United States Patent
Masui et al.

(10) Patent No.: US 8,883,779 B2
(45) Date of Patent: *Nov. 11, 2014

(54) OXAZINE DERIVATIVES AND A PHARMACEUTICAL COMPOSITION FOR INHIBITING BACE1 CONTAINING THEM

(75) Inventors: Moriyasu Masui, Toyonaka (JP);
Yasunori Mitsuoka, Toyonaka (JP);
Syuhei Yoshida, Toyonaka (JP);
Ken-ichi Kusakabe, Toyonaka (JP);
Naohiro Onodera, Toyonaka (JP);
Noriyuki Kurose, Toyonaka (JP)

(73) Assignee: Shinogi & Co., Ltd., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/113,327

(22) PCT Filed: Apr. 25, 2012

(86) PCT No.: PCT/JP2012/061031
§ 371 (c)(1),
(2), (4) Date: Oct. 22, 2013

(87) PCT Pub. No.: WO2012/147763
PCT Pub. Date: Nov. 1, 2012

(65) Prior Publication Data
US 2014/0051691 A1    Feb. 20, 2014

(30) Foreign Application Priority Data

Apr. 26, 2011 (JP) ................................. 2011-098121
Jun. 7, 2011 (JP) ................................. 2011-127185
Dec. 15, 2011 (JP) ................................. 2011-274039

(51) Int. Cl.
*C07D 265/04* (2006.01)
*A61K 31/5355* (2006.01)
*C07D 413/12* (2006.01)
*C07D 413/14* (2006.01)

(52) U.S. Cl.
USPC ........................................ 514/228.8; 544/96

(58) Field of Classification Search
USPC ........................................ 544/96; 514/228.8
See application file for complete search history.

(56) References Cited

U.S. PATENT DOCUMENTS

| | | |
|---|---|---|
| 2,899,426 A | 8/1959 | Bloom |
| 3,115,494 A | 12/1963 | Joseph et al. |
| 3,227,713 A | 1/1966 | Behner |
| 3,235,551 A | 2/1966 | Werner |
| 3,577,428 A | 5/1971 | Suh et al. |
| 3,636,116 A | 1/1972 | Trepanier |
| 3,719,674 A | 3/1973 | Trepanier |
| 3,775,409 A | 11/1973 | Harsanyi et al. |
| 4,049,807 A | 9/1977 | Paulus et al. |
| 4,311,840 A | 1/1982 | Condon |
| 4,895,841 A | 1/1990 | Sugimoto et al. |
| 4,906,626 A | 3/1990 | Amrein et al. |
| 5,100,901 A | 3/1992 | Sugimoto et al. |
| 5,236,942 A | 8/1993 | Miller |
| 5,328,915 A | 7/1994 | Long et al. |
| 5,880,147 A | 3/1999 | Yoshida et al. |
| 5,952,374 A | 9/1999 | Clarkson, Jr. et al. |

(Continued)

FOREIGN PATENT DOCUMENTS

| | | |
|---|---|---|
| CA | 2163724 | 5/1996 |
| CA | 2165386 | 6/1996 |

(Continued)

OTHER PUBLICATIONS

Emilio Testa et al.: "Auf das Zentralnervensystem wirkende Substanzen, XXXVI, Weitere Untersuchungen über die 2-substituierten Azetidine"; Justus Liebigs Annalen Der Chemie, vol. 673, No. 1., May 4, 1964, pp. 60-70 XP055091964.

(Continued)

*Primary Examiner* — Kahsay Habte
(74) *Attorney, Agent, or Firm* — Hamre, Schumann, Mueller & Larson, P.C.

(57) ABSTRACT

The present invention provides a compound of formula (I):

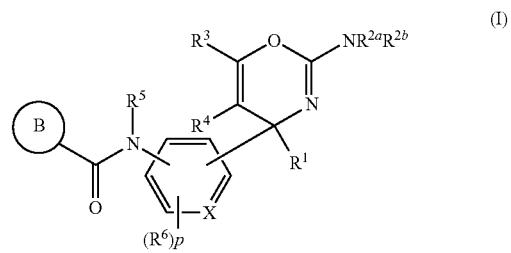

wherein
—X= is —$CR^7$= or —N=,
ring B is a substituted or unsubstituted carbocycle or a substituted or unsubstituted heterocycle,
$R^1$ is substituted or unsubstituted alkyl or the like,
$R^{2a}$ and $R^{2b}$ are each independently hydrogen, substituted or unsubstituted alkyl or the like,
$R^3$ and $R^4$ are each independently hydrogen, halogen, substituted or unsubstituted alkyl or the like,
$R^5$ is hydrogen, substituted or unsubstituted alkyl or the like,
each $R^6$ is independently halogen, hydroxy, substituted or unsubstituted alkyl or the like,
$R^7$ is hydrogen, halogen, hydroxy, substituted or unsubstituted alkyl or the like,
p is an integer of 0 to 3,
or a pharmaceutically acceptable salt thereof which has an effect of inhibiting amyloid β production, especially an effect of inhibiting BACE1, and which is useful as a therapeutic or prophylactic agent for diseases induced by production, secretion and/or deposition of amyloid β proteins.

14 Claims, No Drawings

(56) References Cited

U.S. PATENT DOCUMENTS

| | | |
|---|---|---|
| 6,096,753 A | 8/2000 | Spohr et al. |
| 6,590,123 B2 | 7/2003 | Bekesi et al. |
| 6,713,276 B2 | 3/2004 | Cordell et al. |
| 7,183,070 B2 | 2/2007 | Cordell et al. |
| 7,309,706 B2 | 12/2007 | Rupp et al. |
| 7,326,792 B2 | 2/2008 | Shum et al. |
| 7,414,050 B2 | 8/2008 | Illig et al. |
| 7,763,609 B2 | 7/2010 | Zhu et al. |
| 7,902,238 B2 | 3/2011 | Galley et al. |
| 8,173,642 B2 | 5/2012 | Kobayashi et al. |
| 2002/0019427 A1 | 2/2002 | Carry et al. |
| 2005/0165080 A1 | 7/2005 | Rupp et al. |
| 2006/0173006 A1 | 8/2006 | Sun et al. |
| 2006/183790 A1 | 8/2006 | Cole et al. |
| 2006/183792 A1 | 8/2006 | Fobare et al. |
| 2006/183943 A1 | 8/2006 | Hu et al. |
| 2007/0004730 A1 | 1/2007 | Zhou et al. |
| 2007/0004786 A1 | 1/2007 | Malamas et al. |
| 2007/0027199 A1 | 2/2007 | Malamas et al. |
| 2007/0224656 A1 | 9/2007 | Cordell et al. |
| 2008/0200445 A1 | 8/2008 | Zhu et al. |
| 2009/0023729 A1 | 1/2009 | Nakamuta et al. |
| 2009/0082560 A1 | 3/2009 | Kobayashi et al. |
| 2010/0075957 A1 | 3/2010 | Tamura et al. |
| 2010/0093999 A1 | 4/2010 | Motoki et al. |
| 2010/0125087 A1 | 5/2010 | Holenz et al. |
| 2010/0160290 A1 | 6/2010 | Kobayashi et al. |
| 2010/0234365 A1 | 9/2010 | Liu et al. |
| 2010/0261727 A1 | 10/2010 | Chi et al. |
| 2011/0009395 A1 | 1/2011 | Audia et al. |
| 2011/0046122 A1 | 2/2011 | Andreini et al. |
| 2011/0065695 A1 | 3/2011 | Beauchamp et al. |
| 2011/0190279 A1 | 8/2011 | Hori et al. |
| 2011/0237576 A1 | 9/2011 | Yonezawa et al. |
| 2012/0015961 A1 | 1/2012 | Tamura et al. |
| 2012/0016116 A1 | 1/2012 | Kobayashi et al. |
| 2012/0022249 A1 | 1/2012 | Kobayashi et al. |
| 2012/0172355 A1 | 7/2012 | Tamura et al. |
| 2012/0202828 A1 | 8/2012 | Castro Pineiro et al. |
| 2012/0238548 A1 | 9/2012 | Gabellieri et al. |
| 2012/0238557 A1 | 9/2012 | Masui et al. |
| 2012/0245154 A1 | 9/2012 | Anan et al. |
| 2012/0245155 A1 | 9/2012 | Yoshida et al. |
| 2012/0245157 A1 | 9/2012 | Masui et al. |
| 2012/0253035 A1 | 10/2012 | Narquizian et al. |
| 2012/0258961 A1 | 10/2012 | Suzuki et al. |
| 2012/0258962 A1 | 10/2012 | Hilpert et al. |
| 2012/0295900 A1 | 11/2012 | Hilpert et al. |
| 2013/0210839 A1 | 8/2013 | Masui et al. |
| 2013/0217705 A1 | 8/2013 | Mitsuoka et al. |
| 2013/0303755 A1 | 11/2013 | Kobayashi et al. |

FOREIGN PATENT DOCUMENTS

| | | |
|---|---|---|
| DE | 140144 | 2/1980 |
| EP | 0 798 292 | 10/1995 |
| EP | 0 713 704 | 5/1996 |
| EP | 0 718 294 | 6/1996 |
| EP | 0717040 | 6/1996 |
| EP | 1043312 | 10/2000 |
| EP | 1 283 039 | 2/2003 |
| EP | 1 577 294 | 9/2005 |
| EP | 1942105 | 7/2008 |
| EP | 2147914 | 1/2010 |
| EP | 2151435 | 2/2010 |
| EP | 2233474 | 9/2010 |
| EP | 2305672 | 4/2011 |
| EP | 2332943 | 6/2011 |
| EP | 2 360 155 | 8/2011 |
| EP | 2415756 | 2/2012 |
| GB | 1001093 | 8/1965 |
| JP | 62-120374 | 6/1987 |
| JP | 8-231521 | 9/1996 |
| JP | 9-067355 | 3/1997 |
| JP | 10-505862 | 6/1998 |
| JP | 11-349572 | 12/1999 |
| JP | 2005-509651 | 4/2004 |
| JP | 2004-149429 | 5/2004 |
| JP | 2005-517634 | 6/2005 |
| JP | 2005-526005 | 9/2005 |
| JP | 2005-531520 | 10/2005 |
| JP | 2006-519758 | 8/2006 |
| JP | 2009-051828 | 3/2009 |
| JP | 2009-520685 | 5/2009 |
| WO | WO 94/12165 | 6/1994 |
| WO | WO 95/09619 | 4/1995 |
| WO | WO 96/09286 | 3/1996 |
| WO | WO 96/14842 | 5/1996 |
| WO | WO 96/18608 | 6/1996 |
| WO | WO 97/07098 | 2/1997 |
| WO | 97/14686 | 4/1997 |
| WO | 97/38977 | 10/1997 |
| WO | 99/18960 | 4/1999 |
| WO | 00/00200 | 1/2000 |
| WO | WO 01/19788 | 3/2001 |
| WO | WO 01/78709 | 10/2001 |
| WO | WO 01/87293 | 11/2001 |
| WO | 02/062766 | 8/2002 |
| WO | 02/088101 | 11/2002 |
| WO | WO 02/096897 | 12/2002 |
| WO | 03/040096 | 5/2003 |
| WO | WO 03/039446 | 5/2003 |
| WO | WO 03/040115 | 5/2003 |
| WO | WO 03/040142 | 5/2003 |
| WO | WO 03/082191 | 10/2003 |
| WO | 2004/009549 | 1/2004 |
| WO | WO 2004/014843 | 2/2004 |
| WO | 2004/031154 | 4/2004 |
| WO | 2004/039404 | 5/2004 |
| WO | WO 2004/043916 | 5/2004 |
| WO | WO 2004/096795 | 11/2004 |
| WO | WO 2005/014555 | 2/2005 |
| WO | WO 2005/032493 | 4/2005 |
| WO | 2005/058311 | 6/2005 |
| WO | WO 2005/097767 | 10/2005 |
| WO | WO 2005/111031 | 11/2005 |
| WO | 2005/121100 | 12/2005 |
| WO | 2006/009655 | 1/2006 |
| WO | 2006/023750 | 3/2006 |
| WO | 2006/029850 | 3/2006 |
| WO | WO 2006/041404 | 4/2006 |
| WO | WO 2006/041405 | 4/2006 |
| WO | 2005/065277 | 6/2006 |
| WO | WO 2006/065204 | 6/2006 |
| WO | 2006/076284 | 7/2006 |
| WO | 2006/099379 | 9/2006 |
| WO | WO 2006/138192 | 12/2006 |
| WO | WO 2006/138217 | 12/2006 |
| WO | WO 2006/138265 | 12/2006 |
| WO | WO 2006/138304 | 12/2006 |
| WO | 2007/002220 | 1/2007 |
| WO | WO 2007/005366 | 1/2007 |
| WO | WO 2007/005404 | 1/2007 |
| WO | WO 2007/016012 | 2/2007 |
| WO | WO 2007/038271 | 4/2007 |
| WO | 2007/049532 | 5/2007 |
| WO | 2007/058583 | 5/2007 |
| WO | WO 2007/058580 | 5/2007 |
| WO | WO 2007/058582 | 5/2007 |
| WO | WO 2007/058601 | 5/2007 |
| WO | WO 2007/058602 | 5/2007 |
| WO | WO 2007/073284 | 6/2007 |
| WO | WO 2007/078813 | 7/2007 |
| WO | 2007/092846 | 8/2007 |
| WO | 2007/092854 | 8/2007 |
| WO | WO 2007/114771 | 10/2007 |
| WO | WO 2007/120096 | 10/2007 |
| WO | WO 2007/146225 | 12/2007 |
| WO | WO 2008/011560 | 1/2008 |
| WO | 2008/022024 | 2/2008 |
| WO | 2008/073365 | 6/2008 |
| WO | WO 2008/073370 | 6/2008 |
| WO | 2008/103351 | 8/2008 |

(56) References Cited

FOREIGN PATENT DOCUMENTS

| | | |
|---|---|---|
| WO | 2008/133273 | 11/2008 |
| WO | 2008/133274 | 11/2008 |
| WO | WO 2009/010454 | 1/2009 |
| WO | 2009/064418 | 5/2009 |
| WO | 2009/091016 | 7/2009 |
| WO | 2009/097278 | 8/2009 |
| WO | 2009/097401 | 8/2009 |
| WO | 2009/097578 | 8/2009 |
| WO | 2009/103626 | 8/2009 |
| WO | 2009/131974 | 10/2009 |
| WO | 2009/131975 | 10/2009 |
| WO | 2009/134617 | 11/2009 |
| WO | 2009/151098 | 12/2009 |
| WO | 2010/019392 | 2/2010 |
| WO | 2010/019393 | 2/2010 |
| WO | WO 2010/013302 | 2/2010 |
| WO | WO 2010/013794 | 2/2010 |
| WO | 2010/038686 | 4/2010 |
| WO | 2010/047372 | 4/2010 |
| WO | 2010/056194 | 5/2010 |
| WO | 2010/056195 | 5/2010 |
| WO | 2010/056196 | 5/2010 |
| WO | 2010/113848 | 10/2010 |
| WO | 2010/129864 | 11/2010 |
| WO | WO 2010/128058 | 11/2010 |
| WO | 2011/009897 | 1/2011 |
| WO | 2011/009898 | 1/2011 |
| WO | 2011/009943 | 1/2011 |
| WO | WO 2011/005738 | 1/2011 |
| WO | WO 2011/009943 | 1/2011 |
| WO | WO 2011/020806 | 2/2011 |
| WO | 2011/029803 | 3/2011 |
| WO | WO 2011/044181 | 4/2011 |
| WO | WO 2011/044184 | 4/2011 |
| WO | WO 2011/044185 | 4/2011 |
| WO | WO 2011/044187 | 4/2011 |
| WO | 2011/058763 | 5/2011 |
| WO | 2011/060207 | 5/2011 |
| WO | 2011/069934 | 6/2011 |
| WO | 2011/070029 | 6/2011 |
| WO | 2011/070781 | 6/2011 |
| WO | 2011/071057 | 6/2011 |
| WO | 2011/071109 | 6/2011 |
| WO | 2011/071135 | 6/2011 |
| WO | 2011/077726 | 6/2011 |
| WO | WO 2011/080176 | 7/2011 |
| WO | 2011/138293 | 11/2011 |
| WO | 2011/154431 | 12/2011 |
| WO | WO 2011/154374 | 12/2011 |
| WO | 2012/006953 | 1/2012 |
| WO | WO 2012/000933 | 1/2012 |
| WO | 2012/019966 | 2/2012 |
| WO | 2012/038438 | 3/2012 |
| WO | 2012/057247 | 5/2012 |
| WO | 2012/057248 | 5/2012 |
| WO | 2012/085038 | 6/2012 |
| WO | 2012/093148 | 7/2012 |
| WO | 2012/095469 | 7/2012 |
| WO | 2012/095521 | 7/2012 |
| WO | 2012/098064 | 7/2012 |
| WO | 2012/098213 | 7/2012 |
| WO | 2012/098461 | 7/2012 |
| WO | 2012/104263 | 8/2012 |
| WO | 2012/107371 | 8/2012 |
| WO | 2012/110440 | 8/2012 |
| WO | 2012/110441 | 8/2012 |
| WO | 2012/110459 | 8/2012 |
| WO | 2012/117027 | 9/2012 |
| WO | 2012/119883 | 9/2012 |
| WO | 2012/120023 | 9/2012 |
| WO | 2012/126791 | 9/2012 |
| WO | 2012/136603 | 10/2012 |
| WO | 2012/139993 | 10/2012 |
| WO | 2012/147762 | 11/2012 |
| WO | 2012/147763 | 11/2012 |
| WO | 2012/156284 | 11/2012 |
| WO | 2012/162330 | 11/2012 |
| WO | 2012/162334 | 11/2012 |
| WO | 2012/163790 | 12/2012 |
| WO | 2012/168164 | 12/2012 |
| WO | 2012/168175 | 12/2012 |

OTHER PUBLICATIONS

Portnyagin et al.: Russian Journal of Organic Chemistry, Consultants Bureau, US, vol. 10, Jan. 1, 1974, pp. 95-98, XP009174887.

Database CAPLUS [Online]; Chemical Abstracts Service, Columbus, OH, US; 2006, Bathich, Yaser: "Synthesis of Branched Amino Polyoly and Aminohydroxy Acids: Stereoselective Additiom of C-Nucleophiles ti Isoxazolines and Isoxazolinium Salts and Assignment of Configurations", XP002717806.

Database Registry [Online]; Chemical Abstracts Service, Columbus, OH, US; 3-Pyridinepropanol, .beta., .gamma.-diamino-6-fluoro-.gamma.-(4-fluorophenyl)-, (.beta.-R,.gamma.S)-, Apr. 29, 2004, XP002717807.

Church J et al.: "Anticonvulsant actions of phencyclidine receptor ligands: Correlation with N-Methylaspartate Antagonism in vivo"; General Phamacology, Pergamon Press, Oxford, GB, vol. 21, No. 2, Jan. 1, 1990, pp. 165-170, XP023834032.

Edwards, et al., "Application of Fragment-Based Lead Generation to the Discovery of Novel, Cyclic Amidine β-Secretase Inhibitors with Nanomolar Potency, Cellular Activity, and High Ligand Efficiency", Journal of Medicinal Chemistry, vol. 50, No. 24, 2007, pp. 5912-5925.

Kuo, et al., "A Synthesis of Estrone via Novel Intermediates. Mechanism of the Coupling Reaction of a Vinyl Carbinol with a β Diketone", The Journal of Organic Chemistry, vol. 33, No. 8, Aug. 1968, pp. 3126-3132.

Cohen, et al., "Synthesis of 2-Amino-5,6-dihydro-4,*H*-1,3-thiazines and Related Compounds by Acid Catalyzed Cyclizationof Allylic Isothiuronium Salts", Journal of Heterocyclic Chemistry, vol. 14, 1977, pp. 717-723.

Hünig, et al., "Azofarbstoffe Durch Oxydative Kupplung, XVIII. Synthese von-3-substituierten Thiazolon-(2)-hydrazonen und Thiazolon-(2)-benzolsulfonylhydrazonen", European Journal of Organic Chemistry, vol. 647, No. 1, May 1961, pp. 66-76.

Schaumann, et al., "Cycloadditionsreaktionen von Heterokumulenen, XXIII. Stickstoffhaltige Fünfring-Heterocyclen aus Carbodiimiden oder Keteniminen mit 3-Dimethylamino-2*H*-azirinen", Liebigs Ann. Chem., 1981, pp. 290-305.

Cambie, et al., "*vic*-Iodothiocyanates and Iodoisothiocyanates. Part 2. New Syntheses of Thiazolidin-2-ones and 2-Amino-2-thiazolines", Journal of the Chemical Society, Perkin Transactions I, No. 3, 1979, pp. 765-770.

Fernández, et al., "Syntheses of β-iodourea derivatives of carbohydrates and glycosylamino-oxazolines", Carbohydrate Research, vol. 216, 1991, pp. 21-32.

Fernández, et al., "Syntheses and Spectral Properties of β-Iodoureas and 2-Amino-4,4-diphenyl-2-oxazolines", Journal of Heterocyclic Chemistry, vol. 28, 1991, pp. 777-780.

Liebscher, et al., "2-Arylimino-3-Thiazolines—Formation of Unusual Tautomers of 2-Acylamino-Thiazolines—a Revision", Tetrahedron Letters, vol. 26, No. 35, 1985, pp. 4179-4180.

Koriyama et al., "Reversal of diastereofacial selectivity in the nucleophilic addition reaction to chiral *N*-sulfinimine and application to the synthesis of indrizidine 223AB," Tetrahedron, vol. 58, 2002, pp. 9621-9628.

Fujisawa et al., "Switchover of diastereofacial selectivity in the condensation reaction of optically active *N*-sulfinimine with ester enolate," Tetrahedron Letters, vol. 37, No. 22, 1996, pp. 3881-3884.

Vilaivan et al., "Recent Advances in Catalytic Asymmetric Addition to Imines and Related C=N Systems," Current Organic Chemistry, vol. 9, 2005, pp. 1315-1392.

Hua et al., "*N*-Alkylidenesulfinamides," Sulfur Reports, vol. 21, 1999, pp. 211-239.

Savoca et al., "1,5-Diazabicyclo[4.3.0]non-5-ene[1]," Encyclopedia of Reagents for Organic Synthesis, 2006, 10 pages total.

(56) References Cited

OTHER PUBLICATIONS

Creeke et al., "Synthesis and elaboration of heterocycles via iodocyclisation of unsaturated thioureas," Tetrahedron Letters, 1989, vol. 30, No. 33, pp. 4435-4438.
Mellor et al., A general route to spirocycles by radical additions to exocyclic unsaturated sulphides and related compounds, Tetrahedron Letters, 1991, vol. 32, No. 48, pp. 7111-7114.
Murai et al., "Iodo-cyclization of N-homoallyl thioamides leading to 2,4-diaryl-5,6-dihydro-4H-1,3-thiazines," Chemistry Letters, 2004, vol. 33, No. 5, pp. 508-509.
Singh et al., "Synthesis of heterocyclic compounds via enamines. Part 8.[†] Acid-catalysed transformations in a 4,4,6-trimethyl-1,4-dihydropyrimidine-2(3H)-thione derivatives and related compounds," J. Chem. Soc., Perkin Trans. 1, 1980, pp. 1013-1018.
Kondrat'eva et al., "Noncyclic dimer of 4-methyl-2-dimethlaminooxazole," Izvestiya Akademii Nauk SSSR, Seriya Khimicheskaya, No. 7, Jul. 1977, pp. 1680-1682 (with English translation).
Database Registry [Online], Chemical Abstracts Service, Columbus, Ohio, US; May 29, 2007, "2H-Indol-2-ome,4-(-2-amino-5,6-dihydro-4-methyl-4H-1,3-thiazin-4-y1)-1,3-dihydro-", XP002646872, Database accession No. 935998-84-8.
Schubert et al., "Neue synthesen von 2-Amino-5,6-dihydro-4H-1,3-thiazinen," Archiv der Pharmazie, 1968, vol. 301, No. 10, pp. 750-762.
Huang et al., "Pharmacophore model construction of β-secretase inhibitors," 2008, Acta Chimica Sinica, vol. 66, No. 16, pp. 1889-1897 (English language abstract provided).
Clark, et al., "Antitumor Imidazotetrazines. 32.[1] Synthesis of Novel Imidazotetrazinones and Related Bicyclic Heterocycles to Probe the Mode of Action of the Antitumor Drug Temozolomide", J. Med. Chem., vol. 38, 1995, pp. 1493-1504.
Congreve, et al., "Application of Fragment Screening by X-ray Crystallography to the Discovery of Aminopyridines as Inhibitors of β-Secretase", J. Med. Chem., vol. 50, 2007, pp. 1124-1132.
Huang, et al., "Progress in the Development of Nonpeptidomimetic BACE 1 Inhibitors for Alzheimer's Disease", Current Medicinal Chemistry, vol. 16, 2009, pp. 1806-1820.
Goodyer et al., "Synthesis of N-benzyl- and N-phenyl-2-amino-4,5-dihydrothiazoles and thioureas and evaluation as modulators of the isoforms of nitric oxide synthase," Bioorganic & Medicinal Chemistry, 2003, vol. 11, pp. 4189-4206.
Siddiqui et al., "Some extensions of Von Bruan (BrCN) reaction on organic bases," Proc. Pakistan Acad. Sci., 1988, vol. 25, No. 3, pp. 231-240.
Ozawa et al., Pharmacological actions of 2-Aminoethylisothiuronium (AET) derivatives. I[1], Yakugaku Zasshi, 1968, vol. 88, No. 2, pp. 156-162 (English language abstract provided).
Curtis et al., The byozynsethis of Phenols. Part VIII. The synthesis of (2-carboxy-3,5-dihydroxyphynyl)propan-2-one (C-acetyl-o-orsellinic acid). Journal of the Chemical Society, 1964, pp. 5382-5385.
Burton et al., "Addition reactions of quinones. Part I. The reaction of cysteine and thiourea and its derivatives with some quinones," Journal of the Chemical Society, 1952, pp. 2193-2196.
Matsui, "Yomo bochuzai no kenkyu (the 6th report) Kagaku kozo to yomo shokugai boshi koka tono kankei (III)," Journal of Synthetic Organic Chemistry, Japan, 1950, vol. 8, No. 10, pp. Ho61-Ho65 (and International Search Report issued in PCT/JP2010/055528, which corresponds to co-pending U.S. Appl. No. 13/260,103).
Desai et al., "The condensation of thiocarbamides with monochloroacetic acid and the conversion of arylformamidinethiolacetic acids into pseudothiohydantoin derivatives," Recuil des Travaux Chimiques des Pays-Bas et de la Belgique, 1935, pp. 118-121.
Cole et al., "Acylguanidines as small-molecule beta-secretase inhibitors," J. Med. Chem., 2006, pp. 6158-6161.
Bol'but et al., Heterocyclizations of Functionalized Heterocumulenes with C,N- and C,O-Dinucleophiles: III. Cyclization of N-(1-Aryl-1-chloro-2,2,2-trifluoroethyl)-N'-arylcarbodiimides with 3-Substituted 1-Phenylpyrazol-5- ones, Russian Journal of Organic Chemistry, 2003, vol. 39, No. 12, pp. 1789-1791.
Trepanier et al., "Synthesis and screening for antidepressant activity of some aminoindanooxazolines, aminoindanooxazines, and aminoacenaphthoxazolines," Journal of Medicinal Chemistry, 1970, vol. 13, No. 4, pp. 729-733.
Sayed et al., "α-Enones in heterocyclic synthesis of indazole, thiazine, chromene and quinolone derivatives with their antimicrobial activities," Journal of Chemical Research, 2009, vol. 12, pp. 726-728.
Database Caplus [Online] Chemical Abstracts Service, Columbus, Ohio, US; Xu, Yungen et al: "Preparation of benzimidazolyl and benzothiazolyl isothiourea derivatives as nitric oxide synthase inhibitors", XP002679913, retrieved from STN Database accession No. 2005:46620 abstract Accessed Jul. 13, 2012.
Bol'but et al., "Synthesis of 4-imino-2-trifluoromethyl-3,4-dihydro-2h-Benzo-[1,3]Thiazines" Chemistry of Heterocyclic Compounds, 2001, vol. 37, No. 4, pp. 522-523.
Vovk et al., "Intramolecular thermal cyclization of N-(1-Aryl-1-aryloxy-2,2,2-trifluoroethyl)-N'-arylcarbodiimides" Russian Journal of Organic Chemistry, 2000, vol. 36, No. 12, pp. 1739-1742.
Vovk et al., "Regioselective cyclization of 1-chloroalkylcarbodiimides with 1,1- and 1,2-bifunctional nucleophilic reagents" Russian Journal of Organic Chemistry, 1997, vol. 33, No. 1, pp. 96-102.
Potts et al., "N-Acyl-β-enamino Ketones: Versatile Heterocyclic Synthons" J. Org. Chem., 1983, 48, pp. 623-625.
Rivkin et al., "Piperazinyl pyrimidine derivatives as potent γ-secretase modulators" Bioorganic & Medicinal Chemistry Letters, 2010, 20, pp. 1269-1271.
Rivkin et al,, "Purine derivatives as potent γ-secretase modulators" Bioorganic & Medicinal Chemistry Letters, 2010, 20, pp. 2279-2282.
Vippagunta et al. "Crystalline Solids". Advanced Drug Delivery Reviews, vol. 48, 2001, pp. 3-26.
Gavezzotti. "Are Crystal Structures Predictable". Accounts of Chemical Research, vol. 27, 1994, pp. 309-314.
STN a the Web, RN 79005-45-1, 1964.
Zhu et al., Two novel Diastereoselective Three-Component Reactions of Alkenes or 3,4-Dihydro-(2H)-pyran with Urea/Thiourea-Aldehyde Mixtures: [4 + 2] Cycloaddition vs Biginelli-Type Reaction, Organic Letters, 2006, vol. 8, No. 12, pp. 2599-2602.
Calabrese et al. "NO Synthase and NO-Dependent Signal Pathways in Brain Aging and Neurodegenerative Disorders: The Role of Oxidant/Antioxidant Balance". Neurochemical Balance, vol. 25, No. 9/10, pp. 1315-1341 (2000).
Kavya et al. "Nitric oxide synthase regulation and diversity: Implications in Parkinson's Disease". Nitric Oxide: Biology and Chemistry, vol. 15, No. 4, pp. 280-294 (2006).
Chiou et al. "Review: Effects of Nitric Oxide on Eye Diseases and Their Treatment". Journal of Ocular Pharmacology and Therapeutics, vol. 17, No. 2, pp. 189-198 (2001).
Ishii et al "Suhacute NO generation induced by Alzheimer's β-amyloid in the living brain: reversal by inhibition of the inducible NO synthase". The Federation of American Societies for Experimental Biology Journal, vol. 14, pp. 1485-1489 (2000).
Pak et al. "Morphine via nitric oxide modulates β-amyloid metabolism: a novel protective mechanism for Alzheimer's disease". Medical Science Monitor, vol. 11, No. 10, pp. BR357-BR366 (2005).
Kiselyov et al., "Design and chemical synthesis of [1,2,4]triazol[1,5-c]pyrimidin-5-y1 amines, a novel class of VEGFR-2 kinase inhibitors," 2009, Tetrahedron Letters, vol. 50, pp. 3809-3812.
Mulcahy et al., "A stereoselective synthesis of (+)-Gonyautoxin 3," Journal of the American Chemical Society, 2008, vol. 130, pp. 12630-12631.
"Diphenyl Cyanocarbonimidate," e-EROS Encyclopedia of Reagents for Organic Synthesis, 2001, 2 pages total.
Shafik et al., "Synthesis of novel 2-[2-(substituted amino)phenethyl]-1H-benzimidazoles; 3,4-dihydro and 1,2,3,4-tetrahydropyrimido[1,6-α]-benzimidazoles as potential antiulcer agents," 2004, Pharmazie, vol. 59, No. 12, pp. 899-905.

(56) References Cited

OTHER PUBLICATIONS

Pohl et al., "Synthesis of partially saturated condensed triazoles by reaction of ω-Aminoalkyl-1,2,4-triazoles with electrophiles," Journal fuer Praktische Chemie Chemiker-Zeitung, 1992, vol. 334, pp. 630-636.

Buschauer et al., "Isohistamine und Homologe als Bausteine von $H_2$-Antagonisten," Arzneimittel-Forschung, 1985, vol. 35, pp. 1025-1029 (English language abstract provided).

Buschauer et al., "7,8-Dihydroimidazo[1,2-c]pyrimidin-5(6H)-one, -5(6H)-thione and -5(6H)-ylidencyanamide," Chemische Berichte, 1984, vol. 117, pp. 2597-2614.

Borchers et al., "$H_2$-Antihystaminika, 19. Mitt.[1]) Syntheses und $H_2$-antihistaminische Wirkung $N^α$-substituierter Histamine," Archiv der Pharmazie (Weinheim, Germany), 1984, vol. 317, pp. 455-459.

Cheong et al., "Pharmacophore elucidation for a new series of 2-aryl-pyrazolo-triazolo-pyrimidines as potent human $A_3$ adenosine receptor antagonists," Bioorganic & Medicinal Chemistry Letters, 2011, vol. 21, pp. 2898-2905.

Xu et al., "Copper-catalyzed cascade synthesis of benzimidazoquinazoline derivatives under mild condition," Chemical Communications, 2011, vol. 47, pp. 5596-5598.

Kishore et al., "QSAR of adenosine receptor antagonists: exploring physicochemical requirements for binding of pyrazolo[4,3-e]-1,2,4-triazolo[1,5-c]pyrimidine derivatives with human adenosine $A_3$ receptor subtype," Bioorganic & Medicinal Chemistry Letters, 2011, vol. 21, No. 2, pp. 818-823.

Dolzhenko et al., "8-methyl-2-[4-(trifluoromethyl)phenyl]-8H-pyrazolo[4,3-e][1,2,4]triazolo[1,5-c]-pyrimidin-5-amine methanol disolvate," Acta Crystallographica, Section E: Structure Reports Online, E66(7), 12 pages total, (2010).

Weinhardt et al. "Synthesis and antidepressant profiles of phenyl-substituted 2-amino- and 2-((alkoxycarbonyl)amino)11,4,5,6-tetrahydropyrimidines," Journal of Medicinal Chemistry, vol. 28, No. 6, 1985, pp. 694-698.

Meschino et al., "2-Amino-5,6-dihydro-1,3-oxazines. The reduction of carboxylic esters with sodium borohydride," J. Org. Chem., vol. 28, 1963, pp. 3129-3134.

Poos et al., "2-amino-5-aryl-2-oxazolines. Potent new anorectic agent," J. Med. Chem., vol. 6, 1963, pp. 266-272.

Sandin et al., "A fast and parallel route to cyclic isothioureas and guanidines with use of microwave-assisted chemistry," J. Org. Chem., vol. 69, 2004, pp. 1571-1580.

Weinhardt et al., "Synthesis and central nervous system propreties of 2-[(Alkoxycarbonyl)amino]-4(5)-phenyl-2-imidazolines," Journal of Medicinal Chemistry, vol. 27, No. 5, 1984, pp. 616-627.

Woodgate et al., "A new synthesis of 2-amino-2-thiazolines," Heterocycles, vol. 7, No. 1, 1977, pp. 109-112.

Dörwald, "Side reactions in organic synthesis: a guide to successful synthesis design" 2005 Wiley-VCH Verlag GmbH & Co., KGaA, Wienheim, chapter 1, 32 pages total.

Wermuth; Practice of Medicinal Chemistry, Third Ed., 2008, Elsevier, chapter 15.

Co-pending U.S. Appl. No. 13/887,745, entitled Aminodihydrothiazine Derivatives Substituted With a Cyclic Group, filed May 6, 2013.

Co-pending U.S. Appl. No. 13/952,073, entitled Sulfur-Containing Heterocyclic Derivative Having Beta Secretase Inhibitory Activity, filed Jul. 26, 2013.

Co-pending U.S. Appl. No. 14/070,202 entitled A Pharmaceutical Composition for Treating Alzheimer'S Disease, filed Nov. 1, 2013.

Co-pending U.S. Appl. No. 14/112,400 entitled Pyridine Derivatives and a Pharmaceutical Composition for Inhibiting BACE1 Containing Them, filed Oct. 17, 2013.

Beaton et al., "3,4-dihydro-1-isoquinolinamines: a novel class of nitric oxide synthase inhibitors with a range of isoform selectivity and potency," Bioorganic & Medicinal Chemistry Letters, 2001, vol. 11, pp. 1023-1026.

Beaton et al., "The synthesis of 1-aminodihydroisoquinolines by an imine addition cyclisation reaction," 1998, Tetrahedron Letters, vol. 39, pp. 1227-1230.

Tian et al., "Radiosynthesis of 8-Fluoro-3-(4-[18F]Fluorophenyl)-3,4-Dihydro-1-Isoquinolinamine ([18F]FFDI), a potential PET radiotracer for the inducible nitric oxide synthase," 2008, Current Radiopharmaceuticals, vol. 1, pp. 49-53.

Bathich, "Synthesis of branched amino polyols and amino hydroxy acids: stereoselective addition of C-Nucleophiles to isoxazoline and isoxazolinium salts and assignment of configurations," 2006, pp. 148.

OXAZINE DERIVATIVES AND A PHARMACEUTICAL COMPOSITION FOR INHIBITING BACE1 CONTAINING THEM

FIELD OF THE INVENTION

The present invention relates to a compound having an effect of inhibiting amyloid β production and is useful as a therapeutic or prophylactic agent for diseases induced by production, secretion and/or deposition of amyloid β proteins.

BACKGROUND ART

In the brains of patients with Alzheimer's disease, peptides each consisting of approximately 40 amino acids, called amyloid β proteins, which widely accumulate outside neurons to form insoluble plaques (senile plaques) are observed. These senile plaques are considered to kill neurons and cause the onset of Alzheimer's disease. As therapeutic agents for Alzheimer's disease, agents promoting degradation of amyloid β proteins and amyloid β vaccines have been studied.

Secretases are enzymes which cleave a protein called amyloid precursor protein (APP) within a cell and generate an amyloid β protein. An enzyme which produces N-terminals of amyloid β proteins is called as BACE1 (beta-site APP-cleaving enzyme 1, BACE1). It is considered that production of amyloid β proteins may be suppressed by inhibiting this enzyme, and thus a substance with such an effect can serve as a therapeutic or prophylactic agent for Alzheimer's disease.

Patent Documents 1 to 19 disclose compounds having a structure similar to those of the compounds of the present invention. Each of these document discloses each of these compound is useful as a therapeutic agent for Alzheimer's disease, Alzheimer's relating symptoms or diabetes, but each of these substantially disclosed compounds has a structure different from those of the compounds of the present invention.

PRIOR ART

Patent Document

Patent Document 1: WO2007/049532
Patent Document 2: WO2008/133273
Patent Document 3: WO2008/133274
Patent Document 4: WO2009/151098
Patent Document 5: WO2010/047372
Patent Document 6: WO2011/058763
Patent Document 7: WO2010/128058
Patent Document 8: WO2009/134617
Patent Document 9: WO2011/009898
Patent Document 10: WO2011/009943
Patent Document 11: WO2011/020806
Patent Document 12: WO2011/070029
Patent Document 13: WO2011/069934
Patent Document 14: WO2011/138293
Patent Document 15: WO2007/58583
Patent Document 16: WO2011/154431
Patent Document 17: WO2011/071135
Patent Document 18: WO011/071057
Patent Document 19: WO2011/070781

SUMMARY OF THE INVENTION

Problems to be Solved by the Invention

The present invention provides a compound which has an effect of inhibiting amyloid β production, in particular BACE1 inhibitory effect, and is useful as a therapeutic or prophylactic agent for diseases induced by production, secretion or deposition of amyloid p proteins.

Means for Solving the Problem

The present invention provides:
(1) A compound of formula (I):

[Chemical Formula 1]

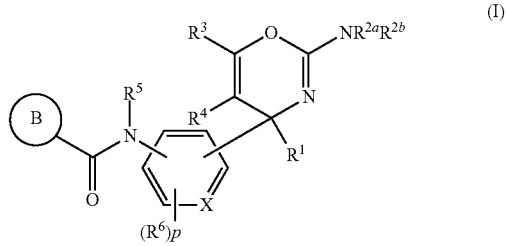

wherein —X= is —CR$^7$= or —N=,
ring B is a substituted or unsubstituted carbocycle or a substituted or unsubstituted heterocycle,
R$^1$ is substituted or unsubstituted alkyl, substituted or unsubstituted alkenyl, substituted or unsubstituted alkynyl, substituted or unsubstituted acyl, cyano, carboxy, substituted or unsubstituted alkoxycarbonyl, substituted or unsubstituted alkenyloxycarbonyl, substituted or unsubstituted alkynyloxycarbonyl, substituted or unsubstituted carbamoyl, substituted or unsubstituted thiocarbamoyl, a substituted or unsubstituted carbocyclic group or a substituted or unsubstituted heterocyclic group,
R$^{2a}$ and R$^{2b}$ are each independently hydrogen, substituted or unsubstituted alkyl, substituted or unsubstituted acyl, substituted or unsubstituted alkoxycarbonyl or substituted or unsubstituted carbamoyl,
R$^3$ and R$^4$ are each independently
hydrogen, halogen, hydroxy, substituted or unsubstituted alkyl, substituted or unsubstituted alkenyl, substituted or unsubstituted alkynyl, substituted or unsubstituted alkoxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, substituted or unsubstituted acyloxy, cyano, nitro, carboxy, substituted or unsubstituted alkoxycarbonyl, substituted or unsubstituted alkenyloxycarbonyl, substituted or unsubstituted alkynyloxycarbonyl, substituted or unsubstituted amino, substituted or unsubstituted carbamoyl, substituted or unsubstituted thiocarbamoyl, substituted or unsubstituted sulfamoyl, substituted or unsubstituted alkylsulfinyl, substituted or unsubstituted alkenylsulfinyl, substituted or unsubstituted alkynylsulfinyl, substituted or unsubstituted alkylsulfonyl, substituted or unsubstituted alkenylsulfonyl, substituted or unsubstituted alkynylsulfonyl, a substituted or unsubstituted carbocyclic group, substituted or unsubstituted carbocycyloxy, substituted or unsubstituted carbocyclylthio, substituted or unsubstituted carbocyclylalkyl, substituted or unsubstituted carbocyclylalkoxy, substituted or unsubstituted carbocyclyloxycarbonyl, substituted or unsubstituted carbocyclylsulfinyl, substituted or unsubstituted carbocyclylsulfonyl, a substituted or unsubstituted heterocyclic group, substituted or unsubstituted heterocyclyloxy, substituted or unsubstituted heterocyclylthio, substituted or unsubstituted heterocyclylalkyl, substituted or unsubstituted heterocyclylalkoxy, substituted or unsubstituted heterocyclyloxycarbonyl, substituted or unsubstituted heterocyclylsulfinyl or substituted or unsubstituted heterocyclylsulfonyl, $R^5$ is hydrogen, substituted or unsubstituted alkyl, substituted or unsubstituted alkenyl, substituted or unsubstituted alkynyl or substituted or unsubstituted acyl, each $R^6$ is independently halogen, hydroxy, substituted or unsubstituted alkyl, substituted or unsubstituted alkenyl, substituted or unsubstituted alkynyl, substituted or unsubstituted alkoxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, substituted or unsubstituted acyloxy, cyano, nitro, carboxy, substituted or unsubstituted alkoxycarbonyl, substituted or unsubstituted alkenyloxycarbonyl, substituted or unsubstituted alkynyloxycarbonyl, substituted or unsubstituted amino, substituted or unsubstituted carbamoyl, substituted or unsubstituted thiocarbamoyl, substituted or unsubstituted sulfamoyl, substituted or unsubstituted alkylsulfinyl, substituted or unsubstituted alkenylsulfinyl, substituted or unsubstituted alkynylsulfinyl, substituted or unsubstituted alkylsulfonyl, substituted or unsubstituted alkenylsulfonyl or substituted or unsubstituted alkynylsulfonyl, $R^7$ is hydrogen, halogen, hydroxy, substituted or unsubstituted alkyl, substituted or unsubstituted alkenyl, substituted or unsubstituted alkynyl, substituted or unsubstituted. alkoxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, substituted or unsubstituted acyloxy, cyano, nitro, carboxy, substituted or unsubstituted alkoxycarbonyl, substituted or unsubstituted alkenyloxycarbonyl, substituted or unsubstituted alkynyloxycarbonyl, substituted or unsubstituted amino, substituted or unsubstituted carbamoyl, substituted or unsubstituted thiocarbamoyl, substituted or unsubstituted sulfamoyl, substituted or unsubstituted alkylsulfinyl, substituted or unsubstituted alkenylsulfinyl, substituted or unsubstituted alkynylsulfinyl, substituted or unsubstituted alkylsulfonyl, substituted or unsubstituted alkenylsulfonyl or substituted or unsubstituted alkynylsulfonyl, p is an integer of 0 to 3, excluding the following compounds:

[Chemical Formula 2]

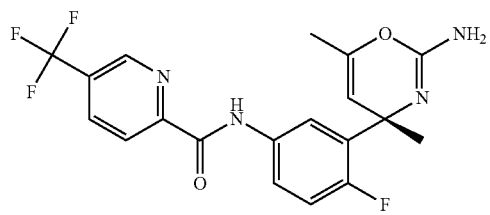

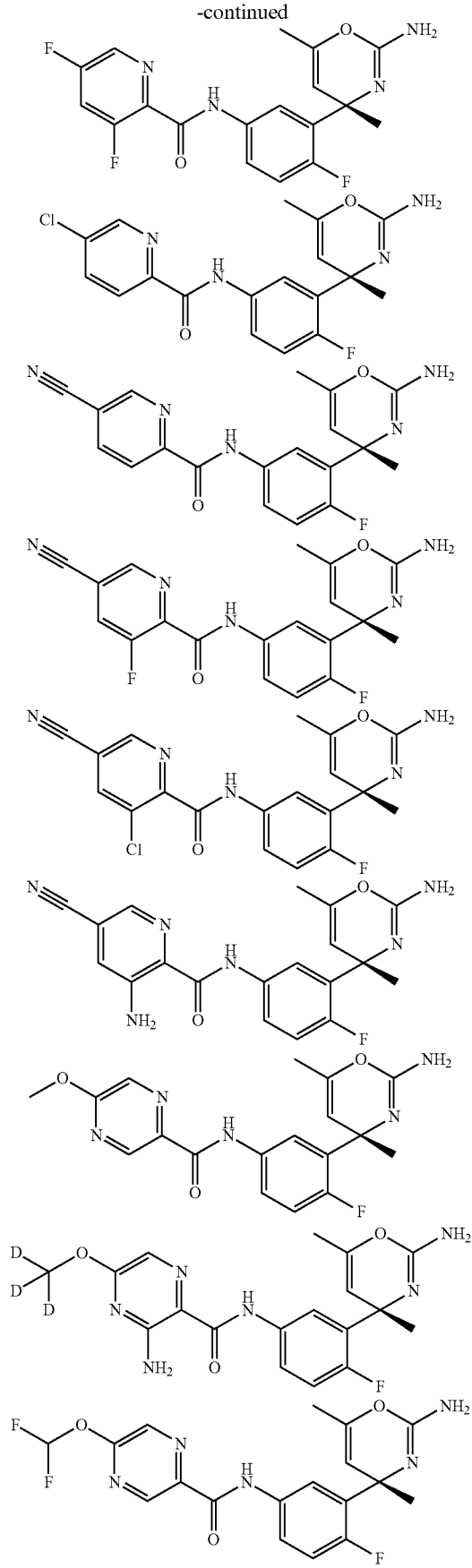

-continued

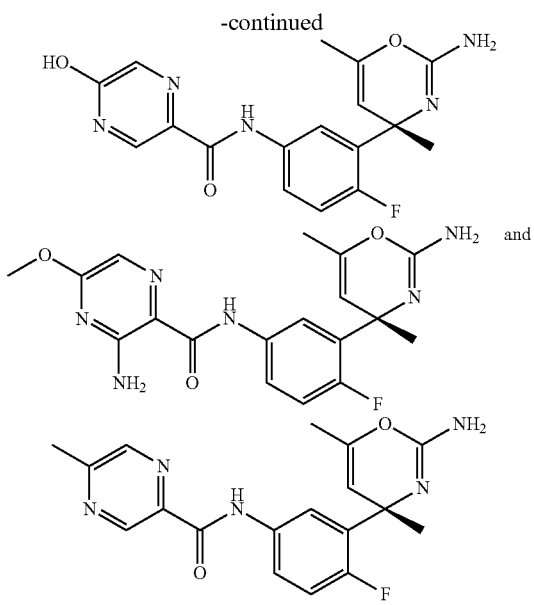

wherein D is deuterium,
or a pharmaceutically acceptable salt thereof.

(2) The compound according to item (1) wherein $R^3$ is hydrogen, halogen or substituted alkyl, or a pharmaceutically acceptable salt thereof.

(3) The compound according to item (1) wherein $R^3$ is alkyl substituted with halogen, or a pharmaceutically acceptable salt thereof.

(4) The compound according to item (1) wherein $R^3$ is methyl, —X= is —$CR^7$=, p is an integer of 0, and one of the following conditions is satisfied:
  1) $R^7$ is chloro,
  2) $R^7$ is fluoro, and ring B is a substituted or unsubstituted carbocycle, or
  3) $R^7$ is fluoro, ring B is substituted heterocycle, and the ring B has at least one substituent selected from dihalogenoalkyl, alkenyl, alkynyl, halogenoethoxy and monohalogenomethoxy,
or a pharmaceutically acceptable salt thereof.

(4') The compound according to any one of items (1) to (4) wherein —X= is —N=, or a pharmaceutically acceptable salt thereof.

(5) The compound according to any one of items (1) to (4) and (4') wherein

[Chemical Formula 3]

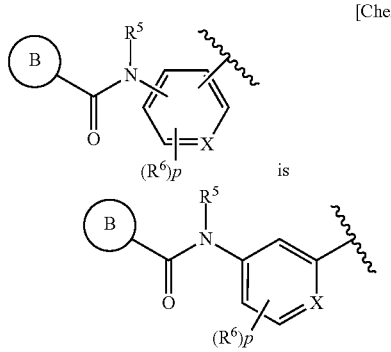

or a pharmaceutically acceptable salt thereof.

(6) The compound according to any one of items (1) to (4), (4') and (5) wherein $R^1$ is C1 to C3 alkyl substituted with halogen, or a pharmaceutically acceptable salt thereof.

(7) The compound according to any one of items (1) to (4), (4'), (5) and (6) wherein $R^1$ is C1 to C3 unsubstituted alkyl, or a pharmaceutically acceptable salt thereof.

(8) The compound according to any one of items (1) to (4), (4'), (5) to (7) wherein ring B is substituted or unsubstituted pyridine, substituted or unsubstituted pyrimidine, substituted or unsubstituted pyrazine, substituted or unsubstituted oxazole, substituted or unsubstituted thiazole, substituted or unsubstituted pyrazole, substituted or unsubstituted benzene, substituted or unsubstituted benzoxazole or substituted or unsubstituted benzothiazole, or a pharmaceutically acceptable salt thereof.

(8') The compound according to any one of items (1) to (4), (4'), (5) to (7) wherein ring B is substituted or unsubstituted pyridine, substituted or unsubstituted pyrimidine, substituted or unsubstituted pyrazine, or substituted or unsubstituted benzene, or a pharmaceutically acceptable salt thereof.

(9) The compound according to any one of items (1) to (4), (4'), (5) to (8) and (8') wherein ring B is optionally substituted with one or more substituents selected from halogen, cyano, hydroxy, nitro, substituted or unsubstituted alkyl, substituted or unsubstituted alkenyl, substituted or unsubstituted alkynyl, substituted or unsubstituted alkoxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted amino and substituted or unsubstituted cycloalkyl, or a pharmaceutically acceptable salt thereof.

(9') The compound according to any one of items (1) to (4), (4'), (5) to (8) and (8') wherein ring B is optionally substituted with one or more substituents selected from halogen, cyano, hydroxy, nitro, substituted or unsubstituted alkyl, substituted or unsubstituted alkenyl, substituted or unsubstituted alkynyl, substituted or unsubstituted alkoxy, substituted or unsubstituted alkenyloxy, substituted or unsubstituted alkynyloxy, substituted or unsubstituted alkylthio, substituted or unsubstituted alkenylthio, substituted or unsubstituted alkynylthio, and substituted or unsubstituted amino, or a pharmaceutically acceptable salt thereof.

(10) The compound according to any one of items (1) to (4), (4'), (5) to (8), (8'), (9) and (9') wherein $R^4$ is hydrogen, or a pharmaceutically acceptable salt thereof.

(11) The compound according to any one of items (1) to (4), (4'), (5) to (8), (8'), (9), (9') and (10) wherein both of $R^{2a}$ and $R^{2b}$ are hydrogen, or a pharmaceutically acceptable salt thereof.

(12) A pharmaceutical composition comprising the compound according to any one of items (1) to (4), (4'), (5) to (8), (8'), (9), (9'), (10) and (11) a pharmaceutically acceptable salt thereof.

(13) A pharmaceutical composition having BACE1 inhibitory activity comprising the compound according to any one of items (1) to (4), (4'), (5) to (8), (8'), (9), (9'), (10) and (11), or a pharmaceutically acceptable salt thereof.

(14) A method for inhibiting BACE1 activity comprising administering the compound according to any one of items (1) to (4), (4'), (5) to (8), (8'), (9), (9'), (10) and (11), or a pharmaceutically acceptable salt thereof.

(15) A compound according to any one of items (1) to (4), (4'), (5) to (8), (8'), (9), (9'), (10) and (11), or a pharmaceutically acceptable salt thereof for use in inhibiting BACE1 activity.

(16) Use of the compound according to any one of items (1) to (4), (4'), (5) to (8), (8'), (9), (9'), (10) and (11), or a pharmaceutically acceptable salt thereof in the manufacture of a medicament for inhibiting BACE1 activity.
(17) A method for treating or preventing diseases induced by production, secretion or deposition of amyloid β proteins comprising administering the compound according to any one of items (1) to (4), (4'), (5) to (8), (8'), (9), (9'), (10) and (11) or a pharmaceutically acceptable salt thereof.
(18) Use of the compound according to any one of items (1) to (4), (4'), (5) to (8), (8'), (9), (9'), (10) and (11) or a pharmaceutically acceptable salt thereof in the manufacture of a medicament for treating or preventing diseases induced by production, secretion or deposition of amyloid β proteins.
(19) A compound according to any one of items (1) to (4), (4'), (5) to (8), (8'), (9), (9'), (10) and (11) or a pharmaceutically acceptable salt thereof for use in a method for treating or preventing diseases induced by production, secretion or deposition of amyloid β proteins.
(20) A method for treating or preventing Alzheimer's disease comprising administering the compound according to any one of items (1) to (4), (4'), (5) to (8), (8'), (9), (9'), (10) and (11) or a pharmaceutically acceptable salt thereof.
(21) Use of the compound according to any one of items (1) to (4), (4'), (5) to (8), (8'), (9), (9'), (10) and (11) or a pharmaceutically acceptable salt thereof in the manufacture of a medicament for treating or preventing Alzheimer's disease.
(22) The compound according to any one of items (1) to (4), (4'), (5) to (8), (8'), (9), (9'), (10) and (11) or a pharmaceutically acceptable salt thereof for use in a method for treating or preventing Alzheimer's disease.
(23) A method, a system, an apparatus, a kit or the like for manufacturing the compound according to any one of items (1) to (4), (4'), (5) to (8), (8'), (9), (9'), (10) and (11) or a pharmaceutically acceptable salt thereof.
(24) A method, a system, an apparatus, a kit or the like for preparing a pharmaceutical composition comprising the compound according to any one of items (1) to (4), (4'), (5) to (8), (8'), (9), (9'), (10) and (11) or a pharmaceutically acceptable salt thereof.
(25) A method, a system, an apparatus, a kit or the like for use the compound according to any one of items (1) to (4), (4'), (5) to (8), (8'), (9), (9'), (10) and (11) or a pharmaceutically acceptable salt thereof.
(26) The pharmaceutical composition according to item (12) or (13) for treating or preventing a disease induced by production, secretion or deposition of amyloid β proteins.
(27) The pharmaceutical composition according to item (12) or (13) for treating or preventing Alzheimer's disease.

Effect of the Invention

The compound of the present invention has BACE1 inhibitory activity and is useful as an agent for treating and/or preventing disease induced by production, secretion or deposition of amyloid β protein such as Alzheimer's disease.

BEST MODE FOR CARRYING OUT THE INVENTION

Each meaning of terms used herein is described below. In the present specification, each term is used in a unified meaning. Both when used alone and in combination with another word, each term is used in the same meaning.

In the present specification, the term "halogen" includes fluorine, chlorine, bromine, and iodine.

The halogen portions in "halogenoalkyl", "dihalogenoalkyl", "halogenoalkoxy", "halogenoethoxy" and "monohalogenomethoxy" are the same as the above "halogen".

In the present specification, the term "alkyl" includes linear or branched alkyl of a carbon number of 1 to 15, for example, a carbon number of 1 to 10, for example, a carbon number of 1 to 6, and for example, a carbon number of 1 to 3. Examples include methyl, ethyl, n-propyl, isopropyl, n-butyl, isobutyl, sec-butyl, tert-butyl, n-pentyl, isopentyl, neopentyl, hexyl, isohexyl, n-heptyl, isoheptyl, n-octyl, isooctyl, n-nonyl, and n-decyl.

The alkyl portions in "alkoxy", "halogenoalkyl", "hydroxyalkyl", "halogenoalkoxy", "hydroxyalkoxy", "alkoxycarbonyl", "halogenoalkoxycarbonyl", "alkylamino", "aminoalkyl", "alkoxyalkoxy", "alkoxyalkenyloxy", "alkoxyalkynyloxy", "alkylcarbonyl", "alkylcarbamoyl", "hydroxy alkylcarbamoyl", "alkoxyimino", "alkylthio", "alkylsulfonyl", "alkylsulfonylamino", "alkylsulfonylalkylamino", "alkylsulfonylimino", "alkylsulfinylamino", "alkylsulfinylalkylamino", "alkylsulfinylimino", "alkylsulfamoyl", "alkylsulfinyl", "carbocyclylalkyl", "carbocyclylalkoxy", "carbocyclylalkoxycarbonyl", "carbocyclylalkylamino", "carbocyclylalkylcarbamoyl", "cycloalkylalkyl", "cycloalkylalkoxy", "cycloalkylalkylamino", "cycloalkylalkoxycarbonyl", "cycloalkylalkylcarbamoyl", "arylalkyl", "arylalkoxy", "arylalkylamino", "arylalkoxycarbonyl", "arylalkylcarbamoyl", "heterocyclylalkyl", "heterocyclylalkoxy", "heterocyclylalkylamino", "heterocyclylalkoxycarbonyl" and "heterocyclylalkylcarbamoyl" are the same as the above "alkyl."

"Substituted or unsubstituted alkyl" and "substituted alkyl" may be substituted with one or more substituents selected from a substituent group α.

As used herein, the substituent group α is a group consisting of halogen, hydroxy, alkoxy, halogenoalkoxy, hydroxyalkoxy, alkoxyalkoxy, acyl, acyloxy, carboxy, alkoxycarbonyl, amino, acylamino, alkylamino, imino, hydroxyimino, alkoxyimino, alkylthio, carbamoyl, alkylcarbamoyl, hydroxyalkylcarbamoyl, sulfamoyl, alkylsulfamoyl, alkylsulfinyl, alkylsulfonyl, alkylsulfonylamino, alkylsulfonylalkylamino, alkylsulfonylimino, alkylsulfinylamino, alkylsulfinylalkylamino, alkylsulfinylimino, cyano, nitro, a carbocyclic group and a heterocyclic group wherein the carbocycle and heterocycle may be each substituted with one or more substituents selected from halogen, alkyl, hydroxy, and alkoxy.

Examples of the substituent of "substituted or unsubstituted alkoxy", "substituted or unsubstituted alkoxycarbonyl", "substituted or unsubstituted alkylthio", "substituted or unsubstituted alkylsulfonyl" and "substituted or unsubstituted alkylsulfinyl" are one or more substituents selected from the above-mentioned substituent group α.

Examples of "halogenoalkyl" are monofluoromethyl, difluoromethyl, trifluoromethyl, monochloromethyl, dichloromethyl, trichloromethyl, monofluoroethyl, difluoroethyl, trifluoroethyl, monochloroethyl, dichloroethyl and trichloroethyl. Examples of "dihalogenoalkyl" are difluoromethyl, difluoroethyl, dichloromethyl and dichloroethyl.

Examples of "halogenoalkoxy" are monofluoromethoxy, difluoromethoxy, trifluoromethoxy, monochloromethoxy, dichloromethoxy, trichloromethoxy, monofluoroethoxy, difluoroethoxy, trifluoroethoxy, monochloroethoxy, dichloroethoxy and trichloroethoxy.

Examples of "halogenoethoxy" are monofluoroethoxy, difluoroethoxy, trifluoroethoxy, monochloro ethoxy, dichloroethoxy and trichloroethoxy.

Examples of "monohalogenomethoxy" are monofluoromethoxy and monochloromethoxy.

The term "alkylidene" includes a divalent group of the above "alkyl" and examples include methylidene, ethylidene, propylidene, isopropylidene, butylidene, pentylidene and hexylidene.

The term "alkenyl" includes linear or branched alkenyl of a carbon number of 2 to 15, for example, a carbon number of 2 to 10, for example, a carbon number of 2 to 6, and for example, a carbon number of 2 to 4, having one or more double bond(s) at any available position. Examples include vinyl, allyl, propenyl, isopropenyl, butenyl, isobutenyl, prenyl, butadienyl, pentenyl, isopentenyl, pentadienyl, hexenyl, isohexenyl, hexadienyl, heptenyl, octenyl, nonenyl, decenyl, undecenyl, dodecenyl, tridecenyl, tetradecenyl and pentadecenyl.

The alkenyl portions in "alkenyloxy", "alkenyloxycarbonyl", "alkenylcarbonyl", "alkoxyalkenyloxy", "alkenylthio", "alkenylamino", "alkenylsulfonyl", and "alkenylsulfinyl" are the same as the above "alkenyl."

The term "alkynyl" includes a linear or branched alkynyl of a carbon number of 2 to 10, for example, a carbon number of 2 to 8, for example, a carbon number 3 to 6, having one or more triple bond(s) at any available position. Examples include ethynyl, propynyl, butynyl, pentynyl, hexynyl, heptynyl, octynyl, nonynyl and decynyl. These may further a double bond at any available position.

The alkynyl portions in "alkynyloxy", "alkynyloxycarbonyl", "alkynylcarbonyl", "alkoxyalkynyloxy", "alkynylthio", "alkynylsulfinyl", "alkynylsulfonyl", and "alkynylamino" are the same as the above "alkynyl."

Examples of the substituent of "substituted or unsubstituted alkenyl", "substituted or unsubstituted alkenyloxy", "substituted or unsubstituted alkenyloxycarbonyl", "substituted or unsubstituted alkenylthio", "substituted or unsubstituted alkenylsulfinyl", "substituted or unsubstituted alkenylsulfonyl", "substituted or unsubstituted alkynyl", "substituted or unsubstituted alkynyloxy", "substituted or unsubstituted alkynylthio", "substituted or unsubstituted alkynyloxycarbonyl", "substituted or unsubstituted alkynylsulfinyl", and "substituted or unsubstituted alkynylsulfonyl" are one or more substituents selected from the above-mentioned substituent group α.

Examples of the substituents of "substituted or unsubstituted amino", "substituted or unsubstituted carbamoyl", "substituted or unsubstituted thiocarbamoyl" and "substituted or unsubstituted sulfamoyl" are one to two substituents selected from alkyl, acyl, hydroxy, alkoxy, alkoxycarbonyl, a carbocyclic group and a heterocyclic group.

The term "acyl" includes formyl, alkylcarbonyl, alkenylcarbonyl, alkynylcarbonyl, carbocyclylcarbonyl, and heterocyclylcarbonyl. Examples are formyl, acetyl, propionyl, butyryl, isobutyryl, valeryl, pivaloyl, hexanoyl, acryloyl, propioloyl, methacryloyl, crotonoyl, benzoyl, cyclohexanecarbonyl, pyridinecarbonyl, furancarbonyl, thiophenecarbonyl, benzothiazolecarbonyl, pyrazinecarbonyl, piperidinecarbonyl and thiomorpholino.

The acyl portions in "acyloxy" and "acylamino" are the same as the above "acyl."

Examples of the substituents of "substituted or unsubstituted acyl" and "substituted or unsubstituted acyloxy" are one or more substituents selected from the substituent group α. The ring portions of carbocyclylcarbonyl and heterocyclylcarbonyl may be substituted with one or more substituents selected from alkyl, substituent group α, and alkyl substituted with one or more substituents selected from substituent group α.

The term "carbocyclic group" includes cycloalkyl, cycloalkenyl, aryl and non-aromatic fused carbocyclyl.

The term "cycloalkyl" includes a carbocyclic group of a carbon number of 3 to 10, for example, a carbon number of 3 to 8, and for example, a carbon number 4 to 8. Examples are cyclopropyl, cyclobutyl, cyclopentyl, cyclohexyl, cycloheptyl, cyclooctyl, cyclononyl and cyclodecyl.

The term "cycloalkane" includes a carbocycle of a carbon number of 3 to 10, for example, a carbon number of 3 to 8, and for example, a carbon number 4 to 8. Examples are cyclopropane, cyclobutane, cyclopentane, cyclohexane, cycloheptane, cyclooctane, cyclononane and cyclodecane.

The cycloalkyl portions in "cycloalkylalkyl", "cycloalkyloxy", "cycloalkylalkoxy", "cycloalkylthio", "cycloalkylamino", "cycloalkylalkylamino", "cycloalkylsulfamoyl", "cycloalkylsulfonyl", "cycloalkylcarbamoyl", "cycloalkylalkylcarbamoyl", "cycloalkylalkoxycarbonyl" and "cycloalkyloxycarbonyl" are the same as that of the above "cycloalkane."

The term "cycloalkenyl" includes a group having one or more double bond(s) at optionally positions in the ring of the above "cycloalkyl". Examples are cyclopropenyl, cyclobutenyl, cyclopentenyl, cyclohexenyl, cycloheptenyl, cyclooctenyl and cyclohexadienyl.

The term "cycloalkene" includes a group having one or more double bond(s) at optionally positions in the ring of the above "cycloalkane". Examples are cyclopropene, cyclobutene, cyclopentene, cyclohexene, cycloheptene, cyclooctene and cyclohexadiene.

The term "aryl" includes phenyl, naphthyl, anthryl and phenanthryl. Specific example is phenyl.

The term "aromatic carbocycle" includes benzene, naphthalene, anthracene, and phenanthrene.

The term "non-aromatic fused carbocyclic group" includes non-aromatic groups wherein two or more rings selected from the above "cycloalkane", "cycloalkene" and "aromatic carbocycle", and at least one ring is "cycloalkane" or "cycloalkene are fused. Examples are indanyl, indenyl, tetrahydronaphthyl and fluorenyl.

The carbocycle portions in "non-aromatic carbocycle" are the same as "cycloalkane", "cycloalkene" or the ring portions of "non-aromatic fused carbocyclic group." Examples are cyclopropane, cyclobutane, cyclopentane, cyclohexane, cycloheptane, cyclooctane, cyclononane, cyclodecane, cyclopropene, cyclobutene, cyclopentene, cyclohexene, cycloheptene, cyclooctene, indane, indene, tetrahydronaphthalene and fluorene.

The carbocycle portions in "carbocycle", "carbocyclyloxy", "carbocyclylalkyl", "carbocyclylalkoxy", "carbocyclylalkoxycarbonyl", "carbocyclylthio", "carbocyclylamino", "carbocyclylalkylamino", "carbocyclylcarbonyl", "carbocyclylsulfamoyl", "carbocyclylsulfonyl", "carbocyclylcarbamoyl", "carbocyclylalkylcarbamoyl", "carbocyclyloxycarbonyl" and "carbocyclylsulfinyl" are the same as that of the above "carbocyclic group."

The aryl portions in "arylalkyl", "aryloxy", "aryloxycarbonyl", "arylalkoxycarbonyl", "arylthio", "arylamino", "arylalkoxy", "arylalkylamino", "arylsulfonyl", "arylsulfamoyl", "arylcarbamoyl" and "arylalkylcarbamoyl" are the same as that of the above "aryl."

The term "heterocyclyl" includes a heterocyclic group comprising one or more rings and having one or more the same or different hetero atom(s) arbitrarily selected from O, S, and N in the ring. Specific examples are 5- or 6-membered heteroaryl such as pyrrolyl, imidazolyl, pyrazolyl, pyridyl, pyridazinyl, pyrimidinyl, pyrazinyl, triazolyl, triazinyl, tetrazolyl, furyl, thienyl, isoxazolyl, oxazolyl, oxadiazolyl, isothiazolyl, thiazolyl, and thiadiazolyl;

non-aromatic heterocyclyl such as dioxanyl, thiiranyl, oxiranyl, oxetanyl, oxathiolanyl, azetidinyl, thianyl, thiazolidinyl, pyrrolidinyl, pyrrolinyl, imidazolidinyl, imidazolinyl, pyrazolidinyl, pyrazolinyl, piperidyl, piperazinyl, morpholinyl, morpholino, thiomorpholinyl, thiomorpholino, dihydropyridyl, tetrahydropyridyl, tetrahydrofuryl, tetrahydropyranyl, dihydrothiazolyl, tetrahydrothiazolyl, tetrahydroisothiazolyl, dihydrooxazinyl, hexahydropyrimidinyl, hexahydroazepinyl, tetrahydrodiazepinyl, tetrahydropyridazinyl, dioxolanyl, dioxazinyl, aziridinyl, dioxolinyl, oxepanyl, thiolanyl, thiinyl, and thiazinyl;

fused bicyclic heterocyclyl such as indolyl, isoindolyl, indazolyl, indolizinyl, indolinyl, isoindolinyl, quinolyl, isoquinolyl, cinnolinyl, phthalazinyl, quinazolinyl, naphthyridinyl, quinoxalinyl, purinyl, pteridinyl, benzopyranyl, benzimidazolyl, benzotriazolyl, benzisooxazolyl, benzoxazolyl, benzoxadiazolyl, benzisothiazolyl, benzothiazolyl, benzothiadiazolyl, benzofuryl, isobenzofuryl, benzothienyl, benzotriazolyl, thienopyridyl, thienopyrrolyl, thienopyrazolyl, thienopyrazinyl, furopyrrolyl, furopyridyl, thienothienyl, imidazopyridyl, imidazopyrazolyl, pyrazolopyridyl, pyrazolopyrazinyl, thiazolopyridyl, oxazolopyridyl, pyrazolopyrimidinyl, pyrazolotriazinyl, pyridazolopyridyl, triazolopyridyl, imidazothiazolyl, pyrazinopyridazinyl, dihydrothiazolopyrimidinyl, tetrahydroquinolyl, tetrahydroisoquinolyl, dihydrobenzofuryl, dihydrobenzoxazinyl, dihydrobenzimidazolyl, tetrahydrobenzothienyl, tetrahydrobenzofuryl, benzodioxolyl, benzodioxonyl, chromanyl, chromenyl, octahydrochromenyl, dihydrobenzodioxinyl, dihydrobenzoxezinyl, dihydrobenzodioxepinyl, and dihydrothienodioxinyl;

fused tricyclic heterocyclyl such as carbazolyl, acridinyl, xanthenyl, phenothiazinyl, phenoxathiinyl, phenoxazinyl, dibenzofuryl, imidazoquinolyl, and tetrahydrocarbazolyl. Specific examples are 5- or 6-membered heteroaryl and non-aromatic heterocyclyl.

The heterocycle portions in "heterocycle", "heterocyclylalkyl", "heterocyclyloxy", "heterocyclylthio", "heterocyclylcarbonyl", "heterocyclylalkoxy", "heterocyclylamino", "heterocyclylsulfamoyl", "heterocyclylsulfonyl", "heterocyclylcarbamoyl", "heterocyclyloxycarbonyl", "heterocyclylalkylamino", "heterocyclylalkoxycarbonyl", "heterocyclylalkylcarbamoyl" and "heterocyclylsulfinyl" are the same as the above "heterocyclyl."

The heterocycle portions in "non-aromatic heterocycle" is the same as the heterocycle portions in the above "non-aromatic heterocyclyl." Specific examples are dioxane, thiirane, oxirane, oxetane, oxathiolane, azetidine, thiane, thiazolidine, pyrrolidine, pyrroline, imidazolidine, imidazoline, pyrazolidine, pyrazoline, piperidine, piperazine, morpholine, thiomorpholine, dihydropyridine, tetrahydropyridine, tetrahydrofuran, tetrahydropyran, dihydrothiazole, tetrahydrothiazole, tetrahydroisothiazole, dihydrooxazine, hexahydroazepine, tetrahydrodiazepine and tetrahydropyridazine.

A bond of the above "heterocyclyl" may be situated on any ring.

The term "heteroaryl" includes aromatic cyclic groups among the above "heterocyclyl."

Examples of the substituent of "substituted or unsubstituted carbocycle", "substituted or unsubstituted heterocycle", "substituted or unsubstituted benzene", "substituted or unsubstituted pyridine", "substituted or unsubstituted pyrimidine", "substituted or unsubstituted pyrazine", "substituted or unsubstituted oxazole", "substituted or unsubstituted thiazole", "substituted or unsubstituted pyrazole", "substituted or unsubstituted benzoxazole" and "substituted or unsubstituted benzothiazole" in ring B include:

a) a group selected from the substituent group a such as halogen, hydroxy, alkoxy, acyl, acyloxy, carboxy, alkoxycarbonyl, carbamoyl, amino, cyano, alkylamino and/or alkylthio;

b) alkyl substituted with one or more groups selected from the substituent group α, hydroxyimino and alkoxyimino, wherein the substituent is, for example, halogen, hydroxy, alkoxy and/or alkoxycarbonyl, or unsubstituted alkyl;

c) aminoalkyl substituted with one or more groups selected from the substituent group α; wherein the substituent is, for example, acyl, alkyl and/or alkoxy;

d) alkenyl substituted with one or more substituents selected from the substituent group α, wherein the substituent is, for example, alkoxycarbonyl, halogen, and/or halogenoalkoxycarbonyl, or unsubstituted alkenyl;

e) alkynyl substituted with one or more substituents selected from the substituent group α, wherein the substituent is, for example, alkoxycarbonyl, or unsubstituted alkynyl;

f) alkoxy substituted with one or more substituents selected from the substituent group α,
    wherein the substituent is, for example, halogen, carbamoyl, alkylcarbamoyl and/or hydroxyalkylcarbamoyl;

g) alkoxyalkoxy substituted with one or more substituents selected from the substituent group α;

h) alkenyloxy substituted with one or more substituents selected from the substituent group α, wherein the substituent is, for example, halogen, hydroxy, amino and/or alkylamino, or unsubstituted alkenyloxy;

i) alkoxyalkenyloxy substituted with one or more substituents selected from the substituent group α;

j) alkynyloxy substituted with one or more substituents selected from the substituent group α, wherein the substituent is, for example, halogen and/or hydroxy, or unsubstituted alkynyloxy;

k) alkoxyalkynyloxy substituted with one or more group(s) selected from the substituent group α;

l) alkylthio substituted with one or more substituents selected from the substituent group α, or unsubstituted alkylthio;

m) alkenylthio substituted with one or more substituents selected from the substituent group α, or unsubstituted alkenylthio;

n) alkynylthio substituted with one or more substituents selected from the substituent group α, or unsubstituted alkynylthio;

o) alkylamino substituted with one or more substituents selected from the substituent group α;

p) alkenylamino substituted with one or more substituents selected from the substituent group α;

q) alkynylamino substituted with one or more substituents selected from the substituent group α;

r) aminooxy substituted with one or more substituents selected from the substituent group α and alkylidene, or unsubstituted aminooxy;

s) acyl substituted with one or more substituents selected from the substituent group α;

t) alkylcarbamoyl substituted with one or more substituents selected from the substituent group α;

u) alkoxycarbonyl substituted with one or more substituents selected from the substituent group α;

v) alkylsulfonyl substituted with one or more substituents selected from the substituent group α, or unsubstituted alkylsulfonyl;

w) alkylsulfinyl substituted with one or more substituents selected from the substituent group α, or unsubstituted alkylsulfinyl;
x) alkylsulfamoyl substituted with one or more substituents selected from the substituent group α;
y) a carbocyclic group such as cycloalkyl and aryl, substituted with one or more substituents selected from the substituent group α, azide, alkyl and halogenoalkyl;
z) a heterocyclic group substituted with one or more substituents selected from the substituent group α, azide, alkyl and halogenoalkyl;
aa) carbocyclylalkyl such as cycloalkylalkyl and arylalkyl, substituted with one or more substituents selected from the substituent group α, azide, alkyl and halogenoalkyl, or unsubstituted carbocyclylalkyl;
ab) heterocyclylalkyl substituted with one or more substituents selected from the substituent group α, azide, alkyl and halogenoalkyl, or unsubstituted heterocyclylalkyl;
ac) carbocyclyloxy such as cycloalkyloxy and aryloxy, substituted with one or more substituents selected from the substituent group α, azide, alkyl and halogenoalkyl, or unsubstituted carbocyclyloxy such as cycloalkyloxy and aryloxy;
ad) heterocyclyloxy substituted with one or more substituents selected from the substituent group α, azide, alkyl and halogenoalkyl, or unsubstituted heterocyclyloxy;
ae) carbocyclylalkoxy such as cycloalkylalkoxy and arylalkoxy, substituted with one or more substituents selected from the substituent group α, azide, alkyl and halogenoalkyl, or unsubstituted carbocyclylalkoxy such as cycloalkylalkoxy and arylalkoxy;
af) heterocyclylalkoxy substituted with one or more substituents selected from the substituent group α, azide, alkyl and halogenoalkyl, or unsubstituted heterocyclylalkoxy;
ag) carbocyclylalkoxycarbonyl such as cycloalkylalkoxycarbonyl and arylalkoxycarbonyl, substituted with one or more substituents selected from the substituent group α, azide, alkyl and halogenoalkyl, or unsubstituted carbocyclylalkoxycarbonyl such as cycloalkylalkoxycarbonyl and arylalkoxycarbonyl;
ah) heterocyclylalkoxycarbonyl substituted with one or more substituents selected from the substituent group α, azide, alkyl and halogenoalkyl, or unsubstituted heterocyclylalkoxycarbonyl;
ai) carbocyclylthio such as cycloalkylthio and arylthio, substituted with one or more substituents selected from the substituent group α, azide, alkyl and halogenoalkyl, or unsubstituted carbocyclylthio such as cycloalkylthio and arylthio;
aj) heterocyclylthio substituted with one or more substituents selected from the substituent group α, azide, alkyl and halogenoalkyl, or unsubstituted heterocyclylthio;
ak) carbocyclylamino such as cycloalkylamino and arylamino, substituted with one or more substituents selected from the substituent group α, azide, alkyl and halogenoalkyl, or unsubstituted carbocyclylamino such as cycloalkylamino and arylamino;
al) heterocyclylamino substituted with one or more substituents selected from the substituent group α, azide, alkyl and halogenoalkyl, or unsubstituted heterocyclylamino; am) carbocyclylalkylamino such as cycloalkylalkylamino and arylalkylamino, substituted with one or more substituents selected from the substituent group α, azide, alkyl and halogenoalkyl or unsubstituted carbocyclylalkylamino;
an) heterocyclylalkylamino substituted with one or more substituents selected from the substituent group α, azide, alkyl and halogenoalkyl, or unsubstituted heterocyclylalkylamino;
ao) carbocyclylsulfamoyl such as cycloalkylsulfamoyl and arylsulfamoyl, substituted with one or more substituents selected from the substituent group α, azide, alkyl and halogenoalkyl, or unsubstituted carbocyclylsulfamoyl;
ap) heterocyclylsulfamoyl substituted with one or more substituents selected from the substituent group α, azide, alkyl and halogenoalkyl, or unsubstituted heterocyclylsulfamoyl;
aq) carbocyclylsulfonyl such as cycloalkylsulfonyl and arylsulfonyl, substituted with one or more substituents selected from the substituent group α, azide, alkyl and halogenoalkyl, or unsubstituted carbocyclylsulfonyl such as cycloalkylsulfonyl and arylsulfonyl;
ar) heterocyclylsulfonyl substituted with one or more substituents selected from the substituent group α, azide, alkyl and halogenoalkyl, or unsubstituted heterocyclylsulfonyl;
as) carbocyclylcarbamoyl such as cycloalkylcarbamoyl and arylcarbamoyl, substituted with one or more substituents selected from the substituent group α, azide, alkyl and halogenoalkyl, or unsubstituted carbocyclylcarbamoyl such as cycloalkylcarbamoyl and arylcarbamoyl;
at) heterocyclylcarbamoyl substituted with one or more substituents selected from the substituent group α, azide, alkyl and halogenoalkyl, or unsubstituted heterocyclylcarbamoyl;
au) carbocyclylalkylcarbamoyl such as cycloalkylalkylcarbamoyl and arylalkylcarbamoyl, substituted with one or more substituents selected from the substituent group α, azide, alkyl and halogenoalkyl, or unsubstituted carbocyclylalkylcarbamoyl such as cycloalkylalkylcarbamoyl and arylalkylcarbamoyl;
av) heterocyclylalkylcarbamoyl substituted with one or more substituents selected from the substituent group α, azide, alkyl and halogenoalkyl, or unsubstituted heterocyclylalkylcarbamoyl;
aw) carbocyclyloxycarbonyl such as cycloalkoxycarbonyl and aryloxycarbonyl, substituted with one or more substituents selected from the substituent group α, azide, alkyl and halogenoalkyl, or unsubstituted carbocyclyloxycarbonyl such as cycloalkoxycarbonyl and aryloxycarbonyl;
ax) heterocyclyloxycarbonyl substituted with one or more substituents selected from the substituent group α, azide, alkyl and halogenoalkyl, or unsubstituted heterocyclyloxycarbonyl;
ay) alkylenedioxy substituted with halogen, or unsubstituted alkylenedioxy;
az) oxo; and
ba) azide.

The aforementioned ring of ring B may be substituted with one or more substituents selected from them.

Examples of the substituents of "substituted or unsubstituted carbocycle", "substituted or unsubstituted benzene", "substituted or unsubstituted heterocycle", "substituted or unsubstituted pyridine", "substituted or unsubstituted pyrimidine", "substituted or unsubstituted pyrazine", "substituted or unsubstituted oxazole", "substituted or unsubstituted thiazole", "substituted or unsubstituted pyrazole", "substituted or unsubstituted benzoxazole" and "substituted or unsubstituted benzothiazole" in ring B include:

halogen;
cyano;
hydroxy;
nitro;
carboxy;
alkyl substituted with one or more substituents selected from the substituent group α; unsubstituted alkyl;
alkenyl substituted with one or more substituents selected from the substituent group α; unsubstituted alkenyl;
alkynyl substituted with one or more substituents selected from the substituent group α; unsubstituted alkynyl;
alkoxy substituted with one or more substituents selected from the substituent group α; unsubstituted alkoxy;

alkenyloxy substituted with one or more substituents selected from the substituent group unsubstituted alkenyloxy;
alkynyloxy substituted with one or more substituents selected from the substituent group unsubstituted alkynyloxy;
alkylthio substituted with one or more substituents selected from the substituent group α; unsubstituted alkylthio;
alkenylthio substituted with one or more substituents selected from the substituent group α;
unsubstituted alkenylthio;
alkynylthio substituted with one or more substituents selected from the substituent group α;
unsubstituted alkynylthio;
amino substituted with one or more substituents selected from the substituent group α;
unsubstituted amino;
alkylamino substituted with one or more substituents selected from the substituent group α;
unsubstituted alkylamino;
cycloalkylamino substituted with one or more substituents selected from the substituent group α,
unsubstituted cycloalkylamino;
carbamoyl substituted with one or more substituents selected from the substituent group α;
unsubstituted carbamoyl;
alkylcarbamoyl substituted with one or more substituents selected from the substituent group α;
unsubstituted alkylcarbamoyl;
alkoxycarbonyl substituted with one or more substituents selected from the substituent group α;
unsubstituted alkoxycarbonyl;
a carbocyclic group substituted with one or more substituents selected from (i) alkyl substituted with one or more substituents selected from the substituent group α, (ii) unsubstituted alkyl and (iii) the substituent group α;
an unsubstituted carbocyclic group.
a heterocyclic group substituted with one or more substituents selected from (i) alkyl substituted with one or more substituents selected from the substituent group α, (ii) unsubstituted alkyl and (iii) the substituent group α; and
an unsubstituted heterocyclic group.

More specifically, examples are one or more substituents selected from halogen, cyano, hydroxy, alkyl, halogenoalkyl, cycloalkylalkyl, alkoxy, halogenoalkoxy, alkoxyalkoxy, cyanoalkoxy, alkenyl, halogenoalkenyl, alkynyl, halogenoalkynyl, alkenyloxy, alkynyloxy, alkylthio, cyanoalkylthio, amino, alkylamino, cycloalkylamino and cycloalkyl.

Examples of the substituents of "an substituted or unsubstituted carbocyclic group", "substituted or unsubstituted carbocyclylthio", "substituted or unsubstituted carbocyclyloxycarbonyl", "substituted or unsubstituted heterocyclyl", "substituted or unsubstituted carbocyclyloxy", "substituted or unsubstituted carbocyclylsulfinyl", "substituted or unsubstituted carbocyclylsulfonyl", "substituted or unsubstituted carbocycle", "substituted or unsubstituted carbocyclylalkyl", "substituted or unsubstituted carbocyclylalkoxy", "substituted or unsubstituted heterocyclyl", "substituted or unsubstituted heterocyclyloxy", "substituted or unsubstituted heterocyclylthio", "substituted or unsubstituted heterocyclyloxycarbonyl", "substituted or unsubstituted heterocyclylsulfinyl", "substituted or unsubstituted heterocyclylsulfonyl", "substituted or unsubstituted heterocycle", "substituted or unsubstituted heterocyclylalkyl" and "substituted or unsubstituted heterocyclylalkoxy" in the groups other than ring B are one or more substituents selected from (i) alkyl substituted with one or more substituents selected from the substituent group α, (ii) unsubstituted alkyl, and (iii) the substituent group α.

The alkylene portion in "alkylenedioxy" includes linear or branched divalent carbon chain of a carbon number 1 to 10, for example, a carbon number of 1 to 6, or a carbon number of 1 to 3. Specific examples are methylenedioxy and dimethylenedioxy.

The compound of the formula (I) is not limited to a specific isomer, and includes all possible isomers such as keto-enol isomers, imine-enamine isomers, diastereoisomers, optical isomers and rotation isomers, racemate and the mixture thereof. For example, the compound of formula (I) in which $R^{2a}$ is hydrogen includes the following tautomers.

[Chemical Formula 4]

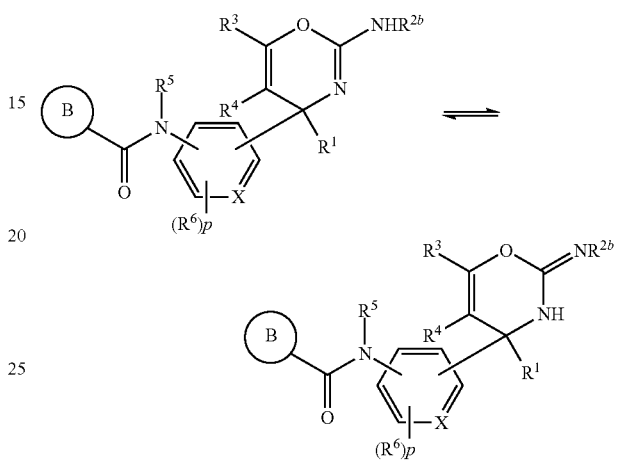

The compound of formula (I) has an asymmetric carbon atom and the compound includes the following optical isomers.

[Chemical Formula 5]

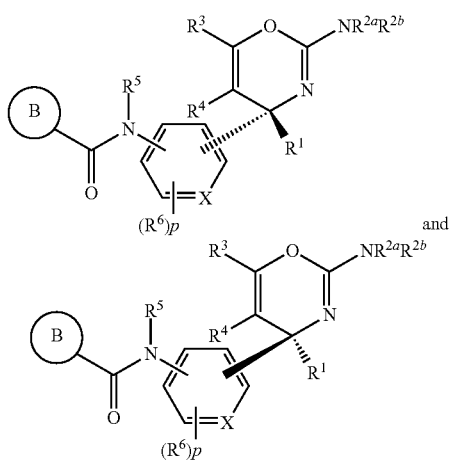

Preferable isomers are as follows.

[Chemical Formula 6]

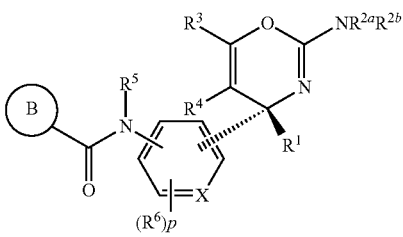

The optical isomer of the compound of formula (I) can be produced by known methods such as separation using chiral chromatography or resolution of a diastereomer by salt formation using a chiral acid or a chiral base.

One or more hydrogen, carbon or other atoms of a compound of formula (I) can be replaced with an isotope of hydrogen, carbon and/or other atoms, respectively. Examples of isotopes include isotopes of hydrogen, carbon, nitrogen, oxygen, phosphorous, sulfur, fluorine, iodine and chlorine, such as $^{2}H$, $^{3}H$, $^{11}C$, $^{13}C$, $^{14}C$, $^{15}N$, $^{18}O$, $^{17}O$, $^{31}P$, $^{32}P$, $^{35}S$, $^{18}F$, $^{128}I$ and $^{36}Cl$, respectively. The compound of formula (I) also includes the compound replaced with such isotopes. The compound replaced with such isotopes is useful also as a medicament, and includes all the radiolabeled compounds of the compound of formula (I). The invention includes "radiolabelling method" for manufacturing the "radiolabeled compound" and the method is useful as a tool of metabolic pharmacokinetic research, the research in binding assay and/or diagnosis.

Radiolabeled compounds of the compound of formula (I) can be prepared by methods known in the art. For example, tritiated compounds of formula (I) can be prepared by introducing tritium into the particular compound of formula (I) such as by catalytic dehalogenation with tritium. This method may include reacting a suitably halogen-substituted precursor of a compound of formula (I) with tritium gas in the presence of a suitable catalyst such as Pd/C, in the presence or absence of a base. Other suitable methods for preparing tritiated compounds can be found in Isotopes in the Physical and Biomedical Sciences, Vol. 1, Labeled Compounds (Part A), Chapter 6 (1987). $^{14}C$-labeled compounds can be prepared by employing starting materials having $^{14}C$ carbon.

As pharmaceutically acceptable salt of the compound of formula (I), examples include salts with alkaline metals (e.g. lithium, sodium and potassium), alkaline earth metals (e.g. calcium and barium), magnesium, transition metal (e.g. zinc and iron), ammonia, organic bases (e.g. trimethylamine, triethylamine, dicyclohexylamine, ethanolamine, diethanolamine, triethanolamine, meglumine, diethanolamine, ethylenediamine, pyridine, picoline, quinoline), and amino acids, and salts with inorganic acids (e.g. hydrochloric acid, sulfuric acid, nitric acid, carbonic acid, hydrobromic acid, phosphoric acid and hydroiodic acid) and organic acids (e.g. formic acid, acetic acid, propionic acid, trifluoroacetic acid, citric acid, lactic acid, tartaric acid, oxalic acid, maleic acid, fumaric acid, mandelic acid, glutaric acid, malic acid, benzoic acid, phthalic acid, ascorbic acid, benzenesulfonic acid, p-toluenesulfonic acid, methanesulfonic acid and ethanesulfonic acid). Specific examples are salts with hydrochloric acid, sulfuric acid, phosphoric acid, tartaric acid, or methanesulfonic acid. These salts may be formed by the usual methods.

The compound of formula (I) of the present invention or its pharmaceutically acceptable salt may form solvate such as hydrate, and/or crystal polymorphs, and the present invention also includes such various solvate and crystal polymorphs. "Solvates" may be those wherein any number of solvent molecules (e.g., water molecules etc.) are coordinated with the compounds of formula (I). When the compounds of formula (I) or pharmaceutically acceptable salts thereof are allowed to stand in the atmosphere, the compounds may absorb water, resulting in attachment of adsorbed water or formation of hydrates. Recrystallization of the compounds of formula (I) or pharmaceutically acceptable salts thereof may produce crystal polymorphs.

The compound of formula (I) of the present invention or its pharmaceutically acceptable salt may form prodrug, and the present invention also includes such various prodrugs. Prodrugs are derivatives of the compounds of the present invention that have chemically or metabolically degradable groups and are compounds that are converted to the pharmaceutically active compounds of the present invention through solvolysis or under physiological conditions in vivo. Prodrugs include compounds that are converted to the compounds of formula (I) through enzymatic oxidation, reduction, hydrolysis and the like under physiological conditions in vivo and compounds that are converted to the compounds of formula (I) through hydrolysis by gastric acid and the like. Methods for selecting and preparing suitable prodrug derivatives are described, for example, in the Design of Prodrugs, Elsevier, Amsterdam 1985. Prodrugs themselves may be active compounds.

When the compounds of formula (I) or pharmaceutically acceptable salts thereof have a hydroxy group, prodrugs include acyloxy derivatives and sulfonyloxy derivatives which can be prepared by reacting a compound having a hydroxy group with a suitable acid halide, suitable acid anhydride, suitable sulfonyl chloride, suitable sulfonylanhydride and mixed anhydride or with a condensing agent. Examples are $CH_3COO$—, $C_2H_5COO$—, t-BuCOO—, $C_{15}H_{31}COO$—, PhCOO—, (m-NaOOCPh)COO—, NaOOCCH$_2$CH$_2$COO—, CH$_3$CH(NH$_2$) COO—, CH$_2$N(CH$_3$)$_2$COO—, CH$_3$SO$_3$—, CH$_3$CH$_2$SO$_3$—, CF$_3$SO$_3$—, CH$_2$FSO$_3$—, CF$_3$CH$_2$SO$_3$—, p-CH$_3$—O-PhSO$_3$—, PhSO$_3$— and p-CHsPhSO$_3$—.

The compound of formula (I) can be prepared, for example, by the general synthetic procedure shown below. The methods for extraction, purification, and the like may be carried out by using the usual method for the experiments of organic chemistry.

The compounds of the present invention can be synthesized in consideration of the condition of the known methods in the art.

In the case that a substituent which inhibits a reaction (e.g. hydroxy, mercapto, amino, formyl, carbonyl and carboxy) exists in any of the above steps, the substituent may be preliminarily protected by, for example, the method described in "Protective Groups in Organic Synthesis, Theodora W Green (John Wiley & Sons)" (hereinafter referred to as Literature A), and the protective group may be removed at an appropriate step.

During all the following steps, the order of the steps to be performed may be appropriately changed. In each step, an intermediate may be isolated and then used in the next step. All of reaction time, reaction temperature, solvents, reagents, protecting groups, etc. are mere exemplification and not limited as long as they do not cause an adverse effect on a reaction.

(General Synthetic Procedure 1)

[Chemical Formula 7]

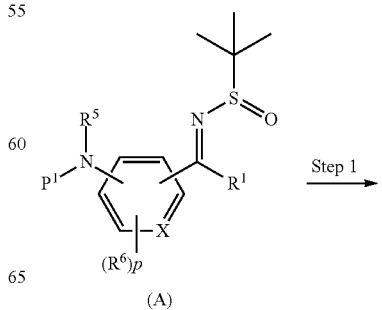

Step 1

(A)

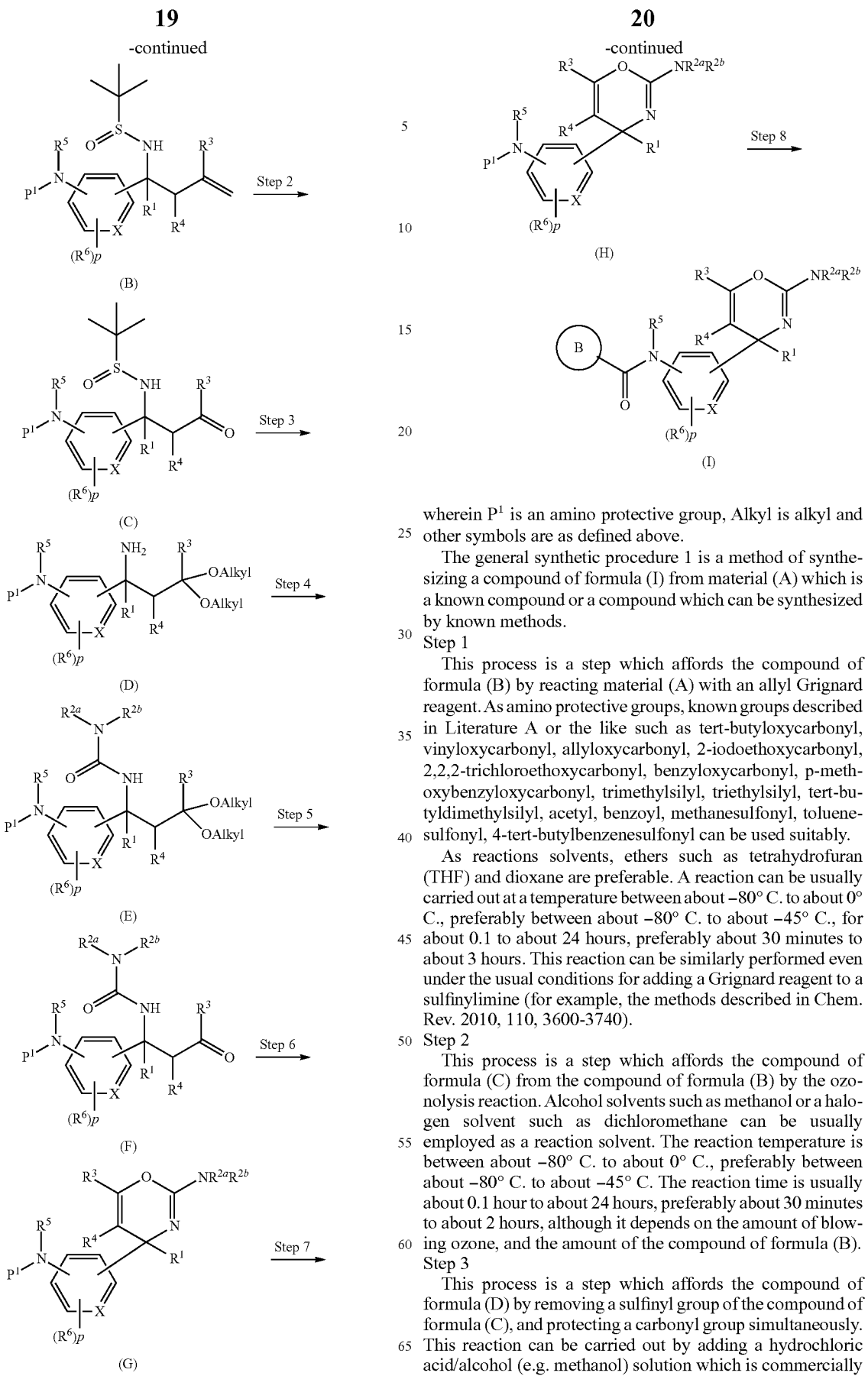

(B), (C), (D), (E), (F), (G), (H), (I)

wherein $P^1$ is an amino protective group, Alkyl is alkyl and other symbols are as defined above.

The general synthetic procedure 1 is a method of synthesizing a compound of formula (I) from material (A) which is a known compound or a compound which can be synthesized by known methods.

Step 1

This process is a step which affords the compound of formula (B) by reacting material (A) with an allyl Grignard reagent. As amino protective groups, known groups described in Literature A or the like such as tert-butyloxycarbonyl, vinyloxycarbonyl, allyloxycarbonyl, 2-iodoethoxycarbonyl, 2,2,2-trichloroethoxycarbonyl, benzyloxycarbonyl, p-methoxybenzyloxycarbonyl, trimethylsilyl, triethylsilyl, tert-butyldimethylsilyl, acetyl, benzoyl, methanesulfonyl, toluenesulfonyl, 4-tert-butylbenzenesulfonyl can be used suitably.

As reactions solvents, ethers such as tetrahydrofuran (THF) and dioxane are preferable. A reaction can be usually carried out at a temperature between about −80° C. to about 0° C., preferably between about −80° C. to about −45° C., for about 0.1 to about 24 hours, preferably about 30 minutes to about 3 hours. This reaction can be similarly performed even under the usual conditions for adding a Grignard reagent to a sulfinylimine (for example, the methods described in Chem. Rev. 2010, 110, 3600-3740).

Step 2

This process is a step which affords the compound of formula (C) from the compound of formula (B) by the ozonolysis reaction. Alcohol solvents such as methanol or a halogen solvent such as dichloromethane can be usually employed as a reaction solvent. The reaction temperature is between about −80° C. to about 0° C., preferably between about −80° C. to about −45° C. The reaction time is usually about 0.1 hour to about 24 hours, preferably about 30 minutes to about 2 hours, although it depends on the amount of blowing ozone, and the amount of the compound of formula (B).

Step 3

This process is a step which affords the compound of formula (D) by removing a sulfinyl group of the compound of formula (C), and protecting a carbonyl group simultaneously. This reaction can be carried out by adding a hydrochloric acid/alcohol (e.g. methanol) solution which is commercially available to a compound (C). Reaction temperature is between about −30° C. to about room temperature, preferably between about 0° C. to about room temperature, and the reaction time is usually about 0.1 hour to about 24 hours, preferably about 10 minutes to about 2 hours.

Step 4

This process is a step which affords the compound of formula (E) by converting the compound of formula (D) to an isocyanate and reacting with an amine of the formula: $NHR^{2a}R^{2b}$. The isocyanate can be synthesized by adding triphosgene to the compound (D) and reacting in the presence of an inorganic base such as potassium carbonate or an organic base such as triethylamine in THF, ethyl acetate, acetonitrile or the mixed solvent these solvents and water. The compound of formula (E) can be afforded by reacting an amine of the formula: $NHR^{2a}R^{2b}$ with the obtained isocyanate. The reaction temperature is between about −30° C. to about room temperature, preferably about 0° C. to about room temperature and the reaction time is usually about 0.1 hour to about 24 hours, preferably about 30 minutes to about 1 hour.

Step 5

This process is a step which affords the compound of formula (F) by deprotecting an acetal or a ketal of formula (E). This reaction is a known method and, for example, can be carried out by the methods described in Literature A.

Step 6

This process is a step which affords the compound of formula (G) by intramolecular cyclization reaction of the compound of formula (F). In this reaction, a known dehydrating agent can be used and a Burgess reagent or diphosphorus pentoxide is preferable. Reactions solvents are not limited if the employed dehydrating agent is not deactivated, and ether solvents such as THF, ethyl acetate or acetonitrile is preferable. When employing a Burgess reagent, an acid such as pyridinium-p-toluene sulfonate can be added for accelerating a reaction. Reaction temperature may be suitably adjusted depending on the progress of the reactions and usually between about 0° C. to about 150° C., preferably about room temperature to about 120° C. Reaction time is usually about 0.1 hour to 24 hours, preferably about 4 hours to about 12 hours.

Step 7

This process is a step which affords the compound of formula (H) by deprotecting a protective group $P^1$ of the compound of formula (G). Deprotection of an amino protective group can be carried out by using known methods such as those described in Literature A.

Step 8

This process is a step which affords the compound of formula (I) by reacting the compound of formula (H) with a compound of ring B—CO₂H or ring B—COCl. The reaction of an amine of formula (H) with a carboxylic acid or an acid chloride such as ring B—CO₂H or ring B—COCl can be carried out under the known conditions. In a condensation reaction with a carboxylic acid of ring B—CO₂H, preferable examples of condensing agents are 1-ethyl-3-(3-dimethylaminopropyl)carbodiimide (WSCD), O-(benzotriazol-1-yl)-N,N,N',N'-tetramethyluronium hexafluorophosphate (HATU) and diphenylphosphoryl chloride. An additive agent such as N,N-dimethyl-4-aminopyridine (DMAP) can be added for accelerating a reaction. The reaction usually can be carried out between about −30° C. to about room temperature, preferably about 0° C. to about room temperature for about 0.1 hour to about 24 hours, preferably about 30 minutes to about 3 hours. When the compound of formula (I) wherein $R^{2a}$ and/or $R^{2b}$ is an amino protective group is obtained, the protective group can be suitably removed using the method such as those described in Literature A or the like.

(General Synthetic Procedure 2)

[Chemical Formula 8]

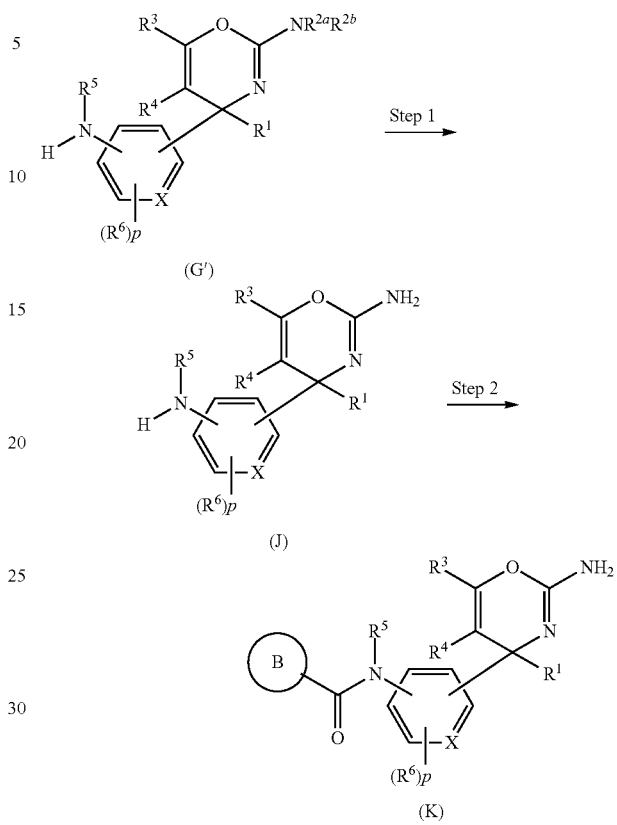

wherein each symbol is as defined above.

General synthetic procedure 2 is a step for synthesizing the compound of formula (K), which is especially preferable when $R^{2a}$ and $R^{2b}$ are hydrogen, by using the compound of formula (G') shown in the above as a starting material.

Step 1

This process is a step for synthesizing the compound of formula (J) by removing $R^{2a}$ and $R^{2b}$ of the compound of formula (G'). When $R^{2a}$ and/or $R^{2b}$ is an amino protective group, the protective group can be removed suitably using the method such as those described in Literature A. When an acid is used in this reaction, a corresponding salt of the compound of formula (J) may be obtained.

Step 2

This process is a step for converting the compound of formula (J) into the compound of formula (K). This process can be carried out in a similar manner as described in Step 8 of the general synthetic procedure 1.

(General Synthetic Procedure 3)

[Chemical Formula 9]

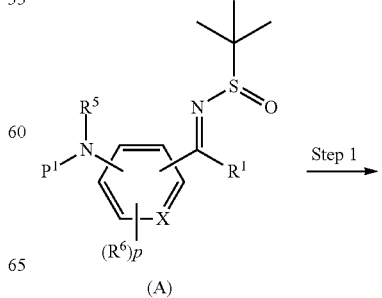

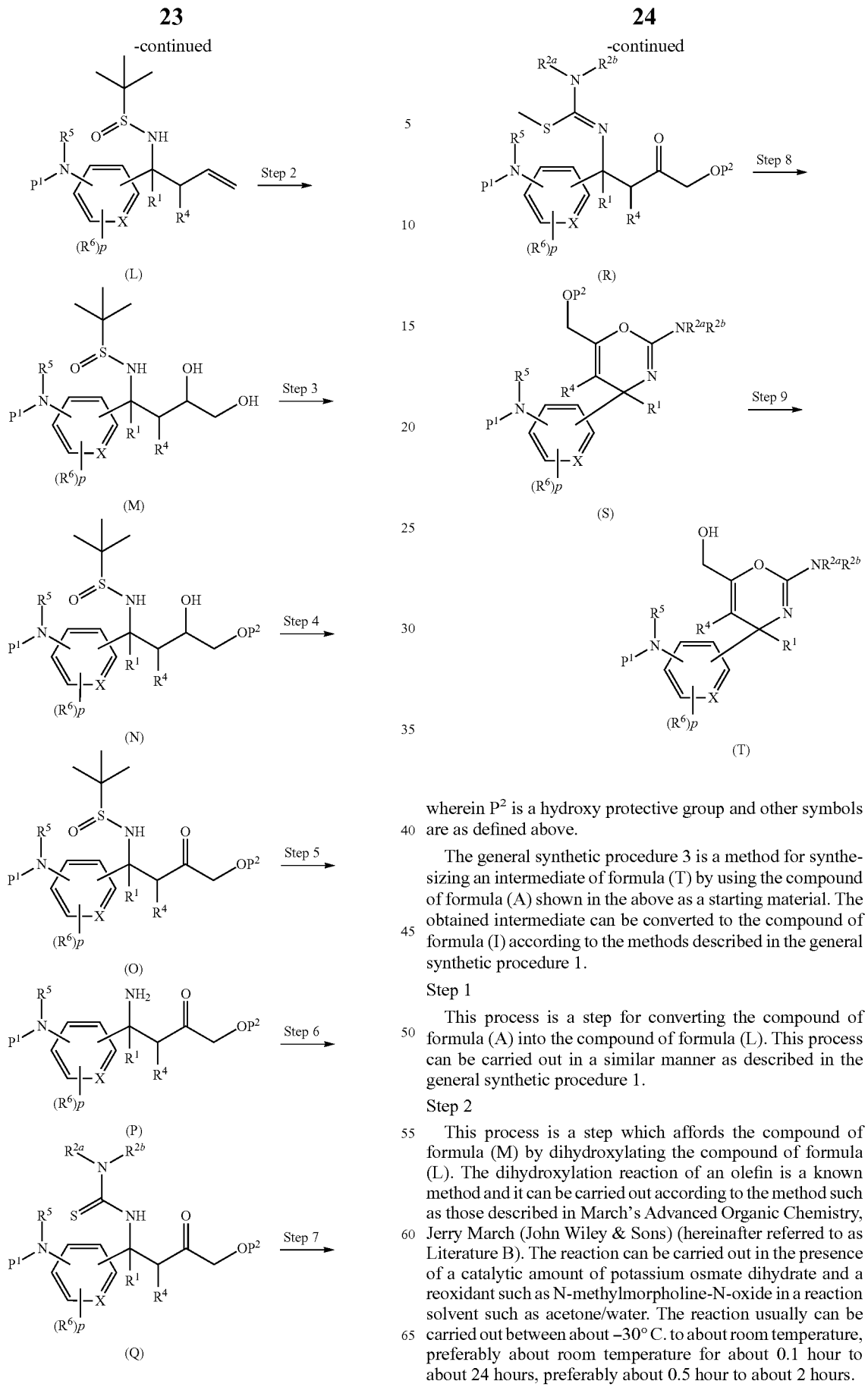

wherein $P^2$ is a hydroxy protective group and other symbols are as defined above.

The general synthetic procedure 3 is a method for synthesizing an intermediate of formula (T) by using the compound of formula (A) shown in the above as a starting material. The obtained intermediate can be converted to the compound of formula (I) according to the methods described in the general synthetic procedure 1.

Step 1

This process is a step for converting the compound of formula (A) into the compound of formula (L). This process can be carried out in a similar manner as described in the general synthetic procedure 1.

Step 2

This process is a step which affords the compound of formula (M) by dihydroxylating the compound of formula (L). The dihydroxylation reaction of an olefin is a known method and it can be carried out according to the method such as those described in March's Advanced Organic Chemistry, Jerry March (John Wiley & Sons) (hereinafter referred to as Literature B). The reaction can be carried out in the presence of a catalytic amount of potassium osmate dihydrate and a reoxidant such as N-methylmorpholine-N-oxide in a reaction solvent such as acetone/water. The reaction usually can be carried out between about −30° C. to about room temperature, preferably about room temperature for about 0.1 hour to about 24 hours, preferably about 0.5 hour to about 2 hours.

Step 3

This process is a step which affords the compound of formula (N) by protecting a hydroxy group of the compound of formula (M) with a protective group $P^2$. This reaction is a known method and it can be carried out according to the conditions such as described in Literature A. As a protective group, a known group such as tert-butyl, triphenylmethyl, benzyl, trimethylsilyl, tert-butyldimethylsilyl, tert-butyldiphenylsilyl, tribenzylsilyl, methoxymethyl, 1-ethoxyethyl, tetrahydropyranyl, tetrahydrothiopyranyl, benzyloxymethyl, methanesulfonyl, p-toluenesulfonyl or acetyl can be used.

When $P^2$ is acetyl, a hydroxy group can be protected by adding acetic anhydride in a reaction solvent such as pyridine, in the presence of a catalytic amount of 4,4-dimethylaminopyridine, if necessary, at a temperature about 0° C. to room temperature, preferably about room temperature. The reaction time is usually about 0.1 hour to 24 hour, preferably about 10 minutes to about 2 hours.

Step 4

This process is a step which affords the compound of formula (O) by oxidizing a hydroxy group of the compound of formula (N). This reaction is a known method and it can be carried out according to the method such as described in Literature B. This reaction can be carried out, for example, in the presence of a Dess-Martin reagent in a solvent such as dichloromethane at a temperature between about 10° C. to about 40° C., preferably about room temperature for about 0.1 hour to about 24 hours, preferably about 0.5 hour to about 2 hours.

Step 5

This process is a step which affords the compound of formula (P) by deprotecting a t-butyl sulfinyl group of the compound of formula (O). This reaction can be carried out in a similar manner as described in Step 3 of the general synthetic procedure 1.

Step 6

This process is a step which affords the compound of formula (O) by converting the compound of formula (P) into a thioisocyanate compound, followed by reacting with an amine of the formula: $NHR^{2a}R^{2b}$. An isocyanate compound can be afforded by adding thiophosgene to the compound of formula (P) in the presence of an inorganic base such as potassium carbonate or an organic base such as triethylamine in a solvent such as THF, ethyl acetate, acetonitrile or mixed solvent of these solvent and water. The compound of formula (O) can be afforded by reacting thus-obtained isocyanate with an amine of the formula: $NHR^{2a}R^{2b}$. The reaction temperature is between about −30° C. to about room temperature, preferably about 0° C. to about room temperature, and the reaction time is usually about 0.1 hour to about 24 hours, preferably about 30 minutes to about 1 hour. The reaction solvent is not limited as long as it does not react with thioisocyanate, and dichloromethane, ethyl acetate, acetonitrile or the like is preferable.

Step 7

This process is a step which affords the compound of formula (R) by methylating a thiocarbonyl group of the compound of formula (Q). This reaction is a known method and it can be carried out according to the method as described in literatures. The reaction usually can be carried out by reacting the compound of formula (Q) with methyl iodide in the presence of an organic base such as N,N-diisopropylethylamine or an inorganic base such as potassium carbonate. The reaction solvent is not limited as long as it does not react with a substrate, and acetonitrile, ethers such as THF, or ethyl acetate is preferable. The reaction temperature is usually between about 0° C. to 100° C., preferably about room temperature to about 50° C. and the reaction time is about 0.1 hour to about 24 hours, preferably about 7 hours to about 24 hours.

Step 8

This process is a step which affords the compound of formula (S) by intramolecular cyclization of the compound of formula (R). This reaction can be carried out by adding an acid such as acetic acid and tosic acid to the compound of formula (R) and heating in a solvent such as t-butanol at a temperature between about room temperature to about 100° C., preferably about 100° C. The reaction time is about 10 hours to 50 hours, preferably about 20 hours to 40 hours and it can be adjusted suitably depending on the progress of the reactions.

Step 9

This process is a step which affords the compound of formula (T) by deprotecting of a protective group $P^2$ of the compound of formula (S). This process is a known method and it can be carried out according to the conditions such as described in Literature A. When $P^2$ is acetyl, the reaction usually can be carried out by adding potassium carbonate in a mixed solution of the compound of formula (S) in water/methanol. The reaction time is about 0.1 hour to about 24 hours, preferably about 2 hours to 6 hours, the reaction temperature is about 0° C. to about 50° C., preferably about room temperature and it can be adjusted suitably depending on the progress of the reactions.

(General Synthetic Procedure 4)

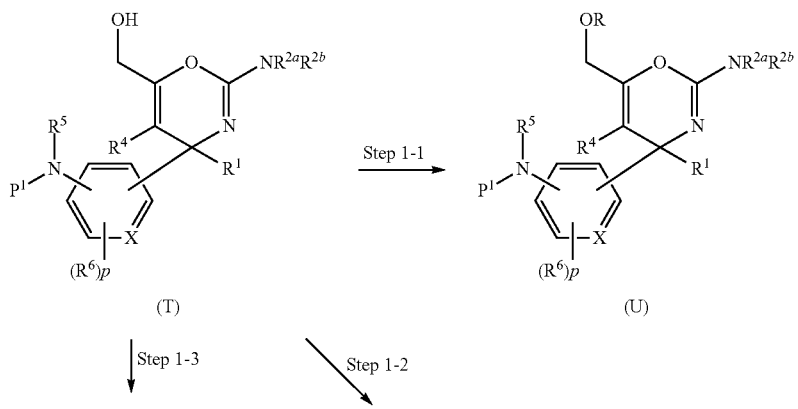

[Chemical Formula 10]

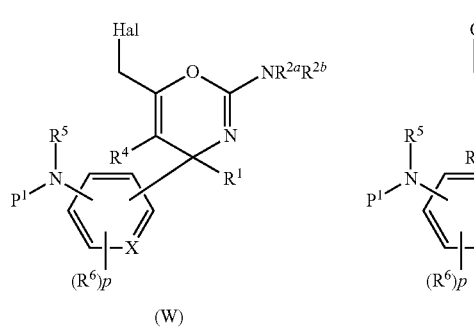

(W)

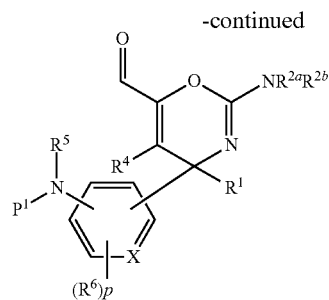

(V)

Step 2

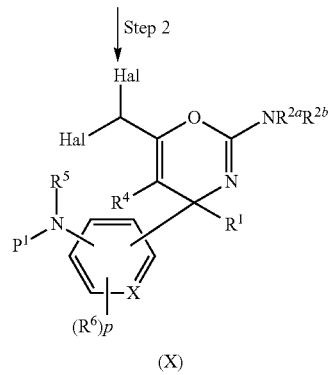

(X)

wherein R alkyl, halogenoalkyl, hydroxyalkyl, alkoxyalkyl, acyloxy or the like, Hal is halogen and other symbols are as defined above.

The general synthetic procedure 4 is a process for synthesizing intermediates of formula (U), (V), (W), or (X) using the above-mentioned compound of formula (T) as a starting material. These intermediates can be converted into the compound of formula (I) according to the method such as those described in the general synthetic procedure 1.

Step 1-1

This process is a step which affords the compound of formula (U) by introducing an R group into a hydroxy group of the compound of formula (T). The reaction of hydroxy and various electrophiles is a known method and it is not limited to a specific electrophile. Examples of electrophiles are alkyl halide, acid chloride, aryl halide and the like. The reaction time is about 0.1 hour to about 24 hours, preferably about 1 hour to about 5 hours and the reaction temperature is about 0° C. to about 80° C., preferably about 0° C. to about room temperature, and it can be suitably carried out according to the methods such as described in Literature B.

The compound (T) can be reacted with various nucleophiles after introducing a leaving group such as methanesulfonyl group into hydroxy of a compound (T). The reaction can be carried out by reacting the compound with a nucleophile such as metal alkoxide in a corresponding alcohol solvent at a temperature between about 0° C. to about 100° C., preferably about room temperature to about 50° C. The reaction time is about 0.1 hour to about 24 hours, preferably about 0.5 hour to about 2 hours and it can be adjusted suitably depending on the progress of the reactions.

Step 1-2

This process is a step which affords the compound of formula (V) by oxidizing a hydroxy group of the compound of formula (T) to convert into an aldehyde group. This reaction is a known method and it can be carried out according to method such as described in Literature B. This reaction can be carried out, for example, in the presence of a Dess-Martin reagent in a solvent such as dichloromethane at a temperature between about 10° C. to about 40° C., preferably about room temperature. The reaction time is about 0.1 hour to about 24 hours, preferably about 0.5 hour to about 4 hours.

Step 1-3

This process is a step which affords the compound of formula (W) by halogenating a hydroxy group of the compound of formula (T). When halogen is fluorine, the reaction can be carried out, for example, using N,N-diethylaminosulfur trifluoride (DAST), bis(2-methoxyethyl)aminosulfurtrifluoride or the like according to known methods such as those described in Synthesis 2002, 2561.

Step 2

This process is a step which affords the compound of formula (X) by halogenating a formyl group of the compound of formula (V). This reaction can be carried out in a similar manner as the above Step 1-3.

The order of above each process to be carried out can be changed suitably, and each intermediate can be used for the next step after isolation.

Optically active compounds of formula (I) can be produced by employing an optically active starting material, by obtaining an optically active intermediate by asymmetry synthesis at a suitable step, or by performing optical resolution of an intermediate or an objective compound, each of which is a racemate, at a suitable step. Examples of a method for optical resolution is separation of an optical isomer using an optically active column; kinetic optical resolution utilizing an enzymatic reaction; crystallization resolution of a diastereomer by salt formation using a chiral acid or a chiral base; and preferential crystallization method.

Specific embodiments of the present invention are illustrated below.

A compound of formula (IA) or (IB):

[Chemical Formula 11]

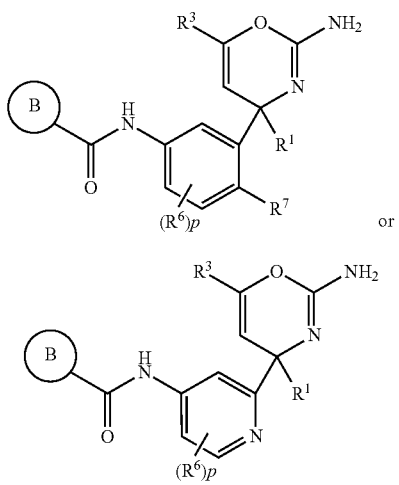

wherein each symbol is as defined above,
or a pharmaceutically acceptable salt thereof.

Specific embodiments ring B, $R^1$, $R^3$ and $R^7$ are illustrated below. All combination of these embodiments are examples of the compounds of formula (IA) and (IB).

Examples of ring B include a substituted or unsubstituted carbocycle or a substituted or unsubstituted heterocycle.

Examples of ring B include a substituted or unsubstituted heterocycle.

Examples of ring B include substituted or unsubstituted pyridine, substituted or unsubstituted pyrimidine, substituted or unsubstituted pyrazine, substituted or unsubstituted oxazole, substituted or unsubstituted thiazole, substituted or unsubstituted pyrazole, substituted or unsubstituted benzene, substituted or unsubstituted benzoxazole, or substituted or unsubstituted benzothiazole.

Examples of ring B include pyridine, pyrimidine, pyrazine, oxazole, thiazole, pyrazole, benzene, benzoxazole or benzothiazole, each of which is optionally substituted with one or more substituents selected from the following groups.
halogen;
cyano;
hydroxy;
nitro;
alkyl substituted with one or more substituents selected from the substituent group α;
unsubstituted alkyl;
alkenyl substituted with one or more substituents selected from the substituent group α;
unsubstituted alkenyl;
alkynyl substituted with one or more substituents selected from the substituent group α;
unsubstituted alkynyl;
alkoxy substituted with one or more substituents selected from the substituent group α;
unsubstituted alkoxy;
alkenyloxy substituted with one or more substituents selected from the substituent group α;
unsubstituted alkenyloxy;
alkynyloxy substituted with one or more substituents selected from the substituent group α;
unsubstituted alkynyloxy;
alkylthio substituted with one or more substituents selected from the substituent group α;
unsubstituted alkylthio;
alkenylthio substituted with one or more substituents selected from the substituent group α;
unsubstituted alkenylthio;
alkynylthio substituted with one or more substituents selected from the substituent group α;
unsubstituted alkynylthio;
unsubstituted amino;
alkylamino substituted with one or more substituents selected from the substituent group α;
unsubstituted alkylamino;
cycloalkylamino substituted with one or more substituents selected from the substituent group α;
unsubstituted cycloalkylamino;
unsubstituted carbamoyl;
alkylcarbamoyl substituted with one or more substituents selected from the substituent group α;
unsubstituted alkylcarbamoyl;
alkoxycarbonyl substituted with one or more substituents selected from the substituent group α;
unsubstituted alkoxycarbonyl;
a carbocyclic group substituted with one or more substituents selected from the substituent group α, alkyl and halogenoalkyl;
an unsubstituted carbocyclic group;
a heterocyclic group substituted with one or more substituents selected from the substituent group α, alkyl and halogenoalkyl; and
an unsubstituted heterocyclic group.

Examples of ring B include pyridine, pyrimidine, pyrazine, oxazole, thiazole, pyrazole, benzene, benzoxazole or benzothiazole, each of which is optionally substituted with one or more substituents selected from the following groups.
halogen, cyano, hydroxy, alkyl, halogenoalkyl, cycloalkylalkyl, alkoxy, halogenoalkoxy, alkoxyalkoxy, cyanoalkoxy, alkenyl, halogenoalkenyl, alkynyl, halogenoalkynyl, alkenyloxy, alkynyloxy, alkylthio, cyanoalkylthio, amino, alkylamino, cycloalkylamino and cycloalkyl.

Examples of ring B include pyridine, pyrazine, oxazole, thiazole, pyrazole, benzoxazole or benzothiazole, each of which is optionally substituted with one or more substituents selected from the following groups.
halogen, cyano, hydroxy, alkyl, halogenoalkyl, cycloalkylalkyl, alkoxy, halogenoalkoxy, alkenyl, halogenoalkenyl, alkynyl, halogenoalkynyl, amino, alkylamino, cycloalkylamino and cycloalkyl.

Examples of ring B include pyridine or pyrazine, each of which is optionally substituted with one or more substituents selected from the following groups.
halogen, cyano, hydroxy, alkyl, halogenoalkyl, cycloalkylalkyl, alkoxy, halogenoalkoxy, alkenyl, halogenoalkenyl, alkynyl, halogenoalkynyl, amino, alkylamino, cycloalkylamino and cycloalkyl.

Examples of ring B include the following groups:

[Chemical Formula 12]

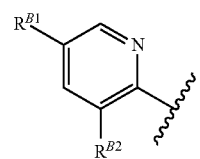

wherein $R^{B1}$ is cyano and $R^{B2}$ is (i) hydroxy, (ii) alkyl optionally substituted with one or more substituents selected from the substituent group c, (iii) alkoxy, (iv) alkynyl, (v) alkylamino, (vi) cycloalkylamino, or (vii) cycloalkyl.

Examples of ring B include the following groups:

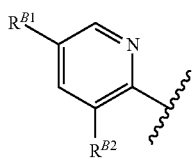

[Chemical Formula 13]

wherein $R^{B1}$ is cyano and $R^{B2}$ is hydroxy, alkyl, halogenoalkyl, cycloalkylalkyl, alkoxy, alkynyl, alkylamino or cycloalkyl.

Examples of ring B include the following groups:

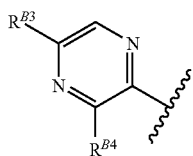

[Chemical Formula 14]

wherein $R^{B3}$ is alkyl, halogenoalkyl or halogenoalkoxy, and $R^{B4}$ is hydrogen, hydroxy, amino, alkylamino or cycloalkylamino.

Examples of ring B include the following groups;

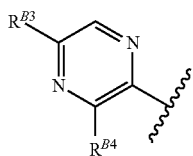

[Chemical Formula 15]

wherein $R^{B3}$ is alkyl, halogenoalkyl or halogenoalkoxy and $R^{B4}$ is hydroxy, amino, alkylamino or cycloalkylamino.

Examples of $R^3$ include hydrogen, halogen, or substituted or unsubstituted alkyl.

Examples of $R^3$ include hydrogen, halogen or substituted alkyl.

Examples of $R^3$ include hydrogen, halogen, halogenoalkyl, hydroxyalkyl, alkoxyalkyl, or halogenoalkoxyalkyl.

Examples of $R^3$ include hydrogen, halogen, halogenoalkyl, or halogenoalkoxyalkyl.

Examples of $R^3$ include halogen, halogenoalkyl, or halogenoalkoxyalkyl.

Examples of $R^3$ include halogenoalkyl.

Examples of $R^1$ include methyl.

Examples of $R^1$ include ethyl.

Examples of $R^1$ include halogenomethyl.

Examples of p include 0.

Examples of p include 1 and examples of $R^6$ include halogen, alkyl, or cyano.

Examples of $R^7$ include hydrogen.

Examples of $R^7$ include halogen.

Examples of $R^7$ include chloro.

Examples of $R^7$ include fluoro.

Examples of $R^7$ include cyano.

Examples of $R^7$ include halogenomethyl.

Examples of $R^7$ include methoxymethyl.

Examples of preferable combination of the substituents of the compounds of formula (IA) or (IB) are as follows:

1) Compound wherein Ring B is substituted or unsubstituted pyridine, substituted or unsubstituted pyrimidine, substituted or unsubstituted pyrazine, substituted or unsubstituted oxazole, substituted or unsubstituted thiazole, substituted or unsubstituted pyrazole, substituted or unsubstituted benzene, substituted or unsubstituted benzoxazole, or substituted or unsubstituted benzothiazole,
$R^3$ is hydrogen, halogen, alkyl, halogenoalkyl, hydroxyalkyl, alkoxyalkyl, or halogenoalkoxyalkyl,
$R^1$ is methyl or halogenomethyl, and
p is 1 and $R^6$ is halogen, alkyl, or cyano, and
if present, $R^7$ is hydrogen or halogen.

2) Compound wherein Ring B is substituted or unsubstituted pyridine, substituted or unsubstituted pyrimidine, substituted or unsubstituted pyrazine, substituted or unsubstituted oxazole, substituted or unsubstituted thiazole, substituted or unsubstituted pyrazole, substituted or unsubstituted benzene, substituted or unsubstituted benzoxazole, or substituted or unsubstituted benzothiazole,
$R^3$ is methyl or halogenomethyl,
$R^1$ is methyl or halogenomethyl,
p is 1 and $R^6$ is halogen, alkyl, or cyano, and
if present, $R^7$ is hydrogen or halogen.

3) Compound wherein Ring B is substituted or unsubstituted pyridine, substituted or unsubstituted pyrimidine, substituted or unsubstituted pyrazine, substituted or unsubstituted oxazole, substituted or unsubstituted thiazole, substituted or unsubstituted pyrazole, substituted or unsubstituted benzene, substituted or unsubstituted benzoxazole, or substituted or unsubstituted benzothiazole,
$R^3$ is hydrogen, halogen, alkyl, halogenoalkyl, hydroxyalkyl, alkoxyalkyl, or halogenoalkoxyalkyl,
$R^1$ is methyl or halogenomethyl,
p is 0, and
if present, $R^7$ is hydrogen or halogen.

4) Compound wherein Ring B is substituted or unsubstituted pyridine, substituted or unsubstituted pyrimidine, substituted or unsubstituted pyrazine, substituted or unsubstituted oxazole, substituted or unsubstituted thiazole, substituted or unsubstituted pyrazole, substituted or unsubstituted benzene, substituted or unsubstituted benzoxazole, or substituted or unsubstituted benzothiazole,
$R^3$ is methyl or halogenomethyl,
$R^1$ is methyl or halogenomethyl,
p is 0, and
if present, $R^7$ is hydrogen or halogen.

5) Compound wherein Ring B is substituted or unsubstituted pyridine, substituted or unsubstituted pyrimidine, substituted or unsubstituted pyrazine, substituted or unsubstituted oxazole, substituted or unsubstituted thiazole, substituted or unsubstituted pyrazole, substituted or unsubstituted benzene, substituted or unsubstituted benzoxazole, or substituted or unsubstituted benzothiazole,
$R^3$ is methyl or halogenomethyl,
$R^1$ is methyl or halogenomethyl,
provided that both of $R^3$ and $R^1$ are not methyl,
p is 0, and
if present, $R^7$ is hydrogen or halogen.

6) Compound wherein Ring B is substituted or unsubstituted pyridine or substituted or unsubstituted pyrazine,
$R^3$ is methyl or halogenomethyl,
$R^1$ is methyl or halogenomethyl,
provided that both of $R^3$ and $R^1$ are not methyl,
p is 0, and
if present, $R^7$ is hydrogen or halogen.

7) Compound wherein Ring B is substituted or unsubstituted pyridine or substituted or unsubstituted pyrazine, wherein the substituents are one or more substituents selected from halogen, cyano, hydroxy, alkyl, halogenoalkyl, cycloalkylalkyl, alkoxy, halogenoalkoxy, alkynyl, amino, alkylamino, cycloalkylamino, and cycloalkyl, $R^3$ is methyl or halogenomethyl, $R^1$ is methyl or halogenomethyl, provided that both of $R^3$ and $R^1$ are not methyl, p is 0, and if present, $R^7$ is hydrogen or halogen.

8) Ring B is substituted or unsubstituted pyridine, substituted or unsubstituted pyrimidine, substituted or unsubstituted pyrazine, substituted or unsubstituted oxazole, substituted or unsubstituted thiazole, substituted or unsubstituted pyrazole, substituted or unsubstituted benzene, substituted or unsubstituted benzoxazole, or substituted or unsubstituted benzothiazole, $R^3$ is halogenomethyl, $R^1$ is methyl, p is 0, and if present, $R^7$ is hydrogen or halogen.

9) Compound wherein Ring B is substituted or unsubstituted pyridine or substituted or unsubstituted pyrazine, $R^3$ is halogenomethyl, $R^1$ is methyl, p is 0, and if present, $R^7$ is hydrogen or halogen.

10) Compound wherein Ring B is substituted or unsubstituted pyridine or substituted or unsubstituted pyrazine, wherein the substituents are one or more substituents selected from halogen, cyano, hydroxy, alkyl, halogenoalkyl, cycloalkylalkyl, alkoxy, halogenoalkoxy, alkynyl, amino, alkylamino, cycloalkylamino, and cycloalkyl, $R^3$ is halogenomethyl, $R^1$ is methyl, p is 0, and if present, $R^7$ is hydrogen or halogen.

11) Compound wherein Ring B is

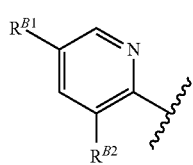

[Chemical Formula 16]

wherein $R^{B1}$ is cyano and $R^{B2}$ is (i) hydroxy, (ii) alkyl optionally substituted with one or more substituents selected from the substituent group α, (iii) alkoxy, (iv) alkynyl, (v) alkylamino, (vi) cycloalkylamino, or (vii) cycloalkyl, $R^3$ is hydrogen, halogen, alkyl, halogenoalkyl, hydroxyalkyl, alkoxyalkyl, or halogenoalkoxyalkyl, $R^1$ is methyl or halogenomethyl, p is 0, and if present, $R^7$ is hydrogen or halogen.

12) Compound wherein Ring B is

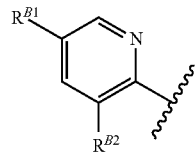

[Chemical Formula 17]

wherein $R^{B1}$ is cyano and $R^{B2}$ is hydroxy, alkyl, halogenoalkyl, cycloalkylalkyl, alkoxy, alkynyl, alkylamino, or cycloalkyl, $R^3$ is hydrogen, halogen, alkyl, halogenoalkyl, hydroxyalkyl, alkoxyalkyl, or halogenoalkoxyalkyl, $R^1$ is methyl or halogenomethyl, p is 0, and if present, $R^7$ is hydrogen or halogen.

13) Compound wherein Ring B is

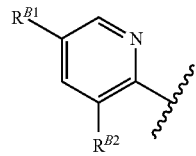

[Chemical Formula 18]

wherein $R^{B1}$ is cyano and $R^{B2}$ is alkyl, halogenoalkyl, cycloalkylalkyl, alkynyl, or cycloalkyl, $R^3$ is hydrogen, halogen, alkyl, halogenoalkyl, hydroxyalkyl, alkoxyalkyl, or halogenoalkoxyalkyl, $R^1$ is methyl or halogenomethyl, p is 0, and if present, $R^7$ is hydrogen or halogen.

14) Compound wherein Ring B is

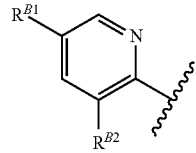

[Chemical Formula 19]

wherein $R^{B1}$ is cyano and $R^{B2}$ is (i) hydroxy, (ii) alkyl optionally substituted with one or more substituents selected from the substituent group α, (iii) alkoxy, (iv) alkynyl, (v) alkylamino, (vi) cycloalkylamino, or (vii) cycloalkyl, $R^3$ is methyl or halogenomethyl, $R^1$ is methyl or halogenomethyl, provided that both of $R^3$ and $R^1$ are not methyl, p is 0, and if present, $R^7$ is hydrogen or halogen.

15) Compound wherein Ring B is

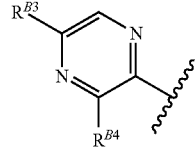

[Chemical Formula 20]

wherein $R^{B3}$ is alkyl, halogenoalkyl or halogenoalkoxy, and
$R^{B4}$ is hydroxy, amino, alkylamino, or cycloalkylamino,
$R^3$ is hydrogen, halogen, alkyl, halogenoalkyl, hydroxyalkyl, alkoxyalkyl, or halogenoalkoxyalkyl,
$R^1$ is methyl or halogenomethyl,
p is 0, and
if present, $R^7$ is hydrogen or halogen.
16) Compound wherein Ring B

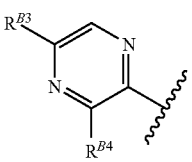

[Chemical Formula 21]

wherein $R^{B3}$ is alkyl, halogenoalkyl, or halogenoalkoxy, and
$R^{B4}$ is hydroxy, amino, alkylamino, or cycloalkylamino,
$R^3$ is hydrogen, halogen, alkyl, halogenoalkyl, hydroxyalkyl, alkoxyalkyl, or halogenoalkoxyalkyl,
$R^1$ is methyl or halogenomethyl,
p is 0, and
if present, $R^7$ is hydrogen or halogen.
17) Compound wherein Ring B is

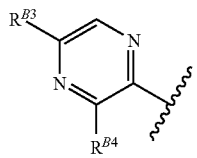

[Chemical Formula 22]

wherein $R^{B3}$ is alkyl, halogenoalkyl or halogenoalkoxy, and
$R^{B4}$ is hydrogen, hydroxy, amino, alkylamino, or cycloalkylamino,
$R^3$ is methyl or halogenomethyl,
$R^1$ is methyl or halogenomethyl,
provided that both of $R^3$ and $R^1$ are not methyl,
p is 0, and
if present, $R^7$ is hydrogen or halogen.
18) Compound wherein Ring B is

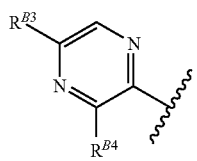

[Chemical Formula 23]

wherein $R^{B3}$ is alkyl, halogenoalkyl, or halogenoalkoxy, and
$R^{B4}$ is hydroxy, amino, alkylamino, or cycloalkylamino,
$R^3$ is methyl or halogenomethyl,
$R^1$ is methyl or halogenomethyl,
provided that both of $R^3$ and $R^1$ are not methyl,
p is 0, and
if present, $R^7$ is hydrogen or halogen.

The compounds of the present invention have BACE1 inhibitory activity, and therefore, are useful as a medicament for treatment, prevention, and/or symptom improvement of the diseases induced by the production, secretion or deposition of amyloid β protein such as dementia of the Alzheimer's type (Alzheimer's disease, senile dementia of Alzheimer type), Down's syndrome, memory impairment, prion disease (Creutzfeldt-Jakob disease), mild cognitive impairment (MCI), Dutch type of hereditary cerebral hemorrhage with amyloidosis, cerebral amyloid angiopathy, other type of degenerative dementia, mixed dementia such as coexist Alzheimer's disease with vascular type dementia, dementia with Parkinson's Disease, dementia with progressive supra-nuclear palsy, dementia with Cortico-basal degeneration, Alzheimer's disease with diffuse Lewy body disease, age-related macular degeneration, Parkinson's Disease and amyloid angiopathy.

The term "treating Alzheimer's disease" includes prevention of progression of MCI and prevention of onset of familial Alzheimer's disease. The term "a pharmaceutical composition for treating Alzheimer's disease" includes a pharmaceutical composition for preventing progression of MCI, and a pharmaceutical composition for preventing onset of the familial Alzheimer's disease.

The compound of the present invention has not only BACE1 inhibitory activity but the beneficialness as a medicament. The compound has any or all of the following superior properties.
a) The compound has weak inhibitory activity for CYP enzymes such as CYP1A2, CYP2C9, CYP2C19, CYP2D6, CYP3A4.
b) The compound show excellent pharmacokinetics such as high bioavailability or moderate clearance.
c) The compound has high metabolic stability.
d) The compound does not show irreversible inhibition to CYP enzyme such as CYP3A4 in the range of the concentration of the measurement conditions described in this description.
e) The compound does not show mutagenesis.
f) The compound has low risk of cardiovascular systems.
g) The compound show high solubility.
h) The compound show high brain distribution.
i) The compound has high oral absorption.
j) The compound has long half-life period.
k) The compound has high protein unbinding ratio.
l) The compound show negative in the Ames test.

Since the compound of the present invention has high inhibitory activity on BACE1 and/or high selectivity on other enzymes, it can be a medicament with reduced side effect. Further, since the compound has high effect of reducing amyloid β production in a cell system, particularly, has high effect of reducing amyloid β production in brain, it can be an excellent medicament. In addition, by converting the compound into an optically active compound having suitable stereochemistry, the compound can be a medicament having a wider safety margin on the side effect.

When a pharmaceutical composition of the present invention is administered, it can be administered orally or parenterally. The composition for oral administration can be administered in usual dosage forms such as tablets, granules, powders, capsules which can be prepared according to the conventional manners. The composition for parenteral administration can be administered suitably in usual parenteral dosage forms such as injections. Since the compounds of the present invention have high oral absorption, they can be preferably administered in an oral dosage form.

A pharmaceutical composition can be formulated by mixing various additive agents for medicaments, if needed, such as excipients, binders, disintegrating agents, and lubricants which are suitable for the formulations with an effective amount of the compound of the present invention.

Although the dosage of a pharmaceutical composition of the present invention should be determined in consideration of the patient's age and body weight, the type and degree of diseases, the administration route and the like, a usual oral dosage for an adult is 0.05 to 100 mg/kg/day and preferable is 0.1 to 10 mg/kg/day. For parenteral administration, although the dosage highly varies with administration routes, a usual dosage is 0.005 to 10 mg/kg/day and preferably 0.01 to 1 mg/kg/day. The dosage may be administered once or several times per day.

The compound of the present invention can be used combining other medicaments for treating Alzheimer's disease such as acetylcholinesterase inhibitor (hereinafter referred to as a concomitant medicament) for the purpose of enforcement of the activity of the compound or reduction of the amount of medication of the compound or the like. In this case, timing of administration of the compound of the present invention and the concomitant medicament is not limited and these may be administered to the subject simultaneously or at regular intervals. Furthermore, the compound of the present invention and concomitant medicament may be administered as two different compositions containing each active ingredient or as a single composition containing both active ingredient.

The dose of the concomitant medicament can be suitably selected on the basis of the dose used on clinical. Moreover, the mix ratio of the compound of the present invention and a concomitant medicament can be suitably selected in consideration of the subject of administration, administration route, target diseases, symptoms, combinations, etc. For example, when the subject of administration is human, the concomitant medicament can be used in the range of 0.01-100 parts by weight relative to 1 part by weight of the compounds of the present invention.

Examples of a concomitant medicament are Donepezil hydrochloride, Tacrine, Galanthamine, Rivastigmine, Zanapezil, Memantine and Vinpocetine.

EXAMPLE

The present invention will be described in more detail with reference to, but not limited to, the following examples and test examples.

In this description, meaning of each abbreviation is as follows:
Me methyl
Boc tert-butoxy Carbonyl
Ms methanesulfonyl
Ac acetyl
TFA trifluoroacetyl
DMF N,N-dimethylformamide
DMAP 4-dimethylaminopyridine
DMSO dimethylsulfoxide
EDC 1-ethyl-3-(3-dimethylaminopropyl)carbodiimide
WSCD-HCl 1-ethyl-3-(3-dimethylaminopropyl)carbodiimide hydrochloride
DAST (diethylamino)sulfur trifluoride
HOBt 1-hydroxybenzotriazole NMR analysis of each Example was performed by 300 MHz using DMSO-$d_6$ and CDCl$_3$.

$^1$H-NMR was measured using tetramethylsilane as an internal standard in deuterochloroform (CDCl$_3$) solvent. Alternatively, it was measured in dimethyl-d6 sulfoxide (DMSO-$d_6$). The δ values were shown by ppm and the coupling constant (J) were shown by Hz. In the data, s means singlet, d means doublet, t means triplet, m means multiplet, br means broad and brs means broad singlet.

"RT" in tables means retention time in LC/MS: liquid column chromatography/mass analysis, and these are measured under the conditions as mentioned below:

Conditions A
Column: XBridge (registered trademark) C18 (5 μm, i.d.4.6× 50 mm) (Waters)
Flow rate: 3 mL/min
UV detection wavelength: 254 nm
Mobile phases: [A] is 0.1% formic acid solution, and [B] is 0.1% formic acid in acetonitrile solvent.
Gradient: linear gradient of 10% to 100% solvent [B] for 3 minutes was performed, and 100% solvent [B] was maintained for 1 minute.

Conditions B
Column: Shim-pack XR-ODS (2.2 μm, i.d.50×3.0 mm) (Shimadzu)
Flow rate: 1.6 mL/min
Columns oven: 50° C.
UV detection wavelength: 254 nm
Mobile phases: [A] is 0.1% formic acid solution, and [B] is 0.1% formic acid in acetonitrile solvent.
Gradient: linear gradient of 10% to 100% solvent [B] for 3 minutes was performed, and 100% solvent [B] was maintained for 1 minute.

Example 1

Synthesis of Compound (I-4)

[Chemical Formula 24]

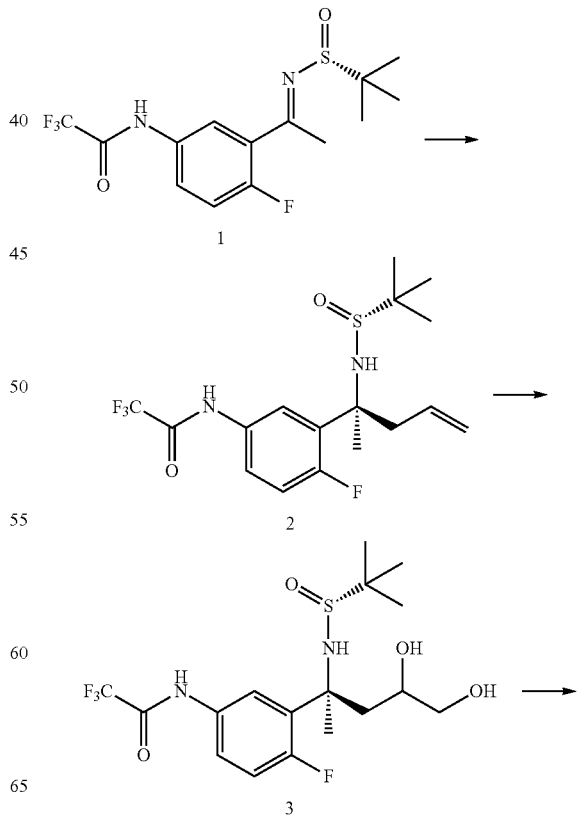

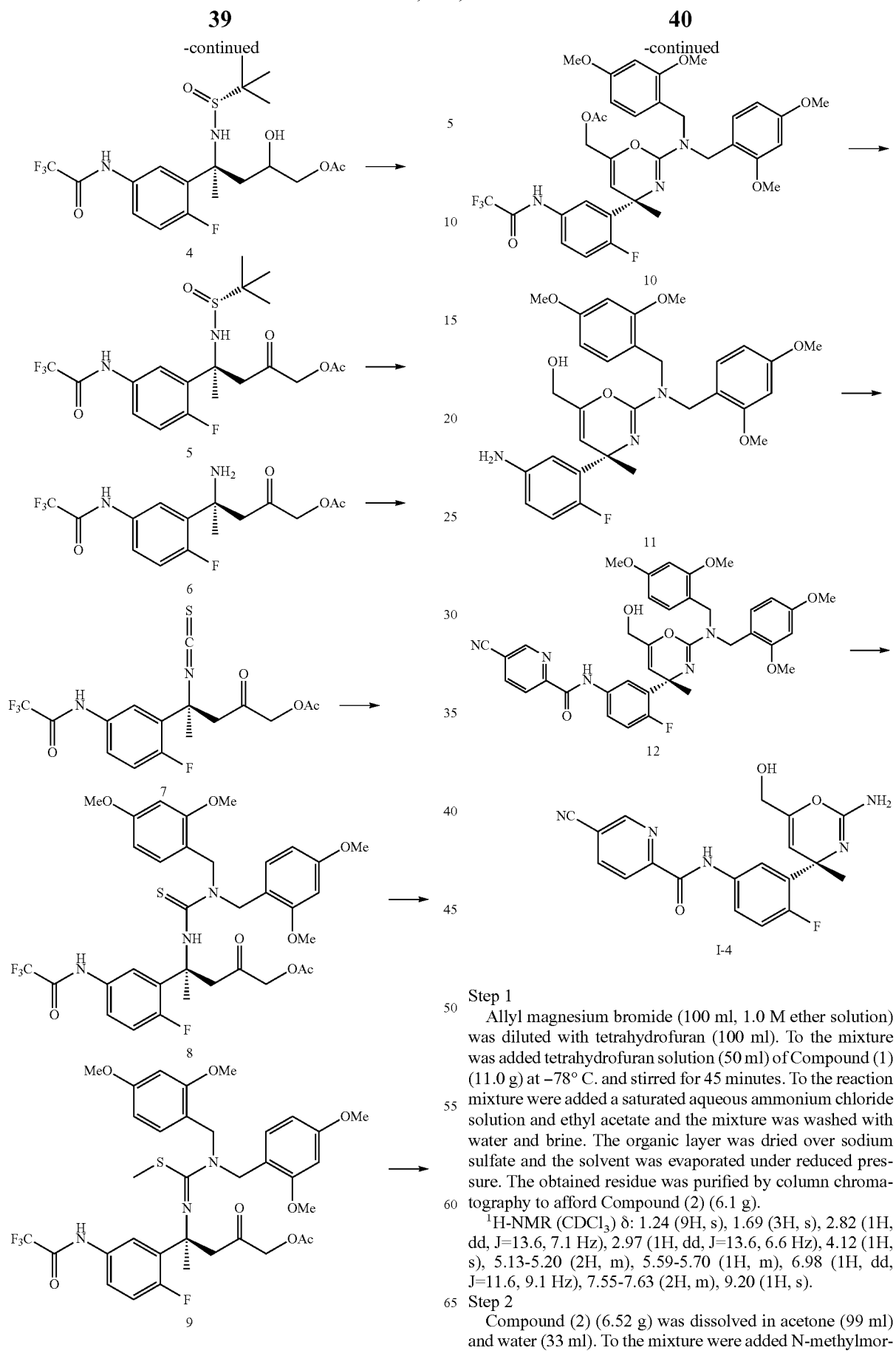

Step 1
Allyl magnesium bromide (100 ml, 1.0 M ether solution) was diluted with tetrahydrofuran (100 ml). To the mixture was added tetrahydrofuran solution (50 ml) of Compound (1) (11.0 g) at −78° C. and stirred for 45 minutes. To the reaction mixture were added a saturated aqueous ammonium chloride solution and ethyl acetate and the mixture was washed with water and brine. The organic layer was dried over sodium sulfate and the solvent was evaporated under reduced pressure. The obtained residue was purified by column chromatography to afford Compound (2) (6.1 g).

$^1$H-NMR (CDCl$_3$) δ: 1.24 (9H, s), 1.69 (3H, s), 2.82 (1H, dd, J=13.6, 7.1 Hz), 2.97 (1H, dd, J=13.6, 6.6 Hz), 4.12 (1H, s), 5.13-5.20 (2H, m), 5.59-5.70 (1H, m), 6.98 (1H, dd, J=11.6, 9.1 Hz), 7.55-7.63 (2H, m), 9.20 (1H, s).

Step 2
Compound (2) (6.52 g) was dissolved in acetone (99 ml) and water (33 ml). To the mixture were added N-methylmorpholine-N-oxide (4.65 g) and potassium osmate dihydrate (244 mg) at room temperature. The mixture was stirred for 6.5 hours and were added a saturated aqueous sodium hydrogen carbonate solution and ethyl acetate. The mixture was washed with brine and dried over sodium sulfate. The solvent was evaporated under reduced pressure to afford diastereo-mixture (3) (8.30 g).

Step 3

The diastereo-mixture (3) (8.30 g) was dissolved in dichloromethane (105 ml). To the solution were added 4-dimethylaminopyridine (202 mg) and pyridine (1.73 ml) at room temperature, and the mixture was stirred for 10 minutes. To the reaction mixture was added anhydrous acetic acid (1.72 ml) in dichloromethane (7.0 ml) at room temperature, and the mixture was stirred for 40 minutes. Then a saturated aqueous ammonium chloride solution and ethyl acetate were added and the mixture was washed with 10% aqueous citric acid solution, water and brine. The organic layer was dried over sodium sulfate and the solvent was evaporated under reduced pressure. The obtained residue was purified by column chromatography to afford the diastereo-mixture (4) (6.20 g).

Step 4

A Dess-Martin reagent (5.71 g) was suspended in dichloromethane (50 ml). To the suspension was added a solution of diastereo-mixture (4) (5.28 g) in dichloromethane (25 ml) at room temperature. The mixture was stirred for 40 minutes and to the mixture were added a saturated aqueous sodium hydrogen carbonate solution, a saturated aqueous sodium thiosulfate solution and ethyl acetate. The mixture was washed with a saturated aqueous sodium hydrogen carbonate solution, water and brine. The organic layer was dried over sodium sulfate and the solvent was evaporated under reduced pressure to afford the crude product (5) (5.13 g).

$^1$H-NMR (CDCl$_3$) δ: 1.29 (9H, s), 1.79 (3H, s), 2.12 (3H, s), 3.35 (1H, d, J=18.2 Hz), 3.54 (1H, d, J=18.2 Hz), 4.54 (1H, d, J=16.2 Hz), 4.74 (1H, d, J=16.2 Hz), 5.15 (1H, s), 7.01-7.06 (1H, m), 7.54-7.55 (1H, m), 7.63-7.65 (1H, m), 8.49 (1H, s).

Step 5

Crude product (5) (4.98 g) was dissolved in methanol (30 ml). To the solution was added 4.0 M aqueous hydrochloric acid solution (3.99 ml) at room temperature. The mixture was stirred for 1 hour and the solvent was evaporated under reduced pressure. Ethyl acetate was added and the mixture was extracted with water. A saturated aqueous sodium hydrogen carbonate solution was added, the mixture was extracted with chloroform, and the organic layer was dried over sodium sulfate. The solvent was evaporated under reduced pressures to afford the crude product (6) (2.62 g).

Step 6

Crude product (6) (2.62 g) was dissolved in ethyl acetate (40 ml). To a solution were added a solution of potassium carbonate (1.99 g) in water (7.0 ml) and a solution of thiophosgene (827 µl) in ethyl acetate (11 ml) at 0° C., and the mixture was stirred for 30 minutes. To the reaction mixture were added water and ethyl acetate, and the mixture was washed with brine. The organic layer was dried over sodium sulfate. The solvent was evaporated under reduced pressure to afford the crude product (7) (2.96 g).

Step 7

The crude product (7) (2.96 g) was dissolved in dichloromethane (40 ml). To the solution was added bis(2,4-dimethoxybenzyl)amine (2.62 g) at room temperature. The mixture was stirred overnight and the solvent was evaporated under reduced pressure. The obtained residue was purified by column chromatography to afford Compound (8) (2.50 g).

$^1$H-NMR (CDCl$_3$) δ: 1.79 (3H, s), 2.18 (3H, s), 3.34 (1H, d, J=16.7 Hz), 3.79-3.80 (14H, m), 4.50 (1H, d, J=16.7 Hz), 4.66-4.78 (4H, m), 6.46-6.50 (4H, m), 6.74 (1H, s), 6.97-7.04 (2H, m), 7.12 (2H, d, J=8.6 Hz), 7.61 (1H, d, J=7.6 Hz), 8.19 (1H, s).

Step 8

Compound (8) (2.39 g) was dissolved in acetonitrile (17 ml). To the solution were added N,N-diisopropylethylamine (1.15 ml) and methyl iodide (413 µl) at room temperature and the mixture was stirred for 20 hours. To the reaction mixture was added methyl iodide (413 µl) and stirred for 7 hours. To the reaction mixture were added water and ethyl acetate, and the mixture was washed with 1.0 M aqueous hydrochloric acid solution, a saturated aqueous sodium hydrogen carbonate solution, water, and brine. The organic layer was dried over sodium sulfate and the solvent was evaporated under reduced pressures to afford the crude product (9) (2.43 g).

$^1$H-NMR (CDCl$_3$) δ: 1.82 (3H, s), 2.05 (3H, s), 2.10 (3H, s), 3.75-3.81 (14H, m), 4.48-4.59 (5H, m), 4.90 (1H, d, J=17.7 Hz), 6.45-6.48 (4H, m), 6.99-7.10 (4H, m), 7.74-7.75 (1H, m), 8.20 (1H, br s).

Step 9

The crude product (9) (4.50 g) was dissolved in t-butanol (90 ml), and acetic acid (6.98 ml) was added at room temperature. The mixture was stirred for 2.5 hours at 90° C. and the solvent was evaporated under reduced pressure. To the residue were added a saturated aqueous sodium hydrogen carbonate solution and ethyl acetate and the mixture was washed with water and brine. The organic layer was dried over sodium sulfate and the solvent was evaporated under reduced pressure. The obtained residue was purified by column chromatography to afford Compound (10) (2.34 g).

$^1$H-NMR (CDCl$_3$) δ: 1.58 (3H, s), 1.92 (3H, s), 3.76-3.79 (12H, m), 4.31 (2H, d, J=15.2 Hz), 4.44 (1H, d, J=13.1 Hz), 4.53 (1H, d, J=13.1 Hz), 4.77 (2H, d, J=15.2 Hz), 5.68 (1H, s), 6.44-6.46 (4H, m), 6.97-7.02 (1H, m), 7.14-7.18 (3H, m), 7.48 (1H, s), 7.82-7.84 (1H, m).

Step 10

Compound (10) (60.5 mg) was dissolved in tetrahydrofuran (0.6 ml), methanol (0.6 ml) and water (0.6 ml). To the solution was added potassium carbonate (48.5 mg) at room temperature, and the mixture was stirred 3.5 hours at 50° C. To the mixture were added water and ethyl acetate, and the mixture was washed with brine. The organic layer was dried over sodium sulfate and the solvent was evaporated under reduced pressure. The obtained residue was purified by chromatography to afford Compound (11) (38.2 mg).

$^1$H-NMR (CDCl$_3$) δ: 1.55 (3H, s), 3.22 (2H, br s), 3.77 (6H, s), 3.80 (6H, s), 3.97 (2H, s), 4.32 (2H, d, J=16.2 Hz), 4.81 (2H, d, J=16.2 Hz), 5.58 (1H, d, J=3.5 Hz), 6.37 (1H, dt, J=8.4, 3.5 Hz), 6.45-6.49 (4H, m), 6.58 (1H, dd, J=6.8, 3.0 Hz), 6.71 (1H, dd, J=11.4, 8.4 Hz), 7.19 (2H, d, J=8.4 Hz).

Step 11

In methanol (0.35 ml) was dissolved 5-cyano picolinic acid monohydrate (37.0 mg). DMT-MM (24.8 mg) was added at room temperature, and the mixture was stirred for 15 minutes. To the mixture was added a solution of Compound (11) (35.0 mg) in methanol (0.7 ml) and the mixture was stirred for 8 hours. To the mixture were added water and ethyl acetate, and the mixture was washed with brine. The organic layer was dried over sodium sulfate and the solvent was evaporated under reduced pressure. The obtained residue was purified by chromatography to afford Compound (12) (20.9 mg).

¹H-NMR (CDCl₃) δ: 1.61 (3H, s), 3.71 (6H, s), 3.78 (6H, s), 3.99 (2H, d, J=5.5 Hz), 4.37 (2H, d, J=16.0 Hz), 4.78 (2H, d, J=16.0 Hz), 5.63 (1H, d, J=3.1 Hz), 6.42-6.45 (4H, m), 7.02 (1H, dd, J=11.1, 8.8 Hz), 7.20 (2H, d, J=8.8 Hz), 7.41 (1H, dd, J=6.7, 2.7 Hz), 8.04-8.09 (1H, m), 8.18 (1H, dd, J=8.1, 1.5 Hz), 8.38 (1H, d, J=8.1 Hz), 8.90 (1H, d, J=1.5 Hz), 9.51 (1H, s).

Step 12

Compound (12) (37.6 mg) was dissolved in trifluoroacetic acid (1.1 ml). To the mixture was added anisole (42 μl) at room temperature, and stirred for 19.5 hours at 80° C. Then, 2.0 M an aqueous sodium carbonate solution (8.5 ml) and ethyl acetate were successively added and the mixture was washed with brine. The organic layer was dried over sodium sulfate and the solvent was evaporated under reduced pressure. The obtained residue was purified by chromatography, precipitated as a solid from ethyl acetate and n-hexane, and collected by filtration to afford Compound (I-4) (13.8 mg).

Example 2

Synthesis of Compound (I-17)

[Chemical Formula 25]

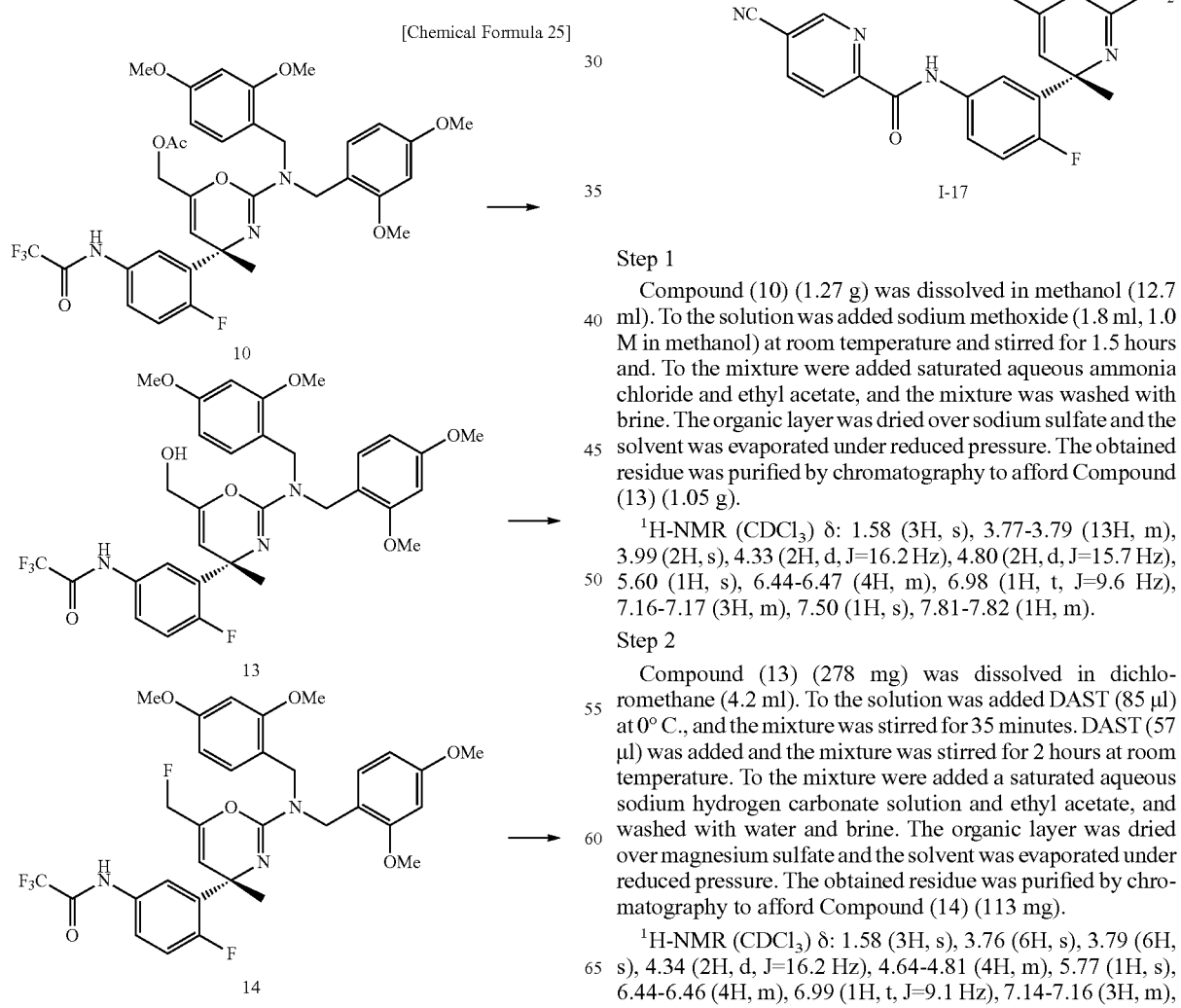

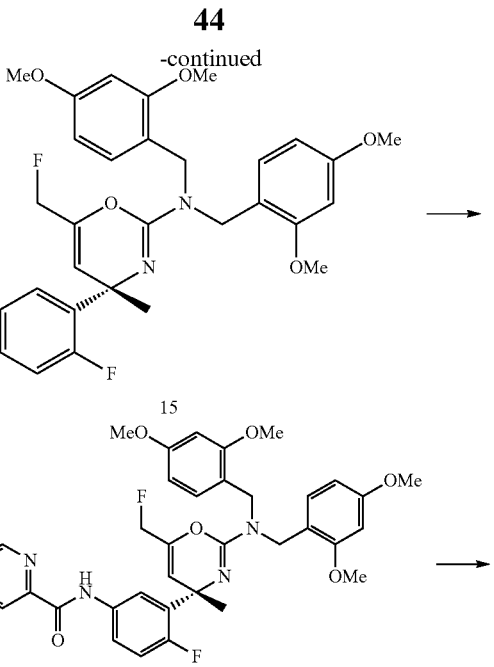

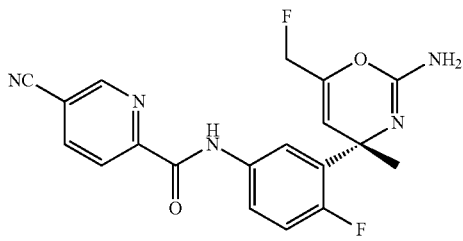

Step 1

Compound (10) (1.27 g) was dissolved in methanol (12.7 ml). To the solution was added sodium methoxide (1.8 ml, 1.0 M in methanol) at room temperature and stirred for 1.5 hours and. To the mixture were added saturated aqueous ammonia chloride and ethyl acetate, and the mixture was washed with brine. The organic layer was dried over sodium sulfate and the solvent was evaporated under reduced pressure. The obtained residue was purified by chromatography to afford Compound (13) (1.05 g).

¹H-NMR (CDCl₃) δ: 1.58 (3H, s), 3.77-3.79 (13H, m), 3.99 (2H, s), 4.33 (2H, d, J=16.2 Hz), 4.80 (2H, d, J=15.7 Hz), 5.60 (1H, s), 6.44-6.47 (4H, m), 6.98 (1H, t, J=9.6 Hz), 7.16-7.17 (3H, m), 7.50 (1H, s), 7.81-7.82 (1H, m).

Step 2

Compound (13) (278 mg) was dissolved in dichloromethane (4.2 ml). To the solution was added DAST (85 μl) at 0° C., and the mixture was stirred for 35 minutes. DAST (57 μl) was added and the mixture was stirred for 2 hours at room temperature. To the mixture were added a saturated aqueous sodium hydrogen carbonate solution and ethyl acetate, and washed with water and brine. The organic layer was dried over magnesium sulfate and the solvent was evaporated under reduced pressure. The obtained residue was purified by chromatography to afford Compound (14) (113 mg).

¹H-NMR (CDCl₃) δ: 1.58 (3H, s), 3.76 (6H, s), 3.79 (6H, s), 4.34 (2H, d, J=16.2 Hz), 4.64-4.81 (4H, m), 5.77 (1H, s), 6.44-6.46 (4H, m), 6.99 (1H, t, J=9.1 Hz), 7.14-7.16 (3H, m), 7.46 (1H, s), 7.84 (1H, br s).

Step 3

Compound (14) (93.5 mg) was dissolved in tetrahydrofuran (0.9 ml), methanol (0.9 ml) and water (0.9 ml). To the solution was added potassium carbonate (39.8 mg) under room temperature, and stirred for 5 hours at 50° C. To the mixture were added water and ethyl acetate, and the mixture was washed with water and brine. The organic layer was dried over sodium sulfate and the solvent was evaporated under reduced pressure. The obtained residue was purified by chromatography to afford Compound (15) (72.2 mg).

$^1$H-NMR (CDCl$_3$) δ: 1.56 (3H, s), 3.22 (2H, s), 3.76 (6H, s), 3.80 (6H, s), 4.33 (2H, d, J=16.0 Hz), 4.67 (2H, d, J=47.9 Hz), 4.79 (2H, d, J=16.0 Hz), 5.74 (1H, dd, J=4.7, 3.2 Hz), 6.37 (1H, dt, J=8.5, 3.2 Hz), 6.45-6.48 (4H, m), 6.56 (1H, dd, J=6.9, 2.9 Hz), 6.71 (1H, dd, J=11.6, 8.5 Hz), 7.17 (1H, s), 7.19 (1H, s).

Step 4

To a solution of compound (15) (60.5 mg) in dimethylformamide (1.0 ml) were added 5-cyano picolinic acid monohydrate (21.8 mg), 1-hydroxybenzotriazole monohydrate (20.1 mg), 4-dimethylaminopyridine (1.3 mg), and WSCD-HCl (25.1 mg). The mixture was stirred for 50 minutes. To the mixture were added sequentially a saturated aqueous sodium hydrogen carbonate solution and ethyl acetate, and the mixture was washed with water and brine. The organic layer was dried over sodium sulfate, and the solvent was evaporated under reduced pressure. The obtained residue was purified by chromatography to afford Compound (16) (72.9 mg).

$^1$H-NMR (CDCl$_3$) δ: 1.62 (3H, s), 3.71 (6H, s), 3.77 (6H, s), 4.39 (2H, d, J=16.0 Hz), 4.70 (4H, d, J=48.1 Hz), 4.77 (4H, d, J=16.0 Hz), 5.80 (1H, dd, J=4.7, 3.1 Hz), 6.41-6.44 (4H, m), 7.02 (1H, dd, J=11.3, 8.8 Hz), 7.18 (2H, s), 7.21 (2H, s), 7.41 (1H, dd, J=6.7, 2.9 Hz), 8.06-8.11 (1H, m), 8.18 (1H, dd, J=8.0, 2.0 Hz), 8.38 (1H, d, J=8.0 Hz), 8.90 (1H, d, J=2.0 Hz), 9.50 (1H, s).

Step 5

Compound (16) (60.1 mg) was dissolved in trifluoroacetic acid (1.8 ml). To the solution was added anisole (67 µl) at room temperature, and stirred for 14 hours at 80° C. To the mixture were added sequentially 2.0 M aqueous sodium carbonate solution (13.5 ml) and ethyl acetate, and the mixture was washed with water and brine. The organic layer was dried over sodium sulfate and the solvent was evaporated under reduced pressure. The obtained residue was purified by chromatography, precipitated as a solid by ethyl acetate and n-hexane, and collected by filtration to afford Compound (I-17) (21.7 mg).

Example 3

Synthesis of Compound (I-2)

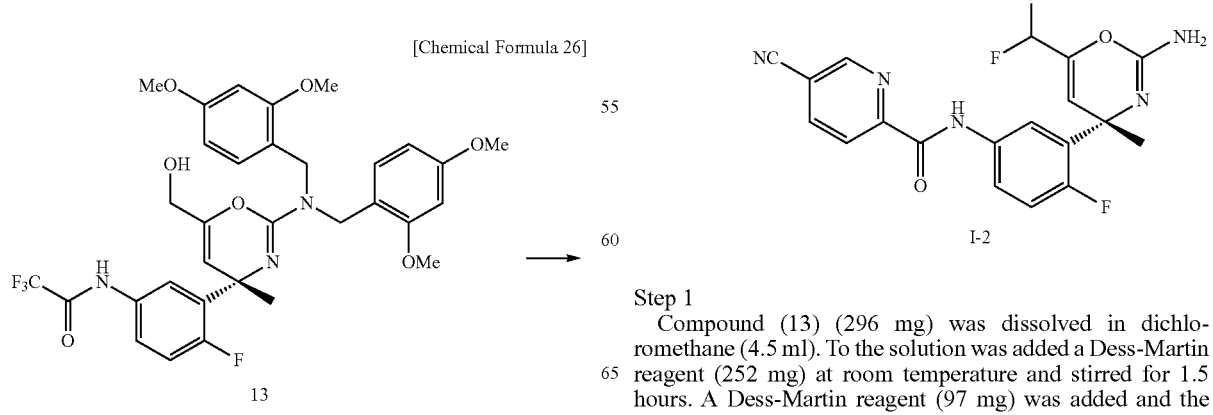

Step 1

Compound (13) (296 mg) was dissolved in dichloromethane (4.5 ml). To the solution was added a Dess-Martin reagent (252 mg) at room temperature and stirred for 1.5 hours. A Dess-Martin reagent (97 mg) was added and the mixture was stirred for 2 hours. An additional Dess-Martin reagent (97 mg) was added and the mixture was stirred for 30 minutes. To the mixture were added a saturated aqueous sodium hydrogen carbonate solution, a saturated aqueous sodium thiosulfate solution, and ethyl acetate. The mixture was washed with a saturated aqueous sodium hydrogen carbonate solution, water and brine. The organic layer was dried over sodium sulfate and the solvent was evaporated under reduced pressure. The obtained residue was purified by column chromatography to afford Compound (17) (289 mg).

$^1$H-NMR (CDCl$_3$) δ: 1.65 (3H, s), 3.76 (6H, s), 3.78 (6H, s), 4.41 (2H, d, J=16.2 Hz), 4.82 (2H, d, J=16.2 Hz), 6.41-6.46 (4H, m), 6.59 (1H, s), 7.03 (1H, t, J=9.9 Hz), 7.15-7.20 (3H, m), 7.45 (1H, s), 7.88 (1H, d, J=6.6 Hz), 9.20 (1H, s).

Step 2

Compound (17) (269 mg) was dissolved in dichloromethane (4.0 ml). To the solution was added DAST (137 μl) at 0° C., and stirred at room temperature for 2.5 hours. To the mixture was added DAST (55 μl), and the mixture was stirred at room temperature for 2 hours. To the mixture were added a saturated aqueous sodium hydrogen carbonate solution and ethyl acetate. The mixture was washed with water and brine and the organic layer was dried over magnesium sulfate. The solvent was evaporated under reduced pressure and the obtained residue was purified by chromatography to afford Compound (18) (82 mg).

$^1$H-NMR (CDCl$_3$) δ: 1.60 (3H, s), 3.76 (6H, s), 3.79 (6H, s), 4.35 (2H, d, J=16.7 Hz), 4.76 (2H, d, J=16.7 Hz), 5.79-6.06 (2H, m), 6.43-6.46 (4H, m), 7.01 (1H, t, J=10.4 Hz), 7.13 (3H, s), 7.15 (3H, s), 7.45 (1H, s), 7.84 (1H, s).

Step 3

Compound (18) (77.7 mg) was dissolved in tetrahydrofuran (0.8 ml), methanol (0.8 ml) and water (0.8 ml). To the solution was added potassium carbonate (32.2 mg) at room temperature, and stirred at 50° C. for 5 hours. To the mixture were added water and ethyl acetate and the mixture was washed with water and brine. The organic layer was dried over sodium sulfate and the solvent was evaporated under reduced pressure. The obtained residue was purified by chromatography to afford Compound (19) (63.3 mg).

$^1$H-NMR (CDCl$_3$) δ: 1.56 (3H, s), 3.22 (2H, br s), 3.76 (6H, s), 3.80 (6H, s), 4.34 (2H, d, J=16.0 Hz), 4.77 (2H, d, J=16.0 Hz), 5.89 (1H, t, J=54.0 Hz), 5.95-5.97 (1H, m), 6.38 (1H, dt, J=8.4, 3.4 Hz), 6.44-6.47 (4H, m), 6.52 (1H, dd, J=6.8, 3.0 Hz), 6.72 (1H, dd, J=11.4, 8.5 Hz), 7.15 (1H, s), 7.18 (1H, s).

Step 4

To a solution of Compound (19) (54.8 mg) in dimethylformamide (0.82 ml) were added 5-cyano picolinic acid monohydrate (19.1 mg), 1-hydroxybenzotriazole monohydrate (17.6 mg), 4-dimethylaminopyridine (1.2 mg), and WSCD-HCl (22.1 mg). The mixture was stirred for 40 minutes. To the mixture were added sequentially a saturated aqueous sodium hydrogen carbonate solution and ethyl acetate and the mixture was washed with water and brine. The organic layer was dried over sodium sulfate, and the solvent was evaporated under reduced pressure. The obtained residue was purified by chromatography to afford Compound (20) (59.0 mg).

$^1$H-NMR (CDCl$_3$) δ: 1.63 (3H, s), 3.71 (6H, s), 3.77 (6H, s), 4.40 (2H, d, J=15.9 Hz), 4.74 (2H, d, J=15.9 Hz), 5.92 (1H, t, J=54.0 Hz), 6.01-6.02 (1H, m), 6.41-6.44 (4H, m), 7.04 (1H, dd, J=11.1, 8.8 Hz), 7.17 (1H, s), 7.19 (1H, s), 7.41 (1H, dd, J=6.9, 2.7 Hz), 8.06-8.12 (1H, m), 8.18 (1H, dd, J=8.1, 2.0 Hz), 8.38 (1H, d, J=8.1 Hz), 8.90 (1H, d, J=2.0 Hz), 9.51 (1H, s).

Step 5

Compound (20) (50.8 mg) was dissolved in trifluoroacetic acid (1.5 ml). To the solution was added anisole (55 μl) at room temperature, and stirred at 80° C. for 15 hours. To the mixture were added sequentially a 2.0 M aqueous sodium carbonate solution (11.3 ml) and ethyl acetate, and the mixture was washed with water and brine. The organic layer was dried over sodium sulfate and the solvent was evaporated under reduced pressure. The obtained residue was purified by chromatography and precipitated as a solid from ethyl acetate and n-hexane and collected by filtration to afford Compound (I-2) (17.6 mg).

Example 4

Synthesis of Compound (I-18)

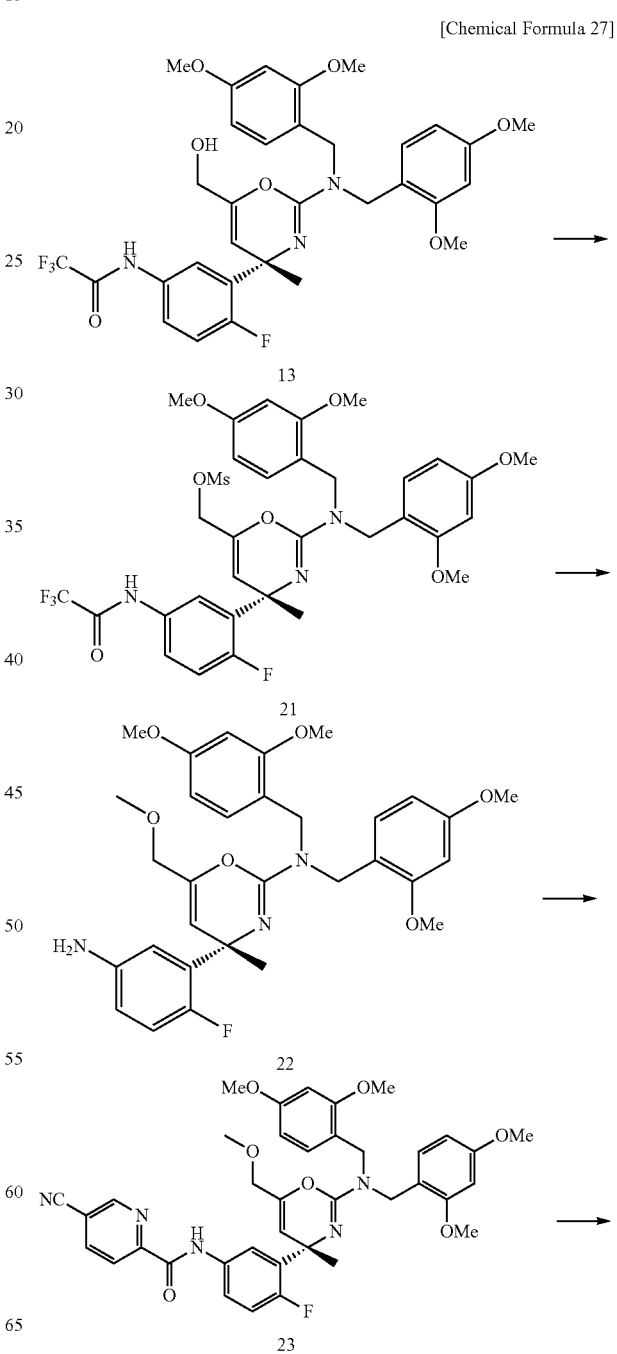

[Chemical Formula 27]

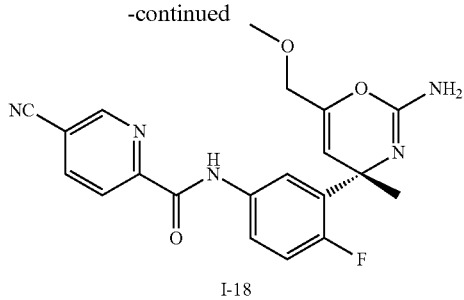

I-18

Step 1

Compound (13) (246 mg) was dissolved in dichloromethane (3.7 ml). To the solution were added triethylamine (79 μl) and methanesulfonyl chloride (44 μl) at room temperature and stirred for 30 minutes. To the reaction mixture were added a saturated aqueous sodium hydrogen carbonate solution and ethyl acetate, and the mixture was washed with water and brine. The organic layer was dried over sodium sulfate and the solvent was evaporated under reduced pressure to afford the crude product (21) (284 mg).

$^1$H-NMR (CDCl$_3$) δ: 1.60 (3H, s), 2.75 (3H, s), 3.77 (6H, s), 3.79 (6H, s), 4.35 (2H, d, J=16.2 Hz), 4.57 (2H, s), 4.79 (2H, d, J=16.2 Hz), 5.83 (1H, s), 6.44-6.46 (4H, m), 7.01 (1H, t, J=9.6 Hz), 7.14-7.19 (3H, m), 7.48 (1H, s), 7.82 (1H, d, J=7.1 Hz).

Step 2

Compound (21) (263 mg) was dissolved in methanol (2.6 ml). To the solution was added sodium methoxide (710 μl, 1.0 M in methanol) at room temperature, and stirred at 40° C. for 3 hours. To the mixture was added sodium methoxide (1.1 ml, 1.0 M in methanol) and stirred at 40° C. for 1.5 hours. To the mixture were added tetrahydrofuran (2.6 ml), water (2.6 ml) and potassium carbonate (100 mg), and the mixture was stirred at 50° C. for 6 hours. To the reaction mixture were added water and ethyl acetate and the mixture was washed with water and brine. The organic layer was dried over sodium sulfate and the solvent was evaporated under reduced pressure. The obtained residue was purified by column chromatography to afford Compound (22) (172 mg).

$^1$H-NMR (CDCl$_3$) δ: 1.55 (3H, s), 3.21 (2H, br s), 3.26 (3H, s), 3.75-3.81 (14H, m), 4.33 (2H, d, J=16.2 Hz), 4.79 (2H, d, J=16.2 Hz), 5.59 (1H, d, J=3.2 Hz), 6.36 (1H, dt, J=8.5, 3.2 Hz), 6.43-6.47 (4H, m), 6.58 (1H, dd, J=6.9, 3.1 Hz), 6.70 (1H, dd, J=11.4, 8.5 Hz), 7.18 (1H, s), 7.21 (1H, s).

Step 3

To a solution of Compound (22) (142 mg) in dimethylformamide (2.1 ml) were added 5-cyano picolinic acid monohydrate (50.1 mg), 1-hydroxybenzotriazole monohydrate (46.2 mg), 4-dimethylaminopyridine (3.d 1 mg) and WSCD-HCl (57.8 mg). The mixture was stirred for 1.5 hours. To the mixture were added sequentially a saturated aqueous sodium hydrogen carbonate solution and ethyl acetate, and the mixture was washed with water and brine. The organic layer was dried over sodium sulfate and the solvent was evaporated under reduced pressure. The obtained residue was purified by chromatography to afford Compound (23) (162 mg).

$^1$H-NMR (CDCl$_3$) δ: 1.61 (3H, s), 3.28 (3H, s), 3.71 (6H, s), 3.76 (6H, s), 3.83 (2H, s), 4.38 (2H, d, J=16.0 Hz), 4.77 (2H, d, J=16.0 Hz), 5.64 (1H, d, J=3.4 Hz), 6.40-6.43 (4H, m), 7.01 (1H, dd, J=11.2, 8.8 Hz), 7.19 (1H, s), 7.22 (1H, s), 7.40 (1H, dd, J=6.7, 2.7 Hz), 8.05-8.10 (1H, m), 8.17 (1H, dd, J=8.2, 2.1 Hz), 8.38 (1H, d, J=8.2 Hz), 8.89-8.90 (1H, m), 9.49 (1H, s).

Step 4

Compound (23) (129 mg) was dissolved in trifluoroacetic acid (3.8 ml). To the solution was added anisole (142 μl) at room temperature and stirred at 80° C. for 14 hours. To the mixture were added sequentially 2.0 M aqueous sodium carbonate solution (29 ml) and ethyl acetate, and the mixture was washed with water and brine. The organic layer was dried over sodium sulfate and the solvent was evaporated under reduced pressure. The obtained residue was purified by chromatography, precipitated as a solid from ethyl acetate and n-hexane, and collected by filtration to afford Compound (I-18) (49.9 mg).

Example 5

Synthesis of Compound (I-16)

[Chemical Formula 28]

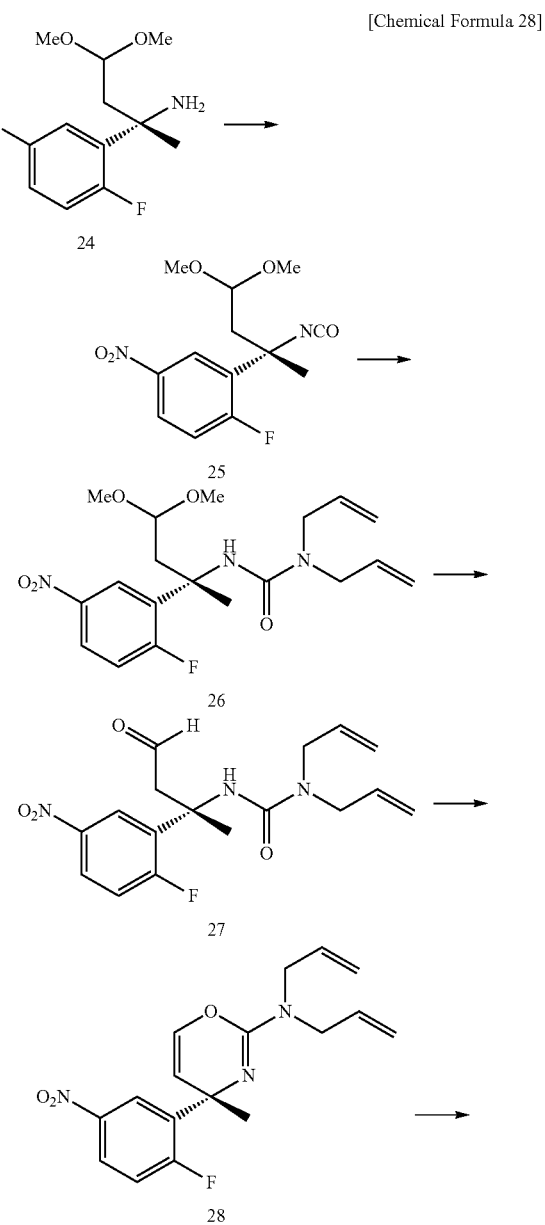

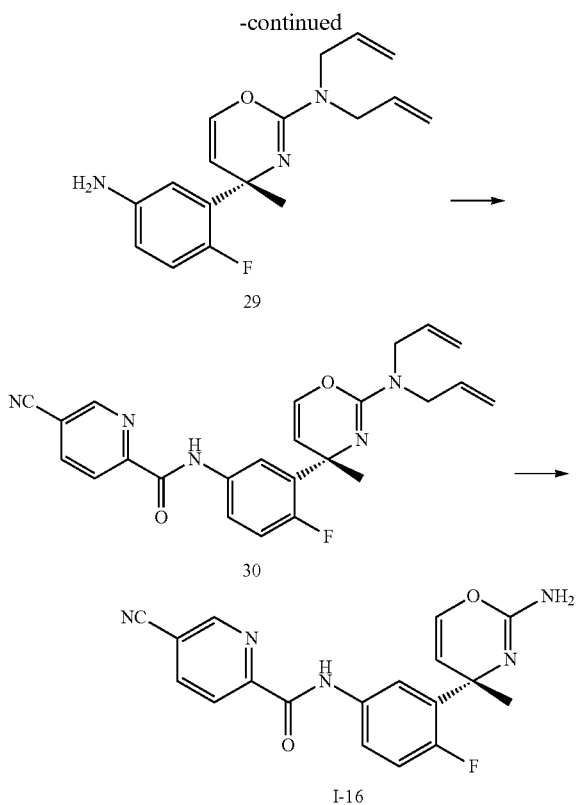

Step 1

Compound (24) (441 mg) which can be prepared according to the methods described in Patent Document 2 or 4 was dissolved in ethyl acetate (8 ml). To the solution were added potassium carbonate (672 mg) and water (4 ml), and the mixture was cooled in a ice bath. To the mixture was added a solution of triphosgene (481 mg) in ethyl acetate (2 ml), and the mixture was stirred at 0° C. for 2 hours. To the reaction mixture was added water, and the mixture was extracted with ethyl acetate. The organic layer was washed with water and saturated brine and dried over anhydrous sodium sulfate. The solvent was evaporated under reduced pressure to afford Compound (25) (481 mg).

$^1$H-NMR (CDCl$_3$) δ: 1.87 (s, 3H), 2.26 (dd, J=14.2, 4.5 Hz, 1H), 2.53 (dd, J=14.2, 6.1 Hz, 1H), 3.09 (s, 3H), 3.30 (s, 3H), 4.38 (dd, J=6.1, 4.5 Hz, 1H), 7.20 (dd, J=11.1, 9.1 Hz, 1H), 8.18-8.23 (m, 1H), 8.52-8.55 (m, 1H).

Step 2

To a solution of Compound (25) (480 mg) in tetrahydrofuran (10 ml) was added diallyl amine (188 mg), and the mixture was stirred at room temperature for 15 hours. To the reaction mixture was added water and the mixture was extracted with ethyl acetate. The organic layer was washed sequentially with water and saturated brine, and dried over anhydrous magnesium sulfate. The solvent was evaporated under reduced pressure and the obtained residue was purified by column chromatography to afford Compound (26) (602 mg).

1H-NMR (CDCl$_3$) δ: 1.98 (s, 3H), 2.05 (dd, J=14.7, 6.1 Hz, 1H), 2.25 (dd, J=14.7, 4.6 Hz, 1H), 3.27 (s, 6H), 3.29 (s, 6H), 3.82-3.94 (m, 4H), 4.19 (dd, J=6.1, 4.6 Hz, 1H), 5.21-5.28 (m, 4H), 5.78-5.88 (m, 2H), 6.41 (s, 1H), 7.14 (dd, J=11.2, 9.1 Hz, 1H), 8.09-8.14 (m, 1H), 8.19-8.23 (m, 1H).

Step 3

To a solution of Compound (26) (400 mg) in acetone (8 ml) was added 1 mol/L sulfuric acid (3.03 ml), and the mixture was stirred at room temperature for 5 hours. To the reaction mixture was added water and extracted with ethyl acetate. The organic layer was washed sequentially with a saturated aqueous sodium hydrogen carbonate solution, water, and a saturated brine, and dried over anhydrous magnesium sulfate. The solvent was evaporated under reduced pressure to afford Compound (27) (351 mg).

$^1$H-NMR (CDCl$_3$) δ: 1.75 (s, 3H), 3.06 (d, J=16.2 Hz, 1H), 3.70 (d, J=16.2 Hz, 1H), 3.83-3.94 (m, 4H), 5.22-5.30 (m, 5H), 5.79-5.89 (m, 2H), 7.17 (dd, J=11.2, 9.1 Hz, 1H), 8.12-8.18 (m, 1H), 8.22-8.28 (m, 1H), 9.74 (s, 1H).

Step 4

To a solution of Compound (27) (263 mg) in acetonitrile (5 ml) was added diphosphorus pentoxide (1.60 g), and the mixture was refluxed for 2 hours. To the reaction mixture was added ice and made alkaline with a saturated aqueous sodium hydrogen carbonate solution. The solution was extracted with ethyl acetate and the organic layer was washed with water and brine. The organic layer was dried over anhydrous magnesium sulfate. The solvent was evaporated under reduced pressure and the obtained residue was purified by column chromatography to afford Compound (28) (51.8 mg).

$^1$H-NMR (CDCl$_3$) δ: 1.59 (s, 3H), 3.85 (dd, J=15.7, 5.6 Hz, 2H), 4.10 (dd, J=15.7, 5.6 Hz, 2H), 5.17-5.22 (m, 4H), 5.54 (dd, J=6.1, 3.5 Hz, 1H), 5.84-5.95 (m, 2H), 6.40 (d, J=6.1 Hz, 1H), 7.11 (dd, J=10.6, 8.6 Hz, 1H), 8.06-8.11 (m, 1H), 8.63-8.66 (m, 1H).

Step 5

To a solution of Compound (28) (55 mg) in toluene (5 ml) were added iron powder (93 mg), ammonium chloride (53.3 mg) and water (1 ml) and stirred at 100° C. for 18 hours. The reaction mixture was made alkaline with water and potassium carbonate, filtered with celite and the filtrate was extracted with ethyl acetate. The organic layer was washed with water and saturated brine and dried over anhydrous magnesium sulfate to afford Compound (29) (50.9 mg).

$^1$H-NMR (CDCl$_3$) δ: 1.55 (s, 3H), 3.49 (br, 2H), 3.86 (dd, J=15.7, 5.6 Hz, 2H), 4.05 (dd, J=15.7, 5.6 Hz, 2H), 5.13-5.21 (m, 4H), 5.55 (dd, J=6.1, 3.0 Hz, 1H), 5.81-5.92 (m, 2H), 6.34 (d, J=6.1 Hz, 1H), 6.43-6.48 (m, 1H), 6.77 (dd, J=11.7, 8.6 Hz, 1H), 6.98-7.01 (m, 1H).

Step 6

In DMF (1 ml) were dissolved Compound (29) (50.9 mg), 5-cyano picolinic acid hydrate (33.7 mg), HOBt hydrate (31.0 mg), and DMAP (2.1 mg). To the solution were added EDC hydrochloride (38.9 mg) and DMF (0.5 ml), and stirred at room temperature for 2 hours. To the reaction mixture was added a saturated aqueous sodium hydrogen carbonate solution, and the mixture was extracted with ethyl acetate. The organic layer was washed sequentially with water, a saturated aqueous sodium hydrogen carbonate solution, water, and saturated brine, and dried over anhydrous magnesium sulfate. The solvent was evaporated under reduced pressure and the obtained residue was purified by chromatography to afford Compound (30) (66.9 mg).

$^1$H-NMR (CDCl$_3$) δ: 1.60 (s, 3H), 3.85 (dd, J=16.2, 5.6 Hz, 2H), 4.15 (dd, J=16.2, 5.6 Hz, 2H), 5.20-5.26 (m, 4H), 5.58 (dd, J=6.1, 3.0 Hz, 1H), 5.88-5.99 (m, 2H), 6.38 (d, J=6.1 Hz, 1H), 7.03 (dd, J=11.2, 8.6 Hz, 1H), 7.74-7.77 (m, 1H), 7.92-7.97 (m, 1H), 8.20 (dd, J=8.1, 2.0 Hz, 1H), 8.43 (dd, J=8.1, 1.0 Hz, 1H), 8.90 (d, J=1.0 Hz, 1H), 9.79 (brs, 1H).

Step 7

To a solution of Compound (30) (66.9 mg) and 1,3-barbituric acid (145 mg) in dichloromethane (1 ml) was added tetrakis(triphenylphosphine)palladium (17.9 mg). The system was degassing with nitrogen and refluxed under nitrogen atmosphere for 4 hours. To the mixture was added tetrakis(triphenylphosphine)palladium (17.9 mg) and refluxed for additional 2 hours. To the reaction mixture was added saturated aqueous sodium hydrogen carbonate solution and extracted with ethyl acetate. The organic layer was washed sequentially with water and a saturated brine and dried over anhydrous magnesium sulfate. The solvent was evaporated under reduced pressure and the obtained residue was purified by column chromatography to afford Compound (I-16) (31.8 mg).

Example 6

Synthesis of Compound (I-31)

[Chemical Formula 29]

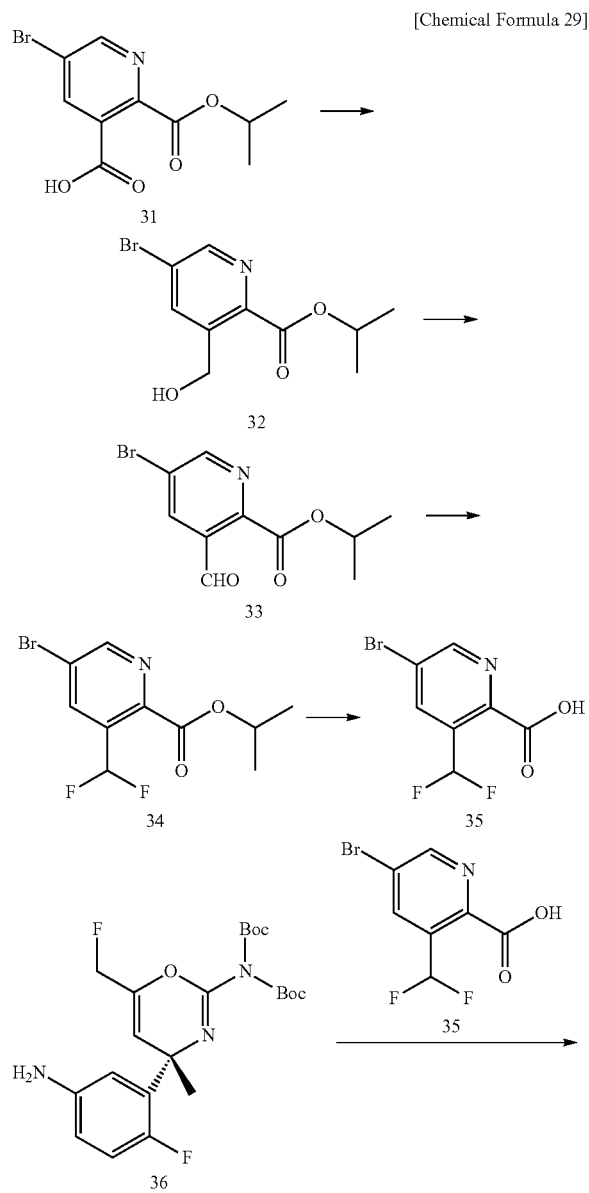

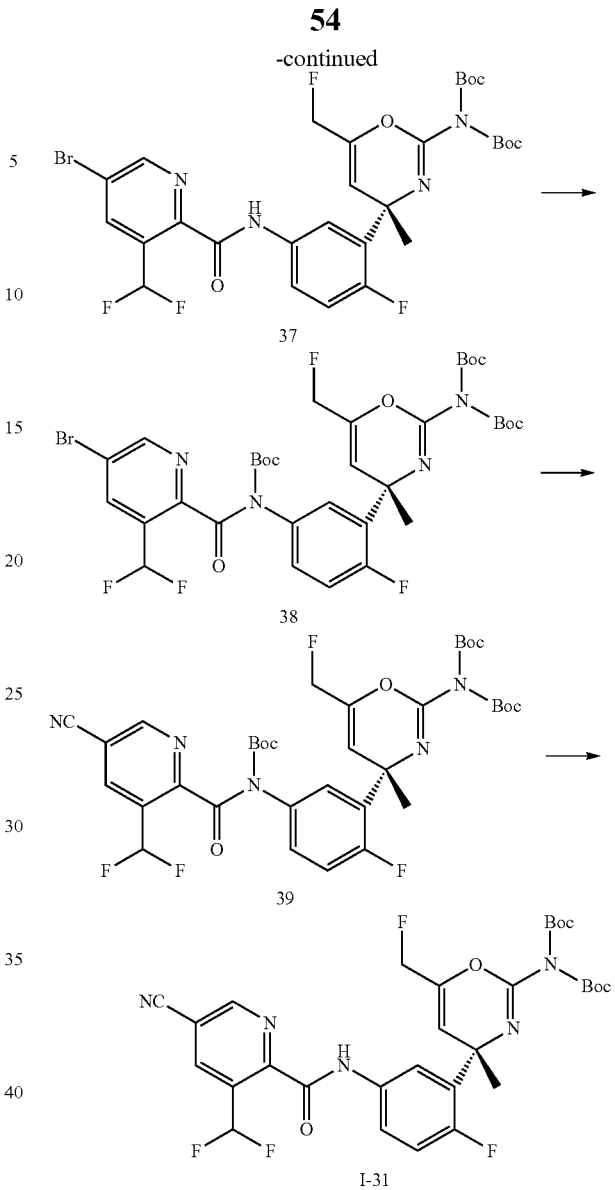

Step 1

Compound 31 (WO2005/077050) (1.15 g, 3.99 mmol) was dissolved in tetrahydrofuran (20 mL) under nitrogen atmosphere. To the solution were added triethylamine (0.67 mL, 4.79 mmol) and isobutyl chloroformate (0.63 mL, 4.79 mmol) under ice-cooling and stirred for 30 minutes. The precipitated salt was collected by filtration and the filtrate was evaporated under reduced pressure. The residue was dissolved in tetrahydrofuran (20 mL), and added dropwise to an aqueous solution (5 mL) of sodium borohydride (317 mg, 8.38 mmol) at −10° C. over 5 minutes. After stirring at the same temperature for 1 hour, the reaction mixture was poured into ice water and extracted with ethyl acetate. The organic layer was washed sequentially with water and a saturated aqueous sodium chloride solution, and the mixture was dried over anhydrous sodium sulfate. The solvent was concentrated under reduced pressure and the obtained residue was chromatographed on silica gel and the fractions eluted with hexane/ethyl acetate=1:1 were collected to afford Compound 32 (763 mg, 70% of yield).

$^1$H NMR (CDCl$_3$) δ: 1.44 (d, J=6.3 Hz, 6H), 3.37 (t, J=5.7 Hz, 1H), 4.83 (d, J=5.7 Hz, 2H), 5.33 (q, J=6.3 Hz, 1H), 8.08 (dd, J=0.3, 2.4 Hz, 1H), 8.71 (dd, J=0.3, 2.1 Hz, 1H).

Step 2

Compound 32 (763 mg, 2.78 mmol) was dissolved in dichloromethane (20 mL). To the solution was added manganese dioxide (2.5 g, 27.8 mmol) and stirred at room temperature for 20 hours. The reaction solution was filtered with celite and the filtrate was evaporated under reduced pressure. The residue was chromatographed on silica gel, and fractions eluted with hexane/ethyl acetate=3:1 were collected to afford Compound 33 (638 mg, 84% of yield).

$^1$H NMR (CDCl$_3$) δ: 1.46 (d, J=6.3 Hz, 6H), 5.93 (q, J=6.3 Hz, 1H), 8.37 (dd, J=0.3, 1.8 Hz, 1H), 8.92 (d, J=2.4 Hz, 1H), 10.58 (t, J=0.3 Hz, 1H).

Step 3

Compound 33 (638 mg, 2.34 mmol) was dissolved in dichloromethane (5 mL). To the solution was added bis(2-methoxyethyl)aminosulfurtrifluoride (1.73 mL, 9.37 mmol) under ice-cooling and stirred at room temperature for 1 hour. The reaction mixture was poured into a saturated aqueous sodium hydrogen carbonate solution and the mixture was extracted with ethyl acetate. The organic layer was washed sequentially with water and a saturated aqueous sodium chloride solution, and dried over anhydrous sodium sulfate. The solvent was concentrated under reduced pressure and the obtained residue was chromatographed on silica gel. Fractions eluted with hexane/ethyl acetate=5:1 were collected to afford Compound 34 (mg 596, 86% of yield).

$^1$H NMR (CDCl$_3$) δ: 1.43 (d, J=6.3 Hz, 6H), 5.34 (q, 6.3 Hz, 1H), 7.45 (t, J=54.9 Hz, 1H), 8.28 (d, J=1.8 Hz, 1H), 8.87 (t, J=0.9 Hz, 1H).

Step 4

Compound 34 (596 mg, 2.02 mmol) was dissolved in tetrahydrofuran/methanol (9 mL, 10:1). To the solution was added a 2 mol/L aqueous sodium hydroxide solution (4.05 mL, 8.10 mol) and stirred at room temperature for 4 hours. The reaction mixtures was made acidic with 2 mol/L hydrochloric acid and extracted with chloroform. The organic layer was washed with a saturated aqueous sodium chloride solution, and dried over anhydrous magnesium sulfate. The solvent was concentrated under reduced pressure to afford Compound 35 (489 mg, 96% of yield).

$^1$H NMR (DMSO-d6) δ: 7.49 (t, J=54.6 Hz, 1H), 8.43 (s, 1H), 8.96 (s, 1H).

Step 5

In N,N-dimethylformamide (1.5 mL) were dissolved Compound 35 (93 mg, 0.369 mmol) and Compound 36 (152 mg, 0.335 mmol). To the solution were added 1-hydroxybenzotriazole (62 mg, 0.402 mmol), 4-dimethylaminopyridine (4.1 mg, 0.034 mmol), and 1-ethyl-3-(3-dimethylaminopropyl) carbodiimide (77 mg, 0.402 mmol), and stirred at room temperature for 4 hours. The reaction mixture was poured into water and extracted with ethyl acetate. The organic layer was washed sequentially with water and saturated aqueous sodium chloride solution, and dried over anhydrous sodium sulfate. The solvent was concentrated under reduced pressure. The residue was chromatographed on silica gel and fractions eluted with hexane/ethyl acetate=3:1 were collected to afford Compound 37 (236 mg, 99% of yield).

MS: m/z=688.9 [(M+H)+].

Step 6

Compound 37 (236 mg, 0.343 mmol) was dissolved in dichloromethane (3 mL). To the solution were added di-tert-butyldicarbonate (0.1 mL, 0.412 mmol) and 4-dimethylaminopyridine (4.1 mg, 0.034 mmol) and stirred at room temperature for 30 minutes. The reaction mixture was concentrated under reduced pressure and the residue was chromatographed on silica gel. Fractions eluted with hexane/ethyl acetate=3:1 were collected to afford Compound 38 (259 mg, 96% of yield).

MS: m/z=788.4 [(M+H)+].

Step 7

Compound 38 (259 mg, 0.329 mmol) and zinc cyanide (58 mg, 0.494 mmol) were dissolved in N-methylpyrrolidone (4 mL) under nitrogen atmosphere. To the solution were added zinc (12.9 mg, 0.198 mmol) and bis(tri-tert-butylphosphine) palladium (50.5 mg, 0.099 mmol) and stirred at 100° C. for 1.5 hours. The reaction mixture was poured into water and extracted with ethyl acetate. The organic layer was washed sequentially with water and saturated aqueous sodium chloride solution, dried over anhydrous sodium sulfate and concentrated under reduced pressure. The residue was chromatographed on silica gel and fractions eluted with hexane/ethyl acetate=3:1 were collected to afford Compound 39 (177 mg, 73% of yield).

MS: m/z=734.1 [(M+H)+].

Step 8

Compound 39 (177 mg, 0.241 mmol) was dissolved in formic acid (0.92 mL) and stirred at room temperature for 16 hours. The reaction mixture was poured into a saturated aqueous sodium carbonate solution under ice-cooling and extracted with ethyl acetate. The organic layer was washed sequentially with water and a saturated aqueous sodium chloride solution, dried over anhydrous sodium sulfate and concentrated under reduced pressure. To the obtained residue was added hexane-ethyl acetate to precipitate a solid, followed by filtration to afford Compound I-31 (90.5 mg, 87% of yield).

$^1$H NMR (CDCl$_3$) δ: 1.52 (3H, s), 4.83 (2H, d, J=47.7 Hz), 5.71 (1H, dd, J=2.1, 5.1 Hz), 5.94 (2H, s), 7.15 (1H, dd, J=9.0, 11.7 Hz), 7.70 (1H, t, J=54.6 Hz), 7.72 (1H, dd, J=3.3, 5.7 Hz), 7.89 (1H, 2.7, 6.6 Hz), 8.85 (1H, s), 9.31 (1H, d, J=0.9 Hz), 10.95 (1H, s).

MS: m/z=434.3 [(M+H)+].

Example 7

Synthesis of Compound (I-78)

[Chemcial Formula 30]

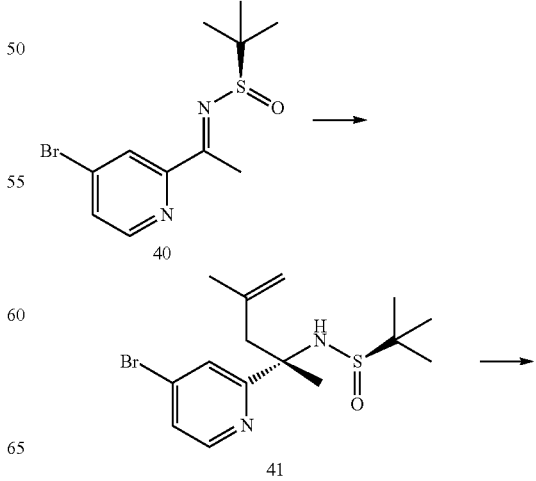

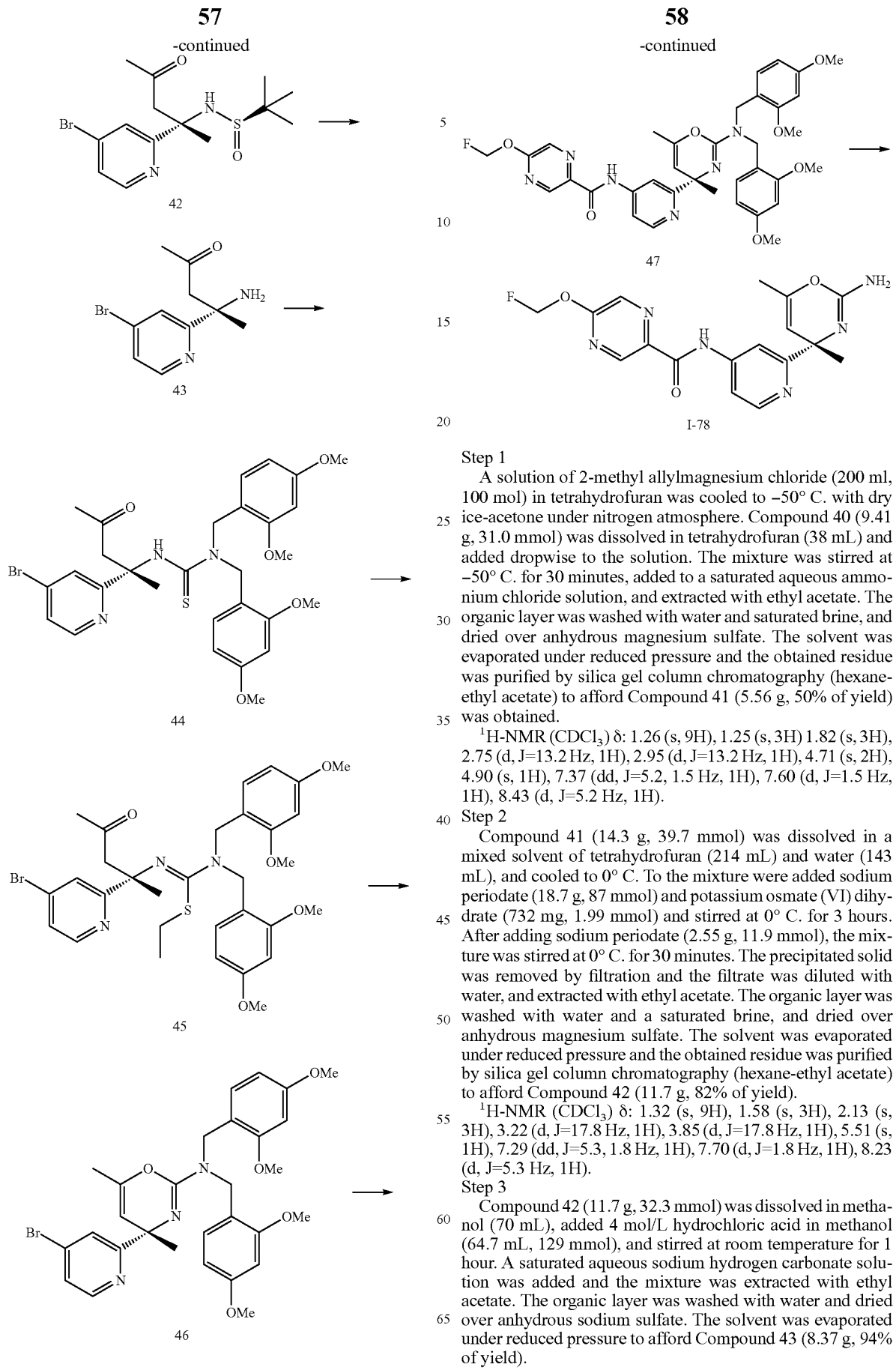

Step 1

A solution of 2-methyl allylmagnesium chloride (200 ml, 100 mol) in tetrahydrofuran was cooled to −50° C. with dry ice-acetone under nitrogen atmosphere. Compound 40 (9.41 g, 31.0 mmol) was dissolved in tetrahydrofuran (38 mL) and added dropwise to the solution. The mixture was stirred at −50° C. for 30 minutes, added to a saturated aqueous ammonium chloride solution, and extracted with ethyl acetate. The organic layer was washed with water and saturated brine, and dried over anhydrous magnesium sulfate. The solvent was evaporated under reduced pressure and the obtained residue was purified by silica gel column chromatography (hexane-ethyl acetate) to afford Compound 41 (5.56 g, 50% of yield) was obtained.

$^1$H-NMR (CDCl$_3$) δ: 1.26 (s, 9H), 1.25 (s, 3H) 1.82 (s, 3H), 2.75 (d, J=13.2 Hz, 1H), 2.95 (d, J=13.2 Hz, 1H), 4.71 (s, 2H), 4.90 (s, 1H), 7.37 (dd, J=5.2, 1.5 Hz, 1H), 7.60 (d, J=1.5 Hz, 1H), 8.43 (d, J=5.2 Hz, 1H).

Step 2

Compound 41 (14.3 g, 39.7 mmol) was dissolved in a mixed solvent of tetrahydrofuran (214 mL) and water (143 mL), and cooled to 0° C. To the mixture were added sodium periodate (18.7 g, 87 mmol) and potassium osmate (VI) dihydrate (732 mg, 1.99 mmol) and stirred at 0° C. for 3 hours. After adding sodium periodate (2.55 g, 11.9 mmol), the mixture was stirred at 0° C. for 30 minutes. The precipitated solid was removed by filtration and the filtrate was diluted with water, and extracted with ethyl acetate. The organic layer was washed with water and a saturated brine, and dried over anhydrous magnesium sulfate. The solvent was evaporated under reduced pressure and the obtained residue was purified by silica gel column chromatography (hexane-ethyl acetate) to afford Compound 42 (11.7 g, 82% of yield).

$^1$H-NMR (CDCl$_3$) δ: 1.32 (s, 9H), 1.58 (s, 3H), 2.13 (s, 3H), 3.22 (d, J=17.8 Hz, 1H), 3.85 (d, J=17.8 Hz, 1H), 5.51 (s, 1H), 7.29 (dd, J=5.3, 1.8 Hz, 1H), 7.70 (d, J=1.8 Hz, 1H), 8.23 (d, J=5.3 Hz, 1H).

Step 3

Compound 42 (11.7 g, 32.3 mmol) was dissolved in methanol (70 mL), added 4 mol/L hydrochloric acid in methanol (64.7 mL, 129 mmol), and stirred at room temperature for 1 hour. A saturated aqueous sodium hydrogen carbonate solution was added and the mixture was extracted with ethyl acetate. The organic layer was washed with water and dried over anhydrous sodium sulfate. The solvent was evaporated under reduced pressure to afford Compound 43 (8.37 g, 94% of yield).

¹H-NMR (CDCl₃) δ: 1.40 (s, 3H), 2.10 (s, 3H), 2.82 (d, J=17.3 Hz, 1H), 3.53 (d, J=17.0 Hz, 1H), 7.30 (dd, J=5.5, 1.8 Hz, 1H), 7.87 (d, J=1.8 Hz, 1H), 8.30 (d, J=5.5 Hz, 1H).

Step 4

Compound 43 (8.24 g, 32.0 mmol) was dissolved in ethyl acetate (82 mL). To the solution were added sodium hydrogen carbonate (13.5 g, 160 mmol) and water (80 mL) and stirred vigorously at 0° C. To the reaction mixture was added dropwise phenyl chlorothionoformate (5.19 mL, 38.5 mmol) and stirred at 0° C. for 1 hour. To the mixture was added bis(2,4-dimethoxybenzyl)amine (12.2 g, 38.5 mmol). The mixture was stirred at 0° C. for 45 minutes, warm to room temperature and stirred for 15 minutes. To the mixture was added a saturated aqueous sodium hydrogen carbonate solution and extracted with ethyl acetate. The organic layer was washed with water and dried over anhydrous sodium sulfate. The solvent was evaporated under reduced pressure and the obtained residue was purified by silica gel column chromatography (hexane-ethyl acetate) to afford Compound 44 (14.9 g, 76% of yield).

¹H-NMR (CDCl₃) δ: 1.71 (s, 3H), 2.13 (s, 3H), 3.80 (s, 6H), 3.81 (s, 6H), 4.02 (s, 2H), 4.91 (s, 4H), 6.44-6.56 (m, 4H), 7.11-7.28 (m, 3H), 7.45 (s, 1H), 8.15 (d, J=5.2 Hz, 1H).

Step 5

Compound 44 (14.9 g, 24.1 mmol) was dissolved in dimethylformamide (170 mL). To the solution were added potassium carbonate (8.34 g, 60.3 mmol) and ethyl iodide (9.75 mL, 121 mmol) and stirred at 80° C. for 7 hours. To the reaction mixture was added water and extracted with ethyl acetate. The organic layer was washed with water and brine and dried over anhydrous sodium sulfate. The solvent was evaporated under reduced pressure, and the obtained residue was purified by silica gel column chromatography (hexane-ethyl acetate) to afford Compound 45 (13.7 g, 88% of yield).

¹H-NMR (CDCl₃) δ: 0.93 (t, J=7.5 Hz, 3H), 1.75 (s, 3H), 2.48-2.69 (m, 1H), 3.05 (d, J=13.0 Hz, 1H), 3.17 (d, J=13.0 Hz, 1H), 3.77 (s, 6H), 3.81 (s, 6H), 4.49 (d, J=15.3 Hz, 2H), 4.57 (d, J=15.3 Hz, 2H), 6.45-6.49 (m, 4H), 7.13 (d, J=8.1 Hz, 2H), 7.18-7.22 (m, 2H), 8.27-8.31 (m, 1H).

Step 6

Compound 45 (13.7 g, 21.3 mmol) was dissolved in t-butylalcohol (480 mL). To the solution was added acetic acid (24.4 mL, 426 mmol) and stirred at 100° C. for 1 hour. The reaction mixture was concentrated to half volume under reduced pressure, washed with a saturated sodium hydrogen carbonate solution, and dried over anhydrous magnesium sulfate. The solvent was evaporated under reduced pressure and the obtained residue was purified by silica gel column chromatography (hexane-ethyl acetate) to afford Compound 46 (5.56 g, 45% of yield).

¹H-NMR (CDCl₃) δ: 1.54 (s, 3H), 1.78 (s, 3H), 3.78 (s, 6H), 3.83 (s, 6H), 4.46 (d, J=16.2 Hz, 2H), 4.68 (d, J=16.2 Hz, 2H), 5.25 (s, 1H), 6.45-6.53 (m, 4H), 7.17-7.29 (m, 3H), 7.73 (d, J=1.4 Hz, 1H), 8.33 (d, J=5.2 Hz, 1H).

Step 7

In dioxane (10 mL) were dissolved 4-bis(diphenylphosphino)-9,9'-dimethylxanthene (120 mg, 0.208 mmol) and tris(dibenzylideneaceton)dipalladium(0) (63.4 mg, 0.069 mmol). After degassing, the mixture was stirred at room temperature for 15 minutes, and cesium carbonate (271 mg, 0.831 mmol) was added. To the mixture was added a suspension of Compound 46 (429 mg, 0.692 mmol) and 5-fluoromethoxypyrazine-2-carboxamide (118 mg) in dioxane (5.0 mL) and stirred at 80° C. for 3 hours, followed by at 90° C. for 7 hours. Insoluble solid was filtered off through celite and filtrate was evaporated under reduced pressure. The obtained residue was purified by silica gel column chromatography (hexane-ethyl acetate) to afford Compound 47 (361 g, 78% of yield).

¹H-NMR (CDCl₃) δ: 1.57 (s, 3H), 1.80 (s, 3H), 3.74 (s, 6H), 3:80 (s, 6H), 4.44 (d, J=16.1 Hz, 2H), 4.76 (d, J=16.1 Hz, 2H), 5.35 (s, 1H), 6.08-6.15 (m, 1H), 6.26-6.32 (m, 1H), 6.44-6.52 (m, 4H), 7.20-7.28 (m, 2H), 7.30-7.33 (m, 1H), 8.03-8.09 (m, 1H), 8.39 (s, 1H), 8.53 (d, J=5.8 Hz, 1H), 9.09 (s, 1H), 9.32 (s, 1H).

Step 8

Compound 47 (347 mg, 0.516 mmol) was dissolved in trifluoroacetic acid (11.9 mL, 154 mmol). To the solution was added anisole (0.395 mL, 3.61 mmol) and stirred at 80° C. for 7 hours. The reaction mixture was added to 1 mol/L aqueous sodium hydroxide solution, extracted with chloroform, and dried over anhydrous magnesium sulfate. The solvent was evaporated under reduced pressure and the obtained residue was purified by amino silica gel column chromatography (hexane-ethyl acetate) to afford Compound I-78 (132 mg, 61% of yield).

¹H-NMR (CDCl₃) δ: 1.59 (s, 3H), 1.82 (s, 3H), 5.26 (s, 1H), 6.16 (d, J=51.0 Hz, 2H), 7.60 (d, J=2.3 Hz, 1H), 7.83 (dd, J=5.4, 2.3 Hz, 1H), 8.30 (s, 1H), 8.54 (d, J=5.7 Hz, 1H), 9.09 (s, 1H), 9.62 (s, 1H).

Example 8

Synthesis of Compound (I-91)

[making 31]

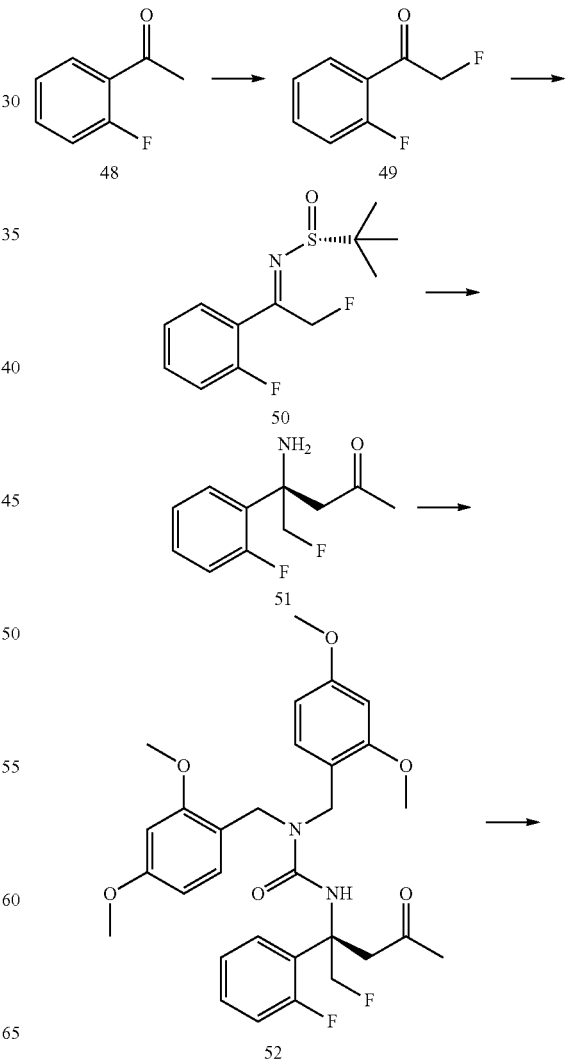

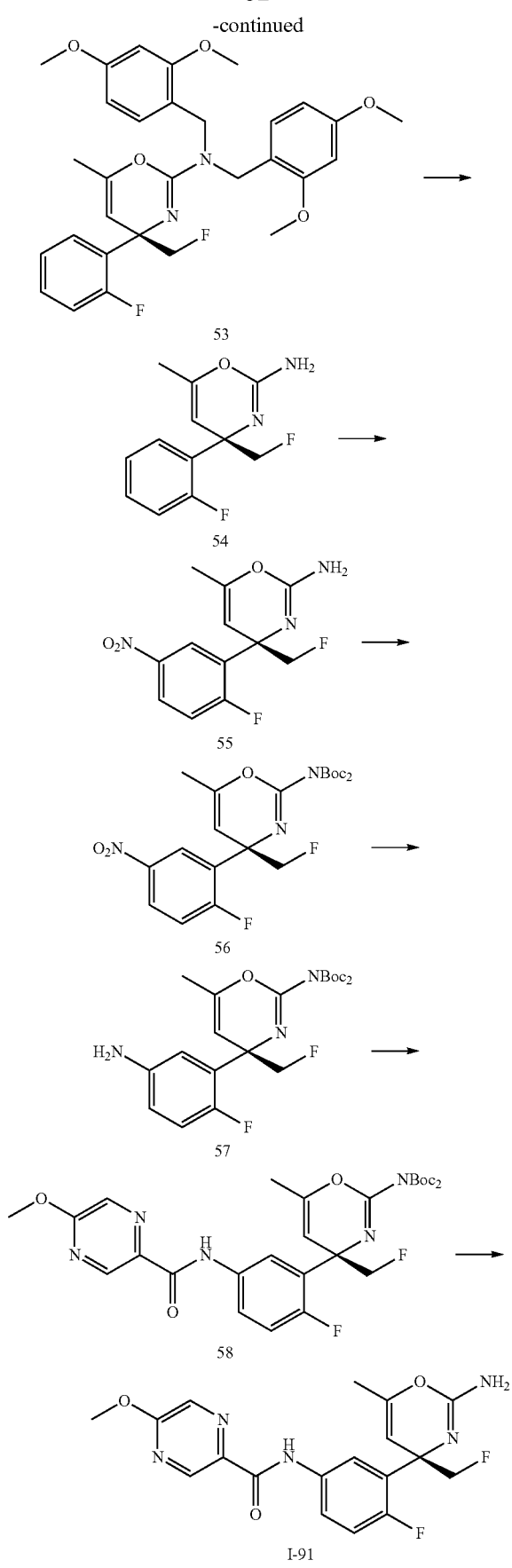

Step 1

To pyridinium bromide perbromide (25.7 g) was added toluene (60 mL) under nitrogen atmosphere, stirred for 10 minutes under ice-cooling. To the mixture was added Compound 48 (10 g), stirred at room temperature for 3.5 hours, and quenched with an aqueous sodium carbonate solution. The organic layer was washed with water and brine and dried over magnesium sulfate. After the extract was filtered, the solvent was evaporated under reduced pressure. The obtained residue was dissolved in acetonitrile (100 mL). To the solution were added potassium fluoride (16.82 g) and 18-crown-ether (1.91 g), and stirred at 90° C. for 12 hours. After stirring at 100° C. for 23 hours, the solvent was evaporated under reduced pressure. To the residue was added water, and extracted with ethyl acetate. The organic layer was washed with brine and dried over magnesium sulfate. The extract was filtered and the solvent was evaporated under reduced pressure. The residue was purified by silica gel column chromatography to afford Compound 49 (3.80 g).

$^1$H-NMR (CDCl$_3$) δ: 5.36 (1H, d, J=3.7 Hz), 5.51 (1H, d, J=3.7 Hz), 7.17 (1H, dd, J=11.1, 8.3 Hz), 7.30 (1H, t, J=7.5 Hz), 7.56-7.63 (1H, m), 8.00-8.06 (1H, m).

Step 2

Compound 49 (1.52 g) was dissolved in toluene (7.6 mL) under nitrogen atmosphere. To the solution were added (R)-2-methylpropane-2-sulfonamide (1.30 g) and tetraethyl orthotitanate (13.75 mL). The mixture was stirred at 80° C. for 70 minutes and diluted with acetonitrile. Water (1.12 mL) was added and filtered through celite. The filtrate was concentrated under reduced pressure and the residue was purified by silica gel column chromatography to afford Compound 50 (1.59 g).

$^1$H-NMR (DMSO-d$_6$) δ: 1.19 (9H, s), 5.60 (2H, dd, J=129.8, 46.2 Hz), 7.27-7.32 (2H, m), 7.48-7.57 (2H, m).

Step 3

Diisopropylamine (15.02 mL) was dissolved in tetrahydrofuran (80 mL) under nitrogen atmosphere. The mixture was stirred at −78° C. for 10 minutes and n-butyllithium hexane solution (1.65 mol/L, 63.9 mL) was added dropwise at the same temperature. After stirred for 30 minutes under ice-cooling, the mixture was stirred at −78° C. for 10 minutes. A solution of t-butyl acetoacetate (8.6 mL) in tetrahydrofuran (34 mL) was added dropwise at the same temperature and the mixture was stirred for 10 minutes. A solution of chlorotitanium triisopropoxide (34.3 g) in tetrahydrofuran (33 mL) was added dropwise and the mixture was stirred for 5 minutes. A solution of Compound 50 (6.83 g) in tetrahydrofuran (33 mL) was added dropwise at the same temperature and the mixture was stirred for 30 minutes. After quenched with an aqueous ammonium chloride solution, the mixture was extracted with ethyl acetate. The organic layer was washed with water and brine and dried over magnesium sulfate. After the extract was filtered, the solvent was evaporated under reduced pressure and roughly purified by silica gel column chromatography. The obtained crude product (8.75 g) was dissolved in a solution of hydrochloric acid in 1,4-dioxane (4 mol/L, 87 mL), and the solution was stirred at 60° C. for 50 minutes. The solvent was evaporated under reduced pressure and the residue was dissolved in an aqueous hydrochloric acid solution (6 mol/L, 87 mL). After stirred at 85° C. for 105 minutes, the mixture was neutralized with an aqueous sodium hydroxide solution and an aqueous sodium carbonate solution under ice-cooling. The reaction solution was extracted with ethyl acetate. The organic layer was washed with brine and dried over magnesium sulfate. The extract was filtered and the solvent was evaporated under reduced pressure. The residue was purified by silica gel column chromatography to afford Compound 51 (3.89 g).

$^1$H-NMR (CDCl$_3$) δ: 2.05 (3H, s), 2.29 (2H, s), 3.17 (2H, dd, J=136.4, 17.2 Hz), 4.55 (2H, ddd, J=47.5, 41.5, 9.0 Hz), 7.01 (1H, dd, J=12.8, 8.1 Hz), 7.17 (1H, dd, J=7.5, 7.5 Hz), 7.23-7.31 (1H, m), 7.62-7.68 (1H, m).

Step 4

Compound 51 (3.69 g) was dissolved in ethyl acetate (64 mL), and an aqueous solution of sodium hydrogen carbonate (5.08 g) in water (31 mL) was added. To the solution was added 4-nitrophenyl chloroformate (3.83 g) under ice-cooling and stirred at the same temperature for 20 minutes. To the solution was added bis(2,4-dimethylbenzyl)amine (6.58 g) at the same temperature and stirred for 20 minutes. After stirred at room temperature for 50 minutes, water was added. The separated organic layer was washed with brine and dried over magnesium sulfate. The extract was filtered and the filtrate was evaporated under reduced pressure. The residue was purified by silica gel column chromatography to afford Compound 52 (9.75 g).

$^1$H-NMR (CDCl$_3$) δ: 2.04 (3H, s), 3.17-3.66 (2H, m), 3.74 (6H, s), 3.80 (6H, s), 4.41 (4H, dd, J=43.2, 16.2 Hz), 5.11 (2H, ddd, J=47.2, 12.8, 9.1 Hz), 6.31 (1H, s), 6.44-6.47 (4H, m), 6.97-7.15 (4H, m), 7.20-7.33 (2H, m).

Step 5

Compound 52 (9.62 g) was dissolved in tetrahydrofuran (192 mL), and a Burgess reagent (8.24 g) was added. The mixture was heated to reflux with stirring for 25 minutes and cold water was added at room temperature. The mixture was extracted with ethyl acetate and washed with brine. The organic layer was dried over magnesium sulfate and the extract was filtered. The filtrate was evaporated under reduced pressure and the residue was purified by silica gel column chromatography to afford Compound 53 (6.71 g).

$^1$H-NMR (CDCl$_3$) δ: 1.79 (3H, s), 3.74 (6H, d, J=0.6 Hz), 3.80 (6H, d, J=0.8 Hz), 4.40 (2H, ddd, J=122.1, 48.0, 8.1 Hz), 4.55 (4H, dd, J=54.9, 15.9 Hz), 5.26-5.27 (1H, m), 6.42-6.45 (4H, m), 6.92-7.02 (2H, m), 7.17 (3H, d, J=7.6 Hz), 7.59 (1H, t, J=7.9 Hz).

Step 6

Compound 53 (6.71 g) was dissolved in trifluoroacetic acid (67 mL). To the solution was added anisole (9.52 mL). After stirred at 80° C. for 17 hours, the mixture was neutralized with an aqueous sodium carbonate solution. The solution was extracted with ethyl acetate and washed with brine. The organic layer was dried over magnesium sulfate and the extract was filtered. The filtrate was evaporated under reduced pressure and the residue was purified by silica gel column chromatography to afford Compound 54 (2.89 g).

$^1$H-NMR (CDCl$_3$) δ: 1.84 (3H, d, J=0.9 Hz), 4.22-4.72 (4H, m), 5.21-5.22 (1H, m), 7.00 (1H, ddd, J=12.1, 8.1, 1.3 Hz), 7.14 (1H, td, J=7.5, 1.3 Hz), 7.20-7.27 (1H, m), 7.63 (1H, td, J=7.8, 1.9 Hz).

Step 7

Compound 54 (305 mg) was dissolved in trifluoroacetic acid (1.8 mL) under ice-cooling. The solution was stirred at −18° C. for 3 minutes. To the mixture were added concentrated sulfuric acid (0.45 mL) and nitric acid (74 μL) dropwise at the same temperature. The mixture was stirred at −13° C. for 20 minutes and neutralized with sodium carbonate solution. It was extracted with ethyl acetate and washed with brine. The organic layer was dried over magnesium sulfate and the extract was filtered. The filtrate was evaporated under reduced pressure and the residue was purified by silica gel column chromatography to afford Compound 55 (317 mg).

$^1$H-NMR (CDCl$_3$) δ: 1.86 (3H, s), 4.27-4.66 (4H, m), 5.17-5.18 (1H, m), 7.16 (1H, dd, J=10.2, 9.0 Hz), 8.15 (1H, ddd, J=9.0, 4.0, 2.8 Hz), 8.60 (1H, dd, J=6.5, 2.8 Hz).

Step 8

Compound 55 (1.28 g) was dissolved in tetrahydrofuran (12 mL). To the solution were added Boc$_2$O (2.62 mL) and DMAP (55 mg) at room temperature. The mixture was stirred at the same temperature for 20.5 hours, and the solvent was removed under reduced pressure. The obtained residue was purified by silica gel column chromatography to afford Compound 56 (2.15 g).

$^1$H-NMR (CDCl$_3$) δ: 1.51 (18H, s), 1.91 (3H, s), 4.35-4.73 (2H, m), 5.13-5.14 (1H, m), 7.20 (1H, dd, J=9.8, 8.9 Hz), 8.19 (1H, ddd, J=8.9, 3.6, 2.9 Hz), 8.58 (1H, dd, J=6.6, 2.9 Hz).

Step 9

Compound 56 (2.15 g) was dissolved in tetrahydrofuran (10.5 mL). To the solution were added ethanol (21 mL) and reduced iron (1.99 g). To the mixture was added an aqueous solution of ammonium chloride (2.85 g) in water (10.5 mL) and stirred at 60° C. for 95 minutes. The reaction mixture was filtered and extracted with ethyl acetate. The organic layer was washed with brine and dried over magnesium sulfate. The extract was filtered and the filtrate was evaporated under reduced pressure. The residue was purified by silica gel column chromatography to afford Compound 57 (1.53 g).

$^1$H-NMR (CDCl$_3$) δ: 1.50 (18H, s), 1.88 (3H, s), 3.54 (2H, br s), 4.49 (2H, ddd, J=80.2, 47.7, 8.8 Hz), 5.16-5.17 (1H, m), 6.52 (1H, dt, J=8.5, 3.3 Hz), 6.82 (1H, dd, J=11.4, 8.5 Hz), 6.92 (1H, dd, J=6.3, 3.3 Hz).

Step 10

Compound 57 (110 mg) was dissolved in dimethylformamide (1.5 mL). To the solution were added 5-methoxy pyrazine-2-carboxamide (44.9 mg), HOBt monohydrate (44.6 mg), DMAP (2.96 mg) and EDC hydrochloride (55.8 g). The mixture was stirred at the same temperature for 40 minutes, quenched with a saturated aqueous sodium hydrogen carbonate solution and extracted with ethyl acetate. The organic layer was washed with brine and dried over magnesium sulfate. The extract was filtered and the filtrate was evaporated under reduced pressure. The residue was purified by silica gel column chromatography to afford Compound 58 (132 mg).

$^1$H-NMR (CDCl$_3$) δ: 1.51 (18H, s), 1.90 (3H, s), 4.06 (3H, s), 4.55 (2H, ddd, J=80.7, 47.4, 8.9 Hz), 5.19-5.21 (1H, m), 7.08 (1H, dd, J=11.1, 9.0 Hz), 7.50 (1H, dd, J=6.5, 2.7 Hz), 8.08-8.09 (1H, m), 8.23 (1H, ddd, J=9.0, 4.2, 2.7 Hz), 8.99 (1H, s), 9.58 (1H, s).

Step 11

Compound 58 (130 mg) was dissolved in formic acid (847 μL) and stirred at room temperature for 3.5 hours. The mixture was neutralized with an aqueous sodium carbonate solution and extracted with ethyl acetate. The organic layer was washed sequentially with water and brine, and dried over magnesium sulfate. The extract was filtered and the solvent was evaporated under reduced pressure. The residue was purified by column chromatography. The obtained crude product was solidified in hexane-ethyl acetate solution and collected by filtration. The obtained white solid was washed with hexane-ethyl acetate solution, air-dried and dried in vacuo to afford Compound I-91 (65 mg).

$^1$H-NMR (CDCl$_3$) δ: 1.85 (3H, s), 4.06 (3H, s), 4.32 (2H, br s), 4.47 (2H, ddd, J=89.7, 47.4, 8.2 Hz), 5.22-5.23 (1H, m), 7.04 (1H, dd, J=11.2, 8.8 Hz), 7.65-7.69 (1H, m), 7.97 (1H, ddd, J=8.8, 4.2, 3.0 Hz), 8.12-8.15 (1H, m), 8.99-9.00 (1H, m), 9.50 (1H, s).

Reference Example 1

Synthesis of Compound (II-1)

[Chemical Formula 32]

Step 1

Compound (31) (465 mg) was dissolved in trifluoroacetic acid (10 ml). To the solution was added anisole (557 mg) at room temperature and stirred at 80° C. for 14 hours. After the reaction mixture was warm to room temperature and neutralized with an aqueous sodium carbonate solution, ethyl acetate was added and the mixture was washed with water and brine. The organic layer was dried over magnesium sulfate. The extract was filtered and the solvent was evaporated under reduced pressure. The residue was purified by silica gel column chromatography to afford Compound (32) (187 mg).

MS; m/z 332 [M$^+$+H]

$^1$H-NMR (CDCl$_3$) δ: 1.57 (3H, d, J=1.1 Hz), 1.79 (3H, d, J=1.1 Hz), 5.24 (1H, dd, J=2.7, 1.2 Hz), 7.03 (1H, dd, J=11.1, 8.7 Hz), 7.53 (1H, dd, J=6.7, 2.9 Hz), 7.66 (1H, ddd, J=8.7, 3.9, 2.9 Hz).

Step 2

Compound (32) (21 mg) was dissolved in tetrahydrofuran (0.50 ml). To the solution were added di-tert-butyl dicarbonate (69 mg) and N,N-dimethyl-4-aminopyridine (4 mg) at room temperature. The mixture was stirred at the same temperature for 3 hours. To the solution were added potassium carbonate (26 mg) and water (0.25 ml), stirred for an additional 2 hours, and left overnight. To the reaction mixture was added ethyl acetate, washed with water and brine and dried over magnesium sulfate. The extract was filtered and the solvent was evaporated under reduced pressure. The obtained residue was dissolved in tetrahydrofuran (0.50 ml). To the solution were added di-tert-butyl dicarbonate (69 mg) and N,N-dimethyl-4-aminopyridine (4 mg) at room temperature and stirred at the same temperature for 1 hour. The solvent was evaporated under reduced pressure and the obtained residue was purified by silica gel column chromatography to afford Compound (33) (37 mg).

MS; m/z 636.6 [M$^+$+H]

Step 3

Compound (33) (80 mg) was dissolved in ethyl acetate (3 ml) under nitrogen atmosphere. To the solution was added toluenesulfonic acid monohydrate (238 mg) at room temperature and stirred at the same temperature for two days. To the reaction mixture was added isopropyl ether (3 ml), and the supernatant was removed. The residue was washed twice with ethyl acetate/isopropyl ether (1/1) solution (2 ml) and the residue was dissolved in dichloromethane (1 ml). To the solution was added isopropyl ether (3 ml) and the supernatant was removed. The residue was dried in vacuo to afford Compound (II-1) (52 mg).

Reference Example 2

Synthesis of Compound (II-2)

[Chemical Formula 33]

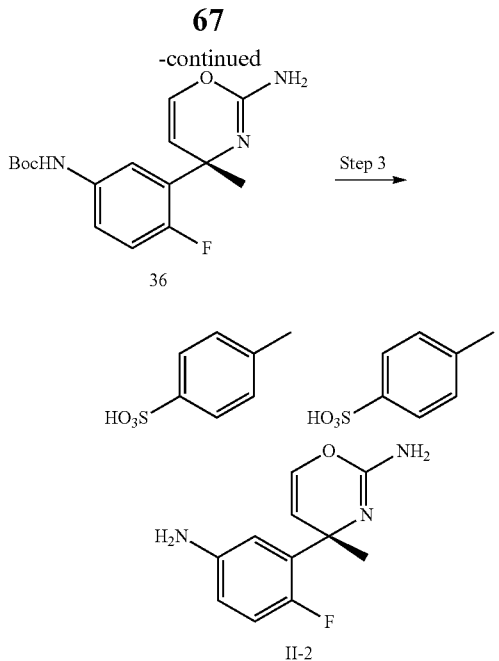

Step 1

Compound (34) (430 mg) was dissolved in tetrahydrofuran (2 ml), methanol (2.5 ml), and water (2.5 ml). To the solution was added potassium carbonate (359 mg) at room temperature. The mixture was stirred with heating at 60° C. for 4 hours. After the completion of the reaction, water (10 ml) was added and extracted with ethyl acetate (20 ml×2). The organic layer was dried over magnesium sulfate and the solvent was concentrated under reduced pressure to afford the oil (319 mg). The obtained oil was used for the next step without purification.

To a solution of the obtained oil (319 mg) in tetrahydrofuran (5 ml) were added triethylamine (0.225 ml) and di-tert-butyl carbonate (0.301 ml) at room temperature and stirred for 24 hours. After the completion of the reaction, a saturated aqueous sodium hydrogen carbonate solution (10 ml) was added and the mixture was extracted with ethyl acetate (20 ml×2). The organic layer was dried over magnesium sulfate and the solvent was concentrated under reduced pressure to afford Compound (35) (342 mg).

MS; m/z 402 [M$^+$+H]

$^1$H-NMR (CDCl$_3$) δ: 1.52 (s, 9H), 1.57 (s, 3H), 3.88 (dd, J=18.0, 6.0 Hz, 2H), 4.04 (dd, J=15.0, 6.0 Hz, 2H), 5.15 (m, 2H), 5.20 (d, J=9.0 Hz, 2H), 5.55 (dd, J=6.0, 3.0 Hz, 1H), 5.91 (m, 2H), 6.34 (m, 1H), 6.35 (m, 1H), 6.91 (dd, J=10.0, 9.0 Hz, 1H), 7.42 (m, 1H), 7.43 (m, 1H).

Step 2

To a solution of Compound (35) (334 mg) in dichloromethane (5 ml) was added 1,3 dimethylbarbituric acid (779 mg) at room temperature. After degassed, Pd(PPh$_3$)$_4$ (96 mg) was added and the mixture was refluxed with heating for 4 hours. After the completion of the reaction, the solvent was evaporated under reduced pressure. The obtained residue was purified by amino column chromatography and silica gel column chromatography to afford Compound (36) (180 mg).

MS; m/z 322 [M$^+$+H]

$^1$H-NMR (CDCl$_3$) δ: 1.51 (s, 9H), 1.62 (s, 3H), 5.52 (dd, J=6.0, 3.0 Hz, 1H), 6.34 (d, J=6.0 Hz, 1H), 6.47 (s, 1H), 6.95 (dd, J=12.0, 9.0 Hz, 1H), 7.26 (m, 1H), 7.44(br, 1H).

Step 3

To a solution of Compound (36) (128 mg) in ethyl acetate (3 ml) was added tosic acid monohydrate (379 mg) and stirred for 20 hours. After the completion of the reaction, diisopropyl ether was added and the obtained solid was washed with ethyl acetate to afford Compound (II-2) (137 mg).

MS; m/z 222 [M$^+$+H]

The following compounds are prepared in a similar manner to the above. In tables, RT means a retention time (min).

TABLE 1-1

| No. | Structure | NMR(solvent: shift value ascending order) | MS [M + 1] | LC/MS RT | LC/MS Method |
|---|---|---|---|---|---|
| I-1 | 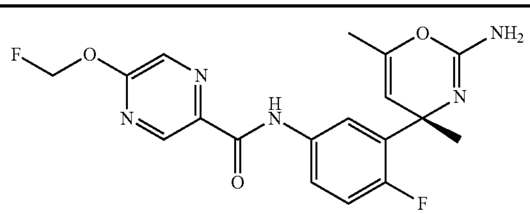 | 1H-NMR (CDCl3) δ: 1.61 (3H, s), 1.80 (3H, d, J = 0.6 Hz), 4.25 (2H, br s), 5.26 (1H, dd, J = 2.4, 1.1 Hz), 6.06 (1H, dd, J = 3.2, 2.0 Hz), 6.23 (1H, dd, J = 3.2, 2.0 Hz), 7.03 (1H, dd, J = 11.3, 8.7 Hz), 7.60 (1H, dd, J = 6.9, 2.9 Hz), 7.88 (1H, ddd, J = 8.7, 4.0, 2.9 Hz), 8.25 (1H, d, J = 0.9 Hz), 9.06 (1H, d, J = 0.9 Hz), 9.47 (1H, br s). | 390 | 1.14 | A |
| I-2 | 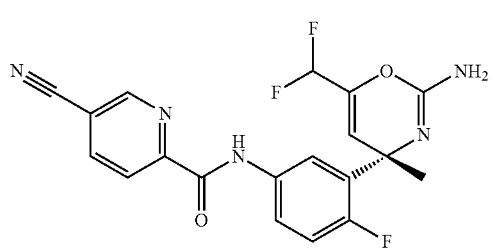 [SMILES: C[C@@]1(c2cc(NC(=O)c3ccc(C#N)cn3)ccc2F)C=C(C(F)F)OC(N)=N1] | 1H-NMR (CDCl3) δ: 1.68 (3H, s), 4.34 (2H, br s), 5.95-5.96 (1H, m), 5.96 (1H, t, J = 53.8 Hz), 7.08 (1H, dd, J = 11.2, 8.6 Hz), 7.73 (1H, dd, J = 6.8, 2.8 Hz), 7.88-7.92 (1H, m), 8.20 (1H, dd, J = 8.1, 2.0 Hz), 8.42 (1H, d, J = 8.1 Hz), 8.88-8.89 (1H, m), 9.85 (1H, s). | 402 | 1.35 | A |

TABLE 1-1-continued

| No. | Structure | NMR(solvent: shift value ascending order) | MS [M + 1] | LC/MS RT | LC/MS Method |
|---|---|---|---|---|---|
| I-3 | 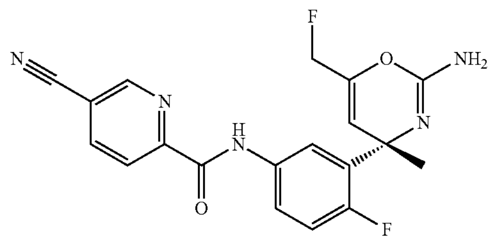 [SMILES: C[C@@]1(c2cc(NC(=O)c3ccc(C#N)cn3)ccc2F)C=C(CF)OC(N)=N1] | 1H-NMR (CDCl3) δ: 1.66 (3H, s), 4.26 (2H, br s), 4.74 (2H, d, J = 47.7 Hz), 5.74 (1H, dd, J = 5.1, 2.5 Hz), 7.06 (1H, dd, J = 11.2, 9.1 Hz), 7.69 (1H, dd, J = 6.8, 2.8 Hz), 7.89-7.93 (1H, m), 8.20 (1H, dd, J = 8.1, 2.0 Hz), 8.42 (1H, d, J = 8.1 Hz), 8.89 (1H, d, J = 2.0 Hz), 9.84 (1H, s). | 384 | 1.26 | A |
| I-4 | 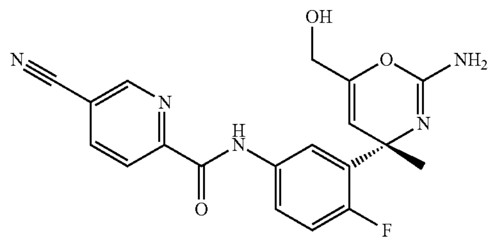 [SMILES: C[C@@]1(c2cc(NC(=O)c3ccc(C#N)cn3)ccc2F)C=C(CO)OC(N)=N1] | 1H-NMR (DMSO-d6) δ: 1.50 (3H, s), 3.80-3.89 (2H, m), 5.09 (1H, t, J = 5.8 Hz), 5.37 (1H, d, J = 3.0 Hz), 5.78 (2H, s), 7.13 (1H, dd, J = 11.4, 8.9 Hz), 7.71-7.75 (1H, m), 7.97 (1H, dd, J = 7.4, 2.8 Hz), 8.28 (1H, d, J = 8.1 Hz), 8.58 (1H, dd, J = 8.1, 2.0 Hz), 9.19-9.20 (1H, m), 10.77 (1H, s). | 382 | 0.91 | A |
| I-5 | 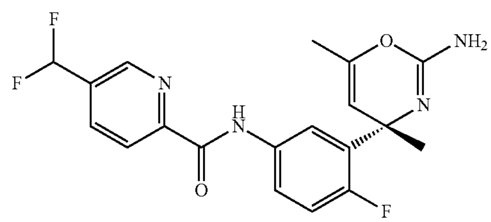 [SMILES: CC1=C[C@@](C)(c2cc(NC(=O)c3ccc(C(F)F)cn3)ccc2F)N=C(N)O1] | 1H-NMR (CDCl3) δ: 1.61 (3H, d, J = 1.0 Hz), 1.80 (3H, d, J = 1.0 Hz), 4.17 (2H, br s), 5.26-5.26 (1H, m), 6.80 (1H, t, J = 55.5 Hz), 7.04 (1H, dd, J = 11.2, 8.6 Hz), 7.63 (1H, dd, J = 6.8, 2.8 Hz), 7.92-7.96 (1H, m), 8.05 (1H, d, J = 8.1 Hz), 8.39 (1H, d, J = 8.1 Hz), 8.75 (1H, s), 9.93 (1H, s). | 391 | 1.22 | A |
| I-6 | 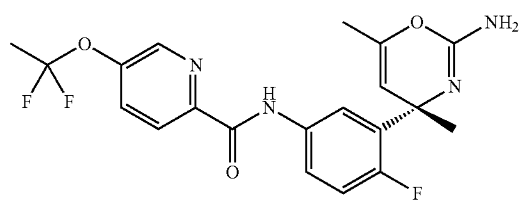 [SMILES: CC1=C[C@@](C)(c2cc(NC(=O)c3ccc(OC(C)(F)F)cn3)ccc2F)N=C(N)O1] | 1H-NMR (CDCl3) δ: 1.61 (3H, d, J = 1.0 Hz), 1.79 (3H, d, J = 1.0 Hz), 2.01 (3H, t, J = 13.4 Hz), 4.16 (2H, br s), 5.25-5.25 (1H, m), 7.02 (1H, dd, J = 11.4, 8.9 Hz), 7.60 (1H, dd, J = 6.8, 2.8 Hz), 7.69-7.71 (1H, m), 7.90-7.94 (1H, m), 8.28 (1H, d, J = 8.6 Hz), 8.45 (1H, d, J = 2.0 Hz), 9.83 (1H, s). | 421 | 1.38 | A |

TABLE 1-2

| No. | Structure | NMR(solvent: shift value ascending order) | MS [M + 1] | LC/MS RT | LC/MS Method |
|---|---|---|---|---|---|
| I-7 | 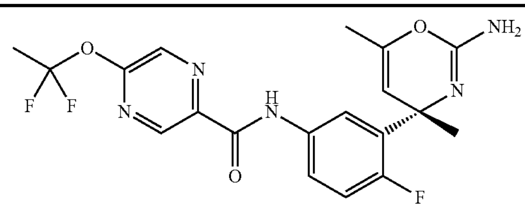 | 1H-NMR (CDCl3) δ: 1.60 (3H, d, J = 1.0 Hz), 1.80 (3H, d, J = 1.0 Hz), 2.13 (3H, t, J = 14.2 Hz), 4.20 (2H, s), 5.25-5.26 (1H, m), 7.04 (1H, dd, J = 11.2, 8.6 Hz), 7.59 (1H, dd, J = 6.8, 2.8 Hz), 7.88-7.92 (1H, m), 8.38 (1H, s), 9.15 (1H, s), 9.47 (1H, s). | 422 | 1.29 | A |
| I-8 | 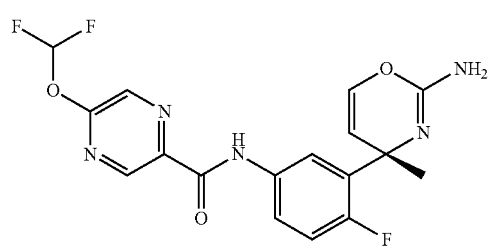 [SMILES: C[C@@]1(c2cc(NC(=O)c3cnc(OC(F)F)cn3)ccc2F)C=COC(N)=N1] | 1H-NMR (CDCl3) δ: 1.65 (3H, s), 5.57 (1H, dd, J = 6.0 Hz, 3.0 Hz), 6.37 (1H, d, J = 6.0 Hz), 7.03 (1H, dd, J = 10.0, 9.0 Hz), 7.50 (1H, t, J = 69.0 Hz), 7.70 (1H, dd, J = 6.0 Hz, 3.0 Hz), 7.84 (1H, m), 8.27 (1H, s), 9.03 (1H, s), 9.45 (1H, s). | 394 | 1.27 | B |

TABLE 1-2-continued

| No. | Structure | NMR(solvent: shift value ascending order) | MS [M + 1] | LC/MS RT | LC/MS Method |
|---|---|---|---|---|---|
| I-9 | 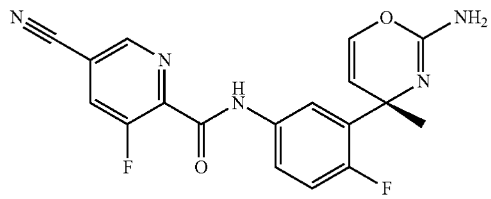 [SMILES: C[C@@]1(c2cc(NC(=O)c3ncc(C#N)cc3F)ccc2F)C=COC(N)=N1] | 1H-NMR (CDCl3) δ: 1.65 (3H, s), 5.57 (1H, dd, J = 6.0 Hz, 3.0 Hz), 6.37 (1H, d, J = 6.0 Hz), 7.06 (1H, dd, J = 12.0 Hz, 9.0 Hz), 7.64 (1H, dd, J = 9.0Hz, 3.0 Hz), 7.91 (1H, m), 7.92 (1H, s), 8.69 (1H, s), 9.65 (1H, s). | 370 | 0.99 | B |
| I-10 | 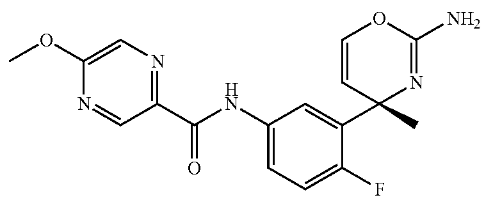 [SMILES: COc1cnc(C(=O)Nc2ccc(F)c([C@]3(C)C=COC(N)=N3)c2)cn1] | 1H-NMR (CDCl3) δ: 1.69 (3H, s), 4.15 (3H, s), 5.59 (1H, dd, J = 6.0 Hz, 3.0 Hz), 6.41 (1H, d, J = 6.0 Hz), 7.08 (1H, J = 12.0 Hz, 9.0 Hz), 7.69 (1H, dd, J = 9.0 Hz, 3.0 Hz), 7.92 (1H, m), 8.18 (1H, s), 9.05 (1H, s), 9.53 (1H, s). | 358 | 1.1 | B |
| I-11 | 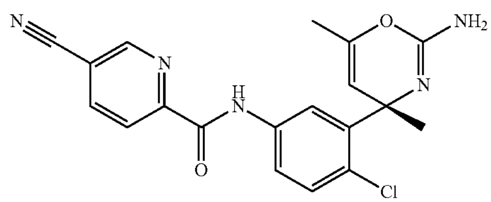 [SMILES: CC1=C[C@@](C)(c2cc(NC(=O)c3ccc(C#N)cn3)ccc2Cl)N=C(N)O1] | 1H-NMR (DMSO-d6) δ: 1.57 (3H, s), 1.76 (3H, s), 5.26 (1H, s), 5.68 (2H, s), 7.36 (1H, d, J = 8.6 Hz), 7.81 (1H, d, J = 8.6 Hz), 8.14 (1H, s), 8.28 (1H, d, J = 8.1 Hz), 8.58 (1H, d, J = 8.1 Hz), 9.20 (1H, s), 10.82 (1H, s). | 382 | 1.26 | B |
| I-12 | 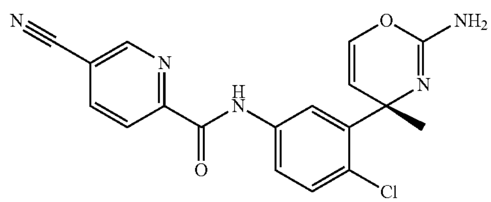 [SMILES: C[C@@]1(c2cc(NC(=O)c3ccc(C#N)cn3)ccc2Cl)C=COC(N)=N1] | 1H-NMR (DMSO-d6) δ: 1.60 (3H, s), 5.54 (1H, d, J = 6.1 Hz), 5.71 (2H, s), 6.56 (1H, d, J = 6.1 Hz), 7.37 (1H, d, J = 8.6 Hz), 7.82 (1H, d, J = 8.6 Hz), 8.17 (1H, s), 8.29 (1H, d, J = 8.6 Hz), 8.58 (1H, d, J = 8.6 Hz), 9.20 (1H, s), 10.83 (1H, s). | 368 | 1.16 | B |
| I-13 | 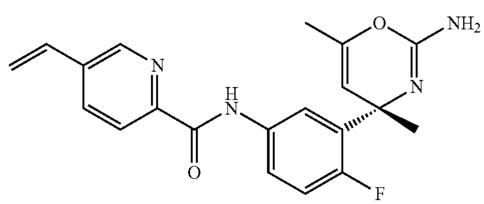 [SMILES: C=Cc1ccc(C(=O)Nc2ccc(F)c([C@]3(C)C=C(C)OC(N)=N3)c2)nc1] | 1H-NMR (CDCl3) δ: 1.69 (3H, s), 1.84 (3H, d, J = 1.0 Hz), 5.29 (1H, br s), 5.52 (1H, d, J = 11.0 Hz), 5.95 (1H, d, J = 17.7 Hz), 6.78 (1H, dd, J = 17.7, 11.0 Hz), 7.05 (1H, dd, J = 11.4, 8.7 Hz), 7.66 (1H, dd, J = 7.0, 2.8 Hz), 7.90-7.95 (2H, m), 8.23 (1H, d, J = 8.2 Hz), 8.60 (1H, d, J = 2.0 Hz), 9.97 (1H, s). | 367 | 1.37 | A |

TABLE 1-3

| No. | Structure | NMR(solvent: shift value ascending order) | MS [M + 1] | LC/MS RT | LC/MS Method |
|---|---|---|---|---|---|
| I-14 | 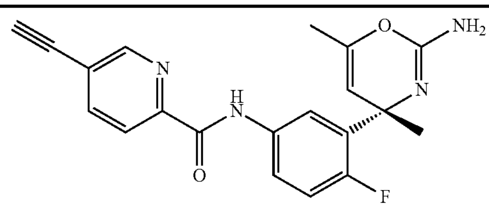 | 1H-NMR (CDCl3) δ: 1.64 (3H, d, J = 0.8 Hz), 1.81 (3H, d, J = 1.0 Hz), 3.37 (1H, s), 5.26-5.27 (1H, br m), 7.03 (1H, dd, J = 11.4, 8.8 Hz), 7.64 (1H, dd, J = 7.0, 2.8 Hz), 7.91 (1H, ddd, J = 8.8, 4.1, 2.8 Hz), 7.94-7.98 (1H, m), 8.24 (1H, dd, J = 8.1, 0.8 Hz), 9.90 (1H, s). | 365 | 1.44 | A |
| I-15 | 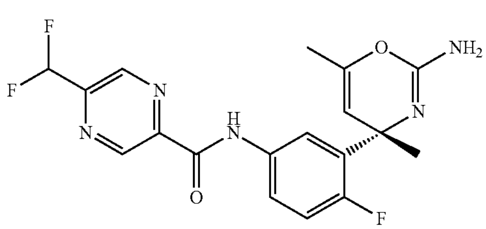 [SMILES: CC1=C[C@@](C)(c2cc(NC(=O)c3cnc(C(F)F)cn3)ccc2F)N=C(N)O1] | 1H-NMR (CDCl3) δ: 1.63 (3H, s), 1.81 (3H, s), 5.28 (1H, br s), 6.78 (1H, t, J = 54.4 Hz), 7.01-7.10 (1H, m), 7.64-7.67 (1H, m), 7.90 (1H, dt, J = 8.6, 3.5 Hz), 8.89 (1H, s), 9.50 (1H, s), 9.62 (1H, s). | | | |

TABLE 1-3-continued

| No. | Structure | NMR(solvent: shift value ascending order) | MS [M + 1] | LC/MS RT | LC/MS Method |
|---|---|---|---|---|---|
| I-16 | 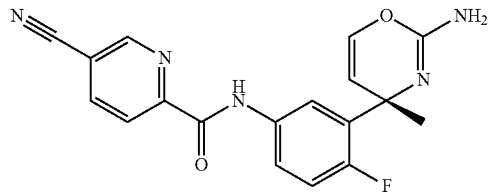 [SMILES: C[C@@]1(c2cc(NC(=O)c3ccc(C#N)cn3)ccc2F)C=COC(N)=N1] | 1H-NMR (CDCl3) δ: 1.56 (3H, brs), 4.11 (2H, br), 5.56 (1H, dd, J = 6.1, 2.5 Hz), 6.37 (1H, d, J = 6.1 Hz), 7.06 (1H, dd, J = 11.2, 8.6 Hz), 7.67 (1H, dd, J = 4.1, 3.0 Hz), 7.91-7.95 (1H, m), 8.20 (1H, dd, J = 8.1, 2.0 Hz), 8.43 (1H, d, J = 8.1 Hz), 8.89 (1H, d, J = 2.0 Hz), 9.85 (1H, s). | 352 | 1.04 | B |
| I-17 | 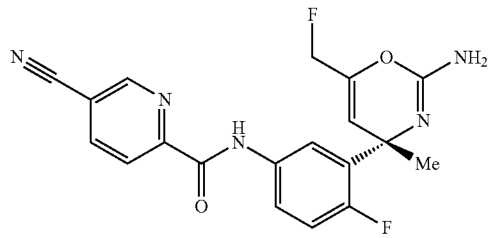 [SMILES: C[C@@]1(c2cc(NC(=O)c3ccc(C#N)cn3)ccc2F)C=C(CF)OC(N)=N1] | 1H-NMR (CDCl3) δ: 1.66 (3H, s), 4.26 (2H, br s), 4.74 (2H, d, J = 47.7 Hz), 5.74 (1H, dd, J = 5.1, 2.5 Hz), 7.06 (1H, dd, J = 11.2, 9.1 Hz), 7.69 (1H, dd, J = 6.8, 2.8 Hz), 7.89-7.93 (1H, m), 8.20 (1H, dd, J = 8.1, 2.0 Hz), 8.42 (1H, d, J = 8.1 Hz), 8.89 (1H, d, J = 2.0 Hz), 9.84 (1H, s) | | | |
| I-18 | 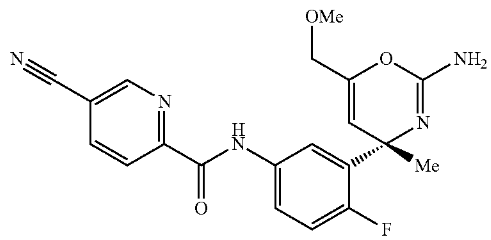 [SMILES: COCC1=C[C@@](C)(c2cc(NC(=O)c3ccc(C#N)cn3)ccc2F)N=C(N)O1] | 1H-NMR (CDCl3) δ: 1.65 (3H, s), 3.35 (3H, s), 3.87 (2H, s), 4.24 (2H, br s), 5.59 (1H, d, J = 2.5 Hz), 7.05 (1H, dd, J = 11.4, 8.9 Hz), 7.67 (1H, dd, J = 6.8, 2.8 Hz), 7.90-7.94 (1H, m), 8.20 (1H, dd, J = 8.1, 2.0 Hz), 8.42 (1H, d, J = 8.1 Hz), 8.89 (1H, d, J = 2.0 Hz), 9.84 (1H, s). | 396 | 1.26 | A |

TABLE 1-4

| No. | Structure | | NMR(solvent: shift value ascending order) | MS [M + 1] | LC/MS RT | LC/MS method |
|---|---|---|---|---|---|---|
| I-19 | 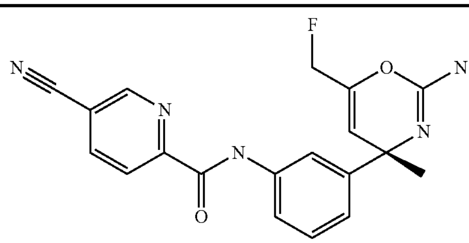 | Chiral | 1H-NMR (CDCl3) d: 1.69 (3H, s), 4.81 (2H, d, J = 47.4 Hz), 5.49 (1H, d, J = 4.2 Hz), 7.27 (1H, m), 7.43 (1H, t, J = 7.8 Hz), 7.78-7.90 (2H, m), 8.24 (1H, dd, J = 8.1, 1.8 Hz), 8.48 (1H, dd, J = 8.1, 0.9 Hz), 8.94 (1H, m), 9.91 (1H, m). | 366 | 1.04 | B |
| I-21 | 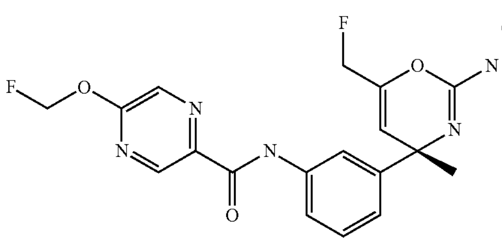 | Chiral | 1H-NMR (CDCl3) d: 1.64 (3H, s), 4.81 (2H, d, J = 47.4 Hz), 5.45 (1H, d, J = 4.2 Hz), 6.15 (2H, d, J = 51 Hz), 7.22 (1H, d; J = 8.1 Hz), 7.37 (1H, d, J = 8.1 Hz), 7.72 (2H, m), 8.29 (1H, s), 9.09 (1H, s), 9.51 (1H, s). | 390 | 1.08 | B |
| I-22 | 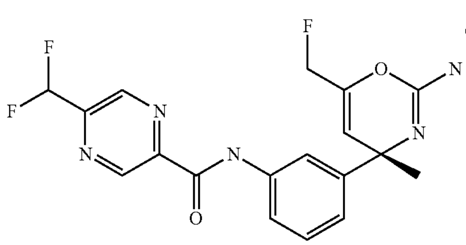 | Chiral | 1H-NMR (CDCl3) d: 1.65 (3H, s), 4.82 (2H, d, J = 47.4 Hz), 5.47 (1H, d, J = 4.2 Hz), 6.79 (1H, t, J = 54.6 Hz), 7.24 (1H, m), 7.39 (1H, d, J = 8.1 Hz), 7.74 (2H, m), 8.92 (1H, s), 9.53 (1H, s), 9.66 (1H, s). | 392 | 1.08 | B |

TABLE 1-4-continued

| No. | Structure | NMR(solvent: shift value ascending order) | MS [M + 1] | LC/MS RT | LC/MS method |
|---|---|---|---|---|---|
| I-23 | Chiral | 1H-NMR (CDCl3) d: 1.63 (3H, s), 4.75 (2H, d, J = 47.7 Hz), 5.43 (1H, d, J = 4.8 Hz), 6.70 (1H, t, J = 52.2 Hz), 7.21 (1H, d, J = 8.1 Hz), 7.64 (2H, m), 8.39 (1H, s), 8.63 (1H, s). | 381 | 1.01 | B |
| I-24 | Chiral | 1H-NMR (CDCl3) d: 1.63 (3H, s), 3.94 (3H, s), 4.75 (2H, d, J = 47.7 Hz), 5.44 (1H, d, J = 4.8 Hz), 7.14 (1H, d, J = 8.1 Hz), 7.46 (1H, s), 7.60 (1H, s), 7.68 (1H, d, J = 8.1 Hz), 9.54 (1H, s).. | 387 | 1.16 | B |

TABLE 1-5

| No. | Structure | NMR(solvent: shift value ascending order) | MS [M + 1] | LC/MS RT | LC/MS method |
|---|---|---|---|---|---|
| I-25 | Chiral | 1H-NMR (CDCl3) d: 1.63 (3H, s), 2.57 (3H, s), 4.65 (2H, td, J = 13.2, 3.9 Hz), 4.75 (2H, d, J = 47.7 Hz), 5.46 (1H, d, J = 4.8 Hz), 6.17 (1H, tt, J = 55.2, 4.2 Hz), 7.20 (1H, d, J = 8.1 Hz), 7.35 (1H, t, J = 8.1Hz), 7.70 (1H, d, J = 8.1Hz), 7.75 (1H, s), 8.84 (1H, s), 9.57 (1H, s). | 436 | 1.34 | B |
| I-26 | Chiral | 1H-NMR (CDCl3) d: 1.63 (3H, s), 2.81 (3H, s), 4.29 (2H, td, J = 12.9, 3.9 Hz), 4.75 (2H, d, J = 47.4 Hz), 5.46 (1H, d, J = 4.8 Hz), 6.13 (1H, tt, J = 55.2, 4.2 Hz), 7.10 (1H, d, J = 2.7 Hz), 7.16 (1H, d, J = 8.1 Hz), 7.34 (1H, t, J = 8.1 Hz), 7.63, (1H, d, J = 8.1 Hz), 8.15 (1H, s), 10.0 (1H, s). | 435 | 1.27 | B |
| I-27 | Chiral | 1H-NMR (CDCl3) d: 1.65 (3H, s), 4.77 (2H, d, J = 47.7 Hz), 5.47 (1H, d, J = 4.5 Hz), 7.24 (1H, d, J = 8.1 Hz), 7.38 (1H, t, J = 8.1 Hz), 7.68 (1H, m), 7.72 (1H, d, J = 8.1 Hz), 8.03 (1H, t, J = 54.9 Hz), 8.54 (1H, s), 8.96 (1H, s), 10.00 (1H, s). | 416 | 1.18 | B |
| I-28 | Chiral | 1H-NMR (CDCl3) d: 1.72 (3H, s), 2.86 (3H, s), 4.80 (2H, d, J = 47.7 Hz), 5.47 (1H, d, J = 4.5 Hz), 7.18 (1H, d, J = 8.1 Hz), 7.38 (1H, t, J = 8.1 Hz), 7.69 (1H, m), 7.73 (1H, d, J = 8.1 Hz), 7.93 (1H, s), 8.72 (1H, s), 10.06 (1H, s). | 380 | 1.1 | B |

TABLE 1-5-continued

| No. | Structure | NMR(solvent: shift value ascending order) | MS [M + 1] | LC/MS RT | LC/MS method |
|---|---|---|---|---|---|
| I-29 | 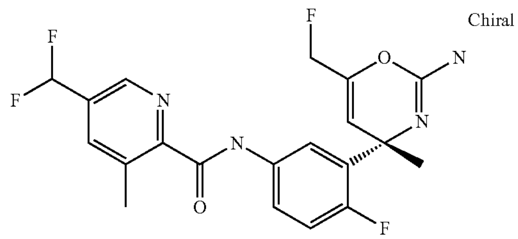 [SMILES: Cc1cc(C(F)F)cnc1C(=O)Nc1ccc(F)c([C@]2(C)C=C(CF)OC(N)=N2)c1] | 1H-NMR (CDCl3) δ: 1.66 (3H, s), 2.80 (3H, s), 4.72 (2H, d, J = 47.7 Hz), 5.75-5.77 (1H, m), 6.72 (1H, t, J = 55.5 Hz), 7.00 (1H, dd, J = 8.7, 11.1 Hz), 7.67-7.73 (2H, m), 7.79-7.84 (1H, m), 8.45 (1H, s). | 423 | 1.25 | B |

TABLE 1-6

| No. | Structure | NMR(solvent: shift value ascending order) | MS [M + 1] | LC/MS RT | LC/MS method |
|---|---|---|---|---|---|
| I-30 | 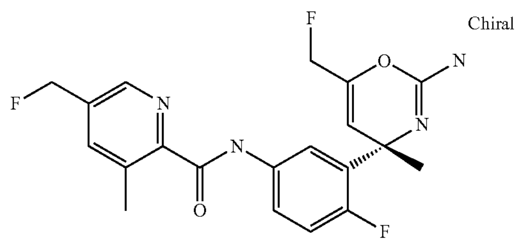 [SMILES: Cc1cc(CF)cnc1C(=O)Nc1ccc(F)c([C@]2(C)C=C(CF)OC(N)=N2)c1] | 1H-NMR (CDCl3) δ: 1.66 (3H, s), 2.80 (3H, s), 4.40 (2H, brs), 4.73 (2H, d, J = 47.7 Hz), 5.46 (2H, d, J = 46.8 Hz), 5.74 (1H, dd, J = 2.4, 4.8 Hz), 7.02 (1H, dd, 9.0, 11.4 Hz), 7.62-7.65 (2H, m), 7.89 (1H, ddd, J = 1.5, 2.7, 8.7 Hz), 8.40 (1H, s), 10.16 (1H, s). | 405 | 1.17 | B |
| I-31 | 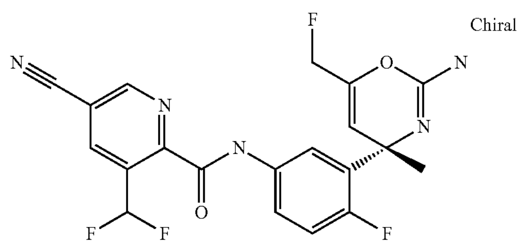 [SMILES: C[C@@]1(c2cc(NC(=O)c3ncc(C#N)cc3C(F)F)ccc2F)C=C(CF)OC(N)=N1] | 1H-NMR (CDCl3) δ: 1.52 (3H, s), 4.83 (2H, d, J = 47.7 Hz), 5.71 (1H, dd, J = 2.1, 5.1 Hz), 5.94 (2H, s), 7.15 (1H, dd, J = 9.0, 11.7 Hz), 7.70 (1H, t, J = 54.6 Hz), 7.72 (1H, dd, J = 3.3, 5.7 Hz), 7.89 (1H, 2.7, 6.6 Hz), 8.85 (1H, s), 9.31 (1H, d, J = 0.9 Hz), 10.95 (1H, s). | 434 | 1.17 | B |
| I-32 | 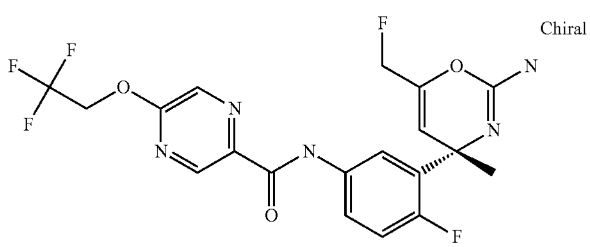 [SMILES: C[C@@]1(c2cc(NC(=O)c3cnc(OCC(F)(F)F)cn3)ccc2F)C=C(CF)OC(N)=N1] | 1H-NMR (CDCl3) δ: 1.66 (3H, s), 473 (2H, d, J = 47.6 Hz), 4.86 (2H, q, J = 8.3 Hz), 5.73 (1H, dd, J = 4.7, 2.4 Hz), 7.04 (1H, dd, J = 11.4, 8.8 Hz), 7.65 (1H, dd, J = 6.9, 2.7 Hz), 7.87 (1H, ddd, J = 8.7, 4.1, 2.9 Hz), 8.29 (1H, d, J = 1.4 Hz), 9.00 (1H, d, J = 1.4 Hz), 9.47 (1H, s). | 459 | 1.27 | B |
| I-33 | 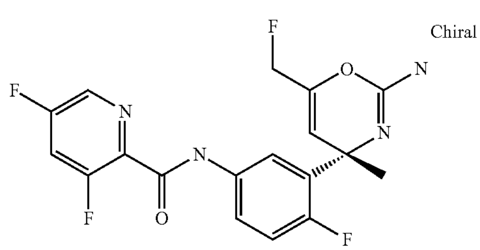 [SMILES: C[C@@]1(c2cc(NC(=O)c3ncc(F)cc3F)ccc2F)C=C(CF)OC(N)=N1] | 1H-NMR (CDCl3) δ: 1.65 (3H, s), 4.73 (2H, d, J = 47.7 Hz), 5.72 (1H, dd, J = 4.9, 2.3 Hz), 7.03 (1H, dd, J = 11.4, 8.8 Hz), 7.34-7.41 (1H, m), 7.60 (1H, dd, J = 6.9, 2.7 Hz), 7.91 (1H, ddd, J = 8.8, 4.2, 2.9 Hz), 8.33 (1H, d, J = 2.1 Hz), 9.58 (1H, s). | 395 | 1 | B |

TABLE 1-6-continued

| No. | Structure | NMR(solvent: shift value ascending order) | MS [M + 1] | LC/MS RT | LC/MS method |
|---|---|---|---|---|---|
| I-34 | Chiral | 1H-NMR (CDCl3) δ: 1.65 (3H, s), 4.73 (2H, d, J = 47.6 Hz), 5.73 (1H, dd, J = 4.9, 2.3 Hz), 7.03 (1H, dd, J = 11.3, 8.8 Hz), 7.56 (1H, dd, J = 6.9, 2.8 Hz), 7.88 (1H, d, J = 2.1 Hz), 7.94 (1H, ddd, J = 8.7, 4.0, 3.0 Hz), 8.44 (1H, d, J= 1.8 Hz), 9.70 (1H, s). | 427 | 1.19 | B |

TABLE 1-7

| No. | Structure | NMR(solvent: shift value ascending order) | MS [M + 1] | LC/MS RT | LC/MS method |
|---|---|---|---|---|---|
| I-35 | Chiral | 1H-NMR (CDCl3) δ; 1.66 (3H, s), 4.73 (2H, d, J = 47.6 Hz), 5.72 (1H, dd, J = 4.4, 2.6 Hz), 7.03 (1H,dd, J= 11.3, 8.8 Hz), 7.05 (1H, d, J = 2.7 Hz), 7.20 (1H, t, J = 60 Hz), 7.60 (1H, dd, J = 6.6, 2.7 Hz), 7.80 (1H, ddd, J = 8.7, 4.0, 2.9 Hz), 7.86 (1H, d, J = 2.7 Hz), 8.62 (1H, s). | 398 | 1 | B |
| I-36 | Chiral | 1H-NMR (CDCl3) δ: 1.66 (3H, s), 4.73 (2H, d, J = 47.6 Hz), 5.73 (1H, dd, J = 4.4, 2.4 Hz), 7.05 (1H, dd, J = 11.1, 8.8 Hz), 7.62 (1H, dd, J = 6.6, 2.8 Hz), 7.90 (1H, ddd, J = 9.2, 4.7, 2.2 Hz), 8.69 (1H, d, J = 1.5 Hz), 9.63 (1H, s). | 402 | 0.99 | B |
| I-37 | Chiral | 1H-NMR (CDCl3) δ: 1.65 (3H, s), 4.73 (2H, d, J = 47.7 Hz), 5.74 (1H, dd, J = 4.7, 2.5 Hz), 7.03 (1H, dd, J = 11.4, 8.9 Hz), 7.51 (1H, dd, J = 6.7, 2.7 Hz), 7.99 (1H, ddd, J = 8.7, 4.2, 2.2 Hz), 8.19 (1H, d, J = 2.3 Hz), 8.69 (1H, d, J = 2.1 Hz), 9.64 (1H, s). | 461 | 1.27 | B |
| I-38 | Chiral | 1H-NMR (CDCl3) δ: 1.72 (3H, s), 4.75 (2H, d, J = 47.4 Hz), 5.41 (2H, d, J = 47.0 Hz), 5.75 (1H, dd, J = 4.5, 2.4 Hz), 7.03 (1H, dd, J = 11.4, 8.8 Hz), 7.63 (1H, dd, J = 7.0, 2.6 Hz), 7.78 (1H, ddd, J = 8.8, 4.1, 2.9 Hz), 8.31 (1H, d, J= 1.4 Hz), 8.69 (1H, s). | 381 | 0.92 | B |

TABLE 1-7-continued

| No. | Structure | NMR(solvent: shift value ascending order) | MS [M + 1] | LC/MS RT | LC/MS method |
|---|---|---|---|---|---|
| I-39 | 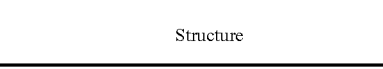 Chiral | 1H-NMR (CDCl3) δ: 1.67 (3H, s), 3.94 (3H, s), 4.74 (2H, d, J = 48.1 Hz), 5.73 (1H, dd, J = 4.7, 2.7 Hz), 7.02 (1H, dd, J = 11.4, 8.7 Hz), 7.46 (1H, s), 7.57 (1H, dd, J = 6.9, 3.0 Hz), 7.80 (1H, ddd, J = 9.1, 4.5, 3.2 Hz), 9.51 (1H, s). | 406 | 1.15 | B |

TABLE 1-8

| No. | Structure | NMR(solvent: shift value ascending order) | MS [M + 1] | LC/MS RT | LC/MS method |
|---|---|---|---|---|---|
| I-40 | Chiral | 1H-NMR (CDCl3) δ: 1.66 (3H, s), 4.73 (2H, d, J = 47.6 Hz), 5.72 (1H, dd, J = 4.7, 2.2 Hz), 7.03 (1H, dd, J = 11.4, 8.9 Hz), 7.61 (1H, dd, J = 6.9, 2.7 Hz), 7.63 (1H, 10.1, 1.8 Hz), 7.90 (1H, ddd, J = 8.7, 4.0, 3.0 Hz), 9.62 (1H, s). | 411 | 1.12 | B |
| I-41 | Chiral | 1H-NMR (CDCl3) δ: 1.66 (3H, s), 4.73 (2H, d, J = 47.6 Hz), 5.74 (1H, dd, J = 4.7, 2.6 Hz), 7.06 (1H, dd, J = 11.3, 8.8 Hz), 7.70 (1H, dd, J = 6.9, 2.9 Hz), 7.88 (1H, ddd, J = 8.8, 4.0, 2.9 Hz), 8.93 (1H, d, J = 1.2 Hz), 9.58 (2H, s). | 428 | 1.2 | B |
| I-42 | Chiral | 1H-NMR (CDCl3) δ: 1.67 (3H, s), 4.74 (2H, d, J = 47.6 Hz), 5.74 (1H, dd, J = 4.7, 2.6 Hz), 5.80 (2H, d, J = 53.4 Hz), 7.04 (1H, dd, J = 11.4, 8.8 Hz), 7.56 (1H, dd, J = 8.6, 2.8 Hz), 7.66 (1H, dd, J = 6.9, 2.8 Hz), 7.90 (1H, ddd, J = 8.8, 4.2, 2.8 Hz), 8.28 (1H, d, J = 8.7 Hz), 8.40 (1H, d, J = 2.7 Hz), 9.58 (1H, s). | 407 | 1.13 | B |
| I-43 | Chiral | 1H-NMR (CDCl3) δ: 1.66 (3H, s), 3.38 (1H, s), 4.75 (2H, d, J = 47.6 Hz), 5.75 (1H, dd, J = 4.5, 2.3 Hz), 7.06 (1H, dd, J = 11.3, 8.8 Hz), 7.69 (1H, dd, J = 6.9, 2.6 Hz), 7.92 (1H, ddd, J = 8.8, 4.0, 2.9 Hz), 7.98 (1H, dd, J = 8.1, 1.9 Hz), 8.24 (1H, d, J = 8.0 Hz), 8.68 (1H, d, J = 1.3 Hz), 9.58 (1H, s). | 383 | 1.16 | B |

TABLE 1-8-continued

| No. | Structure | NMR(solvent: shift value ascending order) | MS [M + 1] | LC/MS RT | LC/MS method |
|---|---|---|---|---|---|
| I-44 | Chiral | 1H-NMR (CDCl3) δ: 1.17-1.20 (4H, m), 1.66 (3H, s), 2.13-2.21 (1H, m), 4.73 (2H, d, J = 47.7 Hz), 5.73 (1H, dd, J = 4.7, 2.5 Hz), 7.04 (1H, dd, J = 11.4, 8.9 Hz), 7.65 (1H, dd, J = 7.0, 2.8 Hz), 7.89 (1H, ddd, J = 8.7, 4.2, 2.9 Hz), 8.43 (1H, d, J = 1.3 Hz), 9.25 (1H, d, J = 1.3 Hz), 9.60 (1H, s). | 400 | 1.2 | B |

TABLE 1-9

| No. | Structure | NMR(solvent: shift value ascending order) | MS [M + 1] | LC/MS RT | LC/MS method |
|---|---|---|---|---|---|
| I-45 | Chiral | 1H-NMR (CDCl3) δ: 1.79 (3H, s), 4.75 (2H, d, J = 47.7 Hz), 5.94 (1H, d, J = 4.7 Hz), 6.15 (2H, d, J = 51.1 Hz), 7.37 (1H, d, J = 9.6 Hz), 7.82-7.85 (2H, m), 8.28 (1H, s), 9.07 (1H, s), 9.52 (1H, s). | 424 | 1.19 | B |
| I-46 | Chiral | 1H-NMR (CDCl3) δ: 1.78 (3H, s), 4.75 (2H, d, J = 47.7 Hz), 5.96 (1H, d, J = 4.7 Hz), 6.78 (1H, t, J = 54.4 Hz), 7.38 (1H, d, J = 8.3 Hz), 7.83-7.90 (2H, m), 8.90 (1H, s), 9.51 (1H, s), 9.65 (1H, s). | 426 | 1.17 | B |
| I-47 | Chiral | 1H-NMR (CDCl3) δ: 1.78 (3H, s), 2.58 (3H, s), 4.65 (3H, td, J = 13.3, 4.1 Hz), 4.75 (2H, d, J = 47.5 Hz), 5.96 (1H, d, J = 4.9 Hz), 6.17 (1H, tt, J = 59.1, 3.9 Hz), 7.36 (1H, d, J = 9.0 Hz), 7.86-7.89 (2H, m), 8.83 (1H, s), 9.57 (1H, s). | 470 | 1.39 | B |
| I-48 | Chiral | 1H-NMR (CDCl3) δ: 1.76 (3H, s), 2.58 (3H, s), 4.52 (3H, td, J = 13.8, 4.1 Hz), 4.74 (2H, d, J = 47.7 Hz), 5.93 (1H, d, J = 4.7 Hz), 6.11 (1H, tt, J = 54.8, 4.2 Hz), 7.33 (1H, d, J = 8.9 Hz), 7.53 (1H, s), 7.75-7.78 (2H, m), 9.54 (1H, s). | 471 | 1.4 | B |

TABLE 1-9-continued

| No. | Structure | NMR(solvent: shift value ascending order) | MS [M + 1] | LC/MS RT | LC/MS method |
|---|---|---|---|---|---|
| I-49 | 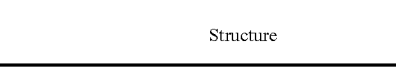 | 1H-NMR (CDCl3) δ: 1.76 (3H, s), 4.75 (2H, d, J = 47.8 Hz), 5.44 (2H, d, J = 47.2 Hz), 5.94 (1H, d, J = 5.2 Hz), 7.35 (1H, d, J = 8.2 Hz), 7.77-7.82 (2H, m), 8.34 (1H, s), 8.68 (1H, s). | 397 | 1.04 | B |

TABLE 1-10

| No. | Structure | NMR(solvent: shift value ascending order) | MS [M + 1] | LC/MS RT | LC/MS method |
|---|---|---|---|---|---|
| I-50 | 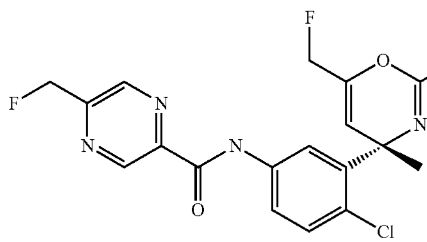 | 1H-NMR (CDCl3) δ: 1.79 (3H, s), 4.76 (2H, d, J = 47.8 Hz), 5.66 (2H, d, J = 46.4 Hz), 5.96 (1H, d, J = 4.9 Hz), 7.37 (1H, d, J = 8.2 Hz), 7.85-7.90 (2H, m), 8.74 (1H, s), 9.43 (1H, s), 9.68 (1H, s). | 408 | 1.09 | B |
| I-51 | 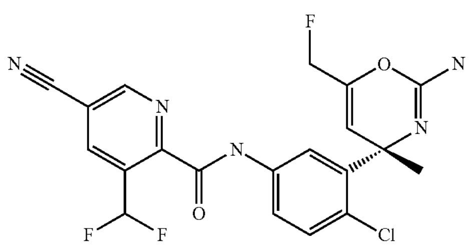 | 1H-NMR (CDCl3) δ: 1.77 (3H, s), 4.75 (2H, d, J = 47.5 Hz), 5.98 (1H, d, J = 4.9 Hz), 7.38 (1H, d, J = 8.2 Hz), 7.83-7.88 (2H, m), 8.01 (1H, t, J = 54.9 Hz), 8.55 (1H, s), 8.96 (1H, s), 10.00 (1H, s). | 450 | 1.33 | B |
| I-52 | 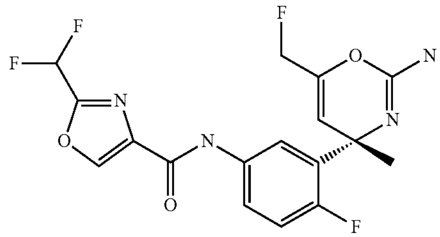 | 1H-NMR (CDCl3) δ: 1.65 (3H, s), 4.73 (2H, d, J = 47.6 Hz), 5.72 (1H, dd, J = 4.7, 2.7 Hz), 6.68 (1H, t, J = 52.4 Hz), 7.03 (1H, dd, J = 11.3, 8.7 Hz), 7.62 (1H, dd, J = 6.8, 2.8 Hz), 7.79 (1H, ddd, J = 8.8, 4.0, 3.2 Hz), 8.37 (1H, s), 8.61 (1H, s). | 399 | 1.02 | B |
| I-54 | 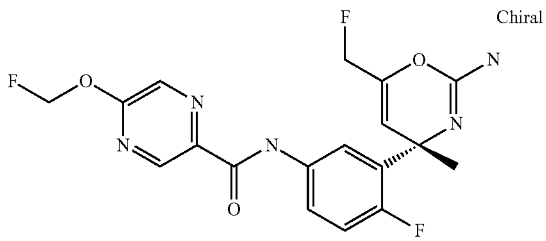 [SMILES: C[C@@]1(c2cc(NC(=O)c3cnc(OCF)cn3)ccc2F)C=C(CF)OC(N)=N1] | 1H-NMR (CDCl3) δ: 1.66 (3H, s), 4.74 (2H, d, J = 47.6 Hz), 5.74 (1H, dd, J = 4.7, 2.4 Hz), 6.15 (2H, d, J = 51.0 Hz), 7.05 (1H, dd, J = 11.4, 8.8 Hz), 7.76 (1H, dd, J = 6.9, 2.7 Hz), 7.88 (1H, ddd, J = 8.8, 4.2, 2.9 Hz), 8.26 (1H, d, J = 1.4 Hz), 9.06 (1H, d, J = 1.4 Hz), 9.48 (1H, s). | 408 | 1.06 | A |

TABLE 1-10-continued

| No. | Structure | NMR(solvent: shift value ascending order) | MS [M + 1] | LC/MS RT | LC/MS method |
|---|---|---|---|---|---|
| I-55 | Chiral | 1H-NMR (CDCl3) δ: 1.67 (3H, s), 4.74 (2H, d, J = 47.6 Hz), 5.74 (1H, dd, J = 4.7, 2.6 Hz), 6.79 (1H, t, J = 54.4 Hz), 7.06 (1H, dd, J = 11.3, 8.8 Hz), 7.69 (1H, dd, J = 6.8, 2.8 Hz), 7.89 (1H, ddd, J = 8.8, 4.2, 2.8 Hz), 8.90 (1H, s), 9.50 (1H, s), 9.62(1H, s). | 410 | 1.08 | B |

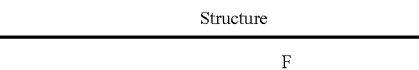

TABLE 1-11

| No. | Structure | NMR(solvent: shift value ascending order) | MS [M + 1] | LC/MS RT | LC/MS method |
|---|---|---|---|---|---|
| I-56 | Chiral | H-NMR (CDCl3) d: 1.66 (3H, s), 4.74 (2H, d, J = 47.7 Hz), 5.65 (2H, d, J = 46.2 Hz), 5.75 (1H, m), 7.04 (1H, dd, J = 11.4, 8.7 Hz), 7.75 (1H, dd, J = 6.9, 2.7 Hz), 7.85 (1H, m), 8.69 (1H, s), 9.40 (1H, s), 9.65 (1H, brs). | 392 | 1.01 | B |
| I-57 | Chiral | H-NMR (CDCl3) d: 1.65 (3H, s), 2.79 (3H, s), 4.29 (2H, td, J = 12.9, 3.9 Hz), 4.73 (2H, d, J = 47.7 Hz), 5.73 (1H, m), 6.13 (1H, tt, J = 54.6, 3.9 Hz), 7.01 (1H, dd, J = 11.4, 8.7 Hz), 7.10 (1H, m), 7.57 (1H, dd, J = 6.9, 2.7 Hz), 7.89 (1H, m), 8.13 (1H, m), 10.01 (1H, brs). | 453 | 1.32 | B |
| I-58 | Chiral | H-NMR (CDCl3) d: 1.65 (3H, s), 2.79 (3H, s), 4.47 (2H, q, J = 7.8 Hz), 4.73 (2H, d, J = 47.7 Hz), 5.74 (1H, m), 7.02 (1H, dd, J = 11.4, 9.0 Hz), 7.13 (1H, d, J = 2.7 Hz), 7.57 (1H, dd, J = 6.9, 2.7 Hz), 7.90 (1H, m), 8.14 (1H, m), 10.00 (1H, brs). | 471 | 1.46 | B |
| I-59 | Chiral | H-NMR (CDCl3) d: 1.66 (3H, s), 2.80 (3H, s), 4.73 (2H, d, J = 47.7 Hz), 5.74 (1H, m), 7.01 (1H, dd, J = 11.4, 9.0 Hz), 7.30 (1H, m), 7.58 (1H, dd, J = 6.9, 3.0 Hz), 7.90 (1H, ddd, J = 9.0, 4.2, 3.0 Hz), 8.22 (1H, m), 10.02 (1H, brs). | 421 | 1.2 | B |
| I-60 | Chiral | 1H-NMR (CDCl3) δ: 1.66 (3H, s), 2.77 (3H, s), 3.33 (1H, s), 4.73 (2H, d, J = 47.6 Hz), 5.73 (1H, dd, J = 4.9, 2.4 Hz), 7.02 (1H, dd, J = 11.4, 8.8 Hz), 7.59 (1H, dd, J = 7.0, 2.7 Hz), 7.71 (1H, dd, J = 1.1 Hz), 7.89 (1H, ddd, J = 8.8, 4.2, 2.8 Hz), 8.49 (1H, d, J = 1.8 Hz), 10.09 (1H, s). | 397 | 1.38 | A |

TABLE 1-12

| No. | Structure | NMR(solvent: shift value ascending order) | MS [M + 1] | LC/MS RT | LC/MS method |
|---|---|---|---|---|---|
| I-61 | 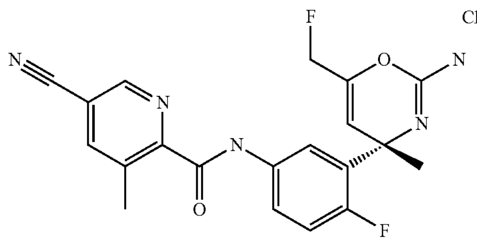 | 1H-NMR (CDCl3) δ: 1.65 (3H, s), 2.81 (3H, s), 4.73 (2H, d, J = 47.7 Hz), 5.75 (1H, dd, J = 4.8, 2.6 Hz), 7.03 (1H, dd, J = 11.3, 8.8 Hz), 7.66 (1H, dd, J = 6.9, 2.7 Hz), 7.84 (1H, ddd, J = 8.8, 4.1, 2.9 Hz), 7.90 (1H, br s), 8.61 (1H, d, J = 1.8 Hz), 9.97 (1H, s). | 398 | 1.19 | A |
| I-62 | 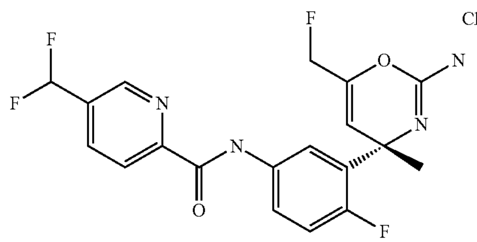 | 1H-NMR (CDCl3) δ: 1.69 (3H, s), 4.75 (2H, d, J = 47.5 Hz), 5.75 (1H, dd, J = 4.7, 2.4 Hz), 6.80 (1H, t, J = 55.5 Hz), 7.06 (1H, dd, J = 11.3, 8.8 Hz), 7.71 (1H, dd, J = 6.9, 2.7 Hz), 7.91 (1H, dt, J = 8.8, 3.4 Hz), 8.05 (1H, dd, J = 8.1, 1.2 Hz), 8.37 (1H, d, J = 8.1 Hz), 8.74 (1H, s), 9.95 (1H, s). | 409 | 1.27 | A |
| I-63 | 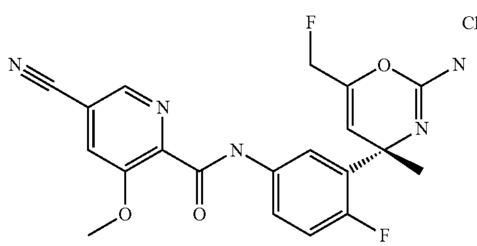 | 1H-NMR (CDCl3) δ: 1.80 (3H, s), 4.03 (4H, s), 4.79 (2H, d, J = 47.2 Hz), 5.79 (1H, dd, J = 4.3, 2.3 Hz), 7.07 (1H, dd, J = 11.4, 8.9 Hz), 7.61 (1H, dd, J = 7.0, 2.8 Hz), 7.64 (1H, d, J = 1.3 Hz), 7.92 (1H, ddd, J = 8.9, 4.2, 2.8 Hz), 8.47 (1H, d, J = 1.5 Hz), 9.69 (1H, s). | 414 | 1.08 | A |
| I-64 | 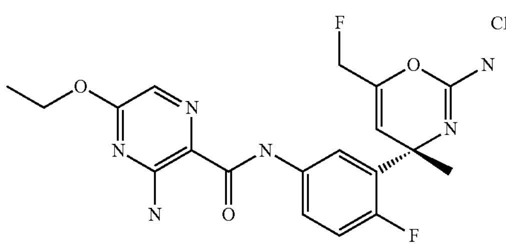 | 1H-NMR (CDCl3) δ: 1.40 (3H, t, J = 7.1 Hz), 1.66 (3H, s), 4.36 (2H, q, J = 7.1 Hz), 4.73 (2H, d, J = 47.7 Hz), 5.73 (1H, dd, J = 4.8, 2.4 Hz), 7.01 (1H, dd, J = 11.5, 8.8 Hz), 7.42 (1H, s), 7.58 (1H, dd, J = 7.1, 2.9 Hz), 7.78 (1H, ddd, J = 8.8, 4.2, 2.9 Hz), 9.50 (1H, s). | 419 | 1.4 | A |
| I-65 | 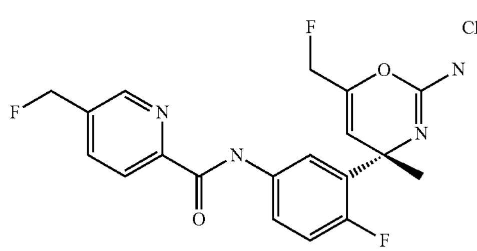 | 1H-NMR (CDCl3) δ: 1.70 (3H, s), 4.75 (2H, d, J = 47.5 Hz), 5.52 (2H, d, J = 47.2 Hz), 5.75 (1H, dd, J = 4.6, 2.4 Hz), 7.05 (1H, dd, J = 11.4, 8.9 Hz), 7.70 (1H, dd, J = 7.0, 2.8 Hz), 7.89-7.94 (2H, m), 8.31 (1H, d, J = 8.1 Hz), 8.61 (1H, s), 9.97 (1H, s). | 391 | 1.26 | A |

TABLE 1-13

| No. | Structure | NMR(solvent: shift value ascending order) | MS [M + 1] | LC/MS RT | LC/MS method |
|---|---|---|---|---|---|
| I-66 | 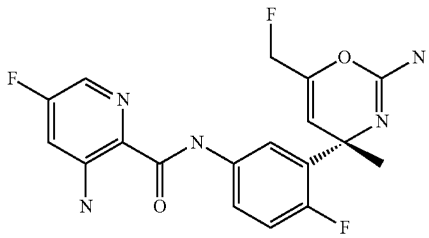 | 1H-NMR (CDCl3) δ: 1.67 (3H, s), 4.73 (2H, d, J = 47.5 Hz), 5.73 (1H, dd, J = 4.7, 2.4 Hz), 6.20 (2H, s), 6.71 (1H, dd, J = 10.1, 2.4 Hz), 7.02 (1H, dd, J = 11.3, 8.8 Hz), 7.61 (1H, dd, J = 7.0, 2.8 Hz), 7.75 (1H, d, J = 2.4 Hz), 7.79 (1H, ddd, J = 8.7, 4.2, 2.9 Hz), 9.81 (1H, s). | 392 | 1.27 | A |
| I-67 | 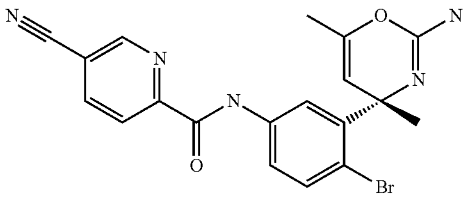 | | 426 | 1.19 | B |
| I-68 | 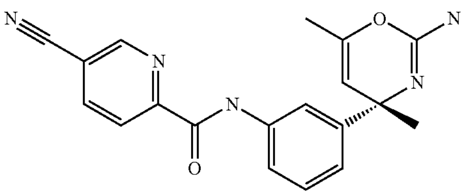 | | 348 | 1.11 | B |
| I-69 | 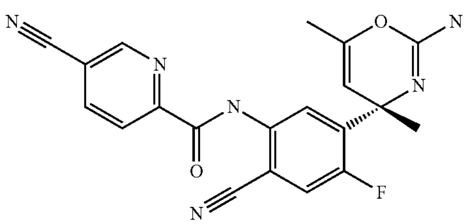 | | 391 | 1.16 | B |
| I-70 | 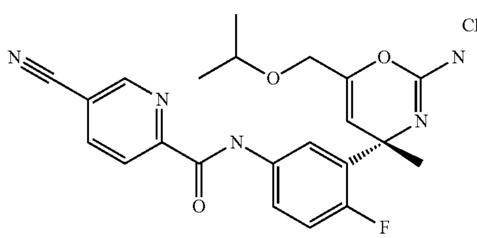 | 1H-NMR (CDCl3) δ: 1.16 (3H, d, J = 6.1 Hz), 1.17 (3H, d, J = 6.1 Hz), 1.64 (3H, s), 3.60-3.69 (1H, m), 3.91 (2H, s), 4.23 (2H, br s), 5.57 (1H, d, J = 2.5 Hz), 7.05 (1H, dd, J = 11.4, 8.9 Hz), 7.66 (1H, dd, J = 6.8, 2.8 Hz), 7.89-7.93 (1H, m), 8.19 (1H, dd, J = 8.1, 2.0 Hz), 8.42 (1H, d, J = 8.1 Hz), 8.88 (1H, d, J = 2.0 Hz), 9.83 (1H, s). | 424 | 1.36 | A |

TABLE 1-14

| No. | Structure | NMR(solvent: shift value ascending order) | MS [M + 1] | LC/MS RT | LC/MS method |
|---|---|---|---|---|---|
| I-71 | 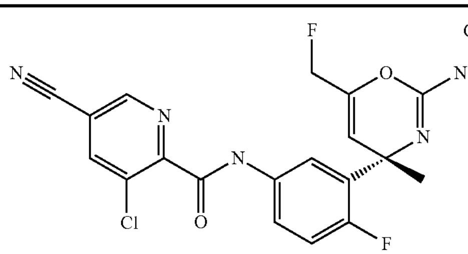 | 1H-NMR (CDCl3) δ: 1.65 (3H, s), 4.23 (2H, br s), 4.73 (2H, d, J = 47.7 Hz), 5.73 (1H, dd, J = 5.1, 2.5 Hz), 7.06 (1H, dd, J = 11.4, 8.9 Hz), 7.59 (1H, dd, J = 6.8, 2.8 Hz), 7.91-7.95 (1H, m), 8.16 (1H, d, J = 2.0 Hz), 8.76 (1H, d, J = 2.0 Hz), 9.67 (1H, s). | 418 | 1.16 | A |

TABLE 1-14-continued

| No. | Structure | NMR(solvent: shift value ascending order) | MS [M + 1] | LC/MS RT | LC/MS method |
|---|---|---|---|---|---|
| I-72 | 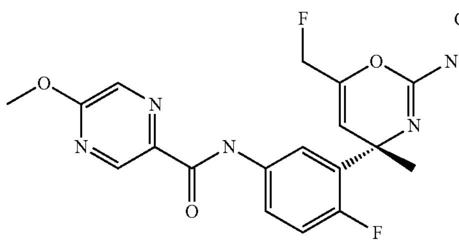 | 1H-NMR (CDCl3) δ: 1.65 (3H, s), 4.07 (3H, s), 4.25 (2H, br s), 4.73 (2H, d, J = 47.7 Hz), 5.73 (1H, dd, J = 4.8, 2.3 Hz), 7.04 (1H, dd, J = 11.4, 8.9 Hz), 7.65 (1H, dd, J = 6.8, 2.8 Hz), 7.86-7.90 (1H, m), 8.14 (1H, d, J = 1.0 Hz), 9.01 (1H, d, J = 1.0 Hz), 9.49 (1H, s). | 390 | 1.17 | A |
| I-73 | 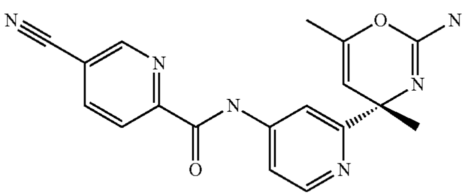 | 1H-NMR (CDCl3) δ: 1.61 (3H, s), 1.84 (3H, s), 5.28 (1H, s), 7.66 (1H, d, J = 1.9 Hz), 7.87 (1H, dd, J = 5.6, 1.8 Hz), 8.25 (1H, dd, = 8.1, 2.1 Hz), 8.46 (1H, d, J = 8.0 Hz), 8.58 (1H, d, J = 5.5 Hz), 8.94 (1H, s), 9.99 (1H, s). | 349 | 0.9 | B |
| I-74 | 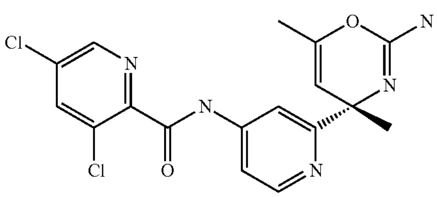 | 1H-NMR (CDCl3) δ: 1.58 (3H, s), 1.82 (3H, s), 5.26 (1H, s), 7.53 (1H, d, J = 2.1 Hz), 7.88 (1H, dd, J = 5.6, 1.9 Hz), 7.92 (1H, dd J = 2.0, 0.8 Hz), 8.50 (1H, dd, J = 2.0, 0.8 Hz), 8.51 (1H, d, J = 5.6 Hz), 9.90 (1H, s). | 392 | 1.08 | B |
| I-75 | 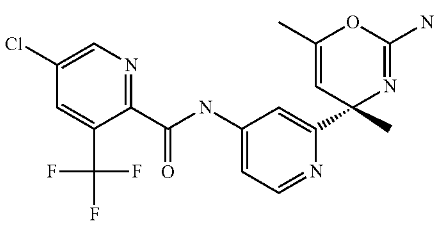 | 1H-NMR (CDCl3) δ: 1.86 (3H, s), 2.01 (3H, s), 5.62 (1H, s), 7.66 (1H, s), 8.14 (1H, t, J = 2.7 Hz), 8.23 (1H, d, J = 1.9 Hz), 8.55 (1H, d, J = 5.8 Hz), 8.81 (1H, d, J = 2.2 Hz), 10.30 (1H, s). | 426 | 1.18 | B |

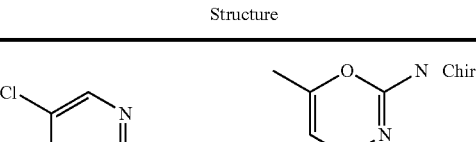

TABLE 1-15

| No. | Structure | NMR(solvent: shift value ascending order) | MS [M + 1] | LC/MS RT | LC/MS method |
|---|---|---|---|---|---|
| I-76 | 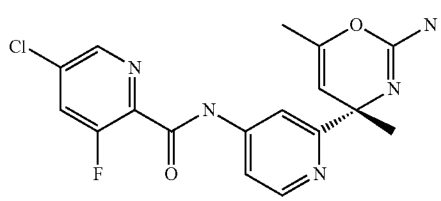 | 1H-NMR (CDCl3) δ: 1.60 (3H, s), 1.84 (3H, s), 4.17 (1H, s), 5.28 (1H, s), 7.60 (1H, d, J = 1.6 Hz), 7.70 (1H, dd, J = 10.2, 1.9 Hz), 7.87 (1H, dd, J = 5.5, 1.9 Hz), 8.45 (1H, d, J = 1.1 Hz), 8.55 (1H, d, J = 5.5 Hz), 9.81 (1H, s). | 376 | 1.17 | B |
| I-77 | 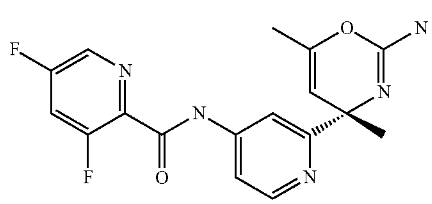 | 1H-NMR (CDCl3) δ: 1.60 (3H, s), 1.84 (3H, s), 5.28 (1H, s), 7.40-7.47 (1H, m), 7.60 (1H, d, J = 1.9 Hz), 7.87 (1H, dd, J = 5.5, 2.2 Hz), 8.39 (1H, d, J = 1.9 Hz), 8.55 (1H, d, J = 5.5 Hz), 9.78 (1H, s). | 360 | 0.94 | B |

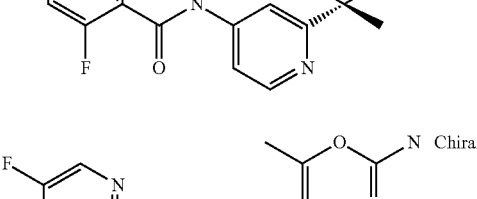

TABLE 1-15-continued

| No. | Structure | NMR(solvent: shift value ascending order) | MS [M + 1] | LC/MS RT | LC/MS method |
|---|---|---|---|---|---|
| I-78 | 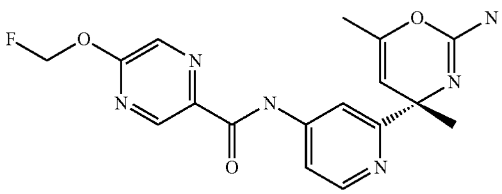 | 1H-NMR (CDCl3) δ: 1.59 (3H, s), 1.82 (3H, s), 5.26 (1H, s), 6.16 (2H, d, J = 51.0 Hz), 7.60 (1H, d, J = 2.3 Hz), 7.83 (1H, dd, J = 5.4, 2.3 Hz), 8.30 (1H, s), 8.54 (1H, d, J = 5.7 Hz), 9.09 (1H, s), 9.62 (1H, s) | 373 | 1.08 | B |
| I-79 | 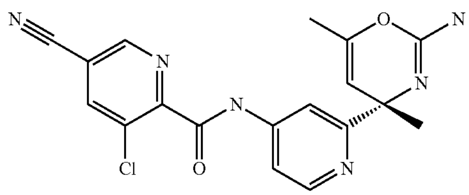 | 1H-NMR (CDCl3) δ: 1.85 (3H, s), 1.99 (3H, s), 5.57 (1H, s), 7.67 (1H, s), 8.09 (1H, d, J = 5.5 Hz), 8.18 (1H, s), 8.56 (1H, d, J = 5.5 Hz), 8.85 (1H, s), 10.43 (1H, s). | 383 | 0.96 | B |
| I-80 | 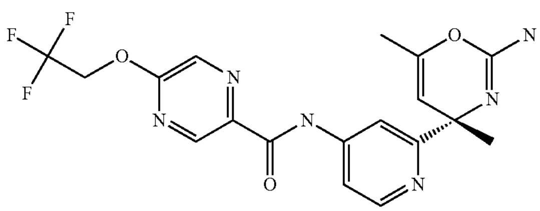 | 1H-NMR (CDCl3) δ: 1.40 (3H, s), 1.63 (3H, s), 4.69 (2H, q, J = 8.2 Hz), 5.07 (1H, s), 7.43 (1H, d, J = 1.9 Hz), 7.63 (1H, dd, J = 5.5, 2.2 Hz), 8.13 (1H, d, J = 1.2 Hz), 8.35 (1H, d, J = 5.5 Hz), 8.84 (1H, d, J = 1.2 Hz), 9.43 (1H, s). | 423 | 1.24 | B |

TABLE 1-16

| No. | Structure | NMR(solvent: shift value ascending order) | MS [M + 1] | LC/MS RT | LC/MS method |
|---|---|---|---|---|---|
| I-81 | 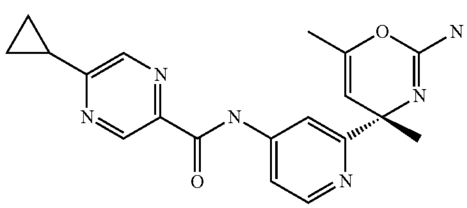 | 1H-NMR (CDCl3) δ: 1.14-1.24 (4H, m), 1.59 (3H, s), 1.82 (3H, s), 2.13-2.24 (1H, m), 5.25 (1H, s), 7.62 (1H, d, J = 2.1 Hz), 7.82 (1H, dd, J = 5.5, 2.1 Hz), 8.44 (1H, d, J = 1.1 Hz), 8.52 (1H, d, J = 5.5 Hz), 9.25 (1H, d, J = 1.2 Hz), 9.74 (1H, s). | 365 | 1.15 | B |
| I-82 | 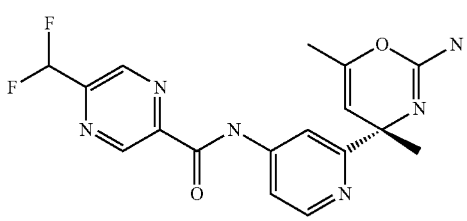 | 1H-NMR (CDCl3) δ: 1.59 (3H, s), 1.82 (3H, d, J = 1.1 Hz), 5.26 (1H, s), 6.80 (1H, t, J = 54.3 Hz), 7.65 (1H, d, J = 2.1 Hz), 7.83 (1H, dd, J = 5.6, 2.1 Hz), 8.56 (1H, d, J = 5.6 Hz), 8.93 (1H, s), 9.52 (1H, d, J = 0.8 Hz), 9.75 (1H, br s). | 375 | 1.01 | B |
| I-83 | 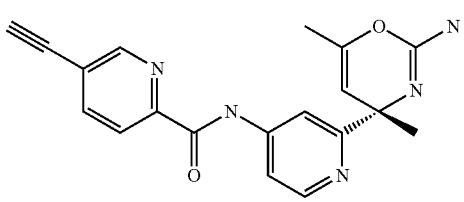 | 1H-NMR (CDCl3) δ: 1.59 (3H, s), 1.82 (3H, s), 3.40 (1H, s), 5.25 (1H, s), 7.61 (1H, d, J = 2.0 Hz), 7.86 (1H, dd, J = 5.5, 2.0 Hz), 7.98 (1H, dd, J = 8.1, 2.0 Hz), 8.25 (1H, d, J = 8.1 Hz), 8.53 (1H, d, J = 5.5 Hz), 8.69 (1H, d, J = 1.8 Hz), 10.04 (1H, s). | 348 | 1.06 | B |

TABLE 1-16-continued

| No. | Structure | NMR(solvent: shift value ascending order) | MS [M + 1] | LC/MS RT | LC/MS method |
|---|---|---|---|---|---|
| I-84 | Chiral | 1H-NMR (CDCl3) δ: 1.58 (3H, s), 1.82 (3H, s), 3.95 (3H, s), 5.25 (1H, s), 7.47 (1H, s), 7.51 (1H, d, J = 2.0 Hz), 7.78 (1H, dd, J = 5.6, 2.2 Hz), 8.48 (1H, d, J = 5.6 Hz), 9.67 (1H, s). | 370 | 1.02 | B |
| I-85 | Chiral | 1H-NMR (CDCl3) δ: 1.61 (3H, s), 1.84 (3H, s), 4.10 (3H, s), 5.28 (1H, s), 7.62 (1H, d, J = 1.7 Hz), 7.86 (1H, dd, J = 5.5, 2.0 Hz), 8.19 (1H, s), 8.55 (1H, d, J = 5.5 Hz), 9.05 (1H, s), 9.66 (1H, s). | 355 | 0.96 | B |

TABLE 1-17

| No. | Structure | NMR(solvent: shift value ascending order) | MS [M + 1] | LC/MS RT | LC/MS method |
|---|---|---|---|---|---|
| I-86 | Chiral | 1H-NMR (CDCl3) δ: 1.69 (3H, s), 4.69 (2H, td, J = 13.4, 3.4 Hz), 4.74 (2H, d, J = 47.7 Hz), 5.76 (1H, dd, J = 4.9, 2.3 Hz), 6.19 (1H, tt, J = 54.9, 4.3 Hz), 7.08 (1H, dd, J = 11.3, 8.8 Hz), 7.67 (1H, dd, J = 6.3, 3.2 Hz), 7.90-7.97 (1H, m), 8.29 (1H, s), 9.04 (1H, s), 9.51 (1H, s). | 440 | 1.2 | B |
| I-87 | Chiral | 1H-NMR (CDCl3) δ: 1.67 (3H, s), 4.55 (2H, td, J = 13.3, 4.2 Hz), 4.76 (2H, d, J = 47.8 Hz), 5.73-5.78 (1H, m), 6.13 (1H, tt, J = 55.3, 4.2 Hz), 7.04 (1H, dd, J = 11.3, 8.8 Hz), 7.53-7.65 (2H, m), 7.76-7.85 (1H, m), 9.52 (1H, s). | 455 | 1.32 | B |
| I-88 | Chiral | 1H-NMR (CDCl3) δ: 1.71 (3H, s), 2.14 (3H, t, J = 18.9 Hz), 4.78 (2H, d, J = 47.7 Hz), 5.78 (1H, dd, J = 4.9, 2.5 Hz), 7.11 (1H, dd, J = 11.2, 8.7 Hz), 7.73 (1H, dd, J = 6.9, 2.9 Hz), 7.95 (1H, ddd, J = 8.7, 4.2, 2.9 Hz), 8.96 (1H, d, J = 1.4 Hz), 9.53 (1H, s), 9.68 (1H, s). | | | |
| I-89 | Chiral | 1H-NMR (CDCl3) δ: 1.85 (3H, s), 4.30 (2H, br s), 4.47 (2H, ddd, J = 88.5, 47.6, 8.4 Hz), 5.22-5.23 (1H, m), 6.05-6.23 (2H, m), 7.05 (1H, dd, J = 11.1, 8.8 Hz), 7.70 (1H, dd, J = 6.4, 2.3 Hz), 7.92-7.97 (1H, m), 8.26-8.28 (1H, m), 9.06-9.07 (1H, m), 9.50 (1H, s). | 408 | 1.29 | A |

TABLE 1-17-continued

| No. | Structure | NMR(solvent: shift value ascending order) | MS [M + 1] | LC/MS RT | LC/MS method |
|---|---|---|---|---|---|
| I-90 | 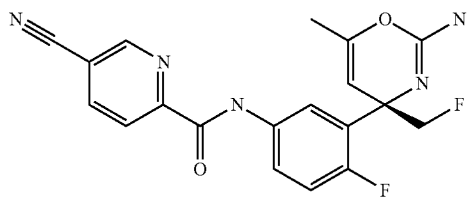 | Chiral 1H-NMR (CDCl3) δ: 1.86 (3H, s), 4.32 (2H, br s), 4.47 (2H, ddd, J = 85.8, 47.5, 8.7 Hz), 5.23 (1H, s), 7.07 (1H, dd, J = 11.1, 8.8 Hz), 7.70-7.74 (1H, m), 7.97-8.02 (1H, m), 8.17-8.20 (1H, m), 8.41 (1H, d, J = 8.1 Hz), 8.87-8.88 (1H, m), 9.85 (1H, s). | 384 | 1.16 | A |

TABLE 1-18

| No. | Structure | NMR(solvent: shift value ascending order) | MS [M + 1] | LC/MS RT | LC/MS method |
|---|---|---|---|---|---|
| I-91 | 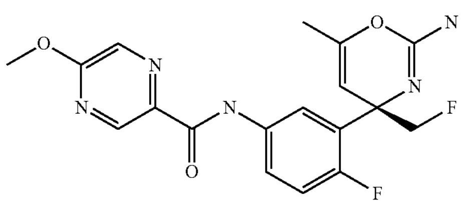 | Chiral 1H-NMR (CDCl3) δ: 1.85 (3H, s), 4.06 (3H, s), 4.32 (2H, br s), 4.47 (2H, ddd, J = 89.7, 47.4, 8.2 Hz), 5.22-5.23 (1H, m), 7.04 (1H, dd, J = 11.2, 8.8 Hz), 7.65-7.69 (1H, m), 7.97 (1H, ddd, J = 8.8, 4.2, 3.0 Hz), 8.12-8.15 (1H, m), 8.99-9.00 (1H, m), 9.50 (1H, s). | 390 | 1.2 | A |
| I-92 | 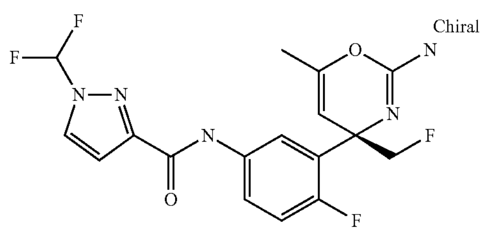 [SMILES: CC1=C[C@@](CF)(c2cc(NC(=O)c3ccn(C(F)F)n3)ccc2F)N=C(N)O1] | Chiral 1H-NMR (CDCl3) δ: 1.85 (3H, s), 4.33 (2H, br s), 4.46 (2H, ddd, J = 88.2, 47.7, 8.6 Hz), 5.22-5.23 (1H, m), 6.98-7.40 (3H, m), 7.61-7.66 (1H, m), 7.85-7.92 (2H, m), 8.64 (1H, s). | 398 | 1.15 | A |
| I-93 | 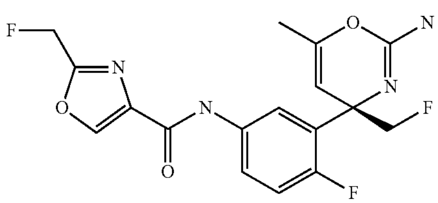 | Chiral 1H-NMR (CDCl3) δ: 1.85 (3H, s), 4.30 (2H, br s), 4.46 (2H, ddd, J = 88.1, 47.0, 8.5 Hz), 5.21-5.22 (1H, m), 5.34-5.51 (2H, m), 7.03 (1H, dd, J = 11.2, 8.8 Hz), 7.62-7.66 (1H, m), 7.89 (1H, ddd, J = 8.8, 4.2, 2.9 Hz), 8.31-8.32 (1H, m), 8.66 (1H, s). | 381 | 1.05 | A |
| I-94 | 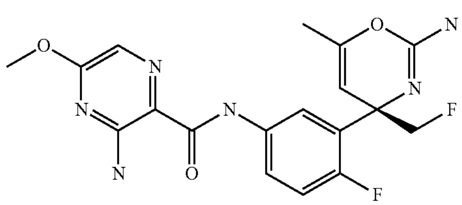 | Chiral 1H-NMR (CDCl3) δ: 1.85 (3H, s), 3.93 (3H, s), 4.30 (2H, br s), 4.46 (2H, ddd, J = 92.5, 47.7, 8.5 Hz), 5.22-5.23 (1H, m), 7.01 (1H, dd, J = 11.3, 8.8 Hz), 7.44-7.45 (1H, m), 7.60-7.64 (1H, m), 7.87 (1H, ddd, J= 8.8, 4.3, 2.4 Hz), 9.51 (1H, s). | 405 | 1.31 | A |
| I-95 | 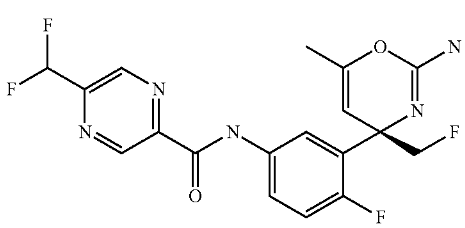 | Chiral 1H-NMR (CDCl3) δ: 1.86 (3H, s), 4.48 (2H, ddd, J = 84.2, 47.6, 8.5 Hz), 5.23-5.24 (1H, m), 6.78 (1H, t, J = 54.4 Hz), 7.07 (1H, dd, J = 11.2, 8.9 Hz), 7.72-7.76 (1H, m), 7.97 (1H, ddd, J = 8.9, 4.0, 3.0 Hz), 8.89-8.90 (1H, m), 9.50 (1H, s), 9.64 (1H, s). | 410 | 1.2 | A |

TABLE 1-18-continued

| No. | Structure | NMR(solvent: shift value ascending order) | MS [M + 1] | LC/MS RT | LC/MS method |
|---|---|---|---|---|---|
| I-96 | 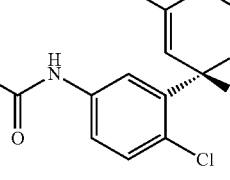 Chiral | 1H-NMR (CDCl3) δ: 1.85 (3H, s), 3.37 (1H, s), 4.22-4.72 (4H, m), 5.23 (1H, d, J = 1.5 Hz), 7.05 (1H, dd, J = 11.3, 8.8 Hz), 7.69-7.72 (1H, m), 7.94-8.03 (2H, m), 8.23 (1H, d, J = 8.1 Hz), 8.67 (1H, d, J = 1.8 Hz), 9.91 (1H, s). | 383 | 1.31 | A |

TABLE 1-19

| No. | Structure | NMR(solvent: shift value ascending order) | MS [M + 1] | LC/MS RT | LC/MS method |
|---|---|---|---|---|---|
| I-97 | 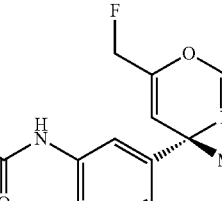 | 1H-NMR (DMSO-d6) δ: 1.62 (3H, s), 4.94 (2H, d, J = 47.6 Hz), 5.78 (1H, d, J = 5.4 Hz), 5.91 (1H, s), 7.39 (1H, d J = 8.7 Hz), 7.85 (1H, dd, J = 8.7, 2.6 Hz), 8.18 (1H, d, J = 2.6 Hz), 8.29 (1H, dd, J = 8.2, 0.8 Hz), 8.59 (1H, dd, J = 8.2, 2.1 Hz), 9.21 (1H, dd, J = 2.1, 0.8 Hz), 10.91 (1H, s). | 400 | 1.1 | B |
| I-98 | 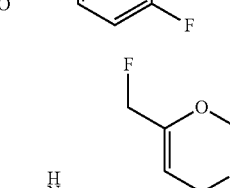 | 1H-NMR (CDCl3) δ: 1.66 (3H, s), 2.77 (3H, s), 4.73 (2H, d, J = 36 Hz), 5.75 (1H, t, J = 3 Hz), 7.02 (1H, dd, J = 3, 9 Hz), 7.60-7.61 (1H, m), 7.62 (1H, d, J = 3 Hz), 7.86-7.88 (1H, m), 8.34 (1H, d, J = 3 Hz), 10.0 (1H, s). | 407 | 1.49 | B |
| I-99 | 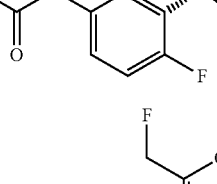 | 1H-NMR (CDCl3) δ: 1.95 (3H, s), 3.46 (1H, s), 4.86 (2H, m), 5.88 (1H, dd, J = 3.8, 2.0 Hz), 7.12 (1H, dd, J = 11.3, 8.8 Hz), 7.64 (1H, dd, J = 7.0, 2.5 Hz), 7.89 (1H, ddd, J = 8.8, 4.3, 2.5 Hz), 7.97 (1H, t, J = 55.0 Hz), 8.33 (1H, brs), 8.77 (1H, brs), 10.15 (1H, s). | 433 | 1.33 | B |
| I-100 | 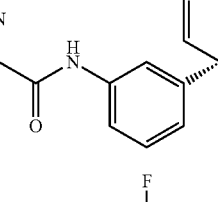 | | 403 | 1.14 | B |
| I-101 | 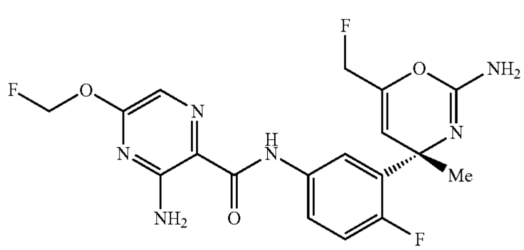 | 1H-NMR (CDCl3) δ: 4.73 (2H, d, J = 47.6 Hz), 5.74 (1H, m), 6.02 (2H, d, J = 51.6 Hz), 7.02 (1H, dd, J = 11.2, 8.8 Hz), 7.52 (1H, s), 7.63 (1H, m), 7.73 (1H, m), 9.50 (1H, s). | 423 | 1.16 | B |

TABLE 1-19-continued

| No. | Structure | NMR(solvent: shift value ascending order) | MS [M + 1] | LC/MS RT | LC/MS method |
| --- | --- | --- | --- | --- | --- |
| I-102 | 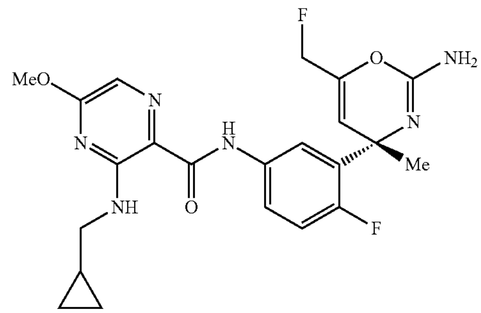 [SMILES: COc1cnc(C(=O)Nc2ccc(F)c([C@]3(C)C=C(CF)OC(N)=N3)c2)c(NCC2CC2)n1] | 1H-NMR (CDCl3) δ: 0.29 (2H, m), 0.56 (2H, m), 1.14 (1H, m), 3.36 (2H, dd, J = 6.8, 5.6 Hz), 3.96 (3H, s), 4.73 (2H, d, J = 47.6 Hz), 5.72 (1H, m), 7.01 (1H, dd, J = 11.2, 8.8 Hz), 7.33 (1H, s), 7.52 (1H, m), 7.82 (1H, m), 8.79 (1H, m), 9.54 (1H, s). | 459 | 1.62 | B |

TABLE 1-20

| No. | Structure | NMR(solvent: shift value ascending order) | MS [M + 1] | LC/MS RT | LC/MS method |
| --- | --- | --- | --- | --- | --- |
| I-103 | 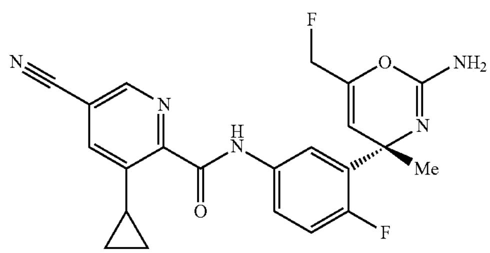 [SMILES: C[C@@]1(c2cc(NC(=O)c3ncc(C#N)cc3C3CC3)ccc2F)C=C(CF)OC(N)=N1] | 1H-NMR (CDCl3) d: 0.76 (2H, m), 1.20-1.22 (2H, m), 1.66 (3H, s), 3.45 (1H, m), 4.74 (2H, d, J = 36 Hz), 5.75 (1H, t, J = 3 Hz), 7.05 (1H, dd, J = 3, 9 Hz), 7.57 (1H, d, J = 3 Hz), 7.68 (1H, m), 7.89 (1H, m), 8.58 (1H, d, J = 3 Hz), 9.96 (1H, s). | 424 | 1.18 | B |
| I-104 | 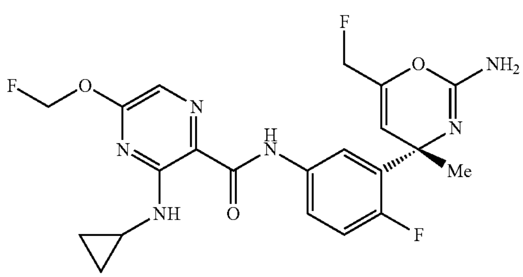 [SMILES: C[C@@]1(c2cc(NC(=O)c3ncc(OCF)nc3NC3CC3)ccc2F)C=C(CF)OC(N)=N1] | | | | |
| I-105 | 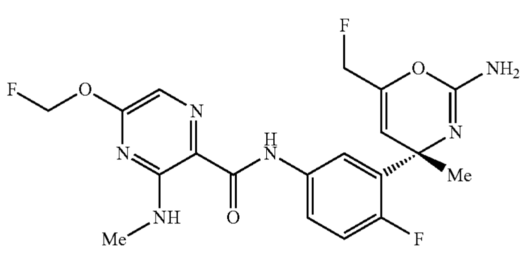 [SMILES: CNc1nc(OCF)cnc1C(=O)Nc1ccc(F)c([C@]2(C)C=C(CF)OC(N)=N2)c1] | | | | |
| I-106 | 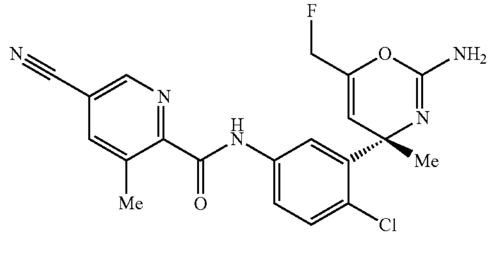 [SMILES: Cc1cc(C#N)cnc1C(=O)Nc1ccc(Cl)c([C@]2(C)C=C(CF)OC(N)=N2)c1] | 1H-NMR (CDCl3) δ: 1.77 (3H, s), 2.86 (3H, s), 4.75 (2H, d, J = 47.7 Hz), 5.96 (1H, d, J = 4.8 Hz), 7.35 (1H, d, J = 8.5 Hz), 7.80 (1H, d, J = 2.0 Hz), 7.87 (1H, dd, 8.7, 2.4 Hz), 7.94 (1H, s), 8.69 (1H, s), 10.04 (1H, s). | 414 | 1.17 | B |

TABLE 1-20-continued

| No. | Structure | NMR(solvent: shift value ascending order) | MS [M + 1] | LC/MS RT | LC/MS method |
|---|---|---|---|---|---|
| I-107 | 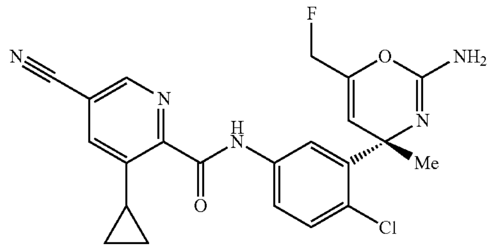 [SMILES: C[C@@]1(c2cc(NC(=O)c3ncc(C#N)cc3C3CC3)ccc2Cl)C=C(CF)OC(N)=N1] | 1H-NMR (CDCl3) δ: 0.76-0.79 (2H, m), 1.21-1.25 (2H, m), 1.77 (3H, s), 3.44-3.49 (1H, m), 4.75 (2H, d, J = 47.9 Hz), 5.97 (1H, d, J = 5.0 Hz), 7.36 (1H, d, J= 8.5 Hz), 7.59 (1H, d, J = 1.5 Hz), 7.82 (1H, d, J = 2.5 Hz), 7.89 (1H, dd, J = 8.7, 2.5 Hz), 8.60 (1H, d, J = 1.8 Hz), 10.01 (1H, s). | 440 | 1.2 | B |
| I-108 | 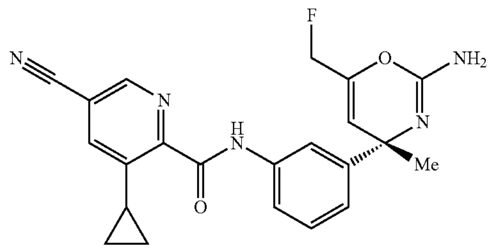 [SMILES: C[C@@]1(c2cccc(NC(=O)c3ncc(C#N)cc3C3CC3)c2)C=C(CF)OC(N)=N1] | 1H-NMR (CDCl3) δ: 0.78 (2H, m), 1.25 (2H, m), 1.64 (3H, s), 3.51 (1H, m), 4.76 (2H, d, J = 47.7 Hz), 5.46 (1H, d, J = 4.8 Hz), 7.22 (1H, m), 7.38 (1H, t, J = 7.9 Hz), 7.60 (1H, d, J = 1.8 Hz), 7.65 (1H, brt, J = 1.9 Hz), 7.77 (1H, m), 8.64 (1H, d, J = 1.8 Hz), 9.99 (1H, s). | 406 | 1.14 | B |

TABLE 1-21

| No. | Structure | NMR(solvent: shift value ascending order) | MS [M + 1] | LC/MS RT | LC/MS method |
|---|---|---|---|---|---|
| I-109 | 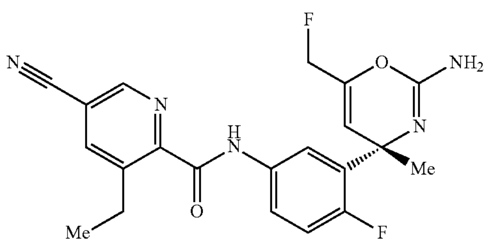 [SMILES: CCc1cc(C#N)cnc1C(=O)Nc1ccc(F)c([C@]2(C)C=C(CF)OC(N)=N2)c1] | 1H-NMR (CDCl3) δ: 1.33 (3H, t, J= 7.2 Hz), 3.32 (2H, q, J = 7.2 Hz), 4.74 (2H, d, J = 47.6 Hz), 5.74 (1H, m), 7.05 (1H, dd, J = 11.2, 8.8 Hz), 7.58 (1H, m), 7.92 (1H, m), 7.97 (1H, s), 8.70 (1H, s), 10.01 (1H, s). | 412 | 1.2 | B |
| I-110 | 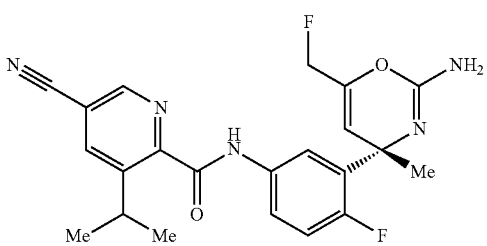 [SMILES: CC(C)c1cc(C#N)cnc1C(=O)Nc1ccc(F)c([C@]2(C)C=C(CF)OC(N)=N2)c1] | | | | |
| I-111 | 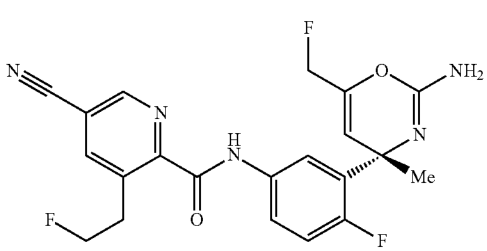 [SMILES: C[C@@]1(c2cc(NC(=O)c3ncc(C#N)cc3CCF)ccc2F)C=C(CF)OC(N)=N1] | | | | |

TABLE 1-21-continued

| No. | Structure | NMR(solvent: shift value ascending order) | MS [M + 1] | LC/MS RT | LC/MS method |
|---|---|---|---|---|---|
| I-112 | 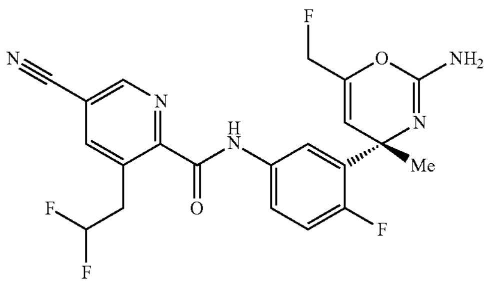 [SMILES: C[C@@]1(c2cc(NC(=O)c3ncc(C#N)cc3CC(F)F)ccc2F)C=C(CF)OC(N)=N1] | | | | |
| I-113 | 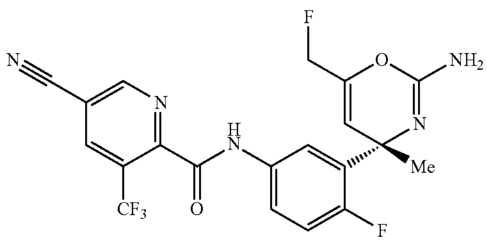 [SMILES: C[C@@]1(c2cc(NC(=O)c3ncc(C#N)cc3C(F)(F)F)ccc2F)C=C(CF)OC(N)=N1] | 1H-NMR (CDCl3) δ: 1.65 (3H, s), 4.74 (2H, d, J = 36 Hz), 5.75 (1H, m), 7.06 (1H, dd, J = 3, 9 Hz), 7.55-7.56 (1H, m), 7.97-7.99 (1H, m), 8.50 (1H, s), 9.02 (1H, s), 9.65 (1H, s) | 452 | 1.14 | B |

TABLE 1-22

| No. | Structure | NMR(solvent: shift value ascending order) | MS [M + 1] | LC/MS RT | LC/MS method |
|---|---|---|---|---|---|
| I-114 | 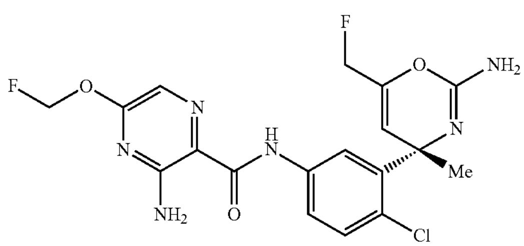 [SMILES: C[C@@]1(c2cc(NC(=O)c3ncc(OCF)nc3N)ccc2Cl)C=C(CF)OC(N)=N1] | 1H NMR (CDCl3) d: 1.76 (3H, s), 4.75 (2H, d, J = 48.0 Hz), 5.94 (1H, m), 6.02 (2H, d, J = 51.6 Hz), 7.33 (1H, d, J = 8.4 Hz), 7.54 (1H, s), 7.75-7.80 (2H, m), 9.56 (1H, s) | 439 | 1.22 | B |
| I-115 | 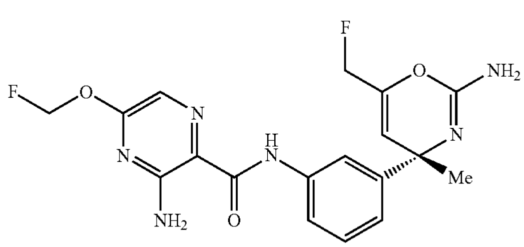 [SMILES: C[C@@]1(c2cccc(NC(=O)c3ncc(OCF)nc3N)c2)C=C(CF)OC(N)=N1] | 1H-NMR: 1.63 (3H, s), 4.76 (2H, d, J = 48 Hz), 5.45 (1H, d, J = 4.0 Hz), 6.03 (2H, d, J = 52 Hz), 7.18 (1H, d, J = 4.0 Hz), 7.35 (1H, t, J = 4.0 Hz), 7.62 (1H,m), 7.67 (1H, d, J = 4.0 Hz), 9.57 (1H, s). | 405 | 1.14 | B |
| I-116 | 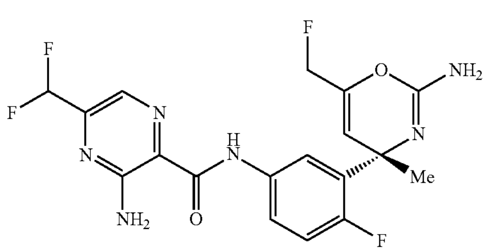 [SMILES: C[C@@]1(c2cc(NC(=O)c3ncc(C(F)F)nc3N)ccc2F)C=C(CF)OC(N)=N1] | 1H-NMR (CDCl3) δ: 1.65 (3H, s), 4.74 (2H, d, J = 47.7 Hz), 5.77 (1H, dd, J = 4.6, 2.6 Hz), 6.49 (1H, t, J = 54.8 Hz), 7.02 (1H, dd, J = 11.2, 8.6 Hz), 7.67-7.72 (2H, m), 8.05 (1H, s), 9.71 (1H, s). | 425 | 1.16 | B |

TABLE 1-22-continued

| No. | Structure | NMR(solvent: shift value ascending order) | MS [M + 1] | LC/MS RT | LC/MS method |
|-----|-----------|-------------------------------------------|------------|----------|--------------|
| I-117 | 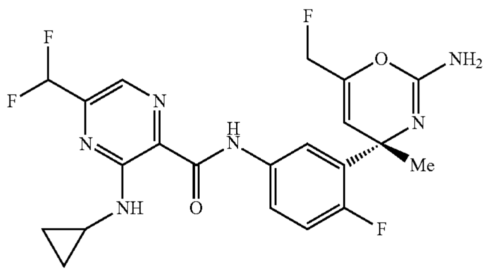 [SMILES: C[C@@]1(c2cc(NC(=O)c3ncc(C(F)F)nc3NC3CC3)ccc2F)C=C(CF)OC(N)=N1] | | | | |
| I-118 | 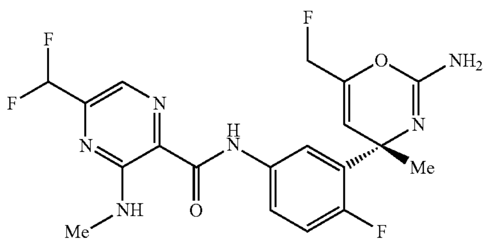 [SMILES: CNc1nc(C(F)F)cnc1C(=O)Nc1ccc(F)c([C@]2(C)C=C(CF)OC(N)=N2)c1] | | | | |

TABLE 1-23

| No. | Structure | NMR(solvent: shift value ascending order) | MS [M + 1] | LC/MS RT | LC/MS method |
|-----|-----------|-------------------------------------------|------------|----------|--------------|
| I-119 | 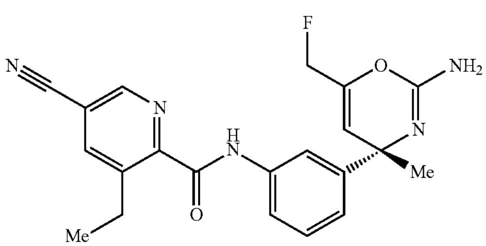 [SMILES: CCc1cc(C#N)cnc1C(=O)Nc1cccc([C@]2(C)C=C(CF)OC(N)=N2)c1] | | | | |
| I-120 | 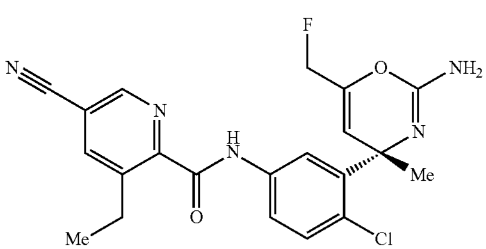 [SMILES: CCc1cc(C#N)cnc1C(=O)Nc1ccc(Cl)c([C@]2(C)C=C(CF)OC(N)=N2)c1] | | | | |
| I-121 | 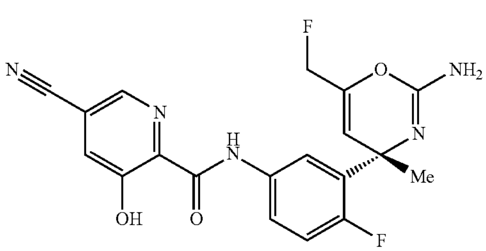 [SMILES: C[C@@]1(c2cc(NC(=O)c3ncc(C#N)cc3O)ccc2F)C=C(CF)OC(N)=N1] | | | | |

TABLE 1-23-continued

| No. | Structure | NMR(solvent: shift value ascending order) | MS [M + 1] | LC/MS RT | LC/MS method |
|---|---|---|---|---|---|
| I-122 | 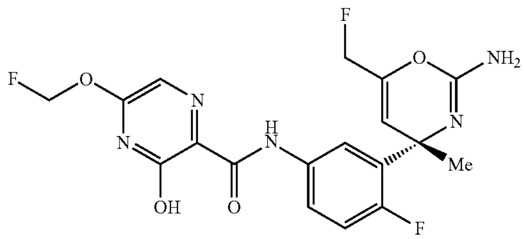 [SMILES: C[C@@]1(c2cc(NC(=O)c3ncc(OCF)nc3O)ccc2F)C=C(CF)OC(N)=N1] | | | | |
| I-123 | 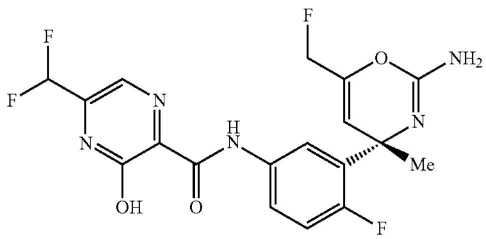 [SMILES: C[C@@]1(c2cc(NC(=O)c3ncc(C(F)F)nc3O)ccc2F)C=C(CF)OC(N)=N1] | | | | |
| I-124 | 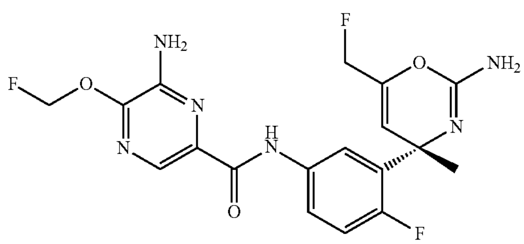 [SMILES: C[C@@]1(c2cc(NC(=O)c3cnc(OCF)c(N)n3)ccc2F)C=C(CF)OC(N)=N1] | 1H-NMR (CDCl3) δ: 1.65 (3H, s), 4.74 (2H, d, J = 47.7 Hz), 5.02 (2H, s), 5.74 (1H, dd, J = 4.8, 2.4 Hz), 6.09 (1H, dd, J = 2.8, 1.7 Hz), 7.04 (1H, dd, J = 11.3, 8.8 Hz), 7.62 (1H, dd, J = 6.9, 2.8 Hz), 7.87-7.91 (1H, m), 9.38 (1H, s). | 423 | 0.98 | B |

TABLE 1-24

| No. | Structure | NMR(solvent: shift value ascending order) | MS [M + 1] | LC/MS RT | LC/MS method |
|---|---|---|---|---|---|
| I-125 | 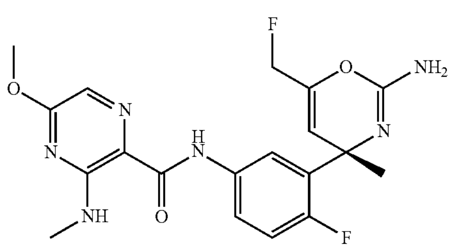 [SMILES: CNc1nc(OC)cnc1C(=O)Nc1ccc(F)c([C@]2(C)C=C(CF)OC(N)=N2)c1] | 1H-NMR (CDCl3) δ: 3.04 (3H, d, J = 4.8 Hz), 3.99 (3H, s), 4.73 (2H, d, J = 48.0 Hz), 5.72 (1H, m), 7.01 (1H, dd, J = 11.2, 8.8 Hz), 7.31 (1H, s), 7.58 (1H, m), 7.77 (1H, m), 8.58 (1H, m), 9.52 (1H, s). | 419 | 1.38 | B |
| I-126 | 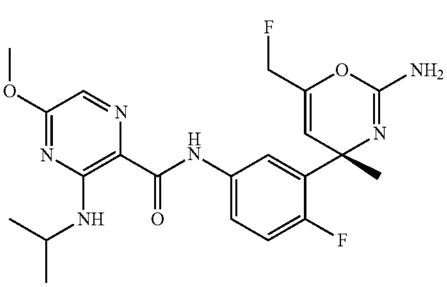 [SMILES: COc1cnc(C(=O)Nc2ccc(F)c([C@]3(C)C=C(CF)OC(N)=N3)c2)c(NC(C)C)n1] | 1H-NMR (CDCl3) δ: 1.29 (6H, d, J = 6.8 Hz), 3.96 (3H, s), 4.25 (1H, m), 4.73 (2H, d, J = 47.6 Hz), 5.72 (1H, m), 7.01 (1H, dd, J = 11.2, 8.8 Hz), 7.32 (1H, s), 7.50 (1H, m), 7.83 (1H, m), 8.58 (1H, m), 9.53 (1H, s). | 447 | 1.56 | B |

TABLE 1-24-continued

| No. | Structure | NMR(solvent: shift value ascending order) | MS [M + 1] | LC/MS RT | LC/MS method |
|---|---|---|---|---|---|
| I-127 | 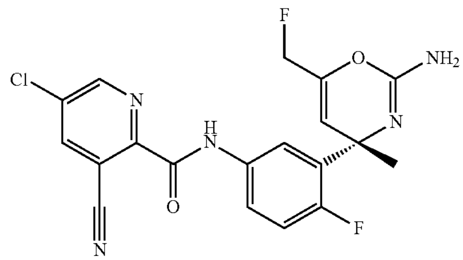 [SMILES: C[C@@]1(c2cc(NC(=O)c3ncc(Cl)cc3C#N)ccc2F)C=C(CF)OC(N)=N1] | 1H-NMR (CDCl3) δ: 1.67 (3H, s), 4.30 (2H, brs), 4.74 (2H, d, J = 36 Hz), 5.72 (1H, t, J = 3 Hz), 7.23-7.27 (2H, m), 7.27 (1H, s), 7.54 (1H, m), 8.33-8.38 (1H, m), 8.91 (1H, s), 9.95 (1H, s). | 418 | 0.92 | B |
| I-128 | 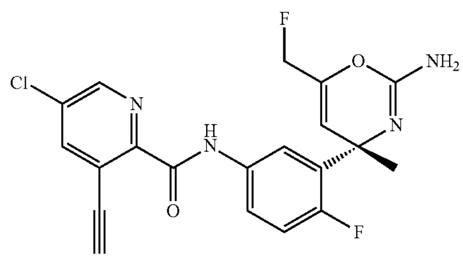 [SMILES: C#Cc1cc(Cl)cnc1C(=O)Nc1ccc(F)c([C@]2(C)C=C(CF)OC(N)=N2)c1] | 1H-NMR (CDCl3) δ: 1.65 (3H, s), 3.70 (1H, s), 4.82 (2H, d, J = 36 Hz), 5.73 (1H, t, J = 3 Hz), 7.03 (1H, dd, J = 3, 9 Hz), 7.54-7.56 (1H, m), 7.98 (1H, d, J = 3 Hz), 8.02-8.46 (1H, m), 8.46 (1H, d, J = 3 Hz), 9.81 (1H, s). | 417 | 1.21 | B |
| I-129 | 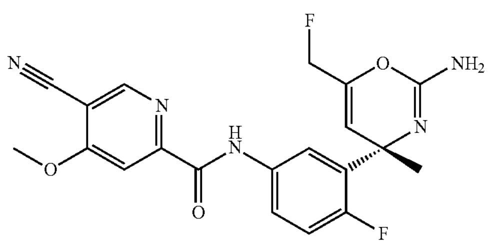 [SMILES: COc1cc(C(=O)Nc2ccc(F)c([C@]3(C)C=C(CF)OC(N)=N3)c2)ncc1C#N] | 1H-NMR (CDCl3) δ: 1.66 (3H, s), 4.09 (3H, s), 4.74 (2H, d, J = 36 Hz), 5.75 (1H, m), 7.06 (1H, dd, J = 3, 9 Hz), 7.76-7.78 (1H, m), 7.83-7.86 (1H, m), 7.90 (1H, s), 8.62 (1H, s), 9.92 (1H, s). | 414 | 1.08 | B |
| I-130 | 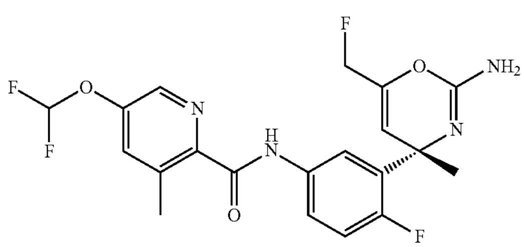 [SMILES: Cc1cc(OC(F)F)cnc1C(=O)Nc1ccc(F)c([C@]2(C)C=C(CF)OC(N)=N2)c1] | 1H-NMR (CDCl3) δ: 1.66 (3H, s), 2.81 (3H, s), 4.74 (2H, d, J = 47.7 Hz), 5.74 (1H, dd, J = 4.9, 2.4 Hz), 6.62 (1H, t, J = 72.2 Hz), 7.03 (1H, dd, J = 11.3, 8.8 Hz), 7.40 (1H, d, J = 2.0 Hz), 7.59 (1H, dd, J = 7.0, 2.8 Hz), 7.90 (1H, ddd, J = 8.7, 4.2, 2.8 Hz), 8.28 (1H, d, J = 2.5 Hz), 10.01 (1H, s). | 439 | 1.24 | B |

TABLE 1-25

| No. | Structure | NMR(solvent: shift value ascending order) | MS [M + 1] | LC/MS RT | LC/MS method |
|---|---|---|---|---|---|
| I-131 | 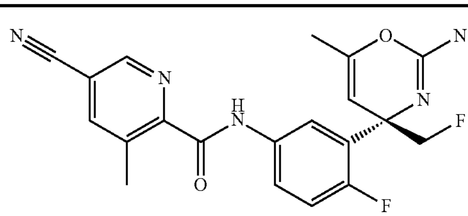 | 1H-NMR (CDCl3) δ: 1.69 (2H, br s), 1.86 (3H, s), 2.84 (3H, s), 4.34 (1H, dd, J = 47.8, 8.7 Hz), 4.62 (1H, ddd, J = 47.8, 8.7, 1.4 Hz), 5.25 (1H, d, J = 1.4 Hz), 7.04 (1H, d, J = 8.8 Hz), 7.07 (1H, d, J = 9.0 Hz), 7.68 (1H, dd, J = 6.8, 2.8 Hz), 7.93 (1H, d, J = 1.0 Hz), 7.97 (1H, ddd, J = 8.8, 4.3, 2.8 Hz), 8.67 (1H, d, J = 1.5 Hz), 10.03 (1H, s). | 398 | 1.07 | B |

TABLE 1-25-continued

| No. | Structure | NMR(solvent: shift value ascending order) | MS [M + 1] | LC/MS RT | LC/MS method |
|---|---|---|---|---|---|
| I-132 | 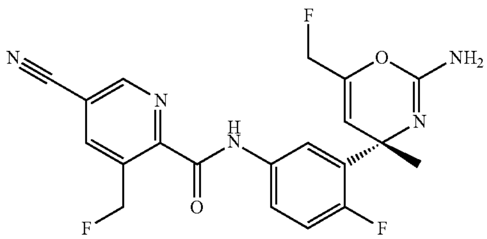 [SMILES: C[C@@]1(c2cc(NC(=O)c3ncc(C#N)cc3CF)ccc2F)C=C(CF)OC(N)=N1] | 1H-NMR (CDCl3) δ: 1.68 (3H, s), 4.75 (2H, d, J = 36 Hz), 5.76 (1H, m), 6.07 (2H, d, J = 36 Hz), 7.04 (1H, dd, J = 6, 6 Hz), 7.65-7.66 (1H, m), 7.79-7.81 (1H, m), 8.43 (1H, s), 8.78 (1H, s), 9.96 (1H, s). | 416 | 1.19 | B |
| I-133 | 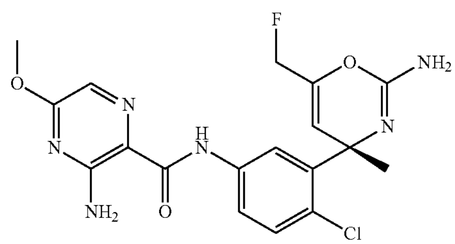 [SMILES: COc1cnc(C(=O)Nc2ccc(Cl)c([C@]3(C)C=C(CF)OC(N)=N3)c2)c(N)n1] | 1H-NMR (CDCl3) δ: 3.95 (3H, s), 4.76 (2H, d, J = 47.6 Hz), 5.93 (1H, d, J = 4.8 Hz), 7.34 (1H, d, J = 8.4 Hz), 7.48 (1H, s), 7.78-7.82 (2H, m), 9.58 (1H, s). | 421 | 1.21 | B |
| I-134 | 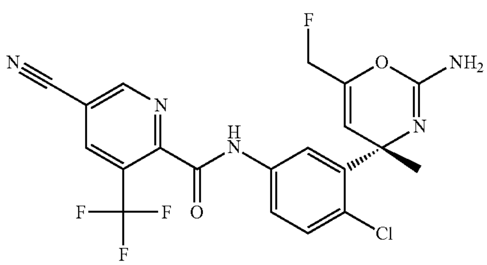 [SMILES: C[C@@]1(c2cc(NC(=O)c3ncc(C#N)cc3C(F)(F)F)ccc2Cl)C=C(CF)OC(N)=N1] | 1H-NMR (CDCl3) δ: 1.80 (3H, s), 4.76 (2H, d, J = 36 Hz), 5.96 (1H, t, J = 3 Hz), 7.37 (1H, d, J = 6 Hz), 7.71 (1H, d, J = 3 Hz), 7.97 (1H, dd, J = 3, 6 Hz), 8.51 (1H, s), 9.05 (1H, s), 9.73 (1H, s). | 468 | 1.22 | B |
| I-135 | 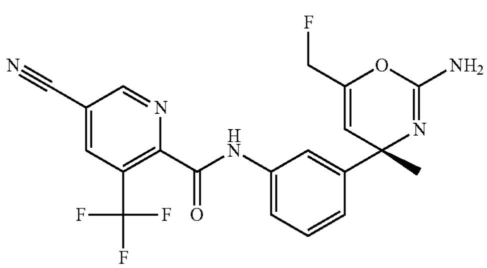 [SMILES: C[C@@]1(c2cccc(NC(=O)c3ncc(C#N)cc3C(F)(F)F)c2)C=C(CF)OC(N)=N1] | 1H-NMR (DMSO-d6): 1.46 (3H, s), 4.83 (2H, d, J = 48 Hz), 5.63 (1H, d, J = 8.0 Hz), 5.87 (2H, m), 7.22 (1H, d, J = 8.0 Hz), 7.33 (1H, t, J = 8.0 Hz), 7.63 (2H, m), 9.06 (1H, s), 9.42 (1H, s), 10.86 (1H, s). | 434 | 1.09 | B |
| I-136 | 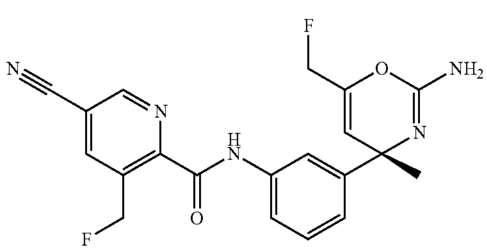 [SMILES: C[C@@]1(c2cccc(NC(=O)c3ncc(C#N)cc3CF)c2)C=C(CF)OC(N)=N1] | 1H-NMR (CDCl3): 1.64 (3H, s), 4.77 (2H, d, J = 47.6 Hz), 5.45 (1H, d, J = 4.8 Hz), 6.12 (2H, d, J = 48.4 Hz), 7.24 (1H, m), 7.38 (1H, t, J = 7.6 Hz), 7.64 (1H, s), 7.72 (1H, d, J = 7.6 Hz), 8.45 (1H, s), 8.85 (1H, s), 10.01(1H, s). | 398 | 1.14 | B |

TABLE 1-26

| No. | Structure | NMR(solvent: shift value ascending order) | MS [M + 1] | LC/MS RT | LC/MS method |
|---|---|---|---|---|---|
| I-142 | 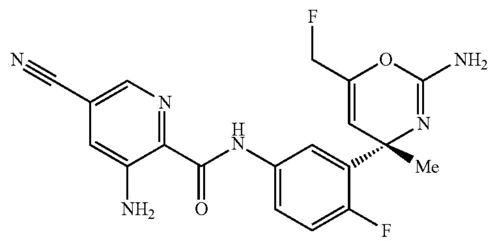 [SMILES: C[C@@]1(c2cc(NC(=O)c3ncc(C#N)cc3N)ccc2F)C=C(CF)OC(N)=N1] | 1H-NMR (CDCl3) δ: 1.66 (3H, s), 4.74 (2H, d, J = 36 Hz), 5.75 (1H, t, J = 3 Hz), 6.40 (2H, brs), 7.03 (1H, dd, J = 3, 6 Hz), 7.29 (1H, d, J = 3 Hz), 7.69-7.74 (2H, m), 8.05 (1H, d, J = 3 Hz), 9.91 (1H, s). | 399 | 1.07 | B |
| I-143 | 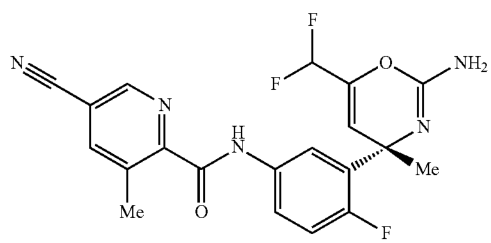 [SMILES: Cc1cc(C#N)cnc1C(=O)Nc1ccc(F)c([C@]2(C)C=C(C(F)F)OC(N)=N2)c1] | 1H-NMR 1.67 (3H, s), 2.85 (3H, s), 5.96 (1H, s), 5.96 (1H, t, J = 56 Hz), 7.06 (1H, dd, J = 12, 8.0 Hz), 7.66 (1H, dd, J = 4.0, 4.0 Hz), 7.89 (1H, m), 7.94 (1H, s), 8.70 (1H, s), 10.01 (1H, s). | 416 | 1.14 | B |
| I-144 | 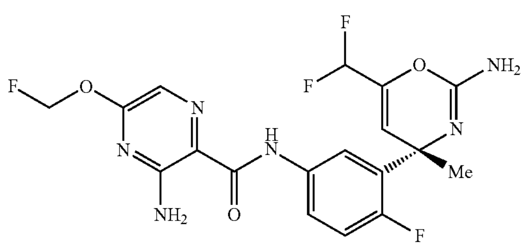 [SMILES: C[C@@]1(c2cc(NC(=O)c3ncc(OCF)nc3N)ccc2F)C=C(C(F)F)OC(N)=N1] | 1H-NMR 1.67 (3H, s), 5.95 (1H, s), 5.95 (1H, t, J = 56 Hz), 6.02 (2H, d, J = 52 Hz), 7.04 (1H, dd, J = 12, 8.0 Hz), 7.55 (1H, s), 7.63 (1H, dd, J = 8.0, 4.0 Hz), 7.78 (1H, m), 9.52 (1H, s). | 441 | 1.29 | B |
| I-145 | 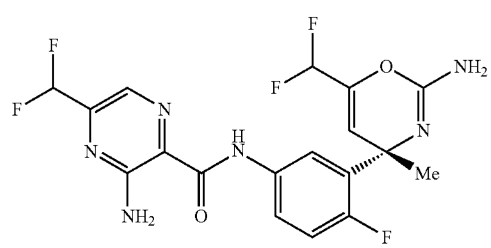 [SMILES: C[C@@]1(c2cc(NC(=O)c3ncc(C(F)F)nc3N)ccc2F)C=C(C(F)F)OC(N)=N1] | | | | |
| I-146 | 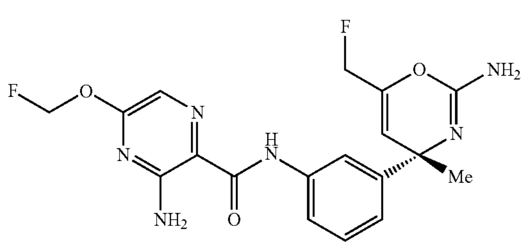 [SMILES: C[C@@]1(c2cccc(NC(=O)c3ncc(OCF)nc3N)c2)C=C(CF)OC(N)=N1] | 1H-NMR (CDCl3) : 1.63 (3H, s), 4.76 (1H, d, J = 48 Hz), 5.45 (1H, d, J = 4.0 Hz), 6.03 (1H, d, J = 52 Hz), 7.18 (1H, d, J = 8.0 Hz), 7.35 (1H, t, J = 8.0 Hz), 7.62 (1H, s), 7.77 (1H, d, J = 8.0 Hz). | 405 | 1.14 | B |
| I-147 | 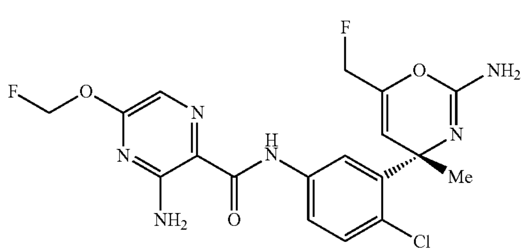 [SMILES: C[C@@]1(c2cc(NC(=O)c3ncc(OCF)nc3N)ccc2Cl)C=C(CF)OC(N)=N1] | 1H-NMR (CDCl3) δ: 4.75 (2H, d, J = 48.0 Hz), 5.94 (1H, m), 6.02 (2H, d, J = 51.6 Hz), 7.33 (1H, d, J = 8.4 Hz), 7.54 (1H, s), 7.75-7.80 (2H, m), 9.56 (1H, s). | 439 | 1.22 | B |

TABLE 1-27

| No. | Structure | NMR(solvent: shift value ascending order) | MS (M+1] | LC/MS RT | LC/MS method |
|---|---|---|---|---|---|
| I-148 | 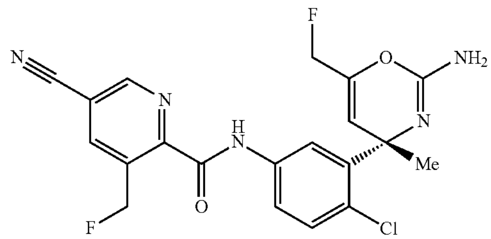 [SMILES: C[C@@]1(c2cc(NC(=O)c3ncc(C#N)cc3CF)ccc2Cl)C=C(CF)OC(N)=N1] | 1H-NMR (CDCl3) δ: 1.78 (3H, s), 4.76 (2H, d, J = 33 Hz), 6.01 (1H, t, J = 3 Hz), 6.08 (2H, d, J = 39 Hz), 7.31 (1H, dd, J = 3, 9 Hz), 7.83 (1H, d, J = 3 Hz), 8.43 (1H, s), 8.76 (1H, s), 9.95 (1H, s). | 432 | 1.19 | B |
| I-149 | 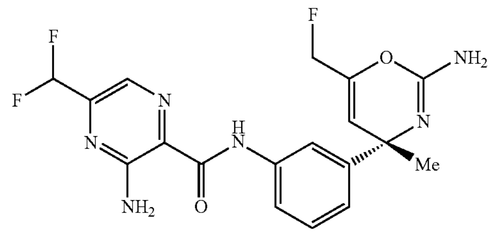 [SMILES: C[C@@]1(c2cccc(NC(=O)c3ncc(C(F)F)nc3N)c2)C=C(CF)OC(N)=N1] | 1H-NMR (CDCl3): 1.67 (3H, s), 4.77 (1H, d, J = 48 Hz), 5.45 (1H, d, J = 4.0 Hz), 6.51 (1H, t, J = 56 Hz), 7.23 (1H, m), 7.37 (1H, m), 7.66 (2H, m), 8.14 (1H, s), 9.80 (1H, s). | 407 | 1.17 | B |
| I-150 | 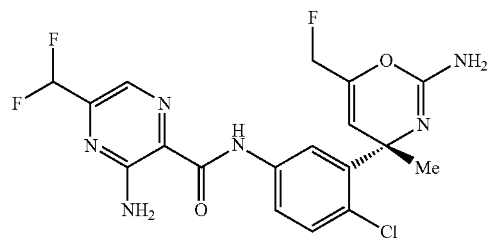 [SMILES: C[C@@]1(c2cc(NC(=O)c3ncc(C(F)F)nc3N)ccc2Cl)C=C(CF)OC(N)=N1] | 1H-NMR (CDCl3): 1.77 (3H, s), 4.8 (1H, d, J = 48 Hz), 5.98 (1H, d, J = 4.0 Hz), 6.51 (1H, t, J = 56 Hz), 7.35 (1H, d, J = 8.0 Hz), 7.77 (1H, d, J = 8.0, 4.0 Hz), 7.85 (1H, d, J = 4.0 Hz), 8.11 (1H, s), 9.79 (1H, s). | 441 | 1.21 | B |
| I-151 | 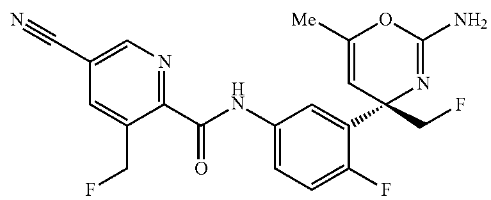 [SMILES: CC1=C[C@@](CF)(c2cc(NC(=O)c3ncc(C#N)cc3CF)ccc2F)N=C(N)O1] | 1H NMR (CDCl3) d: 1.86 (3H, s), 4.34 (1H, dd, J = 47.8, 8.7 Hz), 4.48 (2H, brs), 4.61 (1H, dd, J = 47.8, 8.7 Hz), 5.24 (1H, s), 6.09 (2H, d, J = 48.4 Hz), 7.07 (1H, m), 7.70 (1H, m), 7.91 (1H, m), 8.44 (1H, s), 8.81 (1H, m), 9.99 (1H, s). | 416 | 1.2 | B |
| I-152 | 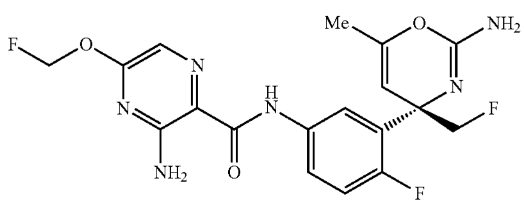 [SMILES: CC1=C[C@@](CF)(c2cc(NC(=O)c3ncc(OCF)nc3N)ccc2F)N=C(N)O1] | 1H-NMR (CDCl3) δ: 1.85 (3H, s), 4.32 (1H, dd, J = 48.0, 9.0 Hz), 4.63 (1H, ddd, J = 47.6, 9.0, 1.6 Hz), 5.24 (1H, m), 6.03 (2H, dq, J = 45.6, 2.0 Hz), 7.03 (1H, dd, J = 11.2, 8.8 Hz), 7.56 (1H, s), 7.65 (1H, m), 7.87 (1H, m), 9.55 (1H, s). | 423 | 1.18 | B |
| I-153 | 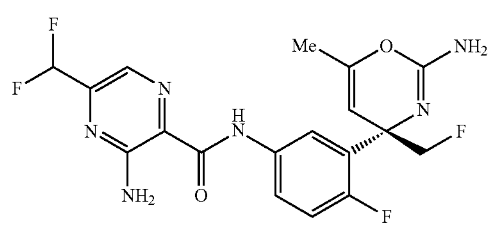 [SMILES: CC1=C[C@@](CF)(c2cc(NC(=O)c3ncc(C(F)F)nc3N)ccc2F)N=C(N)O1] | 1H-NMR (CDCl3): 1.86 (3H, s), 4.34 (1H, dd, J = 48, 8.0 Hz), 4.64 (1H, dd, J = 44, 4.0 Hz), 5.24 (1H, s), 6.51 (1H, t, J = 56 Hz), 7.06 (1H, dd, J = 8.2, 8.0 Hz), 7.70 (1H, m), 7.88 (1H, m), 8.12 (1H, s), 9.78 (1H, s). | 425 | 1.17 | B |

TABLE 1-28

| No. | Structure | NMR(solvent: shift value ascending order) | MS [M + 1] | LC/MS RT | LC/MS method |
|---|---|---|---|---|---|
| I-154 | 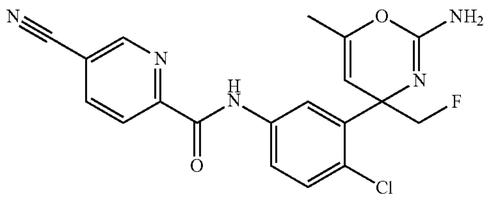 [SMILES: CC1=CC(CF)(c2cc(NC(=O)c3ccc(C#N)cn3)ccc2Cl)N=C(N)O1] | 1H-NMR (CDCl3) δ: 9.90 (1.0H, s), 8.89 (1.0H, t, J = 0.9 Hz), 8.42 (1.0H, d, J = 8.1 Hz), 8.20 (1.0H, dd, J = 8.1, 1.9 Hz), 7.98 (1.0H, dd, J = 8.6, 2.5 Hz), 7.90 (1.0H, d, J = 2.5 Hz), 7.39 (1.0H, d, J = 8.6 Hz), 5.55 (1.0H, d, J = 1.0 Hz), 4.70 (2.0H, ddd, J = 170.0, 47.4, 8.7 Hz), 4.33 (2.0H, br s), 1.87 (3.0H, s). | 400 | 1.14 | B |
| I-155 | 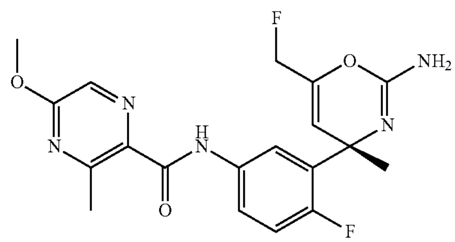 [SMILES: COc1cnc(C(=O)Nc2ccc(F)c([C@]3(C)C=C(CF)OC(N)=N3)c2)c(C)n1] | 1H NMR (CDCl3) d: 1.65 (3H, s), 2.94 (3H, s), 4.04 (3H, s), 4.73 (2H, d, J = 48.0 Hz), 5.73 (1H, m), 7.03 (1H, dd, J = 11.2, 8.8 Hz, 7.66 (1H, m), 7.90 (1H, m), 7.99 (1H, s), 9.78 (1H, s) | 404 | 1.21 | B |
| I-156 | 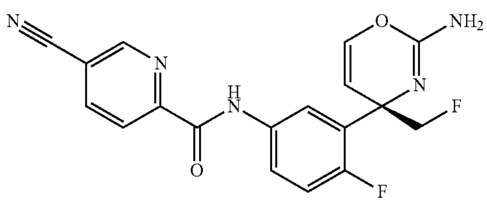 [SMILES: N#Cc1ccc(C(=O)Nc2ccc(F)c([C@]3(CF)C=COC(N)=N3)c2)nc1] | 1H NMR (CDCl3) d: 4.32 (2H, brs), 4.32 (1H, ddd, J = 47.6, 8.5, 1.1 Hz), 4.66 (1H, ddd, J = 47.6, 8.5, 1.5 Hz), 5.56 (1H, dd, J = 6.3, 2.9 Hz), 6.56 (1H, d, J = 6.3 Hz), 7.09 (1H, dd, J = 11.3, 8.9 Hz), 7.78 (1H, dd, J = 6.7, 2.8 Hz), 8.01 (1H, ddd, J = 8.9, 4.1, 2.8 Hz), 8.21 (1H, dd, J = 8.2, 2.0 Hz), 8.42 (1H, dd, J = 8.2, 0.9 Hz), 8.89 (1H, dd, J = 2.0, 0.9 Hz), 9.89 (1H, s). | 370 | 0.94 | B |
| I-157 | 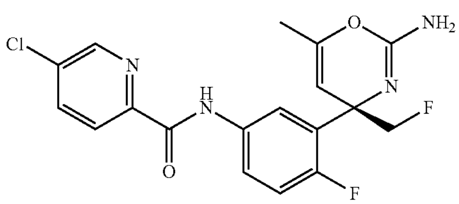 [SMILES: CC1=C[C@@](CF)(c2cc(NC(=O)c3ccc(Cl)cn3)ccc2F)N=C(N)O1] | 1H NMR (CDCl3) d: 1.86 (3H, d, J = 0.9 Hz), 4.33 (1H, dd, J = 47.7, 8.5 Hz), 4.35 (2H, brs), 4.63 (1H, ddd, J = 47.7, 8.5, 1.6 Hz), 5.24 (1H, m), 7.06 (1H, dd, J = 11.3, 8.8 Hz), 7.71 (1H, dd, J = 6.8, 2.9 Hz), 7.88 (1H, dd, J = 8.4, 2.3 Hz), 8.00 (1H, ddd, J = 8.8, 4.1, 2.9 Hz), 8.24 (1H, d, J = 8.4 Hz), 8.56 (1H, d, J = 2.3 Hz), 9.85 (1H, s). | 393 | 1.19 | B |
| I-158 | 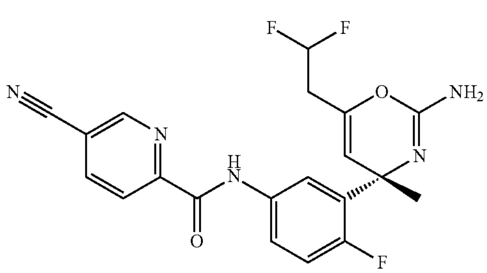 [SMILES: C[C@@]1(c2cc(NC(=O)c3ccc(C#N)cn3)ccc2F)C=C(CC(F)F)OC(N)=N1] | 1H NMR (CDCl3) d: 1.57 (3H, s), 2.65 (2H, dt, J = 6, 12 Hz), 4.25 (2H, brs), 5.48 (1H, d, J = 3 Hz,) 5.93 (1H, tt, J = 3, 42 Hz), 7.05 (1H, dd, J = 6, 12 Hz), 7.68-7.71 (1H, m), 7.86-7.90 (1H, m), 8.20 (1H, dd, J = 3, 6 Hz), 8.41 (1H, d, J = 6 Hz), 8.87 (1H, d, J = 3 Hz), 9.84 (1H, s). | 416 | 1.08 | B |

TABLE 1-29

| No. | Structure | NMR(solvent: shift value ascending order) | MS [M + 1] | LC/MS RT | LC/MS method |
|---|---|---|---|---|---|
| I-159 | 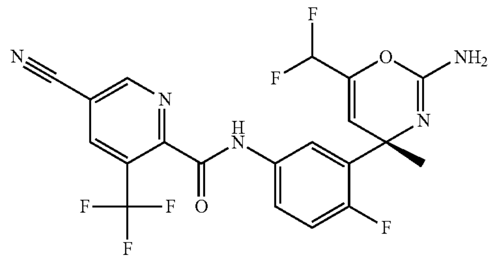 [SMILES: C[C@@]1(c2cc(NC(=O)c3ncc(C#N)cc3C(F)(F)F)ccc2F)C=C(C(F)F)OC(N)=N1] | 1H-NMR 1.67 (3H, s), 5.96 (1H, s), 5.96 (1H, t, J = 56 Hz), 7.08 (1H, dd, J = 12, 8.0 Hz), 7.61 (1H, dd, J = 4.0, 4.0 Hz), 7.95 (1H, m), 8.50 (1H, s), 9.01 (1H, s), 9.64 (1H, s). | 470 | 1.19 | B |
| I-160 | 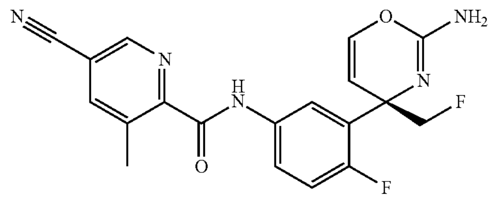 [SMILES: Cc1cc(C#N)cnc1C(=O)Nc1ccc(F)c([C@]2(CF)C=COC(N)=N2)c1] | 1H NMR (CDCl3) d: 2.86 (3H, s), 4.27 (2H, brs), 4.31 (1H, dd, J = 47.7, 8.5 Hz), 4.66 (1H, ddd, J = 47.7, 8.5, 1.3 Hz), 5.55 (1H, dd, J = 6.3, 3.0 Hz), 6.55 (1H, d, J = 6.3 Hz), 7.07 (1H, dd, J = 11.1, 8.8 Hz), 7.69 (1H, dd, J = 6.5, 2.8 Hz), 7.94 (1H, d, J = 1.5 Hz), 8.00 (1H, ddd, J = 8.8, 4.2, 2.8 Hz), 8.71 (1H, d, J = 1.5 Hz), 10.05 (1H, s). | 384 | 1.01 | B |
| I-161 | 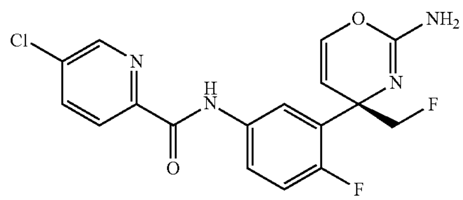 [SMILES: NC1=N[C@](CF)(c2cc(NC(=O)c3ccc(Cl)cn3)ccc2F)C=CO1] | 1H NMR (CDCl3) d: 4.26 (2H, brs), 4.31 (1H, ddd, J = 47.8, 8.7, 1.0 Hz), 4.67 (1H, ddd, J = 47.8, 8.7, 1.6 Hz), 5.55 (1H, dd, J = 6.4, 2.8 Hz), 6.56 (1H, d, J = 6.4 Hz), 7.07 (1H, dd, J = 11.3, 8.9 Hz), 7.75 (1H, dd, J = 6.7, 2.8 Hz), 7.89 (1H, dd, J = 8.4, 2.4 Hz), 8.01 (1H, ddd, J = 8.9, 4.3, 2.8 Hz), 8.25 (1H, d, J = 8.4 Hz), 8.57 (1H, d, J = 2.4 Hz), 9.86 (1H, s). | 379 | 1.08 | B |
| I-162 | 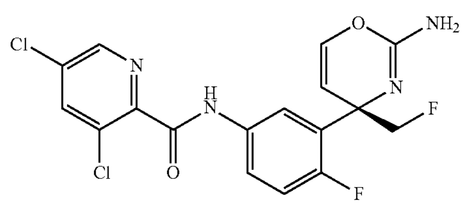 [SMILES: NC1=N[C@](CF)(c2cc(NC(=O)c3ncc(Cl)cc3Cl)ccc2F)C=CO1] | 1H NMR (CDCl3) d: 4.29 (2H, brs), 4.31 (1H, dd, J = 47.7, 8.5 Hz), 4.66 (1H, ddd, J = 47.4, 8.5, 1.3 Hz), 5.55 (1H, dd, J = 6.3, 2.8 Hz), 6.55 (1H, d, J = 6.3 Hz), 7.06 (1H, dd, J = 11.3, 8.8 Hz), 7.65 (1H, dd, J = 6.5, 2.8 Hz), 7.91 (1H, d, J = 2.0 Hz), 8.05 (1H, ddd, J = 8.8, 4.2, 2.8 Hz), 8.47 (1H, d, J = 2.0 Hz), 9.77 (1H, s). | 413 | 1.18 | B |
| I-163 | 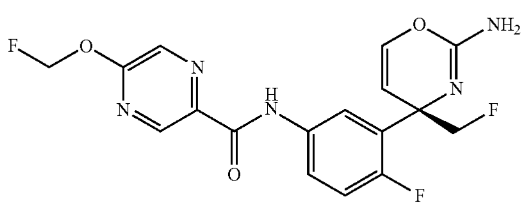 [SMILES: NC1=N[C@](CF)(c2cc(NC(=O)c3cnc(OCF)cn3)ccc2F)C=CO1] | 1H NMR (CDCl3) d: 4.30 (2H, brs), 4.32 (1H, dd, J = 47.7, 8.5 Hz), 4.66 (1H, ddd, J = 47.7, 8.5, 1.5 Hz), 5.55 (1H, dd, J = 6.3, 2.8 Hz), 6.09 (1H, m), 6.22 (1H, m), 6.55 (1H, d, J = 6.3 Hz), 7.07 (1H, dd, J = 11.3, 8.8 Hz), 7.75 (1H, dd, J = 6.5, 2.8 Hz), 7.98 (1H, ddd, J = 8.8, 4.1, 2.8 Hz), 8.29 (1H, d, J = 1.3 Hz), 9.08 (1H, d, J = 1.3 Hz), 9.52 (1H, s). | 394 | 1.03 | B |

TABLE 1-30

| No. | Structure | NMR(solvent: shift value ascending order) | MS [M + 1] | LC/MS RT | LC/MS method |
|---|---|---|---|---|---|
| I-164 | 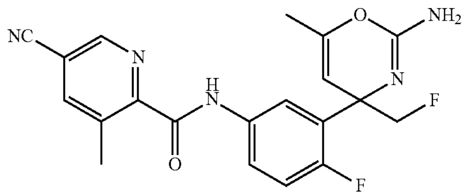 [SMILES: CC1=CC(CF)(c2cc(NC(=O)c3ncc(C#N)cc3C)ccc2F)N=C(N)O1] | 1H-NMR (CDCl3) δ: 10.08 (1.0H, s), 8.69 (1.0H, d, J = 1.3 Hz), 7.98 (1.0H, dd, J = 8.7, 2.6 Hz), 7.94 (1.0H, d, J = 1.3 Hz), 7.82 (1.0H, d, J = 2.6 Hz), 7.36 (1.0H, d, J = 8.7 Hz), 5.56 (1.0H, d, J = 1.0 Hz), 4.70 (2.0H, ddd, J = 167.3, 47.5, 8.7 Hz), 4.41 (2.0H, br s), 2.85 (3.0H, s), 1.87 (3.0H, s). | 414 | 1.22 | B |
| I-165 | 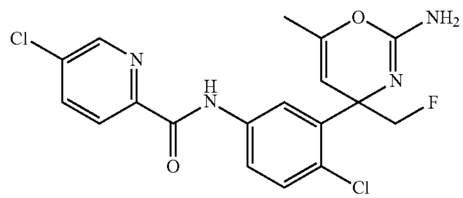 [SMILES: CC1=CC(CF)(c2cc(NC(=O)c3ccc(Cl)cn3)ccc2Cl)N=C(N)O1] | 1H-NMR (CDCl3) δ: 9.89 (1.0H, s), 8.56 (1.0H, d, J = 2.1 Hz), 8.24 (1.0H, d, J = 8.4 Hz), 7.98 (1.0H, dd, J = 8.6, 2.7 Hz), 7.90-7.87 (2.0H, m), 7.37 (1.0H, d, J = 8.6 Hz), 5.55 (1.0H, d, J = 0.9 Hz), 4.70 (2.0H, ddd, J = 182.2, 47.5, 8.7 Hz), 4.33 (1.6H, br s), 1.87 (3.0H, s). | 409 | 1.33 | B |
| I-166 | 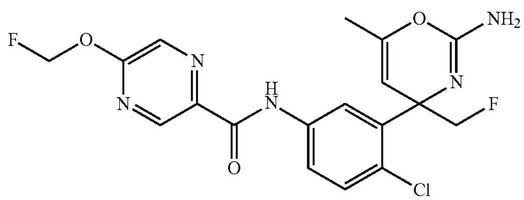 [SMILES: CC1=CC(CF)(c2cc(NC(=O)c3cnc(OCF)cn3)ccc2Cl)N=C(N)O1] | 1H-NMR (CDCl3) δ: 9.55 (1.0H, s), 9.07 (1.0H, d, J = 1.1 Hz), 8.28 (1.0H, d, J = 1.1 Hz), 7.97 (1.0H, dd, J = 8.6, 2.6 Hz), 7.87 (1.0H, d, J = 2.6 Hz), 7.37 (1.0H, d, J = 8.6 Hz), 6.15 (2.0H, ddd, J = 51.1, 4.9, 1.9 Hz), 5.55 (1.0H, d, J = 0.9 Hz), 4.70 (2.0H, ddd, J = 175.5, 47.5, 8.7 Hz), 4.37 (2.0H, br s), 1.86 (3.0H, s). | 424 | 1.17 | B |
| I-167 | 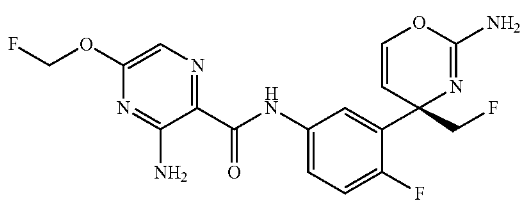 [SMILES: NC1=N[C@](CF)(c2cc(NC(=O)c3ncc(OCF)nc3N)ccc2F)C=CO1] | 1H NMR (CDCl3) d: 4.28 (2H, brs), 4.31 (1H, ddd, J = 47.7, 8.6, 1.0 Hz), 4.66 (1H, ddd, J = 47.7, 8.6, 1.5 Hz), 5.55 (1H, dd, J = 6.3, 2.8 Hz), 5.96 (1H, m), 6.09 (1H, m), 6.55 (1H, d, J = 6.3 Hz), 7.05 (1H, dd, J = 11.3, 8.8 Hz), 7.56 (1H, s), 7.69 (1H, dd, J = 6.7, 2.9 Hz), 7.88 (1H, ddd, J = 8.8, 4.3, 2.9 Hz), 9.56 (1H, s). | 409 | 1.13 | B |
| I-168 | 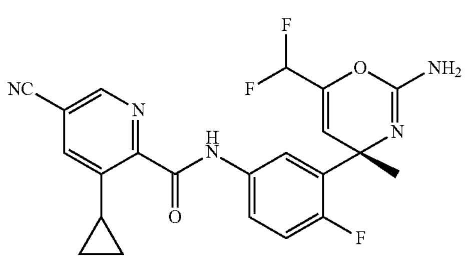 [SMILES: C[C@@]1(c2cc(NC(=O)c3ncc(C#N)cc3C3CC3)ccc2F)C=C(C(F)F)OC(N)=N1] | 1H-NMR 0.78 (2H, m), 1.23 (2H, m), 1.67 (3H, s), 3.48 (1H, m), 5.96 (1H, m), 5.96 (1H, t, J = 56 Hz), 7.07 (1H, dd, J = 12, 8.0 Hz), 7.59 (1H, s), 7.65 (1H, dd, J = 8.0, 4.0 Hz), 7.91 (1H, m), 8.62 (1H, s), 9.97 (1H, s). | 442 | 1.31 | B |

TABLE 1-31

| No. | Structure | NMR(solvent: shift value ascending order) | MS [M + 1] | LC/MS RT | LC/MS method |
|---|---|---|---|---|---|
| I-169 | 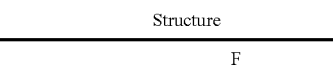 | 1H-NMR 1.67 (3H, s), 5.95 (1H, d, J = 4.0 Hz), 5.96 (1H, t, J = 56 Hz), 7.06 (1H, dd, J = 12, 8.0 Hz), 7.62 (1H, dd, J = 8.0, 4.0 Hz), 7.92 (1H, m), 8.45 (1H, s), 9.74 (1H, s). | 445 | 1.26 | B |

TABLE 1-31-continued

| No. | Structure | NMR(solvent: shift value ascending order) | MS [M + 1] | LC/MS RT | LC/MS method |
|---|---|---|---|---|---|
| I-170 | (structure) | 1H-NMR 1.67 (3H, s), 5.95 (1H, m), 5.96 (1H, t, J = 56 Hz), 7.06 (1H, dd, J = 8.0 , 4.0 Hz), 7.73 (1H, m), 7.88 (1H, m), 8.24 (1H, d, J = 8.0 Hz), 8.55 (1H, d, J = 4.0 Hz), 9.83 (1H, s). | 411 | 1.3 | B |
| II-1 | (structure) 2TsOH | 1H-NMR (CD3OD) δ: 1.85 (3H, s), 2.01 (3H, d, J = 1.1 Hz), 2.36 (6H, s), 5.44 (1H, t, J = 1.0 Hz), 7.22 (4H, d, J = 8.2 Hz), 7.36 (1H, dd, J = 11.4, 8.7 Hz), 7.46 (1H, ddd, J = 8.7, 4.2, 2.7 Hz), 7.54 (1H, dd, J = 6.9, 2.7 Hz), 7.67 (4H, d, J = 8.2 Hz). | 236 | 0.45 | A |
| II-2 | (structure) 2TsOH | 1H-NMR (DMSO-d6) δ: 1.79 (s, 3H), 2.29 (s, 6H), 5.69 (d, J = 6.0 Hz, 1H), 6.99 (d, 1H, J = 6.0 Hz,1H), 7.12 (d, J = 9.0 Hz, 4H), 7.21 (m, 2H), 7.31 (m, 1H), 7.47 (d, J = 9.0 Hz, 4H), 8.60 (br, 1H), 9.30 (br, 1H), 10.4 (br, 1H). | | | |
| II-3 | (structure) 2HCl | 1H-NMR (MeOD) δ: 1.99 (3H, s), 5.02 (2H, d, J = 47.1 Hz), 6.04 (1H, d, J = 4.6 Hz), 7.43 (1H, dd, J = 11.4, 8.9 Hz), 7.49-7.53 (1H, m), 7.56 (1H, dd, J = 7.1, 2.5 Hz). | 254 | 0.4 | A |

TABLE 1-32

| No. | Structure | NMR(solvent: shift value ascending order) | MS [M + 1] | LC/MS RT | LC/MS method |
|---|---|---|---|---|---|
| II-4 | (structure) 2HCl | 1H-NMR (MeOD) δ: 1.94 (3H, s), 3.38 (3H, s), 4.08 (2H, s), 5.79 (1H, s), 7.39 (1H, dd, J = 11.7, 8.6 Hz), 7.45-7.49 (1H, m), 7.53 (1H, dd, J = 6.6, 2.5 Hz). | 266 | 0.52 | A |

TABLE 1-32-continued

| No. | Structure | NMR(solvent: shift value ascending order) | MS [M + 1] | LC/MS RT | LC/MS method |
|---|---|---|---|---|---|
| II-5 | 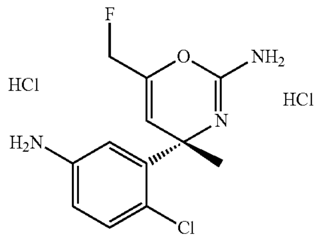 [SMILES: Cl ; C[C@@]1(c2cc(N)ccc2Cl)C=C(CF)OC(N)=N1 ; Cl] | 1H-NMR (DMSO-d6) δ: 1.85 (3H, s), 5.03 (2H, d, J = 47.2 Hz), 5.94 (1H, d, J = 4.6 Hz), 6.91 (1H, d, J = 7.4 Hz), 7.17 (1H, s), 7.32 (1H, d, J = 8.4 Hz), 8.67 (1H, br s), 9.42 (1H, br s), 10.74 (1H, s). | 270 | 0.7 | B |
| II-6 | 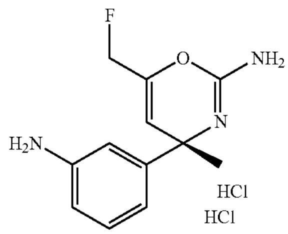 [SMILES: C[C@@]1(c2cccc(N)c2)C=C(CF)OC(N)=N1 ; Cl ; Cl] | 1H-NMR (DMSO-d6) d: 1.79 (3H, s), 5.05 (2H, d, J = 47.2 Hz), 6.15, (1H, d, J = 4.0 Hz), 7.20 (1H, m), 7.29-7.31 (2H, m), 7.46 (1H, t, J = 8.0 Hz), 8.88 (1H, br), 9.60 (1H, br), 11.2 (1H, br). | 236 | 0.47 | B |
| II-7 | 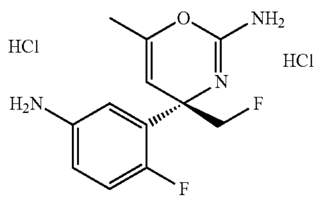 [SMILES: Cl ; CC1=C[C@@](CF)(c2cc(N)ccc2F)N=C(N)O1 ; Cl] | 1H-NMR (DMSO-d6) δ: 2.00 (3H, s), 4.87 (2H, d, J = 46.6 Hz), 5.55 (1H, s), 7.28-7.40 (3H, m), 8.84 (1H, br s), 9.66 (1H, br s). | 254 | 0.4 | B |

[Chemical Formula 34]

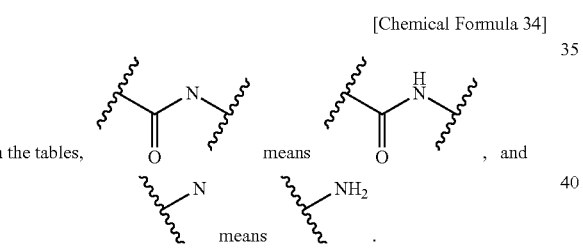

In the tables, [structure] means [structure], and [structure] means [structure].

The following compounds can be synthesized in a similar manner to the above. Compounds wherein the combination of

[Chemical Formula 35]

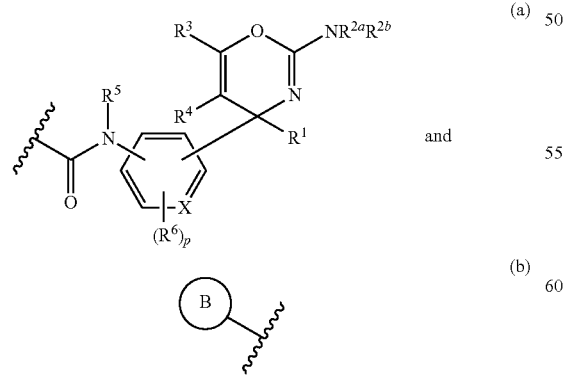

(a)

(b)

i.e., (a, b) is any of the followings. (a1) to (a7) and (b1) to (b105) mean the following groups.

[Chemical Formula 36]

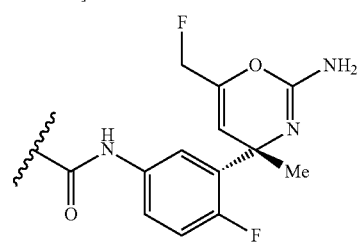

(a1)

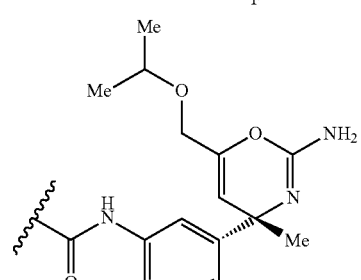

(a2)

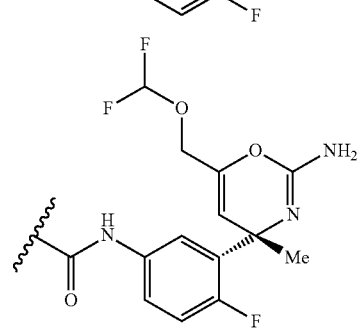

(a3)

-continued
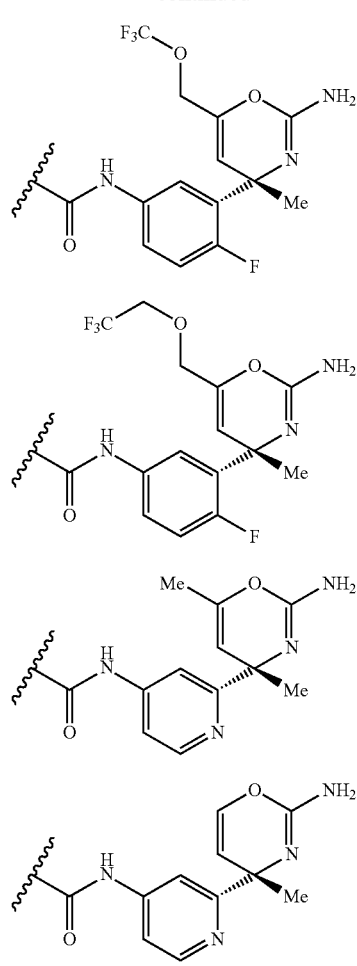
[Chemical Formula 37]
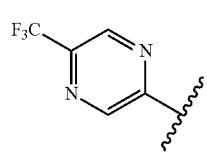
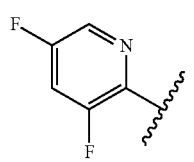
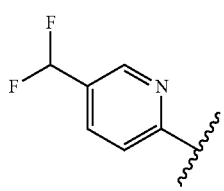
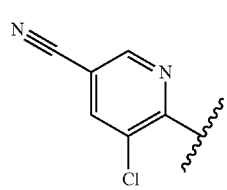
-continued
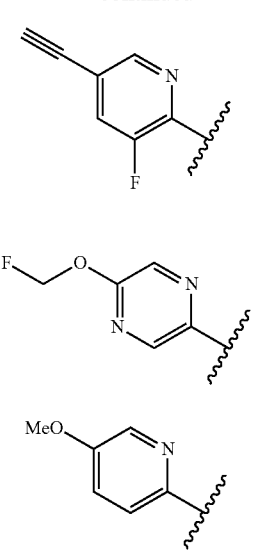
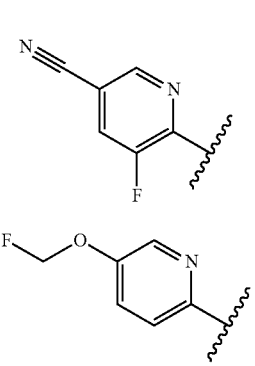

-continued
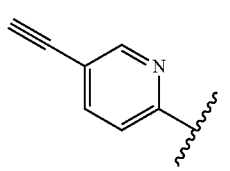 (b14)
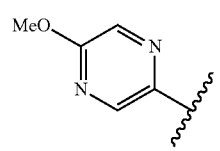 (b15)
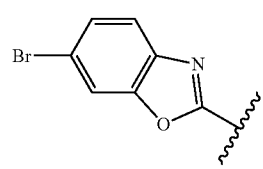 (b16)
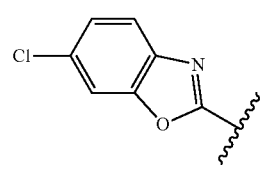 (b17)
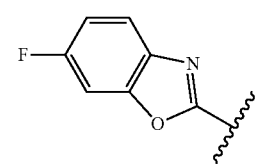 (b18)
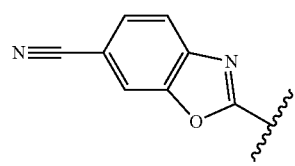 (b19)
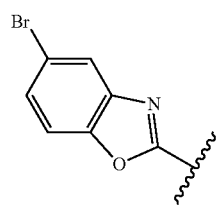 (b20)
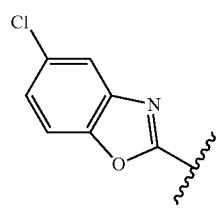 (b21)
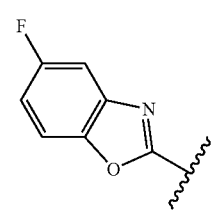 (b22)
-continued
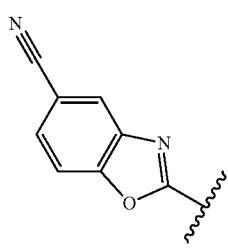 (b23)
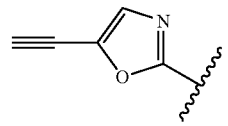 (b24)
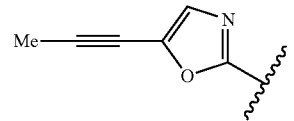 (b25)
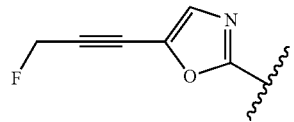 (b26)
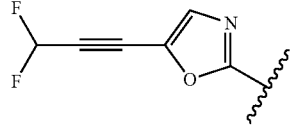 (b27)
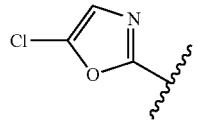 (b28)
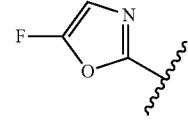 (b29)
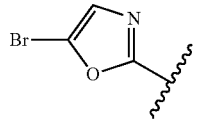 (b30)
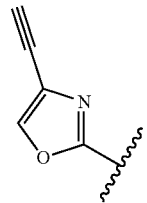 (b31)

(b32) 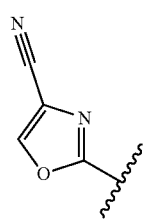
(b33) 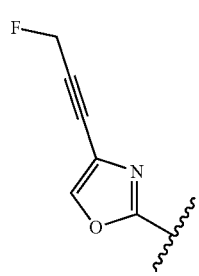
(b34) 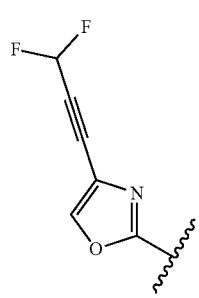
(b35) 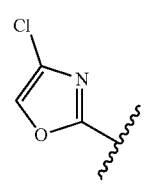
(b36) 
(b37) 
[Chemical Formula 38]
(b38) 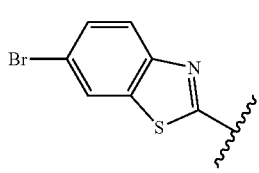
(b39) 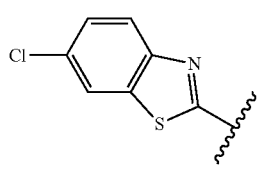
(b40) 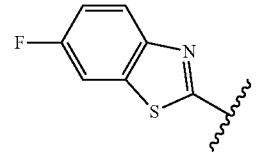
(b41) 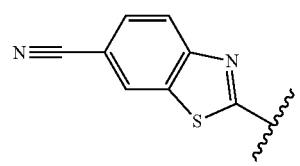
(b42) 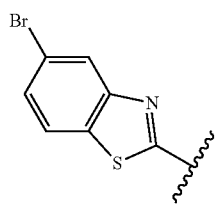
(b43)
(b44)
(b45)
(b46)

-continued
(b47) 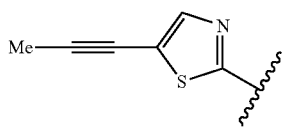
(b48) 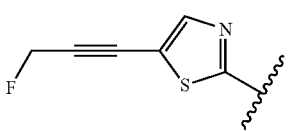
(b49) 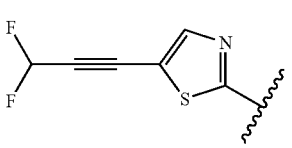
(b50) 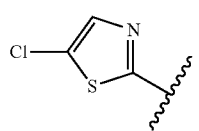
(b51) 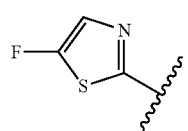
(b52) 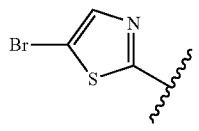
(b53) 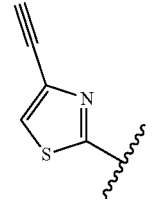
(b54) 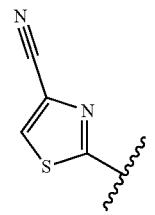
(b55) 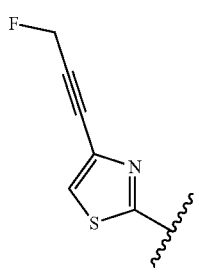
-continued
(b56) 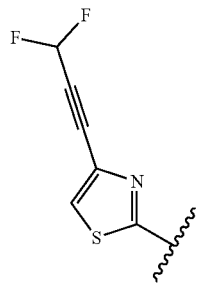
(b57) 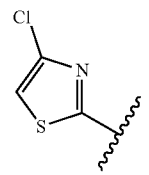
(b58) 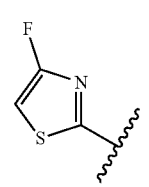
(b59) 
(b60) 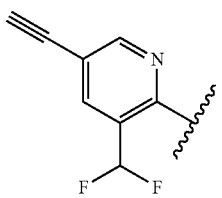
(b61) 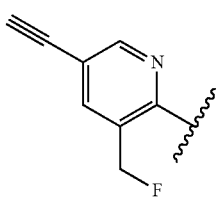
(b62) 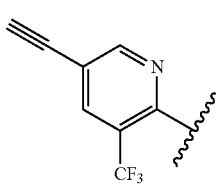
(b63) 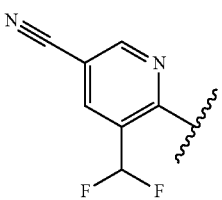

-continued (b64) (b73)
(b65) (b74)
(b66) (b75)
(b67) (b76)
(b68) (b77)
(b69) (b78)

[Chemical Formula 39]

(b79)
(b70) (b80)
(b71) (b81)
(b72) (b82)

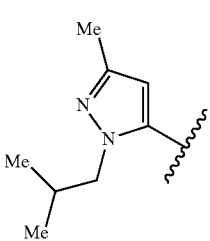
(b83)
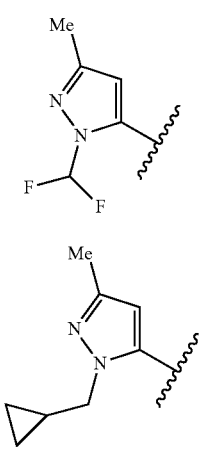
(b84)
(b85)
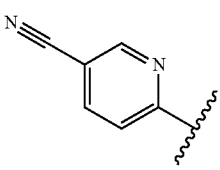
(b86)
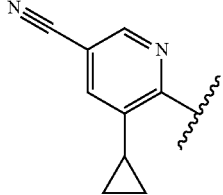
(b87)
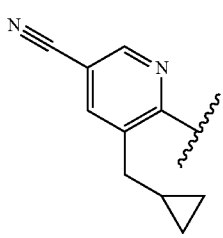
(b88)
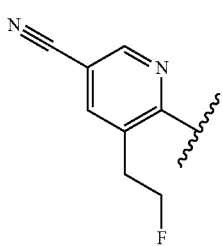
(b89)
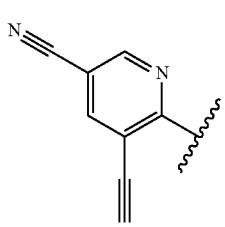
(b90)
(b91)
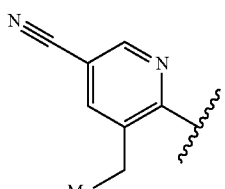
(b92)
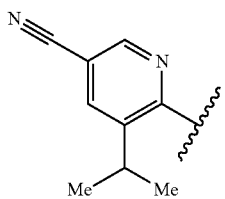
(b93)
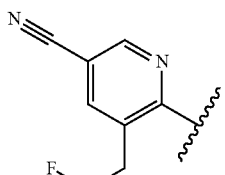
(b94)
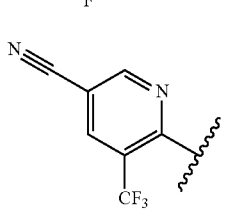
(b95)
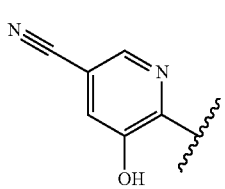
(b96)

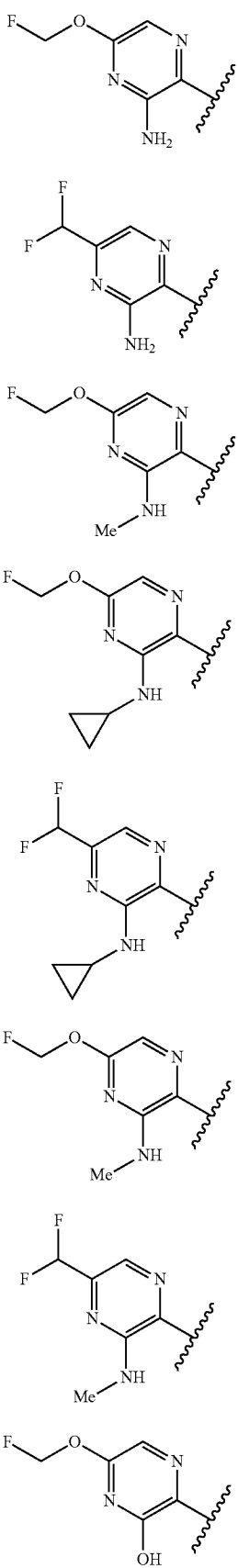

(a,b)=(a1,b1), (a1,b2), (a1,b3), (a1,b4), (a1,b5), (a1,b6), (a1,b7), (a1,b8), (a1,b9), (a1,b10), (a1,b11), (a1,b12), (a1,b13), (a1,b14), (a1,b15), (a1,b16), (a1,b17), (a1,b18), (a1,b19), (a1,b20), (a1,b21), (a1,b22), (a1,b23), (a1,b24), (a1,b25), (a1,b26), (a1,b27), (a1,b28), (a1,b29), (a1,b30), (a1,b31), (a1,b32), (a1,b33), (a1,b34), (a1,b35), (a1,b36), (a1,b37), (a1,b38), (a1,b39), (a1,b40), (a1,b41), (a1,b42), (a1,b43), (a1,b44), (a1,b45), (a1,b46), (a1,b47), (a1,b48), (a1,b49), (a1,b50), (a1,b51), (a1,b52), (a1,b53), (a1,b54), (a1,b55), (a1,b56), (a1,b57), (a1,b58), (a1,b59), (a1,b60), (a1,b61), (a1,b62), (a1,b63), (a1,b64), (a1,b65), (a1,b66), (a1,b67), (a1,b68), (a1,b69), (a1,b70), (a1,b71), (a1,b72), (a1,b73), (a1,b74), (a1,b75), (a1,b76), (a1,b77), (a1,b78), (a1,b79), (a1,b80), (a1,b81), (a1,b82), (a1,b83), (a1,b84), (a1,b85), (a1,b86), (a1,b87), (a1,b88), (a1,b89), (a1,b90), (a1,b91), (a1,b92), (a1,b93), (a1,b94), (a1,b95), (a1,b96), (a1,b97), (a1,b98), (a1,b99), (a1,b100), (a1,b101), (a1,b102), (a1,b103), (a1,b104), (a1,b105), (a2,b1), (a2,b2), (a2,b3), (a2,b4), (a2,b5), (a2,b6), (a2,b7), (a2,b8), (a2,b9), (a2,b10), (a2,b11), (a2,b12), (a2,b13), (a2,b14), (a2,b15), (a2,b16), (a2,b17), (a2,b18), (a2,b19), (a2,b20), (a2,b21), (a2,b22), (a2,b23), (a2,b24), (a2,b25), (a2,b26), (a2,b27), (a2,b28), (a2,b29), (a2,b30), (a2,b31), (a2,b32), (a2,b33), (a2,b34), (a2,b35), (a2,b36), (a2,b37), (a2,b38), (a2,b39), (a2,b40), (a2,b41), (a2,b42), (a2,b43), (a2,b44), (a2,b45), (a2,b46), (a2,b47), (a2,b48), (a2,b49), (a2,b50), (a2,b51), (a2,b52), (a2,b53), (a2,b54), (a2,b55), (a2,b56), (a2,b57), (a2,b58), (a2,b59), (a2,b60), (a2,b61), (a2,b62), (a2,b63), (a2,b64), (a2,b65), (a2,b66), (a2,b67), (a2,b68), (a2,b69), (a2,b70), (a2,b71), (a2,b72), (a2,b73), (a2,b74), (a2,b75), (a2,b76), (a2,b77), (a2,b78), (a2,b79), (a2,b80), (a2,b81), (a2,b82), (a2,b83), (a2,b84), (a2,b85), (a2,b86), (a2,b87), (a2,b88), (a2,b89), (a2,b90), (a2,b91), (a2,b92), (a2,b93), (a2,b94), (a2,b95), (a2,b96), (a2,b97), (a2,b98), (a2,b99), (a2,b100), (a2,b101), (a2,b102), (a2,b103), (a2,b104), (a2,b105), (a3,b1), (a3,b2), (a3,b3), (a3,b4), (a3,b5), (a3,b6), (a3,b7), (a3,b8), (a3,b9), (a3,b10), (a3,b11), (a3,b12), (a3,b13), (a3,b14), (a3,b15), (a3,b16), (a3,b17), (a3,b18), (a3,b19), (a3,b20), (a3,b21), (a3,b22), (a3,b23), (a3,b24), (a3,b25), (a3,b26), (a3,b27), (a3,b28), (a3,b29), (a3,b30), (a3,b31), (a3,b32), (a3,b33), (a3,b34), (a3,b35), (a3,b36), (a3,b37), (a3,b38), (a3,b39), (a3,b40), (a3,b41), (a3,b42), (a3,b43), (a3,b44), (a3,b45), (a3,b46), (a3,b47), (a3,b48), (a3,b49), (a3,b50), (a3,b51), (a3,b52), (a3,b53), (a3,b54), (a3,b55), (a3,b56), (a3,b57), (a3,b58), (a3,b59), (a3,b60), (a3,b61), (a3,b62), (a3,b63), (a3,b64), (a3,b65), (a3,b66), (a3,b67), (a3,b68), (a3,b69), (a3,b70), (a3,b71), (a3,b72), (a3,b73), (a3,b74), (a3,b75), (a3,b76), (a3,b77), (a3,b78), (a3,b79), (a3,b80), (a3,b81), (a3,b82), (a3,b83), (a3,b84), (a3,b85), (a3,b86), (a3,b87), (a3,b88), (a3,b89), (a3,b90), (a3,b91), (a3,b92), (a3,b93), (a3,b94), (a3,b95), (a3,b96), (a3,b97), (a3,b98), (a3,b99), (a3,b100), (a3,b101), (a3,b102), (a3,b103), (a3,b104), (a3,b105), (a4,b1), (a4,b2), (a4,b3), (a4,b4), (a4,b5), (a4,b6), (a4,b7), (a4,b8), (a4,b9), (a4,b10), (a4,b11), (a4,b12), (a4,b13), (a4,b14), (a4,b15), (a4,b16), (a4,b17), (a4,b18), (a4,b19), (a4,b20), (a4,b21), (a4,b22), (a4,b23), (a4,b24), (a4, b25), (a4,b26), (a4,b27), (a4,b28), (a4,b29), (a4,b30), (a4, b31), (a4,b32), (a4,b33), (a4,b34), (a4,b35), (a4,b36), (a4, b37), (a4,b38), (a4,b39), (a4,b40), (a4,b41), (a4,b42), (a4, b43), (a4,b44), (a4,b45), (a4,b46), (a4,b47), (a4,b48), (a4, b49), (a4,b50), (a4,b51), (a4,b52), (a4,b53), (a4,b54), (a4, b55), (a4,b56), (a4,b57), (a4,b58), (a4,b59), (a4,b60), (a4, b61), (a4,b62), (a4,b63), (a4,b64), (a4,b65), (a4,b66), (a4, b67), (a4,b68), (a4,b69), (a4,b70), (a4,b71), (a4,b72), (a4, b73), (a4,b74), (a4,b75), (a4,b76), (a4,b77), (a4,b78), (a4, b79), (a4,b80), (a4,b81), (a4,b82), (a4,b83), (a4,b84), (a4, b85), (a4,b86), (a4,b87), (a4,b88), (a4,b89), (a4,b90), (a4, b91), (a4,b92), (a4,b93), (a4,b94), (a4,b95), (a4,b96), (a4, b97), (a4,b98), (a4,b99), (a4,b100), (a4,b101), (a4,b102), (a4,b103), (a4,b104), (a4,b105), (a5,b1), (a5,b2), (a5,b3), (a5,b4), (a5,b5), (a5,b6), (a5,b7), (a5,b8), (a5,b9), (a5,b10), (a5,b11), (a5,b12), (a5,b13), (a5,b14), (a5,b15), (a5,b16), (a5,b17), (a5,b18), (a5,b19), (a5,b20), (a5,b21), (a5,b22), (a5,b23), (a5,b24), (a5,b25), (a5,b26), (a5,b27), (a5,b28), (a5,b29), (a5,b30), (a5,b31), (a5,b32), (a5,b33), (a5,b34), (a5,b35), (a5,b36), (a5,b37), (a5,b38), (a5,b39), (a5,b40), (a5,b41), (a5,b42), (a5,b43), (a5,b44), (a5,b45), (a5,b46), (a5,b47), (a5,b48), (a5,b49), (a5,b50), (a5,b51), (a5,b52), (a5,b53), (a5,b54), (a5,b55), (a5,b56), (a5,b57), (a5,b58), (a5,b59), (a5,b60), (a5,b61), (a5,b62), (a5,b63), (a5,b64), (a5,b65), (a5,b66), (a5,b67), (a5,b68), (a5,b69), (a5,b70), (a5,b71), (a5,b72), (a5,b73), (a5,b74), (a5,b75), (a5,b76), (a5,b77), (a5,b78), (a5,b79), (a5,b80), (a5,b81), (a5,b82), (a5,b83), (a5,b84), (a5,b85), (a5,b86), (a5,b87), (a5,b88), (a5,b89), (a5,b90), (a5,b91), (a5,b92), (a5,b93), (a5,b94), (a5,b95), (a5,b96), (a5,b97), (a5,b98); (a5,b99), (a5,b10), (a5,b101), (a5,b102), (a5,b103), (a5,b104), (a5,b105), (a6, b1), (a6,b2), (a6,b3), (a6,b4), (a6,b5), (a6,b6), (a6,b7), (a6, b8), (a6,b9), (a6,b10), (a6,b11), (a6,b12), (a6,b13), (a6,b14), (a6,b15), (a6,b16), (a6,b17), (a6,b18), (a6,b19), (a6,b20), (a6,b21), (a6,b22), (a6,b23), (a6,b24), (a6,b25), (a6,b26), (a6,b27), (a6,b28), (a6,b29), (a6,b30), (a6,b31), (a6,b32), (a6,b33), (a6,b34), (a6,b35), (a6,b36), (a6,b37), (a6,b38), (a6,b39), (a6,b40), (a6,b41), (a6,b42), (a6,b43), (a6,b44), (a6,b45), (a6,b46), (a6,b47), (a6,b48), (a6,b49), (a6,b50), (a6,b51), (a6,b52), (a6,b53), (a6,b54), (a6,b55), (a6,b56), (a6,b57), (a6,b58), (a6,b59), (a6,b60), (a6,b61), (a6,b62), (a6,b63), (a6,b64), (a6,b65), (a6,b66), (a6,b67), (a6,b68), (a6,b69), (a6,b70), (a6,b71), (a6,b72), (a6,b73), (a6,b74), (a6,b75), (a6,b76), (a6,b77), (a6,b78), (a6,b79), (a6,b80), (a6,b81), (a6,b82), (a6,b83), (a6,b84), (a6,b85), (a6,b86), (a6,b87), (a6,b88), (a6,b89), (a6,b90), (a6,b91), (a6,b92), (a6,b93), (a6,b94), (a6,b95), (a6,b96), (a6,b97), (a6,b98), (a6,b99), (a6,b100), (a6,b101), (a6,b102), (a6,b103), (a6, b104), (a6,b105), (a7,b1), (a7,b2), (a7,b3), (a7,b4), (a7,b5), (a7,b6), (a7,b7), (a7,b8), (a7,b9), (a7,b10), (a7,b11), (a7, b12), (a7,b13), (a7,b14), (a7,b15), (a7,b16), (a7,b17), (a7, b18), (a7,b19), (a7,b20), (a7,b21), (a7,b22), (a7,b23), (a7, b24), (a7,b25), (a7,b26), (a7,b27), (a7,b28), (a7,b29), (a7, b30), (a7,b31), (a7,b32), (a7,b33), (a7,b34), (a7,b35), (a7, b36), (a7,b37), (a7,b38), (a7,b39), (a7,b40), (a7,b41), (a7, b42), (a7,b43), (a7,b44), (a7,b45), (a7,b46), (a7,b47), (a7, b48), (a7,b49), (a7,b50), (a7,b51), (a7,b52), (a7,b53), (a7, b54), (a7,b55), (a7,b56), (a7,b57), (a7,b58), (a7,b59), (a7, b60), (a7,b61), (a7,b62), (a7,b63), (a7,b64), (a7,b65), (a7, b66), (a7,b67), (a7,b68), (a7,b69), (a7,b70), (a7,b71), (a7, b72), (a7,b73), (a7,b74), (a7,b75), (a7,b76), (a7,b77), (a7, b78), (a7,b79), (a7,b80), (a7,b81), (a7,b82), (a7,b83), (a7, b84), (a7,b85), (a7,b86), (a7,b87), (a7,b88), (a7,b89), (a7, b90), (a7,b91), (a7,b92), (a7,b93), (a7,b94), (a7,b95), (a7, b96), (a7,b97), (a7,b98), (a7,b99), (a7,b100), (a7,b101), (a7, b102), (a7,b103), (a7,b104), (a7,b105).

Test Examples for the present compound are mentioned below.

Test Example 1

Assay of BACE1 Inhibiting Activity 48.5 μL of substrate peptide solution (Biotin-XSEVNLDAEFRHDSGC-Eu: X=ε-amino-n-caproic acid, Eu=Europium cryptate) was added to each well of 96-hole half-area plate (a black plate: Costar), and after addition of 0.5 μl of the compound of the present invention (DMSO solution) and 1 μl of Recombinant human BACE1(R&D Systems), the reaction mixture was incubated at 30° C. for 3.5 hours. The substrate peptide was synthesized by reacting Cryptate TBP-COOH mono SMP (CIS bio international) with Biotin-XSEVNLDAEFRHDSGC (Peptide Institute, Inc.). The final concentrations of the substrate peptide and Recombinant human BACE1 were adjusted to 18 nmol/L and 7.4 nmol/L, respectively, and the reaction was performed in sodium acetate buffer (50 mmol/L sodium acetate, pH 5.0, 0.008% Triton X-100).

After the incubation for reaction, 50 μl of 8.0 μg/ml Streptavidin-XL665 (CIS bio international) dissolved in phosphate buffer (150 mmol/L $K_2HPO_4$—$KH_2PO_4$, pH 7.0, 0.008% Triton X-100, 0.8 mol/L KF) was added to each well and left stand at 30° C. for 45 minutes. After then, fluorescence intensity was measured (excitation wavelength: 320 nm, measuring wavelength: 620 nm and 665 nm) using Wallac 1420 multilabel counter (Perkin Elmer life sciences). Enzymatic activity was determined from counting ratio of each wavelength (10,000×Count 665/Count 620) and 50% inhibitory concentration against the enzymatic activity ($IC_{50}$) was calculated.

Compound I-2:$IC_{50}$ value 0.0053 μmol/L
Compound I-4:$IC_{50}$ value 0.0106 μmol/L
Compound I-8:$IC_{50}$ value 0.0103 μmol/L
Compound I-11:$IC_{50}$ value 0.064 μmol/L Compounds I-1,3,5,9-10, 12-19, 21-24, 27-43, 45, 46, 48-52, 54-68, 70-80, 83-101, 103, 106-109, 113, 116, 128, 130-136, 142, 143, 144, and 146 to 170 also showed the $IC_{50}$ values of 1 μmol/L or less.

Test Example 2

Measurement of β-Amyloid (Aβ) Production Inhibitory Effect in Cell

Neuroblastoma SH-SY5Y cells (SH/APPwt) with human wild-type β-APP excessively expressed therein are prepared at 8×10⁵ cells/mL, and 150 μl portions thereof are inoculated into each well of a 96-well culture plate (Falcon). The cells are cultured for 2 hours at 37° C. in a 5% gaseous carbon dioxide incubator. Then, a solution which have been preliminarily prepared by adding and suspending the compound of the present invention (DMSO (dimethyl sulfoxide) solution) so as to be 2 μl/50 μl medium is added to the cell sap. Namely, the final DMSO concentration is 1%, and the amount of the cell culture is 200 μl. After the incubation is performed for 24 hours from the addition of the test compound, 100 μl of the culture supernatant is collected from each fraction. The amount of the Aβ in each fraction is measured.

The Aβ amount is measured as follows. 10 μl of a homogeneous time resolved fluorescence (HTRF) measurement reagent (Amyloid β I-40 peptide; CIS bio international) and 10 μl of the culture supernatant are put into a 384-well half area microplate (black microplate, Costar) and mixed with each other, and then left standing overnight at 4° C. while the light is shielded. Then, the fluorescence intensity (excitation wavelength: 337 nm, measurement wavelength: 620 nm and 665 nm) is measured with a micro plate reader (Artemis K-101; FURUNO ELECTRIC). The Aβ amount is determined from the count rate at each measurement wavelength (10000×Count 665/Count 620), and the amount needed to inhibit Aβ production by 50% ($IC_{50}$) is calculated from at least six different dosages.

Test Example 3

Lowering Effect on Brain β Amyloid in Rats

Compound of the present invention is suspended in 0.5%-methylcellulose, the final concentration is adjusted to 2 mg/mL, and this is orally administered to male Crl:SD rat (7 to 9 weeks old) at 10 mg/kg. In a vehicle control group, only 0.5% methylcellulose is administered, and an administration test is performed at 3 to 8 animals per group. A brain is isolated 3 hours after administration, a cerebral hemisphere is isolated, a weight thereof is measured, the hemisphere is rapidly frozen in liquid nitrogen, and stored at −80° C. until extraction date. The frozen cerebral hemisphere is transferred to a homogenizer manufactured by Teflon (registered trademark) under ice cooling, a 4-fold volume of a weight of an extraction buffer (containing 1% CHAPS ({3-[(3-chloroamidopropyl)dimethylammonio]1-propanesulfonate}), 20 mmol/L Tris-HCl (pH 8.0), 150 mmol/L NaCl, Complete (Roche) protease inhibitor) is added, up and down movement is repeated, and this is homogenized to solubilize for 2 minutes. The suspension is transferred to a centrifugation tube, allowed to stand on an ice for 3 hours or more and, thereafter centrifuged at 100,000×g, 4° C. for 20 minutes. After centrifugation, the supernatant is transferred to an ELISA plate (product No. 294-62501, Wako Junyaku Kogyo) for measuring β amyloid 40. ELISA measurement is performed according to the attached instruction. The lowering effect is calculated as a ratio compared to the brain β amyloid 40 level of vehicle control group of each test.

Test Example 4

CYP3A4 Fluorescent MBI Test

The CYP3A4 fluorescent MBI test is a test of investigating enhancement of CYP3A4 inhibition of a compound by a metabolism reaction. 7-benzyloxytrifluoromethylcoumarin (7-BFC) is debenzylated by the CYP3A4 enzyme (enzyme expressed in *Escherichia coli*) and 7-hydroxytrifluoromethylcoumarin (7-HFC) is produced as a fluorescing metabolite. The test is performed using 7-HFC production reaction as an index.

The reaction conditions are as follows: substrate, 5.6 µmol/L 7-BFC; pre-reaction time, 0 or 30 minutes; substrate reaction time, 15 minutes; reaction temperature, 25° C. (room temperature); CYP3A4 content (expressed in *Escherichia coli*), at pre-reaction time 62.5 pmol/mL, at reaction time 6.25 pmol/mL (at 10-fold dilution); concentrations of the compound of the present invention, 0.625, 1.25, 2.5, 5, 10, 20 µmol/L (six points).

An enzyme in a K-Pi buffer (pH 7.4) and a compound of the present invention solution as a pre-reaction solution were added to a 96-well plate at the composition of the pre-reaction. A part of pre-reaction solution was transferred to another 96-well plate, and 1/10 diluted by a substrate in a K-Pi buffer. NADPH as a co-factor was added to initiate a reaction as an index (without preincubation). After a predetermined time of a reaction, acetonitrile/0.5 mol/L Tris (trishydroxyaminomethane)=4/1(v/v) solution was added to stop the reaction. On the other hand, NADPH was also added to a remaining pre-reaction solution in order to initiate a preincubation (with preincubation). After a predetermined time of a preincubation, a part was transferred to another 96-well plate, and 1/10 diluted by a substrate in a K-Pi buffer in order to initiate a reaction as an index. After a predetermined time of a reaction, acetonitrile/0.5 mol/L Tris (trishydroxyaminomethane)=4/1 (v/v) solution was added to stop the reaction. Fluorescent values of 7-HFC as a metabolite were measured in each index reaction plate with a fluorescent plate reader. (Ex=420 nm, Em=535 nm).

The sample adding DMSO to a reaction system instead of compound of the present invention solution was adopted as a control (100%) because DMSO is used as a solvent to dissolve a compound of the present invention. Remaining activity (%) was calculated at each concentration of the compound of the present invention added as the solution, and $IC_{50}$ was calculated by reverse-presumption by a logistic model using a concentration and an inhibition rate. When a difference subtracting $IC_{50}$ values with preincubation from that without $IC_{50}$ value is 5 µM or more, this was defined as (+) and, when the difference is 3 µM or less, this was defined as (−).
Compound I-1: (−)

Test Example 5

CYP Inhibition Test

The test is to assess the inhibitory effect of a compound of the present invention towards typical substrate metabolism reactions on CYP enzymes in human liver microsomes. The commercially available pooled human liver microsomes were used.

The marker reactions on human main five CYP enzymes (CYP1A2, 2C9, 2C19, 2D6, and 3A4) were used as follows; 7-ethoxyresorufin O-deethylation (CYP1A2), tolbutamide methyl-hydroxylation (CYP2C9), mephenyloin 4'-hydroxylation (CYP2C19), dextromethorphan O-demethylation (CYP2D6), and terfenadine hydroxylation (CYP3A4

The reaction conditions were as follows: substrate, 0.5 µmol/L ethoxyresorufin (CYP1A2), 100 µmol/L tolbutamide (CYP2C9), 50 µmol/L S-mephenyloin (CYP2C19), 5 µmol/L dextromethorphan (CYP2D6), 1 µmol/L terfenadine (CYP3A4); reaction time, 15 minutes; reaction temperature, 37° C.; enzyme, pooled human liver microsomes 0.2 mg protein/mL; concentrations of the compound of the present invention, 1, 5, 10, 20 µmol/L (four points).

Five kinds of substrates, human liver microsomes, or a compound of the present invention in 50 mmol/L Hepes buffer was added to a 96-well plate at the composition as described above as a reaction solution. NADPH as a cofactor was added to this 96-well plate in order to initiate metabolism reactions. After the incubation at 37° C. for 15 minutes, a methanol/acetonitrile=1/1 (v/v) solution was added to stop the reaction. After the centrifugation at 3000 rpm for 15 minutes, resorufin (CYP1A2 metabolite) in the supernatant was quantified by a fluorescent plate reader, and hydroxytolbutamide (CYP2C9 metabolite), 4'-hydroxymephenyloin (CYP2C19 metabolite), dextrorphan (CYP2D6 metabolite), and terfenadine alcohol metabolite (CYP3A4 metabolite) in the supernatant were quantified by LC/MS/MS.

The sample adding DMSO to a reaction system instead of compound of the present invention solution is adopted as a control (100%) because DMSO was used as a solvent to dissolve a compound of the present invention. Remaining activity (%) was calculated at each concentration of a compound of the present invention, and $IC_{50}$ value was calculated by reverse presumption by a logistic model using a concentration and an inhibition rate.

Compound I-9: five kinds >20 µM

Test Example 6

Fluctuation Ames Test

The mutagenicity of the compound of the present invention is evaluated.

Each 20 µL of freeze-stored *Salmonella typhimurium* (TA98 and TA100 strain) is inoculated in 10 mL of liquid nutrient medium (2.5% Oxoid nutrient broth No. 2), and the cultures are incubated at 37° C. under shaking for 10 hours. 9 mL of TA98 culture is centrifuged (2000×g, 10 minutes) to remove medium, and the bacteria is suspended in 9 mL of Micro F buffer ($K_2HPO_4$: 3.5 g/L, $KH_2PO_4$: 1 g/L, $(NH_4)_2SO_4$: 1 g/L, trisodium citrate dihydrate: 0.25 g/L, $MgSO_4.7H_2O$: 0.1 g/L), and the suspension is added to 110 mL of Exposure medium (Micro F buffer containing Biotin: 8 µg/mL, histidine: 0.2 µg/mL, glucose: 8 mg/mL). 3.16 mL of TA100 culture is added to 120 mL of Exposure medium to prepare the test bacterial solution. 588 µL of the test bacterial solution (or mixed solution of 498 µl of the test bacterial solution and 90 µL of the S9 mix in the case with metabolic activation system) are mixed with each 12 µL of the following solution: DMSO solution of the compound of the present invention (several stage dilution from maximum dose 50 mg/mL at 2 to 3-fold ratio); DMSO as negative control; 50 µg/mL of 4-nitroquinoline-1-oxide DMSO solution as positive control for TA98 without metabolic activation system; 0.25 µg/mL of 2-(2-furyl)-3-(5-nitro-2-furyl)acrylamide DMSO solution as positive control for TA100 without metabolic activation system; 40 µg/mL of 2-aminoanthracene DMSO solution as positive control for TA98 with metabolic activation system; or 20 µg/mL of 2-aminoanthracene DMSO solution as positive control for TA100 with metabolic activation system. A mixed solution is incubated at 37° C. under shaking for 90 minutes. 460 µL of the bacterial solution exposed to the compound of the present invention is mixed with 2300 µL of Indicator medium (Micro F buffer containing biotin: 8 µg/mL, histidine: 0.2 µg/mL, glucose: 8 mg/mL, Bromo Cresol Purple: 37.5 µg/mL), each 50 µL is dispensed into 48 wells/dose in the microwell plates, and is subjected to stationary cultivation at 37° C. for 3 days. A well containing the bacteria, which has obtained the ability of proliferation by mutation in the gene coding amino acid (histidine) synthetase, turns the color from purple to yellow due to pH change. The mutagenicity is evaluated by counting the number of the yellow wells among the 48 total wells per dose and comparing with the negative control group. (−) means that mutagenicity is negative and (+) means positive.

Test Example 7-1

Solubility Test

A 2-fold dilution series (12 points) of a 10 mM solution of a compound of the present invention in DMSO was added to a medium (JP-I, JP-II) (2%), and solubility was assessed by 3 stages (High; >40 µM, Medium; 3-40 µM, Low; <3 µM) from a turbidity after 4 hours.

Compound I-5: High (JP-II)

Test Example 7-2

Solubility Test

The solubility of each compound of the present invention is determined under 1% DMSO addition conditions. A 10 mmol/L solution of the compound is prepared with DMSO, and 6 µL of the compound of the present invention solution is added to 594 µL of an artificial intestinal juice (water and 118 mL of 0.2 mol/L NaOH reagent are added to 250 mL of 0.2 mol/L potassium dihydrogen phosphate reagent to reach 1000 mL) with a pH of 6.8. The mixture is left standing for 16 hours at 25° C., and the mixture is vacuum-filtered. The filtrate is two-fold diluted with methanol/water=1/1 (v/v), and the compound concentration in the filtrate is measured with HPLC or LC/MS/MS by the absolute calibration method.

Test Example 8

Metabolism Stability Test

Using a commercially available pooled human liver microsomes, a compound of the present invention is reacted for a constant time, a remaining rate is calculated by comparing a reacted sample and an unreacted sample, thereby, a degree of metabolism in liver was assessed.

A reaction was performed (oxidative reaction) at 37° C. for 0 minute or 30 minutes in the presence of 1 mmol/L NADPH in 0.2 mL of a buffer (50 mmol/L Tris-HCl pH 7.4, 150 mmol/L potassium chloride, 10 mmol/L magnesium chloride) containing 0.5 mg protein/mL of human liver microsomes. After the reaction, 50 µL of the reaction solution was added to 100 µL of a methanol/acetonitrile=1/1 (v/v), mixed and centrifuged at 3000 rpm for 15 minutes. The compound of the present invention in the supernatant was quantified by LC/MS/MS, and a remaining amount of the compound of the present invention after the reaction was calculated, letting a compound amount at 0 minute reaction time to be 100%.

Compound I-8: 99%

Test Example 9 hERG Test

For the purpose of assessing risk of an electrocardiogram QT interval prolongation, effects on delayed rectifier K+ current ($I_{Kr}$), which plays an important role in the ventricular repolarization process of the compound of the present invention, is studied using HEK293 cells expressing human ether-a-go-go related gene (hERG) channel.

A cell is retained at a membrane potential of −80 mV by whole cell patch clamp method using an automated patch clamp system (PatchXpress 7000A, Axon Instruments Inc.). $I_{Kr}$ induced by depolarization pulse stimulation at +40 mV for 2 seconds and, further, repolarization pulse stimulation at −50 mV for 2 seconds is recorded. After the generated current is stabilized, extracellular solution (NaCl: 135 mmol/L, KCl: 5.4 mmol/L, $NaH_2PO_4$: 0.3 mmol/L, $CaCl_2.2H_2O$: 1.8 mmol/L, $MgCl_2.6H_2O$: 1 mmol/L, glucose: 10 mmol/L, HEPES (4-(2-hydroxyethyl)-1-piperazine ethanesulfonic acid): 10 mmol/L, pH=7.4) in which the compound of the present invention have been dissolved at an objective concentration is applied to the cell under the room temperature condition for 10 minutes. From the recording $I_{Kr}$, an absolute value of the tail peak current is measured based on the current value at the resting membrane potential using an analysis software (DataXpress ver. 1, Molecular Devices Corporation). Further, the % inhibition relative to the tail peak current before application of the compound of the present invention is calculated, and compared with the vehicle-applied group (0.1% dimethyl sulfoxide solution) to assess influence of the compound of the present invention on $I_{Kr}$.

Test Example 10

Powder Solubility Test

Appropriate amounts of the compound of the present invention are put into appropriate containers. 200 µL of JP 1st fluid (Dissolve 2.0 g of sodium chloride in 7.0 mL of hydrochloric acid and water to make 1000 mL), 200 µL of JP 2nd fluid (A mixture of phosphate buffer (pH 6.8) and water (1:1)), and 200 µL of JP 2nd fluid containing 20 mmol/L of sodium taurocholate (TCA) (TCA 1.08 g and JP 2nd fluid to make 100 mL) are added to the respective containers. When the compound of the present invention is dissolved after the addition of the test fluid, the bulk powder is added as appropriate. The containers are sealed, and shaken for 1 hour at 37° C. The mixtures are filtered, and 100 µL of methanol is added to each of the filtrate (100 µL) so that the filtrates are two-fold diluted. The dilution ratio may be changed if necessary. After confirming that there is no bubbles and precipitates in the diluted solution, the containers are sealed and shaken. Quantification is performed by HPLC with an absolute calibration method.

Test Example 11

BA Test

Materials and Methods for Studies on Oral Absorption
(1) Animal: mouse or SD rat
(2) Breeding conditions: mouse or SD rat was allowed to free access to the sterilized tap water and the solid food.
(3) Dose and grouping: orally or intravenously administered at a predetermined dose; grouping was as follows (Dose depends on the compound)
Oral administration: 1 to 30 mg/kg (n=2 to 3)
Intravenous administration: 0.5 to 10 mg/kg (n=2 to 3)
(4) Preparation of dosing formulation: for oral administration, in a solution or a suspension state; for intravenous administration, in a solubilized state
(5) Dosing method: in oral administration, forcedly and intragastrically administer using a syringe attached a flexible feeding tube; in intravenous administration, administer from caudal vein using a syringe attached with a needle
(6) Evaluation items: blood was collected at the scheduled time, and the plasma concentration of the compound of the present invention was measured by LC/MS/MS
(7) Statistical analysis: regarding the transition of the plasma concentration of the compound of the present invention, the area under the plasma concentration-time curve (AUC) was calculated by non-linear least squares program WinNonlin (Registered trademark), and the bioavailability (BA) of the compound of the present invention was calculated from the AUCs of the oral administration group and intravenous administration group
Compound I-16: 98.3%

Test Example 12

Brain Distribution Studies

Compound of the present invention is intravenously administered to a rat at 0.5 mg/mL/kg dosage. 30 minutes later, all blood is drawn from the abdominal aorta under isoflurane anesthesia for death from exsanguination.

The brain is enucleated and 20-25% of homogenate thereof is prepared with distilled water.

The obtained blood is used as plasma after centrifuging. The control plasma is added to the brain sample at 1:1. The control brain homogenate is added to the plasma samples at 1:1. Each sample is measured using LC/MS/MS. The obtained area ratio (a brain/plasma) is used for the brain Kp value.

Test Example 13

Ames Test

Ames test is performed by using Salmonellas (*Salmonella typhimurium*) TA 98, TA100, TA1535 and TA1537 and *Escherichia coli*WP2uvrA as test strains with or without metabolic activation in the pre-incubation method to check the presence or absence of gene mutagenicity of compounds of the present invention.

Test Example 14

P-gp Substrate Test

Compound of the present invention is added in the culture insert of the Transwell wherein human MDR1 expressing cells or parent cells are monolayer cultivated, and reacted for a predetermined period of times. The compound of the present invention is investigated whether a P-gp substrate or not by comparing Efflux Ratio (ER) values of MDR1 expressing cells and parent cells. Here, ER is calculated from the membrane permeability coefficients of the direction from Basolateral side to Apical side (B to A) and the direction from Apical side to Basolateral side (A to B)) of MDR1 expressing cells and parent cells.

Formulation Examples

The following Formulation Examples are only exemplified and not intended to limit the scope of the present invention.

Formulation Example 1

Tablet

| | |
|---|---|
| Compound of the present invention | 15 mg |
| Lactose | 15 mg |
| Calcium stearate | 3 mg |

All of the above ingredients except for calcium stearate are uniformly mixed. Then the mixture is crushed, granulated and dried to obtain a suitable size of granules. Then, calcium stearate is added to the granules. Finally, tableting is performed under a compression force.

Formulation Example 2

Capsules

| Compound of the present invention | 10 mg |
|---|---|
| Magnesium stearate | 10 mg |
| Lactose | 80 mg |

The above ingredients are mixed uniformly to obtain powders or fine granules, and then the obtained mixture is filled in capsules.

Formulation Example 3

Granules

| Compound of the present invention | 30 g |
|---|---|
| Lactose | 265 g |
| Magnesium stearate | 5 g |

After the above ingredients are mixed uniformly, the mixture is compressed. The compressed matters are crushed, granulated and sieved to obtain suitable size of granules.

[Industrial Applicability]

The compound of the present invention can be a useful therapeutic or prophylactic agent for diseases induced by production, secretion and/or deposition of amyloid β proteins.

The invention claimed is:
1. A compound of formula (I):

[Chemical Formula 1]

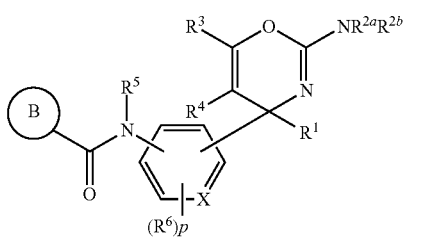

wherein —X═ is —CR$^7$═ or —N═,
ring B is a substituted or unsubstituted carbocycle or a substituted or unsubstituted heterocycle,
R$^1$ is substituted or unsubstituted alkyl, substituted or unsubstituted alkenyl, substituted or unsubstituted alkynyl, substituted or unsubstituted acyl, cyano, carboxy, substituted or unsubstituted alkoxycarbonyl, substituted or unsubstituted alkenyloxycarbonyl, substituted or unsubstituted alkynyloxycarbonyl, substituted or unsubstituted carbamoyl, substituted or unsubstituted thiocarbamoyl, a substituted or unsubstituted carbocyclic group or a substituted or unsubstituted heterocyclic group,
R$^{2a}$ and R$^{2b}$ are each independently hydrogen, substituted or unsubstituted alkyl, substituted or unsubstituted acyl, substituted or unsubstituted alkoxycarbonyl or substituted or unsubstituted carbamoyl,
R$^3$ and R$^4$ are each independently hydrogen, halogen, hydroxy, substituted or unsubstituted alkyl, substituted or unsubstituted alkenyl, substituted or unsubstituted alkynyl, substituted or unsubstituted alkoxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, substituted or unsubstituted acyloxy, cyano, nitro, carboxy, substituted or unsubstituted alkoxycarbonyl, substituted or unsubstituted alkenyloxycarbonyl, substituted or unsubstituted alkynyloxycarbonyl, substituted or unsubstituted amino, substituted or unsubstituted carbamoyl, substituted or unsubstituted thiocarbamoyl, substituted or unsubstituted sulfamoyl, substituted or unsubstituted alkylsulfinyl, substituted or unsubstituted alkenylsulfinyl, substituted or unsubstituted alkynylsulfinyl, substituted or unsubstituted alkylsulfonyl, substituted or unsubstituted alkenylsulfonyl, substituted or unsubstituted alkynylsulfonyl, a substituted or unsubstituted carbocyclic group, substituted or unsubstituted carbocyclyloxy, substituted or unsubstituted carbocyclylthio, substituted or unsubstituted carbocyclylalkyl, substituted or unsubstituted carbocyclylalkoxy, substituted or unsubstituted carbocyclyloxycarbonyl, substituted or unsubstituted carbocyclylsulfinyl, substituted or unsubstituted carbocyclylsulfonyl, a substituted or unsubstituted heterocyclic group, substituted or unsubstituted heterocyclyloxy, substituted or unsubstituted heterocyclylthio, substituted or unsubstituted heterocyclylalkyl, substituted or unsubstituted heterocyclylalkoxy, substituted or unsubstituted heterocyclyloxycarbonyl, substituted or unsubstituted heterocyclylsulfinyl or substituted or unsubstituted heterocyclylsulfonyl,
R$^5$ is hydrogen, substituted or unsubstituted alkyl, substituted or unsubstituted alkenyl, substituted or unsubstituted alkynyl or substituted or unsubstituted acyl,
each R$^6$ is independently halogen, hydroxy, substituted or unsubstituted alkyl, substituted or unsubstituted alkenyl, substituted or unsubstituted alkynyl, substituted or unsubstituted alkoxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, substituted or unsubstituted acyloxy, cyano, nitro, carboxy, substituted or unsubstituted alkoxycarbonyl, substituted or unsubstituted alkenyloxycarbonyl, substituted or unsubstituted alkynyloxycarbonyl, substituted or unsubstituted amino, substituted or unsubstituted carbamoyl, substituted or unsubstituted thiocarbamoyl, substituted or unsubstituted sulfamoyl, substituted or unsubstituted alkylsulfinyl, substituted or unsubstituted alkenylsulfinyl, substituted or unsubstituted alkynylsulfinyl, substituted or unsubstituted alkylsulfonyl, substituted or unsubstituted alkenylsulfonyl or substituted or unsubstituted alkynylsulfonyl,
R$^7$ is hydrogen, halogen, hydroxy, substituted or unsubstituted alkyl, substituted or unsubstituted alkenyl, substituted or unsubstituted alkynyl, substituted or unsubstituted alkoxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, substituted or unsubstituted acyloxy, cyano, nitro, carboxy, substituted or unsubstituted alkoxycarbonyl, substituted or unsubstituted alkenyloxycarbonyl, substituted or unsubstituted alkynyloxycarbonyl, substituted or unsubstituted amino, substituted or unsubstituted carbamoyl, substituted or unsubstituted thiocarbamoyl, substituted or unsubstituted sulfamoyl, substituted or unsubstituted alkylsulfinyl, substituted or unsubstituted alkenylsulfinyl, substituted or unsubstituted alkynylsulfinyl, substituted or unsubstituted alkylsulfonyl, substituted or unsubstituted alkenylsulfonyl or substituted or unsubstituted alkynylsulfonyl, and p is an integer of 0 to 3, wherein the substituents of "a substituted or unsubstituted carbocycle" and "a substituted or unsubstituted heterocycle" in ring B are one or more selected from a) a group selected from the substituent group α, wherein the substituent group α is a group consisting of halogen, hydroxy, alkoxy, halogenoalkoxy, hydroxyalkoxy, alkoxyalkoxy, acyl, acyloxy, carboxy, alkoxycarbonyl, amino, acylamino, alkylamino, imino, hydroxyimino, alkoxyimino, alkylthio, carbamoyl, alkylcarbamoyl, hydroxyalkylcarbamoyl, sulfamoyl, alkylsulfamoyl, alkylsulfinyl, alkylsulfonyl, alkylsulfonylamino, alkylsulfonylalkylamino, alkylsulfonylimino, alkylsulfinylamino, alkylsulfinylalkylamino, alkylsulfonylimino, cyano, nitro, a carbocyclic group and a heterocyclic group wherein the carbocycle and heterocycle may be each substituted with one or more substituents selected from halogen, alkyl, hydroxy, and alkoxy, b) alkyl substituted with one or more groups selected from the substituent group α, hydroxyimino and alkoxyimino, or unsubstituted alkyl;

c) aminoalkyl substituted with one or more groups selected from the substituent group α, d) alkenyl substituted with one or more substituents selected from the substituent group α, or unsubstituted alkenyl;

e) alkynyl substituted with one or more substituents selected from the substituent group α, or unsubstituted alkynyl;

f) alkoxy substituted with one or more substituents selected from the substituent group α, g) alkoxyalkoxy substituted with one or more substituents selected from the substituent group α, h) alkenyloxy substituted with one or more substituents selected from the substituent group α, or unsubstituted alkenyloxy;

i) alkoxyalkenyloxy substituted with one or more substituents selected from the substituent group α;

j) alkynyloxy substituted with one or more substituents selected from the substituent group α, or unsubstituted alkynyloxy;

k) alkoxyalkynyloxy substituted with one or more group(s) selected from the substituent group α;

l) alkylthio substituted with one or more substituents selected from the substituent group α, or unsubstituted alkylthio;

m) alkenylthio substituted with one or more substituents selected from the substituent group α, or unsubstituted alkenylthio;

n) alkynylthio substituted with one or more substituents selected from the substituent group α, or unsubstituted alkynylthio;

o) alkylamino substituted with one or more substituents selected from the substituent group α;

p) alkenylamino substituted with one or more substituents selected from the substituent group α;

q) alkynylamino substituted with one or more substituents selected from the substituent group α;

r) aminooxy substituted with one or more substituents selected from the substituent group α and alkylidene, or unsubstituted aminooxy;

s) acyl substituted with one or more substituents selected from the substituent group α;

t) alkylcarbamoyl substituted with one or more substituents selected from the substituent group α;

u) alkoxycarbonyl substituted with one or more substituents selected from the substituent group α;

v) alkylsulfonyl substituted with one or more substituents selected from the substituent group α, or unsubstituted alkylsulfonyl;

w) alkylsulfinyl substituted with one or more substituents selected from the substituent group α, or unsubstituted alkylsulfinyl;

x) alkylsulfamoyl substituted with one or more substituents selected from the substituent group α;

y) a carbocyclic group substituted with one or more substituents selected from the substituent group α, azide, alkyl and halogenoalkyl;

z) a heterocyclic group substituted with one or more substituents selected from the substituent group α, azide, alkyl and halogenoalkyl;

aa) carbocyclylalkyl substituted with one or more substituents selected from the substituent group α, azide, alkyl and halogenoalkyl, or unsubstituted carbocyclylalkyl;

ab) heterocyclylalkyl substituted with one or more substituents selected from the substituent group α, azide, alkyl and halogenoalkyl, or unsubstituted heterocyclylalkyl;

ac) carbocyclyloxy substituted with one or more substituents selected from the substituent group α, azide, alkyl and halogenoalkyl, or unsubstituted carbocyclyloxy;

ad) heterocyclyloxy substituted with one or more substituents selected from the substituent group α, azide, alkyl and halogenoalkyl, or unsubstituted heterocyclyloxy;

ae) carbocyclylalkoxy substituted with one or more substituents selected from the substituent group α, azide, alkyl and halogenoalkyl, or unsubstituted carbocyclylalkoxy;

af) heterocyclylalkoxy substituted with one or more substituents selected from the substituent group α, azide, alkyl and halogenoalkyl, or unsubstituted heterocyclylalkoxy;

ag) carbocyclylalkoxycarbonyl substituted with one or more substituents selected from the substituent group α, azide, alkyl and halogenoalkyl, or unsubstituted carbocyclylalkoxycarbonyl;

ah) heterocyclylalkoxycarbonyl substituted with one or more substituents selected from the substituent group α, azide, alkyl and halogenoalkyl, or unsubstituted heterocyclylalkoxycarbonyl;

ai) carbocyclylthio substituted with one or more substituents selected from the substituent group α, azide, alkyl and halogenoalkyl, or unsubstituted carbocyclylthio;

aj) heterocyclylthio substituted with one or more substituents selected from the substituent group α, azide, alkyl and halogenoalkyl, or unsubstituted heterocyclylthio;

ak) carbocyclylamino substituted with one or more substituents selected from the substituent group α, azide, alkyl and halogenoalkyl, or unsubstituted carbocyclylamino;

al) heterocyclylamino substituted with one or more substituents selected from the substituent group α, azide, alkyl and halogenoalkyl, or unsubstituted heterocyclylamino;
am) carbocyclylalkylamino substituted with one or more substituents selected from the substituent group α, azide, alkyl and halogenoalkyl or unsubstituted carbocyclylalkylamino;
an) heterocyclylalkylamino substituted with one or more substituents selected from the substituent group α, azide, alkyl and halogenoalkyl, or unsubstituted heterocyclylalkylamino;
ao) carbocyclylsulfamoyl substituted with one or more substituents selected from the substituent group α, azide, alkyl and halogenoalkyl, or unsubstituted carbocyclylsulfamoyl;
ap) heterocyclylsulfamoyl substituted with one or more substituents selected from the substituent group α, azide, alkyl and halogenoalkyl, or unsubstituted heterocyclylsulfamoyl;
aq) carbocyclylsulfonyl substituted with one or more substituents selected from the substituent group α, azide, alkyl and halogenoalkyl, or unsubstituted carbocyclylsulfonyl;
ar) heterocyclylsulfonyl substituted with one or more substituents selected from the substituent group α, azide, alkyl and halogenoalkyl, or unsubstituted heterocyclylsulfonyl;
as) carbocyclylcarbamoyl substituted with one or more substituents selected from the substituent group α, azide, alkyl and halogenoalkyl, or unsubstituted carbocyclylcarbamoyl;
at) heterocyclylcarbamoyl substituted with one or more substituents selected from the substituent group α, azide, alkyl and halogenoalkyl, or unsubstituted heterocyclylcarbamoyl;
au) carbocyclylalkylcarbamoyl substituted with one or more substituents selected from the substituent group α, azide, alkyl and halogenoalkyl, or unsubstituted carbocyclylalkylcarbamoyl;
av) heterocyclylalkylcarbamoyl substituted with one or more substituents selected from the substituent group α, azide, alkyl and halogenoalkyl, or unsubstituted heterocyclylalkylcarbamoyl;
aw) carbocyclyloxycarbonyl substituted with one or more substituents selected from the substituent group α, azide, alkyl and halogenoalkyl, or unsubstituted carbocyclyloxycarbonyl;
ax) heterocyclyloxycarbonyl substituted with one or more substituents selected from the substituent group α, azide, alkyl and halogenoalkyl, or unsubstituted heterocyclyloxycarbonyl;
ay) alkylenedioxy substituted with halogen, or unsubstituted alkylenedioxy;
az) oxo; and
ba) azide,
the substituents of "substituted or unsubstituted alkyl", "substituted or unsubstituted alkoxy", "substituted or unsubstituted alkoxycarbonyl", "substituted or unsubstituted alkylthio", "substituted or unsubstituted alkylsulfonyl", "substituted or unsubstituted alkylsulfinyl", "substituted or unsubstituted alkenyl", "substituted or unsubstituted alkenyloxy", "substituted or unsubstituted alkenyloxycarbonyl", "substituted or unsubstituted alkenylthio", "substituted or unsubstituted alkenylsulfinyl", "substituted or unsubstituted alkenylsulfonyl", "substituted or unsubstituted alkynyl", "substituted or unsubstituted alkynyloxy", "substituted or unsubstituted alkynylthio", "substituted or unsubstituted alkynyloxycarbonyl", "substituted or unsubstituted alkynylsulfinyl", and "substituted or unsubstituted alkynylsulfonyl" are one or more substituents selected from the substituent group α, the substituents of "substituted or unsubstituted amino", "substituted or unsubstituted carbamoyl", "substituted or unsubstituted thiocarbamoyl" and "substituted or unsubstituted sulfamoyl" are one to two substituents selected from alkyl, acyl, hydroxy, alkoxy, alkoxycarbonyl, a carbocyclic group and a heterocyclic group, the term "acyl" includes formyl, alkylcarbonyl, alkenylcarbonyl, alkynylcarbonyl, carbocyclylcarbonyl, and/or heterocyclylcarbonyl, the substituents of "substituted or unsubstituted acyl" and "substituted or unsubstituted , acyloxy" are one or more substituents selected from the substituent group α, and the ring portions of carbocyclylcarbonyl and heterocyclylcarbonyl may be substituted with one or more substituents selected from alkyl, substituent group α, and alkyl substituted with one or more substituents selected from substituent group α, the substituents of "a substituted or unsubstituted carbocyclic group", "substituted or unsubstituted carbocyclylthio", "substituted or unsubstituted carbocyclyloxycarbonyl", "substituted or unsubstituted carbocyclyloxy", "substituted or unsubstituted carbocyclylsulfinyl", "substituted or unsubstituted carbocyclylsulfonyl", "substituted or unsubstituted heterocyclic group", "substituted or unsubstituted heterocyclyloxy", "substituted or unsubstituted heterocyclylthio", "substituted or unsubstituted heterocyclyloxycarbonyl", "substituted or unsubstituted heterocyclylsulfinyl", "substituted or unsubstituted heterocyclylsulfonyl", "substituted or unsubstituted heterocyclylalkyl" and "substituted or unsubstituted heterocyclylalkoxy" in the groups other than ring B are one or more substituents selected from (i) alkyl substituted with one or more substituents selected from the substituent group α, (ii) unsubstituted alkyl, and (iii) the substituent group α, excluding the following compounds:

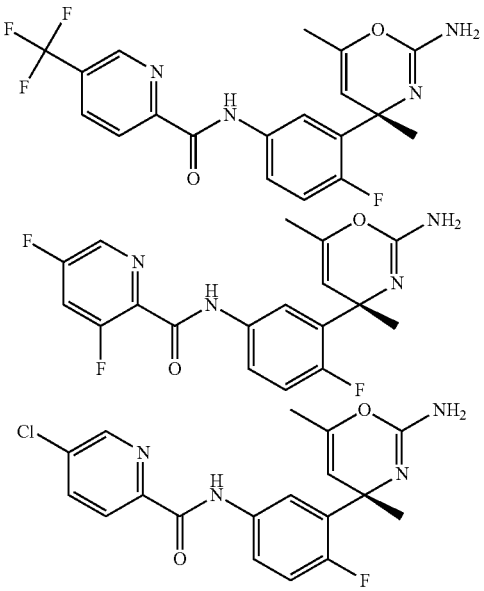

-continued

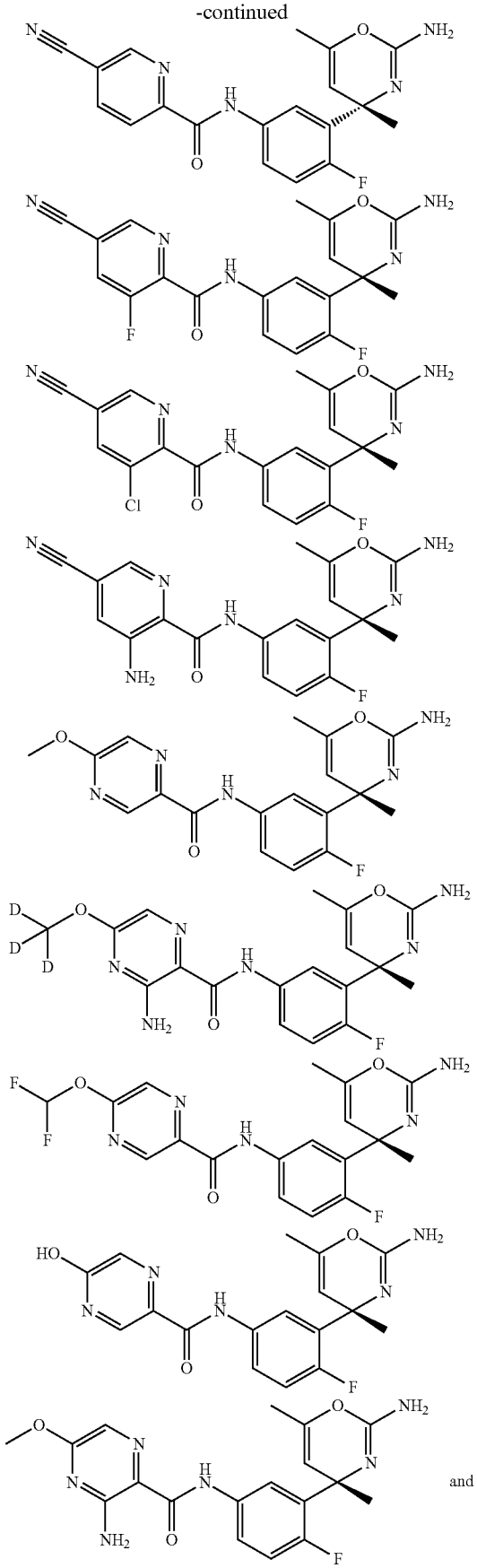

-continued

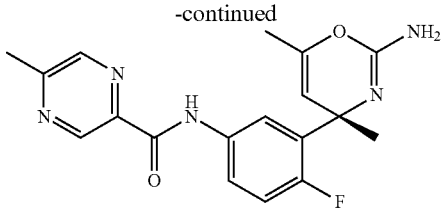

and wherein D means deuterium,
or a pharmaceutically acceptable salt thereof.

2. The compound according to claim 1, wherein $R^3$ is hydrogen, halogen, or substituted alkyl, or a pharmaceutically acceptable salt thereof.

3. The compound according to claim 1, wherein $R^3$ is alkyl substituted with halogen, or a pharmaceutically acceptable salt thereof.

4. The compound according to claim 1, wherein $R^3$ is methyl, —X═is —$CR^7$═, p is an integer of 0, and one of the following conditions is satisfied:
1) $R^7$ is chloro,
2) $R^7$ is fluoro, and ring B is a substituted or unsubstituted carbocycle, or
3) $R^7$ is fluoro, ring B is a substituted heterocycle, and the ring B has at least one substituent selected from dihalogenoalkyl, alkenyl, alkynyl, halogenoethoxy and monohalogenomethoxy,
wherein the substituents of "a substituted or unsubstituted carbocycle" and "substituted heterocycle" in ring B are one or more selected from a) to ba) as defined in claim 1, or a pharmaceutically acceptable salt thereof.

5. The compound according to claim 1, wherein

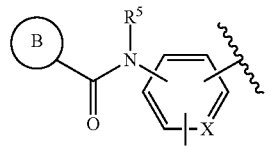 is or a pharmaceutically acceptable salt thereof.

6. The compound according to claim 1, wherein $R^1$ is C1 to C3 alkyl substituted with halogen, or a pharmaceutically acceptable salt thereof.

7. The compound according to claim 1, wherein $R^1$ is C1 to C3 unsubstituted alkyl, or a pharmaceutically acceptable salt thereof.

8. The compound according to claim 1, wherein ring B is substituted or unsubstituted pyridine, substituted or unsubstituted pyrimidine, substituted or unsubstituted pyrazine, substituted or unsubstituted oxazole, substituted or unsubstituted thiazole, substituted or unsubstituted pyrazole, substituted or unsubstituted benzene, substituted or unsubstituted benzoxazole or substituted or unsubstituted benzothiazole,
wherein the substituents of "substituted or unsubstituted pyridine", "substituted or unsubstituted pyrimidine", "substituted or unsubstituted pyrazine", "substituted or unsubstituted oxazole", "substituted or unsubstituted thiazole", "substituted or unsubstituted pyrazole", "substituted or unsubstituted benzene", "substituted or unsubstituted benzoxazole" and "substituted or unsubstituted benzothiazole" are one or more selected from a) to ba) as defined in claim 1, or a pharmaceutically acceptable salt thereof.

9. The compound according to claim 1, wherein ring B is optionally substituted with one or more substituent(s) selected from halogen, cyano, hydroxy, nitro,
- b) alkyl substituted with one or more groups selected from the substituent group α, hydroxyimino and alkoxyimino, or unsubstituted alkyl;
- d) alkenyl substituted with one or more substituents selected from the substituent group α, or unsubstituted alkenyl;
- e) alkynyl substituted with one or more substituents selected from the substituent group α, or unsubstituted alkynyl;
- f) alkoxy substituted with one or more substituents selected from the substituent group α or unsubstituted alkoxy,
- h) alkenyloxy substituted with one or more substituents selected from the substituent group α, or unsubstituted alkenyloxy;
- j) alkynyloxy substituted with one or more substituents selected from the substituent group α, or unsubstituted alkynyloxy;
- l) alkylthio substituted with one or more substituents selected from the substituent group α, or unsubstituted alkylthio;
- m) alkenylthio substituted with one or more substituents selected from the substituent group α, or unsubstituted alkenylthio;
- n) alkynylthio substituted with one or more substituents selected from the substituent group α, or unsubstituted alkynylthio;
- a) amino, acylamino, alkylamino, alkylsulfonylamino, alkylsulfonylalkylamino, alkylsulfinylamino, alkylsulfinylalkylamino;
- o) alkylamino substituted with one or more substituents selected from the substituent group α;
- p) alkenylamino substituted with one or more substituents selected from the substituent group α;
- q) alkynylamino substituted with one or more substituents selected from the substituent group α;
- ak) carbocyclylamino substituted with one or more substituents selected from the substituent group α, azide, alkyl and halogenoalkyl, or unsubstituted carbocyclylamino;
- al) heterocyclylamino substituted with one or more substituents selected from the substituent group α, azide, alkyl and halogenoalkyl, or unsubstituted heterocyclylamino;
- am) carbocyclylalkylamino substituted with one or more substituents selected from the substituent group α, azide, alkyl and halogenoalkyl or unsubstituted carbocyclylalkylamino;
- an) heterocyclylalkylamino substituted with one or more substituents selected from the substituent group α, azide, alkyl and halogenoalkyl, or unsubstituted heterocyclylalkylamino; and
- y) cycloalkyl, substituted with one or more substituents selected from the substituent group α, azide, alkyl and halogenoalkyl, or unsubstituted cycloalkyl, or a pharmaceutically acceptable salt thereof.

10. The compound according to claim 1, wherein $R^4$ is hydrogen, or a pharmaceutically acceptable salt thereof.

11. The compound according to claim 1, wherein both of $R^{2a}$ and $R^{2b}$ are hydrogen, or a pharmaceutically acceptable salt thereof.

12. A pharmaceutical composition comprising the compound according to claim 1, or a pharmaceutically acceptable salt thereof.

13. A pharmaceutical composition having BACE1 inhibitory activity comprising the compound according to claim 1, or a pharmaceutically acceptable salt thereof.

14. A method for treating and/or improving a symptom of dementia of the Alzheimer's type, Alzheimer's disease, senile dementia of Alzheimer type, Down's syndrome, memory impairment, prion disease (Creutzfeldt-Jakob disease), mild cognitive impairment (MCI), Dutch type of hereditary cerebral hemorrhage with amyloidosis, cerebral amyloid angiopathy, Alzheimer's disease with vascular type dementia, dementia with Parkinson's Disease, dementia with progressive supranuclear palsy, dementia with Cortico-basal degeneration, Alzheimer's disease with diffuse Lewy body disease, age-related macular degeneration, Parkinson's Disease or amyloid angiopathy, comprising administering the compound according to claim 1, or a pharmaceutically acceptable salt thereof.

* * * * *